US009168286B2

(12) United States Patent
Chevrier et al.

(10) Patent No.: US 9,168,286 B2
(45) Date of Patent: Oct. 27, 2015

(54) METHODS AND COMPOSITIONS FOR USE IN TREATMENT OF PATIENTS WITH AUTOANTIBODY POSITIVE DISEASE

(75) Inventors: Marc Chevrier, Collegeville, PA (US); William W. Freimuth, Gaithersburg, MD (US); Zhenshao Zhong, Potomac, MD (US); Daniel Odenheimer, Potomac, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 895 days.

(21) Appl. No.: 12/135,025

(22) Filed: Jun. 6, 2008

(65) Prior Publication Data

US 2009/0148462 A1    Jun. 11, 2009

Related U.S. Application Data

(63) Continuation-in-part of application No. 11/543,024, filed on Oct. 5, 2006, now abandoned.

(60) Provisional application No. 60/929,109, filed on Jun. 13, 2007, provisional application No. 60/725,625, filed on Oct. 13, 2005, provisional application No. 60/735,967, filed on Nov. 14, 2005, provisional application No. 60/776,664, filed on Feb. 27, 2006, provisional application No. 60/781,387, filed on Mar. 13, 2006, provisional application No. 60/787,557, filed on Mar. 31, 2006, provisional application No. 60/797,360, filed on May 4, 2006, provisional application No. 60/814,870, filed on Jun. 20, 2006, provisional application No. 60/815,558, filed on Jun. 22, 2006, provisional application No. 60/815,827, filed on Jun. 23, 2006, provisional application No. 60/834,150, filed on Jul. 31, 2006, provisional application No. 60/725,626, filed on Oct. 13, 2005, provisional application No. 60/735,988, filed on Nov. 14, 2005, provisional application No. 60/776,665, filed on Feb. 27, 2006, provisional application No. 60/797,351, filed on May 4, 2006, provisional application No. 60/814,869, filed on Jun. 20, 2006, provisional application No. 60/815,559, filed on Jun. 22, 2006, provisional application No. 60/834,152, filed on Jul. 31, 2006, provisional application No. 60/725,627, filed on Oct. 13, 2005, provisional application No. 60/735,964, filed on Nov. 14, 2005, provisional application No. 60/776,658, filed on Feb. 27, 2006, provisional application No. 60/725,629, filed on Oct. 13, 2005, provisional application No. 60/735,963, filed on Nov. 14, 2005, provisional application No. 60/776,660, filed on Feb. 27, 2006, provisional application No. 60/725,628, filed on Oct. 13, 2005, provisional application No. 60/735,987, filed on Nov. 14, 2005, provisional application No. 60/776,659, filed on Feb. 27, 2006.

(51) Int. Cl.
| | | |
|---|---|---|
| A61K 39/00 | (2006.01) |
| A61K 39/395 | (2006.01) |
| A61P 25/00 | (2006.01) |
| A61K 38/19 | (2006.01) |
| C07K 14/705 | (2006.01) |
| C07K 16/28 | (2006.01) |
| A61K 38/00 | (2006.01) |

(52) U.S. Cl.
CPC ........... *A61K 38/19* (2013.01); *C07K 14/70575* (2013.01); *C07K 16/2875* (2013.01); *C07K 16/2887* (2013.01); *A61K 38/00* (2013.01); *A61K 2039/505* (2013.01); *A61K 2039/507* (2013.01); *C07K 2316/96* (2013.01); *C07K 2317/56* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 5,223,409 A | 6/1993 | Ladner et al. |
| 5,281,704 A | 1/1994 | Love |
| 5,403,484 A | 4/1995 | Ladner et al. |
| 5,416,202 A | 5/1995 | Bernhard et al. |

(Continued)

FOREIGN PATENT DOCUMENTS

| | | |
|---|---|---|
| CA | 2 665 133 A1 | 5/1998 |
| EP | 0 439 095 A2 | 7/1991 |

(Continued)

OTHER PUBLICATIONS

El-Hallak et al., J Pediatric, 150-376-82, Apr. 2007.*

(Continued)

*Primary Examiner* — Daniel E Kolker
*Assistant Examiner* — Stacey N MacFarlane
(74) *Attorney, Agent, or Firm* — Duke M. Fitch; John Lemanowicz; William R. Majarian

(57) ABSTRACT

The present invention relates to methods and compositions for use in treatment of patients with autoantibody positive disease. In a specific embodiment, the present invention relates to a method of treating a patient that has an ANA titer of 1:80 or greater and/or greater than or equal to 30 IU/ml of anti-dsDNA antibodies in his/her blood plasma or serum comprising administering a therapeutically effective amount of an immunomodulatory agent, such as an antagonist of Neutrokine-alpha. Additionally provided is a method of reducing the frequency and/or quantity of corticosteroid administration to patients. In preferred embodiments, the patient has systemic lupus erythematosus. Methods for determining if a lupus patient is responding to medical treatment are also provided.

15 Claims, 1 Drawing Sheet

(56) References Cited

U.S. PATENT DOCUMENTS

| | | | |
|---|---|---|---|
| 5,474,981 | A | 12/1995 | Leder et al. |
| 5,571,698 | A | 11/1996 | Ladner et al. |
| 5,576,195 | A | 11/1996 | Robinson et al. |
| 5,589,499 | A | 12/1996 | Weth |
| 5,595,721 | A | 1/1997 | Kasminski et al. |
| 5,605,671 | A | 2/1997 | Lyle |
| 5,635,384 | A | 6/1997 | Walsh et al. |
| 5,643,575 | A | 7/1997 | Martinez et al. |
| 5,795,724 | A | 8/1998 | Hillman et al. |
| 5,846,818 | A | 12/1998 | Robinson et al. |
| 5,869,045 | A | 2/1999 | Hellstrom et al. |
| 5,869,331 | A | 2/1999 | Dornburg |
| 5,948,619 | A | 9/1999 | Bandman et al. |
| 5,962,301 | A | 10/1999 | Horvitz et al. |
| 5,969,102 | A | 10/1999 | Bram et al. |
| 6,207,160 | B1 | 3/2001 | Victoria et al. |
| 6,297,367 | B1 | 10/2001 | Tribouley |
| 6,403,770 | B1 | 6/2002 | Yu |
| 6,475,987 | B1 | 11/2002 | Shu |
| 6,541,224 | B2 | 4/2003 | Yu |
| 6,562,579 | B1 | 5/2003 | Yu et al. |
| 6,635,482 | B1 | 10/2003 | Yu et al. |
| 6,689,579 | B1 | 2/2004 | Yu et al. |
| 6,716,576 | B1 | 4/2004 | Yu et al. |
| 6,774,106 | B2 | 8/2004 | Theill |
| 6,812,327 | B1 | 11/2004 | Yu |
| 6,869,605 | B2 | 3/2005 | Browning et al. |
| 6,875,846 | B2 | 4/2005 | Rennert et al. |
| 6,881,401 | B1 | 4/2005 | Yu |
| 7,083,785 | B2 | 8/2006 | Browning et al. |
| 7,118,872 | B2 | 10/2006 | Beltzer et al. |
| 7,220,840 | B2 | 5/2007 | Ruben et al. |
| 7,241,576 | B2 | 7/2007 | Aggarwal |
| 7,259,137 | B2 | 8/2007 | Min et al. |
| 7,317,089 | B2 | 1/2008 | Kikly |
| 7,399,593 | B1 | 7/2008 | Farrow et al. |
| 7,691,804 | B2 | 4/2010 | Jeffrey et al. |
| 2001/0010925 | A1 | 8/2001 | Wiley |
| 2002/0037852 | A1 | 3/2002 | Browning et al. |
| 2002/0039557 | A1 | 4/2002 | White |
| 2002/0055624 | A1 | 5/2002 | Wiley |
| 2002/0115112 | A1 | 8/2002 | Yu et al. |
| 2002/0150579 | A1 | 10/2002 | Kimberly et al. |
| 2002/0165156 | A1 | 11/2002 | Browning et al. |
| 2002/0172674 | A1 | 11/2002 | Jeffrey et al. |
| 2003/0012783 | A1 | 1/2003 | Kindsvogel |
| 2003/0022233 | A1 | 1/2003 | Goodwin |
| 2003/0023038 | A1 | 1/2003 | Rennert et al. |
| 2003/0059937 | A1 | 3/2003 | Ruben et al. |
| 2003/0091565 | A1 | 5/2003 | Beltzer et al. |
| 2003/0095967 | A1 | 5/2003 | MacKay et al. |
| 2003/0148445 | A1 | 8/2003 | Shu |
| 2003/0166546 | A1 | 9/2003 | Aggarwal |
| 2003/0175208 | A1 | 9/2003 | Yu et al. |
| 2003/0194743 | A1 | 10/2003 | Beltzer et al. |
| 2003/0223996 | A1 | 12/2003 | Ruben et al. |
| 2004/0175801 | A1 | 9/2004 | Yu et al. |
| 2004/0175802 | A1 | 9/2004 | Yu et al. |
| 2005/0070694 | A1 | 3/2005 | Gelfanova et al. |
| 2005/0100548 | A1 | 5/2005 | Browning et al. |
| 2005/0163775 | A1 | 7/2005 | Chan et al. |
| 2005/0169924 | A1 | 8/2005 | Browning et al. |
| 2005/0175611 | A1 | 8/2005 | Mahler et al. |
| 2005/0186637 | A1 | 8/2005 | Yu et al. |
| 2005/0214543 | A1 | 9/2005 | Koumura et al. |
| 2005/0244411 | A1 | 11/2005 | MacKay et al. |
| 2005/0255532 | A1 | 11/2005 | Ruben et al. |
| 2006/0062789 | A1 | 3/2006 | Ruben et al. |
| 2006/0079457 | A1 | 4/2006 | Browning et al. |
| 2006/0084608 | A1 | 4/2006 | Beltzer et al. |
| 2006/0171919 | A1 | 8/2006 | Rosenblum et al. |
| 2006/0193859 | A1 | 8/2006 | Yu et al. |
| 2006/0198784 | A1 | 9/2006 | Yu et al. |
| 2007/0086979 | A1 | 4/2007 | Chevrier et al. |
| 2007/0212733 | A1 | 9/2007 | Martin |
| 2007/0293434 | A9 | 12/2007 | Beltzer et al. |
| 2008/0254030 | A1 | 10/2008 | Mackay et al. |
| 2008/0260737 | A1 | 10/2008 | Ponce et al. |
| 2008/0267965 | A1 | 10/2008 | Kalled et al. |
| 2009/0068201 | A1 | 3/2009 | Yu et al. |
| 2009/0081213 | A1 | 3/2009 | Chevrier et al. |
| 2009/0081231 | A1 | 3/2009 | Chevrier et al. |
| 2009/0098129 | A1 | 4/2009 | Farrow et al. |
| 2009/0104189 | A1 | 4/2009 | Yu et al. |
| 2009/0110676 | A1 | 4/2009 | Mackay et al. |
| 2009/0169565 | A1 | 7/2009 | Yu et al. |
| 2009/0215071 | A1 | 8/2009 | Cachero et al. |
| 2009/0221008 | A1 | 9/2009 | Yu et al. |
| 2010/0003259 | A1 | 1/2010 | Ruben et al. |
| 2010/0040627 | A1 | 2/2010 | Jeffrey et al. |
| 2010/0111953 | A1 | 5/2010 | Ruben et al. |
| 2010/0144058 | A1 | 6/2010 | Beltzer et al. |
| 2010/0196360 | A9 | 8/2010 | Yu et al. |
| 2010/0261194 | A1 | 10/2010 | Yu et al. |
| 2010/0261207 | A9 | 10/2010 | Yu et al. |
| 2010/0330073 | A1 | 12/2010 | Yu et al. |
| 2011/0014190 | A1 | 1/2011 | Migone et al. |
| 2011/0052590 | A1 | 3/2011 | Yu et al. |

FOREIGN PATENT DOCUMENTS

| | | |
|---|---|---|
| EP | 0 869 180 A1 | 10/1998 |
| EP | 0 921 194 A2 | 6/1999 |
| EP | 0 577 752 B1 | 7/2000 |
| EP | 1 157 110 A1 | 11/2001 |
| EP | 1 294 769 A2 | 3/2003 |
| EP | 1 294 949 A2 | 3/2003 |
| EP | 1 309 718 A2 | 5/2003 |
| EP | 1 146 892 B1 | 8/2003 |
| EP | 1 141 274 B1 | 9/2003 |
| EP | 1 354 598 A3 | 10/2003 |
| EP | 1 415 659 A1 | 5/2004 |
| EP | 1 456 347 A2 | 9/2004 |
| EP | 1 507 793 A1 | 2/2005 |
| EP | 1 577 391 A1 | 9/2005 |
| EP | 0 910 635 B1 | 8/2007 |
| EP | 1 860 190 A2 | 11/2007 |
| GB | 9828628.9 | 12/1998 |
| WO | WO 93/21232 A1 | 10/1993 |
| WO | WO 94/20540 A1 | 9/1994 |
| WO | WO 95/07297 A1 | 3/1995 |
| WO | WO 95/20398 A1 | 8/1995 |
| WO | WO 95/24414 A1 | 9/1995 |
| WO | WO 95/24466 A1 | 9/1995 |
| WO | WO 95/31468 A1 | 11/1995 |
| WO | WO 96/14328 A1 | 5/1996 |
| WO | WO 96/34095 A1 | 10/1996 |
| WO | WO 97/33902 A1 | 9/1997 |
| WO | WO 97/34911 A1 | 9/1997 |
| WO | WO 97/46251 A1 | 12/1997 |
| WO | WO 97/49726 A1 | 12/1997 |
| WO | WO 98/07880 A1 | 2/1998 |
| WO | WO 98/18921 A1 | 5/1998 |
| WO | WO 98/27114 A2 | 6/1998 |
| WO | WO 98/39361 A1 | 9/1998 |
| WO | WO 98/50547 A2 | 11/1998 |
| WO | WO 98/55620 A1 | 12/1998 |
| WO | WO 98/55621 A1 | 12/1998 |
| WO | WO 98/55623 A1 | 12/1998 |
| WO | WO 99/10494 A2 | 3/1999 |
| WO | WO 99/11791 A1 | 3/1999 |
| WO | WO 99/12964 A2 | 3/1999 |
| WO | WO 99/33980 A2 | 7/1999 |
| WO | WO 99/35170 A2 | 7/1999 |
| WO | WO 99/46295 A1 | 9/1999 |
| WO | WO 99/47538 A1 | 9/1999 |
| WO | WO 99/60127 A2 | 11/1999 |
| WO | WO 00/26244 A2 | 5/2000 |
| WO | WO 00/39295 A1 | 7/2000 |
| WO | WO 00/40716 A2 | 7/2000 |
| WO | WO 00/43032 A2 | 7/2000 |
| WO | WO 00/45836 A1 | 8/2000 |
| WO | WO 00/47740 A2 | 8/2000 |
| WO | WO 00/50597 A2 | 8/2000 |

(56) References Cited

FOREIGN PATENT DOCUMENTS

| | | |
|---|---|---|
| WO | WO 00/58362 A1 | 10/2000 |
| WO | WO 00/60079 A2 | 10/2000 |
| WO | WO 00/67034 A1 | 11/2000 |
| WO | WO 00/68378 A1 | 11/2000 |
| WO | WO 00/77256 A1 | 12/2000 |
| WO | WO 01/12812 A2 | 2/2001 |
| WO | WO 01/24811 A1 | 4/2001 |
| WO | WO 01/40466 A2 | 6/2001 |
| WO | WO 01/60397 A1 | 8/2001 |
| WO | WO 01/81417 A2 | 11/2001 |
| WO | WO 01/87977 A2 | 11/2001 |
| WO | WO 02/02641 A1 | 1/2002 |
| WO | WO0202641 * | 1/2002 |
| WO | WO 02/16411 A2 | 2/2002 |
| WO | WO 02/18620 A2 | 3/2002 |
| WO | WO 02/24909 A2 | 3/2002 |
| WO | WO 02/38766 A2 | 5/2002 |
| WO | WO 02/066516 A3 | 8/2002 |
| WO | WO 02/092620 A2 | 11/2002 |
| WO | WO 02/094852 A2 | 11/2002 |
| WO | WO 03/016468 A2 | 2/2003 |
| WO | WO 03/030833 A2 | 4/2003 |
| WO | WO 03/033658 A2 | 4/2003 |
| WO | WO 03/055979 A2 | 7/2003 |
| WO | WO 03/089569 A2 | 10/2003 |
| WO | WO 2004/058309 A1 | 7/2004 |
| WO | WO 2004/074511 A1 | 9/2004 |
| WO | WO 2005/005462 A3 | 1/2005 |
| WO | WO 2005/042009 A1 | 5/2005 |
| WO | WO 2007/123765 | 11/2007 |
| WO | WO 2007/142667 | 12/2007 |
| WO | WO 2009/132058 A2 | 10/2009 |
| WO | WO 2010/093993 A2 | 8/2010 |

OTHER PUBLICATIONS

Tan et al. Arthritis and Rheumatism, 40(9):1601-1611, 1997.*
Keystone, E., Arthritis Research and Therapy, 7 (Suppl 3):S13-S18, May 18, 2005.*
Petri et al. New Engl J Med., 353(24):2550-2558, (2005).*
Mariz et al., Arthritis and Rheumatism, 63(1): 191-200, Jan. 2011.*
Gonzalez et al., Clinical Biochemistry, 35:463-469, 2002.*
Fortin et al., J Rheumatology, 22:2078-2083, 1995.*
Cambridge Antibody Technology website printed Mar. 7, 2007 submitted in UK Revocation suit HC06CO2687.
EFPIA website printed Sep. 12, 2007 submitted in UK Revocation suit HC06CO2687.
First Expert Report of Dr. Rolf Apweiler dated May 29, 2007 in support of Eli Lilly in UK Revocation suit HC06CO2687.
Second Expert Report of Dr. Rolf Apweiler dated Jun. 23, 2007 in support of Eli Lilly in UK Revocation suit HC06CO2687.
Fourth Expert Report of Dr. Rolf Apweiler dated Dec. 11, 2007 in support of Eli Lilly in UK Revocation suit HC06CO2687.
Witness Statement of Dr. David E. Cash dated Nov. 14, 2006 in support of Human Genome Sciences in UK Revocation suit HC06CO2687.
Witness Statement of Christa Pennachio dated Apr. 23, 2007 in support of Human Genome Sciences in UK Revocation suit HC06CO2687.
Witness Statement of Christa Pennachio dated May 15, 2007 in support of Eli Lilly in UK Revocation suit HC06CO2687.
Witness Statement of Dr. Stuart Farrow dated Jun. 1, 2007 in support of Human Genome Sciences in UK Revocation suit HC06CO2687.
Witness Statement of Dr. William F. Heath dated Jun. 27, 2007 in support of Eli Lilly in UK Revocation suit HC06CO2687.
First Witness Statement of Mark Hodgson dated Nov. 6, 2007 in support of Eli Lilly in UK Revocation suit HC06CO2687.
*Bhagwat* v. *Hrastar*, Interference No. 105,516, Paper 67 at 4 (Nov. 7, 2007). Filed in Patent Interference 105,652 (HGS Exhibit 2034).
Information Disclosure Statement dated Sep. 28, 2006 from file history of the RDF Involved Application. Filed in Patent Interference 105,652 (HGS Exhibit 2035).
Supplemental Information Disclosure Statement dated Mar. 7, 2007 from file history of the RDF Involved Application. Filed in Patent Interference 105,652 (HGS Exhibit 2036).
Supplemental Information Disclosure Statement dated May 29, 2008 from file history of the RDF Involved Application. Filed in Patent Interference 105,652 (HGS Exhibit 2037).
*Ex parte Jellá*, Appeal No. 2008-1619 (BPAI Nov. 3, 2008). Filed in Patent Interference 105,652 (HGS Exhibit 2038).
Declaration of Michael Rosenblum, submitted by RDF on Dec. 12, 2003 in inter partes Reexamination No. 95/000,016 involving U.S. Pat. No. 6,376,217, entitled "Fusion Proteins and Polynucleotides Encoding Gelonin Sequences." Filed in Patent Interference 105,652 (HGS Exhibit 2039).
HGS Objections to RDF Evidence filed in Patent Interference 105,652. Filed in the United States Patent Office on Jan. 30, 2009. (HGS Exhibit 2042).
Stirpe et al., *Biotechnology*, 10(4):405-12 (1992). Filed in Patent Interference 105,652 (RDF Exhibit 1008).
Rosenblum et al., *J. Interferon Cytokine Res.*, 15(6):547-55 (1995). Filed in Patent Interference 105,652 (RDF Exhibit 1009).
Rosenblum Declaration dated Jan. 23, 2009. Filed in Patent Interference 105,652 (RDF Exhibit 1010).
Dr. Arthur Chin Louie letter dated Sep. 5, 2001. Filed in Patent Interference 105,652 (RDF Exhibit 1012).
Page 53 of Mi-ae Lyu notebook dated Oct. 7, 2003. Filed in Patent Interference 105,652 (RDF Exhibit 1013).
Page 60 of Mi-ae Lyu notebook dated Oct. 17, 2003. Filed in Patent Interference 105,652 (RDF Exhibit 1014).
Page 1-3 of Lawrence Cheung notebook dated Jan. 27, 2004. Filed in Patent Interference 105,652 (RDF Exhibit 1015).
Page 23 of Lawrence Cheung notebook dated Apr. 14, 2004. Filed in Patent Interference 105,652 (RDF Exhibit 1016).
*Noelle* v. *Lederman*, 2001 Pat. App. LEXIS 8 (2001). Filed in Patent Interference 105,652 (RDF Exhibit 1017).
U.S. Appl. No. 60/122,388, Yu et al.
U.S. Appl. No. 60/543,261, Yu et al.
U.S. Appl. No. 60/580,387, Yu et al.
U.S. Appl. No. 60/617,191, Yu et al.
U.S. Appl. No. 60/649,478, Rosenblum et al.
U.S. Appl. No. 11/054,539, filed Aug. 25, 2005, Yu et al.
U.S. Appl. No. 11/345,661, filed Aug. 3, 2006, Rosenblum et al.
Freimuth, "Lessons learned from the Phase 2 belimumab SLE study: development of an SLE responder index," Jun. 1, 2009.
Stohl, W., "A therapeutic role for BLyS antagonists," *Lupus*, 13:317-322 (2004).
Letter of Suspension issued in U.S. Appl. No. 09/589,288, dated May 9, 2005.
Requirement for Restriction/Election issued in U.S. Appl. No. 12/210,134, dated Jun. 24, 2009.
Requirement for Restriction/Election issued in U.S. Appl. No. 12/393,693, dated Jun. 25, 2009.
International Preliminary Examination Report issued in PCT Patent Application No. PCT/US06/38756, dated May 29, 2009.
Bendig, "Humanization of Rodent Monoclonal Antibodies by CDR Grafting," (Methods: A Comparison to Methods in Enzymology 1995; 8:83-93).
Yu Priority Statement filed in Patent Interference 105,652. Filed in the United States Patent Office on Jan. 23, 2009.
Yu Substantive Motion 1 filed in Patent Interference 105,652. Filed in the United States Patent Office on Jan. 23, 2009.
Rosenblum Preliminary Motion 1 filed in Patent Interference 105,652. Filed in the United States Patent Office on Jan. 23, 2009.
Rosenblum Re-filed Preliminary Motion 1 filed in Patent Interference 105,652. Filed in the United States Patent Office on Jan. 23, 2009.
Rosenblum Substantive Motion 2 filed in Patent Interference 105,652. Filed in the United States Patent Office on Jan. 23, 2009.
Yu Responsive Motion 2 filed in Patent Interference 105,652. Filed in the United States Patent Office on Feb. 19, 2009.
Yu Opposition 1 filed in Patent Interference 105,652. Filed in the United States Patent Office on Apr. 1, 2009.
Yu Opposition 2 filed in Patent Interference 105,652. Filed in the United States Patent Office on Apr. 1, 2009.

(56) References Cited

OTHER PUBLICATIONS

Rosenblum Opposition 1 filed in Patent Interference 105,652. Filed in the United States Patent Office on Apr. 1, 2009.
Rosenblum Opposition 2 filed in Patent Interference 105,652. Filed in the United States Patent Office on Apr. 1, 2009.
Yu Reply 1 filed in Patent Interference 105,652. Filed in the United States Patent Office on Apr. 24, 2009.
Yu Reply 2 filed in Patent Interference 105,652. Filed in the United States Patent Office on Apr. 24, 2009.
Rosenblum Reply 1 filed in Patent Interference 105,652. Filed in the United States Patent Office on Apr. 24, 2009.
Rosenblum Reply 2 filed in Patent Interference 105,652. Filed in the United States Patent Office on Apr. 24, 2009.
Helmkamp et al., "High Specific Activity Iodination of γ-Globulin with Iodine-131 Monochloride," *Cancer Res.*, 20:1495-1500 (1960). Filed in Patent Interference 105,652 (HGS Exhibit 2010).
Langone, "Radioiodination by Use of the Bolton-Hunter and Related Reagents" *Methods in Enzymology*, 70:221-247 (1980). Filed in Patent Interference 105,652 (HGS Exhibit 2011).
Office Communication mailed Jun. 23, 2008 in the HGS Involved Application. Filed in Patent Interference 105,652 (HGS Exhibit 2014).
Executed Declaration and Information Disclosure Statement date-stamped Apr. 12, 2006 from Application File of the RDF Involved Application. Filed in Patent Intererence 105,652 (HGS Exhibit 2016).
Riccobene et al., "Rapid and Specific Targeting of 125I-Labeled B Lymphocyte Stimulator to Lymphoid Tissues and B Cell Tumors in Mice," *J. Nuc. Med.*, 44(3):422-433 (Mar. 2003). Filed in Patent Interference 105,652 (HGS Exhibit 2019).
Murray et al., "Variables Influencing Tumor Uptake of Anti-Melanoma Monoclonal Antibodies Radioiodinated Using Para-Iodobenzoyl (PIB) Conjugate," *J. Nucl. Med.*, 32(2) 279-287 (Feb. 1991). Filed in Patent Interference 105,652 (HGS Exhibit 2020).
Lyu et al., "The Growth Factor Toxin Construct rGel/BLyS Specifically Targets Tumor Cells Expressing BAFF-R, TACI, and BCMA," Abstract 1517, Am. Assoc. for Cancer Res. 96th Annual Meeting, Anaheim, CA (Apr. 16-20, 2005). Filed in Patent Interference 105,652 (HGS Exhibit 2022).
Information Disclosure Statement dated Feb. 20, 2007 from file history of the RDF Involved Application. Filed in Patent Interference 105,652 (HGS Exhibit 2023).
Shen et al., "Construction and Expression of a New Fusion Protein, Thymosin α1-cBLyS, in *E. coli*," *Biotech. Lett.*, 27:143-148 (2005). Filed in Patent Interference 105,652 (HGS Exhibit 2024).
Cao et al., "Construction and Characterization of Bi-functional EGFP/sBAFF Fusion Protein," *Biochimie*, 88:629-635 (2006). Filed in Patent Interference 105,652 (HGS Exhibit 2025).
Transcript of Deposition of Michael Rosenblum, dated Feb. 26, 2009. Filed in Patent Interference 105,652 (HGS Exhibit 2026).
Lyu et al., "The immunocytokine scFv23/TNF targeting HER-2/neu induces synergistic cytotoxic effects with 5-fluorouracil in TNF-resistant pancreatic cancer cell lines," *Biochem. Pharmacol.*, 75:836-846 (2008). Filed in Patent Interference 105,652 (HGS Exhibit 2027).
Rosenblum et al., "Design, Expression, Purification, and Characterization, in Vitro and in Vivo, of an Antimelanoma Single-chain Fv Antibody Fused to the Toxin Gelonin," *Cancer Res.*, 63:3995-4002 (2003). Filed in Patent Interference 105,652 (HGS Exhibit 2028).
Kim et al., "Overexpression of biologically active VEGF121 fusion proteins in *Escherichia coli*," *J. Biotechnol.*, 128:638-647 (2007). Filed in Patent Interference 105,652 (HGS Exhibit 2029).
Veenendaal et al., "In vitro and in vivo studies of a VEGF121/rGelonin chimeric fusion toxin targeting the neovasculature of solid tumors," *Proc. Natl. Acad. Sci.*, 99(12):7866-7871 (Jun. 2002). Filed in Patent Interference 105,652 (HGS Exhibit 2030).
Liu et al., "Targeted delivery of human pro-apoptotic enzymes to tumor cells: In vitro studies describing a novel class of recombinant highly cytotoxic agents," *Mol. Cancer Ther.*, 2(12):1341-1350 (2003). Filed in Patent Interference 105,652 (HGS Exhibit 2031).
*Wesley Jessen Corp.* v. *Bausch & Lomb, Inc.*, 209 F. Supp. 2d. 348, 398 (D. Del. 2002), aff'd 56 Fed. Appx. 503 (Fed. Cir. 2003). Filed in Patent Interference 105,652 (HGS Exhibit 2033).
Rosenblum Curriculum Vitae. Filed in Patent Interference 105,652 (RDF Exhibit 1011).
HGS Amendment and Reply dated Aug. 2, 2007, U.S. Appl. No. 11/054,539. Filed in Patent Interference 105,652 (RDF Exhibit 1018).
Dr. Arthur Chin Louie letter dated Sep. 5, 2001 with facsimile cover sheet. Filed in Patent Interference 105,652 (RDF Supplemental Exhibit 1012).
Yu Miscellaneous Motion 3 filed in Patent Interference 105,652. Filed in the United States Patent Office on May 6, 2009.
HGS Miscellaneous Motion 3 (to exclude RDF Exhibitis 1010 and 1013-1016) filed in Patent Interference 105,652. Filed in the United States Patent Office on May 6, 2009.
RDF Miscellaneous Motion 1 (Motion to Exclude Evidence) filed in Patent Interference 105,652. Filed in the United States Patent Office on May 6, 2009.
HGS Opposition 1A (Opposing RDF Miscellaneous Motion 1 to exclude evidence) filed in Patent Inteference 105,652. Filed in the United States Patent Office on May 14, 2009.
RDF Opposition to HGS Miscellaneous Motion 3 (Motion to Exclude) filed in Patent Interference 105,652. Filed in the United States Patent Office on May 14, 2009.
HGS Reply 3 (to exclude RDF Exhibits 1010 and 1013-1016) filed in Patent Interference 105,652. Filed in the United States Patent Office on May 21, 2009.
HGS Exhibit List (as of May 28, 2009) filed in Patent Interference 105,652. Filed in the United States Patent Office on May 28, 2009.
HGS Demonstratives from Oral Hearing dated Jul. 2, 2009 in Patent Interference 105,652.
Daniel et al., *Virology*, "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity Is Drastically Influenced by the Nature of the Protein Carrier," 202:540-549 (1994).
Lederman et al., *Mol. Immunol.*, "A single amino acid substitution in a common African allele of the CD4 molecule ablates binding of the monoclonal antibody, OKT4," 28(11):1171-1181 (1991).
Li et al., *Proc. Natl. Acad. Sci. USA*, "β-Endorphin omission analogs:Dissociation of immunoreactivity from other biological activities," 77(6):3211-3214 (1980).
Neri et al., *Clin. Cancer Res.*, "Neutralizing B-Cell-Activating Factor Antibody Improves Survival and Inhibits Osteoclastogenesis in a Severe Combined Immunodeficient Human Multiple Myeloma Model," 13(19):5903-5909 (2007).
Shivakumar et al., *Clin. Lymphoma Myeloma*, "Targeting B-Lymphocyte Stimulator/B-Cell Activating Factor and a Proliferation-Inducing Ligand in Hematologic Malignancies," 7(2):106-108 (2006).
Advisory Action issued in U.S. Appl. No. 11/232,439, dated Aug. 14, 2009.
Non-Final Rejection issued in U.S. Appl. No. 11/232,439, dated Nov. 5, 2009.
Examiner Interview Summary issued in U.S. Appl. No. 09/589,288, dated Jul. 14, 2009.
Notice of Allowance issued in U.S. Appl. No. 09/589,288, dated Jul. 27, 2009.
Corrected Notice of Allowance issued in U.S. Appl. No. 09/589,288, dated Sep. 22, 2009.
Non-Final Rejection issued in U.S. Appl. No. 12/170,333, dated Sep. 17, 2009.
Non-Final Rejection issued in U.S. Appl. No. 12/210,134, dated Nov. 30, 2009.
Cope et al., *Curr. Opin. Immunol.*, "Emerging approaches for the therapy of autoimmune and chronic inflammatory disease," 16: 780-786 (2004).
Requirement for Restriction/Election issued in U.S. Appl. No. 12/552,915, dated Dec. 1, 2009.
Better et al, "T Cell-targeted Immunofusion Proteins from *Escherichia coli*", *The Journal of Biological Chemistry*, 270(25): 14951-14957 (1995).

(56) References Cited

OTHER PUBLICATIONS

Extended European Search Report, European Application No. 06851283.9 dated Nov. 3, 2009.
Aguirre-Cruz et al., *J. Neurooncol.*, "Clinical relevance of non-neuronal auto-antibodies in patients with anti-Hu or anti-Yo paraneoplastic diseases," 71(1):39-41 (2005).
Eriksson et al., *Ann. Rheum. Dis.*, "Autoantibody formation in patients with rheumatoid arthritis treated with anti-TNFalpha," 64(3):403-407 (2005).
Keystone, *Arthritis Res. Ther.*, "B cell targeted therapies," 7(3):S13-S18 (2005).
Myckatyn et al., *J. Rheumatol.*, "Outcome of positive antinuclear antibodies in individuals without connective tissue disease," 30(4):736-739 (2003).
Notification of decision of the Technical Board of Appeals in Appeal Case T 18/09-3.3.08 in EP Patent 0 939 804, dated Dec. 1, 2009.
Notice of Allowance issued in U.S. Appl. No. 11/054,515, dated Dec. 21, 2009.
Nichols et al., *Eur. J. Cancer*, "Interleukin-2 Fusion Protein: An Investigational Therapy for Interleukin-2 Receptor Expressing Malignancies," 33(1):S34-S36 (1997).
Sweeney et al., *Bioconjug. Chem.*, "Interleukin 7 (IL-7) Receptor-Specific Cell Killing by $DAB_{389}$ IL-7: A Novel Agent for the Elimination of IL-7 Receptor Positive Cells," 9:201-207 (1998).
Alcami et al., *J. Immunol.*, "Blockade of Chemokine Activity by a Soluble Chemokine Binding Protein from Vaccinia Virus," 160:624-633 (1998).
Fleming et al., *J. Mol. Recognit.*, "Discovery of High-Affinity Peptide Binders to BLyS by Phage Display," 18:94-102 (2005).
Sun et al., *Biochem. Biophys. Res. Commun.*, "A Novel BLyS Antagonist Peptide Designed Based on the 3-D Complex Structure of BCMA and BLyS," 346:1158-1162 (2006).
Requirement for Restriction/Election issued in U.S. Appl. No. 12/135,025, dated Mar. 9, 2010.
Non-Final Rejection issued in U.S. Appl. No. 12/552,915, dated Apr. 8, 2010.
Requirement for Restriction/Election issued in U.S. Appl. No. 12/605,202, dated Apr. 8, 2010.
Transcript of Oral Hearing, dated Sep. 4, 2009. Filed in Patent Interference 105,652.
Aggarwal et al., *Eur. Cytokine Netw.*, 7(2): 93-124 (1996).
Arai et al., *Annu. Rev. Biochem.*, 59: 783-836 (1990).
Baumann et al., *J. Biol. Chem.*, 268(12): 8414-8417 (1993).
Collins et al., *Proc. Natl. Acad. Sci. USA*, 83: 446-450 (1986).
Fujio et al., *Blood*, 95(7): 2204-2211 (2000).
Gearing et al., *Embo. J.*, 10(10): 2839-2848 (1991).
Ginaldi et al., *J. Clin. Pathol.*, 51: 364-369 (1998).
Holmes et al., *Science*, 253: 1278-1280 (1991).
Huntington et al., *Int. Immunol.*, 18(10): 1473-1485 (2006).
Janeway et al., *Immunobiology: The Immune System in Health and Disease*, Current Biology Ltd./Garland Publishing, London. pp. 2:31, 7:1-7:41 (1996).
Kawaguchi et al., *J. Allergy Clin. Immunol.*, 114(6): 1265-1273 (2004).
Lasagni et al., *Blood*, 109(10): 4127-4134 (2007).
Lavie et al., *J. Pathol.*, 202: 496-502 (2004).
Lawn et al., *Cell*, 15: 1157-1174 (1978).
Maniatis et al., *Cell*, 15: 687-701 (1978).
Miyajima et al., *Annu. Rev. Immunol.*, 10: 295-331 (1992).
Pabst et al., *Anat. Embryol.*, 192: 293-299 (1995).
Ranges et al., *J. Exp. Med.*, 167: 1472-1478 (1988).
Rochman et al. *J. Immunol.*, 178: 6720-6724 (2007).
Shan et al., *Physiol. Res.*, 55: 301-307 (2006).
Siegel et al., *Nat. Immunol.*, 1(6): 469-474 (2000).
Stein et al., *J. Clin. Invest.*, 109: 1587-1598 (2002).
Stoeckle et al., *New Biol.*, 2(4): 313-323 (1990).
Wang et al., *Nat. Immunol.*, 2(7): 632-637 (2001).
Waterston et al., *Nat. Genet.*, 1: 114-123 (1992).
Xu et al., *Acta Biochim. Biophys. Sin.*, 39(12): 964-973 (2007).
Xu et al., *Transplant. Proc.*, 41: 1552-1556 (2009).
Yokota et al., *J. Immunol.*, 140(2): 531-536 (1988).
Yoshimoto et al., *Int. Immunol.*, 18(7): 1189-1196 (2006).
Eli Lilly letter on Statement on Grounds of Appeal filed before Technical Board of Appeals in Opposition of EP Patent No. 0 939 804 (Filed in the European Patent Office on May 1, 2009).
HGS Press Release, Human Genome Sciences and GlaxoSmithKline Announce Positive Phase 3 Study Results for Benlysta™ (Jul. 20, 2009).
Declaration of Amy Hamilton filed in Opposition of EP Patent No. 0 939 804 (Filed in the European Patent Office on Jul. 23, 2009).
Eli Lilly letter to Technical Board of Appeals regarding Response to Appeal in Opposition of EP Patent No. 0 939 804 (Filed in the European Patent Office on Jul. 23, 2009).
Eli Lilly Response to Appeal filed before Technical Board of Appeals in Opposition of EP Patent No. 0 939 804 (Filed in the European Patent Office on Jul. 23, 2009).
Declaration and Curriculum Vitae of Dr. Thomas Lane Rothstein filed in Opposition of EP Patent No. 0 939 804 (Filed in the European Patent Office on Jul. 27, 2009).
Second Declaration of Dr. John Calley filed in Opposition of EP Patent No. 0 939 804 (Filed in the European Patent Office on Jul. 27, 2009).
Signed Declaration of Dr. Thomas Lane Rothstein filed in Opposition of EP Patent No. 0 939 804 (Filed in the European Patent Office on Jul. 27, 2009).
HGS letter on Grounds of Appeal update filed before Technical Board of Appeals in Opposition of EP Patent No. 0 939 804 (Filed in the European Patent Office on Jul. 31, 2009).
Preliminary Opinion of the Board of Appeal in Appeal Case T 18/09-3.3.08 in EP Patent 0939804 (Aug. 24, 2009).
Auxiliary Request I filed before Technical Board of Appeals in Opposition of EP Patent No. 0 939 804 (Filed in the European Patent Office on Sep. 30, 2009).
Auxiliary Request II filed before Technical Board of Appeals in Opposition of EP Patent No. 0 939 804 (Filed in the European Patent Office on Sep. 30, 2009).
Auxiliary Request III filed before Technical Board of Appeals in Opposition of EP Patent No. 0 939 804 (Filed in the European Patent Office on Sep. 30, 2009).
Auxiliary Request IV filed before Technical Board of Appeals in Opposition of EP Patent No. 0 939 804 (Filed in the European Patent Office on Sep. 30, 2009).
Auxiliary Request V filed before Technical Board of Appeals in Opposition of EP Patent No. 0 939 804 (Filed in the European Patent Office on Sep. 30, 2009).
Eli Lilly Reply to Preliminary Opinion filed before Technical Board of Appeals in Opposition of EP Patent No. 0 939 804 (Filed in the European Patent Office on Sep. 30, 2009).
Further Declaration of Dr. John Calley filed in Opposition of EP Patent No. 0 939 804 (Filed in the European Patent Office on Sep. 30, 2009).
HGS Reply to Preliminary Opinion filed before Technical Board of Appeals in Opposition of EP Patent No. 0 939 804 (Filed in the European Patent Office on Sep. 30, 2009).
Main Request filed before Technical Board of Appeals in Opposition of EP Patent No. 0 939 804 (Filed in the European Patent Office on Sep. 30, 2009).
Second Declaration of Dr. Garnett Herrel Kelsoe III and list of annexes filed before Technical Board of Appeals in Opposition of EP Patent No. 0 939 804 (Filed in the European Patent Office on Sep. 30, 2009).
Second Declaration of Dr. Randolph J. Noelle filed before Technical Board of Appeals in Opposition of EP Patent No. 0 939 804 (Filed in the European Patent Office on Sep. 30, 2009).
Second Declaration of Dr. Stuart Farrow filed before Technical Board of Appeals in Opposition of EP Patent No. 0 939 804 (Filed in the European Patent Office on Sep. 30, 2009).
Summary of Respondent's Proposed Experiments filed before Technical Board of Appeals in Opposition of EP Patent No. 0 939 804 (Filed in the European Patent Office on Sep. 30, 2009).
Third Declaration of Dr. Andrew Martin and Appendix 1 filed before Technical Board of Appeals in Opposition of EP Patent No. 0 939 804 (Filed in the European Patent Office on Sep. 30, 2009).

(56) References Cited

OTHER PUBLICATIONS

Minutes of the Oral Proceedings before the Opposition Division, issued by the European Patent Office in the matter of Eli Lilly's Opposition of EP 0 939 804 (Oct. 26, 2009).
Eli Lilly's Skeleton Argument on appeal in UK Revocation suit HC06C02687 (Oct. 30, 2009).
Human Genome Science's Consolidated Skeleton Argument on appeal in UK Revocation suit HC06C02687 (Dec. 2009).
Eli Lilly's Note on the Decision of the TBA in T18/09 in UK Revocation suit HC06C02687 (Dec. 4, 2009).
Eli Lilly's Note on why the Decision of the TBA in T18/09 is different on the Facts in UK Revocation suit HC06C02687 (Dec. 11, 2009).
Human Genome Science's mark-up of Eli Lilly's Note on why the Decision of the TBA in T18/09 is different on the Facts in UK Revocation suit HC06C02687 (Dec. 11, 2009).
Human Genome Science's Note on why the Invention is susceptible of Industrial Application in UK Revocation suit HC06C02687 (Dec. 10, 2009).
Human Genome Science's Note on paragraph 26 of Judgment by Mr Justice Kitchin in UK Revocation suit HC06C02687 (Dec. 2009).
Human Genome Science's Reply Note in UK Revocation suit HC06C02687 (Dec. 11, 2009).
Approved Judgment by Mr Justice Jacob on appeal from the Chancery Division in UK Revocation suit HC06C02687 (Feb. 9, 2010).
Notification of decision of the Technical Board of Appeals in Appeal Case T 18/09-3.3.08 in EP Patent 0 939 804 (Oct. 21, 2009).
HGS Press Release, "Human Genome Sciences and GlaxoSmithKline Announce Topline 76-Week Results of Phase 3 Trial of Benlysta™ in Systemic Lupus Erythematosus" (Apr. 20, 2010).
Requirement for Restriction/Election issued in U.S. Appl. No. 12/701,301, dated May 3, 2010.
Final Rejection issued in U.S. Appl. No. 12/170,333, dated May 28, 2010.
Final Rejection issued in U.S. Appl. No. 12/393,693, dated May 28, 2010.
U.S. Appl. No. 08/984,396, Hurle et al.
U.S. Appl. No. 09/912,293, Rosen et al.
U.S. Appl. No. 60/033,601, Gorman.
U.S. Appl. No. 60/041,797, Hurle et al.
U.S. Appl. No. 60/048,776, Masiakowsky et al.
U.S. Appl. No. 60/058,786, Tschopp.
U.S. Appl. No. 60/066,386, Masiakowsky et al.
U.S. Appl. No. 60/066,577, Song.
U.S. Appl. No. 60/068,959, Tribouley et al.
U.S. Appl. No. 60/096,173, Song.
U.S. Appl. No. 60/106,976, Lenardo et al.
U.S. Appl. No. 60/117,169, McKay et al.
U.S. Appl. No. 60/143,228, MacKay et al.
Biogen Inc. and Apoxis SA's Response (including Annexes A and B and the Main Request containing a substitute set of claims) to Human Genome Sciences and Serono's Oppositions of EP Patent No. 1146892. The Response was filed in the European Patent Office on Mar. 14, 2005.
Biogen's Observations in preparation for oral proceedings in defense of the Opposition of EP Patent No. 1146892 lodged by Merck Serono, S.A., and Human Genome Sciences, Inc. The Observations in preparation for oral proceedings was filed in the European Patent Office on Jan. 19, 2007.
Declaration of Dr. Fritz Melchers dated Dec. 1, 2006 in support of Browning et al. in Patent Interference No. 105,485.
Declaration of Dr. Mark S. Schlissel dated Dec. 1, 2006 in support of Browning et al. in Patent Interference No. 105,485.
Second Declaration of Dr. Mark S. Schlissel dated Feb. 8, 2007 in support of Browning et al. in Patent Interference No. 105,485.
Third Declaration of Dr. Mark S. Schlissel dated Apr. 15, 2007.
Declaration of Dr. Randolph J. Noelle dated Feb. 12, 2007 in support of Yu et al. in Patent Interference No. 105,485.
Declaration of Dr. Rodger G. Smith dated and filed on Dec. 14, 2004.
Second Declaration of Dr. Rodger G. Smith dated and filed on Aug. 4, 2005.
Declaration of Dr. Georg Friedrich Melchers dated Jan. 19, 2007 filed in support of EP Patent No. 1146892 in the Opposition to EP Patent No. 1146892 lodged by Merck Serono, S.A., and Human Genome Sciences, Inc.
Declaration of Dr. Carl F. Ware dated and filed on Apr. 16, 2007.
Declaration of Dr. Raif S. Geha dated and filed on Apr. 16, 2007.
European Search Report, European Application No. EP 05 01 2261, mailed Aug. 8, 2005.
Supplementary European Search Report, European Application No. EP 02 78 6413, mailed Dec. 20, 2005.
Supplementary Partial European Search Report, European Application No. EP 00 90 8739, mailed Jun. 30, 2005.
Genbank Accession No. P01374 (Jul. 21, 1986).
Genbank Accession No. CAA25649 (Jul. 12, 1993).
GenBank Accession No. T87299 (Mar. 17, 1995).
GenBank Accession No. R16882 (Apr. 14, 1995).
GenBank Accession No. R16934 (Apr. 14, 1995).
GenBank Accession No. D79690 (Feb. 9, 1996).
GenBank Accession No. G30081 (Oct. 5, 1996).
GenBank Accession No. AA422749 (Oct. 16, 1997).
GenBank Accession No. AA166695 (Nov. 9, 1997).
GenBank Accession No. AA682496 (Dec. 19, 1997).
GenBank Accession No. AA906714 (Jun. 9, 1998).
GenBank Accession No. AI82472 (Oct. 8, 1998).
GenBank Accession No. AF186114 (Jan. 13, 2000).
GenBank Accession No. AF134715 (Mar. 28, 2000).
Genbank Accession No. Q9Y275 (Feb. 21, 2001).
HGS Backgrounder, "B Lymphocyte Stimulator" dated Oct. 30, 2000.
HGS Backgrounder "Systemic Lupus Erythematosus" dated Nov. 1, 2000.
HGS Backgrounder "Immunoglobulin-A-Deficiency" dated Sep. 2001.
HGS Press Release "Human Genome Sciences Announces the Discovery of a Novel immune Stimulant" dated Jul. 8, 1999.
HGS Press Release "Human Genome Sciences Announces Advance in Hodgkins Lymphoma" dated Jul. 14, 1999.
HGS Press Release "New Anti-Angiogenic Proteins Discovered" dated Aug. 5, 1999.
HGS Press Release "Human Genome Sciences Reports 1999 Financial Results" dated Feb. 10, 2000.
HGS Press Release "Human Genome Sciences Reports First Quarter Financial Results" dated Apr. 27, 2000.
HGS Press Release "Human Genome Sciences and Cambridge Antibody Technology Commit to Exclusive Development of Anti-BLyS Antibodies" dated Oct. 30, 2000.
HGS Press Release "High Levels of BlyS Implicated in Lupus and Rheumatoid Arthritis Patients" dated Oct. 30, 2000.
HGS Press Release "Human Genome Sciences and Dow Agree to Develop HGS' Radiolabeled B-Lymphocyte Stimulator" dated Oct. 30, 2000.
HGS Press Release "Human Genome Sciences Reports Financial Results for Fourth Quarter and Full Year 2000" dated Feb. 15, 2001.
HGS Press Release "Human Genome Sciences Completes Construction of Antibody Manufacturing Facility" dated Feb. 21, 2001.
HGS Press Release "Human Genome Sciences Receives Orphan Drug Designation for BlyS Therapeutic Protein for Treatment of Common Variable Immunodeficiency" dated Feb. 27, 2001.
HGS Press Release "Human Genome Sciences Breaks Ground for a Large Scale Manufacturing Plant" dated Oct. 17, 2001.
HGS Press Release "Human Genome Sciences Initiates Trial of a New Drug for Systemic Lupus Erythematosus and Other Autoimmune Diseases" dated Nov. 1, 2001.
HGS Press Release "Human Genome Sciences Data Support Potential of Lymphostat-B as Treatment for Autoimmune Diseases" dated Nov. 14, 2001.
HGS Press Release "Human Genome Sciences Presents Data as American Society of Hematology Meeting" dated Dec. 9, 2001.
HGS Press Release Human Genome Sciences Files Investigational New Drug Application for Lymphorad[131], dated Jan. 23, 2002.

(56) References Cited

OTHER PUBLICATIONS

HGS Press Release "Human Genome Sciences Reports Financial Results for Full Year and Fourth Quarter 2001" dated Feb. 14, 2002.
HGS Press Release "Human Genome Sciences Provides Update of Company Progress" dated Apr. 30, 2002.
HGS Press Release "Human Genome Sciences Announces Clearance of Investigational New Drug Application for Lymphorad[131], A New Anticancer Drug for the Treatment of B-Cell Tumors" dated May 14, 2002.
HGS Press Release "Human Genome Sciences Describes Activity of New cancer Drug at American Society of Clinical Oncology Meeting" dated May 20, 2002.
HGS Press Release "Human Genome Sciences and Cambridge Antibody Technology Commit to Exclusive Development of Antibody to Trial Receptor-2" dated May 20, 2002.
HGS Press Release "Human Genome Sciences Announces Second Quarter 2002 Financial Results" dated Jul. 25, 2002.
HGS Press Release "Human Genome Sciences Reports Progress in Clinical Trials of Five Drugs at JP Morgan H&Q Conference" dated Jan. 6, 2003.
HGS Press Release "Human Genome Sciences Reports Financial Results for Full Year and Fourth Quarter 2002" dated Feb. 14, 2003.
HGS Press Release "Results of Phase 1 Clinical Trial Demonstrate that Lymphostat-B™ is Safe and Biologically Active in Patients with Systemic Lupus Erythematosus" dated Apr. 21, 2003.
HGS Press Release Human Genome Sciences Reports Financial Results for First Quarter of 2003, dated Apr. 24, 2003.
HGS Press Release "Human Genome Sciences Provides Update of Company Progress" dated May 12, 2003.
HGS Press Release "Human Genome Sciences Updates Progress of Clinical Programs at Bio 2003" dated Jun. 25, 2003.
HGS Press Release "Human Genome Sciences Initiates Phase 2 Clinical Trial of Lymphostat-B™ for the Treatment of Systemic Lupus Erythematosus" dated Sep. 25, 2003.
HGS Press Release, "Human Genome Sciences Reports Results of Phase 1 Clinical Trial of Lymphostat-B™ in Patients with Systemic Lupus Erythematosus" dated Oct. 28, 2003.
HGS Press Release "Human Genome Sciences Reports Third Quarter 2003 Financial Results" dated Oct. 28, 2003.
HGS Press Release "Human Genome Sciences Reports Interim Results of Phase 1 Clinical Trials of Lymphorad™[131] at 45th Annual Meeting of the American Society of Hematology" dated Dec. 9, 2003.
HGS Press Release "Human Genome Sciences Initiates Phase 2 Clinical Trial of Lymphostat-B™ for the Treatment of Rheumatoid Arthritis" dated Jan. 8, 2004.
HGS Press Release "Human Genome Sciences Updates Progress of Six Drugs in Clinical Trials at JPMorgan Conference" dated Jan. 12, 2004.
HGS Press Release "Human Genome Sciences Reports Financial Results for Fourth Quarter and Full Year 2003" dated Feb. 10, 2004.
HGS Press Release "Human Genome Sciences Announces Selection of Lymphostat-B™ for Participation in FDA's Continuous Marketing Application Pilot 2 Program" dated Mar. 4, 2004.
HGS Press Release "Human Genome Sciences Completes Patient Enrollment in a Phase 2 Clinical Trial of Lymphostat-B™ for the Treatment of Rheumatoid Arthritis" dated Jul. 29, 2004.
HGS Press Release "Human Genome Sciences Completes Patient Enrollment in a Phase 2 Clinical Trial of Lymphostat-B™ for the Treatment of Systemic Lupus Erythematosus" dated Jul. 29, 2004.
HGS Press Release "Human Genome Sciences Reports on Progress of Clinical Trials and Announces Goals for 2005 at JPMorgan Healthcare Conference" dated Jan. 10, 2005.
HGS Press Release "Human Genome Sciences Reports Results of a Phase 2 Clinical Trial of Lymphostat-B™ in Patients with Rheumatoid Arthritis" dated Apr. 6, 2005.
HGS Press Release GlaxoSmithKline Exercises Option to Lymphostat-B™, dated Jul. 7, 2005.
HGS Press Release, "Human Genome Sciences to Sponsor Conference Call to Discuss Phase 2 Clinical Results of Lymphostat-B™ in Systemic Lupus Erythematosus" dated Oct. 5, 2005.
HGS Press Release "Human Genome Sciences Reports Results of a Phase 2 Clinical Trial of Lymphostat-B™ in Patients with Systemic Lupus Erythematosus" dated Oct. 5, 2005.
HGS Press Release "Human Genome Sciences Reports on Progress Toward Commercialization and Announces 2006 Goals at JPMorgan Healthcare Conference" dated Jan. 10, 2006.
HGS Press Release "Human Genome Sciences Announces Full Presentation of Results of Phase 2 Clinical Trial of Lymphostat-B™ in Systemic Lupus Erythematosus" dated Jun. 22, 2006.
Human Genome Sciences, Inc.'s Reply filed in the European Patent Office on Nov. 4, 2005 in conjunction with its Opposition of EP Patent No. 1 141 274 and supporting documents D41-D43.
Serono International SA's Reply filed in the European Patent Office on Aug. 24, 2005 in conjunction with its Opposition of EP Patent No. 1 146 892.
Zymogenetics' Observation in Reply (158 pages) to Opposition of EP Patent No. 1441274 lodged by Clorixa Corporation, Human Genome Sciences, Inc., Genentech, Inc., and Biogen Idec., Inc. The Observations in Reply was filed in the European Patent Office on Jun. 7, 2005.
Ashkenazi, et al., *Nature Immonol.*, "Response," 1:179 (2000).
Baker et al., *Arthritis & Rheumatism*, "Generation and Characterization of LymphoStat-B, a Human Monoclonal Antibody that Antagonizes the Bioactivities of B Lymphocyte Stimulator," 48(11):3253-3285 (2003).
Baker et al. *Autoimmun. Rev.*, "Blys—an essential survival factor for B cells: basic biology, links to pathology and therapeutic target," 3(5):365-375 (2004).
Ballow et al., *JAMA*, "Immunopharmacology: immunomodulation and immunotherapy," 278(22):2008-17 (1997).
Batten et al., *J. Ex. Med.*, "BAFF Mediates Survival of Periperal Immature B Lymphocytes," 192:1453-65 (2000).
Baumgarth, *Nature Immunol.*, "Secreted IgM versus BIyS in germinal center formation," 1:179 (2000).
Bork et al., *Trends in Genetics*, "Go hunting in sequence databases but watch out for the traps," 12:425-7 (1996).
Bork et al., *Genome Res.*, "Powers and pitfalls in sequence analysis: the 70% hurdle," 10(4):398-400 (2000).
Brenner, *Trends Genet.*, "SE, Errors in genome annotation," 15(4):132-3 (1999).
Cheema et al., *Arthritis and Rheumatism*, "Elevated Serum B. Lymphocyte Stimulator Levels in Patients with Systemic Immune-Based Rheumatic Diseases," 44:1313-1319 (2001).
Chen et al., Gene, "Expression vectors for affinity purification and radiolabeling of proteins using *Eschericha coli* as host," 139:73-75 (1994).
Cyster, *Nature Immunol.*, "B cells on the Front Line," 1:9-10 (2000).
Denardo et al., *Clinical Cancer Res.*, "Comparison of 1,4,7,10-Tetraazacyclododecane-N,N',n",N'''-tetraacetic acid (DOTA)-Peptide-ChL6, a Novel Immunoconjugate with Catabolizable Linker, to 2 iminothioland-2'-p-(Bromoacetamido)benzyl]-DOTA-ChL6 in Breast Cancer Xenografts," 4(10):2483-2490 (1998).
Do et al., *J. Exp. Med.*, "Attenuation of Apoptosis Underlies B Lymphocyte Stimulator Enhancement of Humoral Immune Response," 192:953-964 (2000).
Doerks et al., *Trends Genet.*, "Protein annotation: detective work for function prediction," 14(6):248-50 (1998).
Dorner et al., *Arthritis Res.*, "B cells, BAFF/zTNF4, TACI, and systemic lupus erythematosus," 3:197-99 (2001).
Egner, *J. Clin. Pathol.* "The use of laboratory tests in the diagnosis of SLE," 53(6):424-32 (2000).
Ferguson et al., *Human Molecular Genetics*, "Cloning of Tabby, the murine homolog of the human EDA gene: evidence for a membrane-associated protein with a short collagenous domain," 6(9):1589-94 (1997).
Furie et al., 67th Annual American College of Rheumatology Scientific Meeting, "Safety, Pharmacokinetic and Pharmacodynamic Results of a Phase 1 Single and Double Dose-Escalation Study of LymphoStat-B (Human Monoclonal Antibody to BLyS) in SIE Patients," Oct. 23-28, 2003, Orlando, FL.

(56) References Cited

OTHER PUBLICATIONS

Groom et al. *J. Clin. Invest.*, "Association of BAFF/FLyS overexpression and altered B cells differentiation with Sjogren's Syndrome," 109:59-68 (2002).
Gross et al., *Nature*, "TACI and BCMA are receptors for a TNF homologue implicated in B-cell autoimmune disease," 404:995-999 (2000).
Hatzoglou et al., *J. Immunol.*, "TNF Receptor Family Member CBMA (B Cell Maturation) Associates with TNF Receptor-Associated Factor (TRAF) 1, TRAF2, TRAF3 and Activates NF-$_k$B, Elk-1, c-Jun N-Terminal Kinase, and p38 Mitogen-Activated Protein Kinase," 165:1322-1330 (2000).
Heppeler et al., *Curr. Med. Chem.*, "Receptor Targeting for Tumor Localisation and Therapy with Radiopeptides," 9(7):971-994 (2000).
Hu et al., *Genomics*, "Characterization of TNFRSFI9, a novel member of the tumor necrosis factor receptor superfamily," 62:103-107 (1999).
Huard et al., *J. Immunology*, "T cell costimulation by the TNF ligand BAFF," 167(11):6225-31 (2001).
Jiang et al., *Immunogenetics*, "Polymorphism and chromosomal mapping of the mouse gene for B-cell activating factor belonging to the tumor necrosis factor family (Baff) and association with the autoimmune phenotype," 53(9):810-813 (2001).
Kabat et al., *Sequences of Proteins of Immunological Interest*, Fourth Edition, pp. 44, 53-54, 63, 69-70 and 76 (1987).
Kanakaraj et al., *Cytokine*, "BlyS binds to B Cells With High Affinity and Induces Activation of the Transcription Factors NF-$_k$B and Elf-1," 13:25-31 (2001).
Karpusas et al., *J. Molec. Biol.*, "Crystal Structure of Extracellular Human BAFF, a TNF Family Member that Stimulates B. Lymphocytes," 315(5):1145-1154 (2002).
Kayagaki et al., *Immunity*, "BAFF/BLyS receptor 3 binds the B cell survival factor BAFF ligand through a discrete surface loop and promotes processing of NF-kappaB2," 10:515-24 (2002).
Kehrl et al., *J. Exp. Med.*, "Effect of tumor necrosis factor alpha on mitogen-activated human B cells," 166:786-791 (1987).
Khare et al., *PNAS*, "Severe B Cell Hyperplasia and autoimmune disease in TALL-1 transgenic mice," 97:3370-3375 (2000).
Laabi et al., *Science Magazine*, "Lymphocyte Survival—Ignorane is BlyS," 289:883 (2001).
Liu et al. *Cell*, "Crystal Structure of sTALL-1 Reveals a Virus-like Assembly of TNF Family Ligands," 108(3):383-394 (2002).
Liu et al., *Nature*, "Ligand Receptor Binding revealed by the TNF family member Tall-1," 421:49-56 (2003).
Lotz et al., *J. Leukoc. Biol.*, "The nerve growth factor/tumor necrosis factor receptor family," 60:1-7 (1996).
MacKay et al., *J. Exp. Med.*, "Mice Transgenic for BAFF Develop Lymphocytic Disorders Along with Autoimmune Manifestations," 190:1697-1710 (1999).
Marriette et al., 65th Annual American College of Rheumatology Scientific Meeting, "A Role for B Lymphocyte Stimulator (TALL-1, BAFF, Thank, $_z$TNF4) in Sjögren's Syndrome," (Nov. 2001).
Marsters et al., *Current Biology*, "Interaction of the TNF homologues BlyS and APRIL with the TNF receptor homologues BCMA and TACI," 10:785-788 (2000).
McGhee, *BMC Pediatr*, "Clinical utility of antinuclear antibody tests in children," 4:13 (2004).
Moore et al., *Science*, "BLyS: Member of the Tumor Necrosis Factor Family and B Lymphocyte Stimulator," 285: 260-263 (1999).
Mukhopadhyay et al., *J. Biol. Chem.*, "Identification and characterization of a novel cytokine, THANK, a TNF Homologue that activates Apoptosis, Nuclear factor-kappaB, and c-Jun NH2-terminal Kinase," 274:15978-15981 (1999).
Nardelli et al., *Immunobiology*, "Synthesis and release of B-lymphocyte stimulator from myeloid cells," 97:198-204 (2001).
Nardelli et al., *Leukemia and Lymphoma*, "B Lymphocyte Stimulator (BLyS): A Therapeutic Trichotomy for the treatment of B lymphocyte diseases," 43:1367-73 (2002).

Ngo et al., *The Protein Folding Problem and Tertiary Structure Prediction*, "Computational Complexity, Protein Structure and the Levinthal Paradox," pp. 492-495 (1994).
Oren et al., *Nature Struct. Biol.*, "Structural basis of BlyS receptor recognition," 9(4):288-292 (2002).
Parry et al. *J. Pharmacol. Exp. Therap.*, "Pharmacokinetics and immunological Effects of Exogenously administered Recombinant Human B Lymphocyte Stimulator (BlyS) in Mice," 296:396-404 (2001).
Schiemann et al., *Science*, "An essential role for BAFF in the normal development of B cells through a BCMA-independent pathway," 293(5537):2111-2114 (2001).
Schneider et al., *J. Exp. Med.*, "BAFF, a Novel Ligand of the Tumor Necrosis Factor Family, Stimulates B Cell Growth," 189:1747:1756 (1999).
Shu et al., *J. Leukoc. Biol.*, "TALL-1 is a novel member of the TNF Family that is Down-regulated by Mitogens," 65:680-683 (1999).
Siegel et al., *Nat. Immunol.*, "To B or not to B: TNF family signally in Lymphocytes," 2:577-8 (2001).
Skolnick et al., *Trends Biotechnol.*, "From genes to protein structure and function: novel applications of computational approaches in the genomic era," 18(1):34-9 (2000).
Smith et al. *Nat. Biotechnol.*, "The challenges of genome sequence annotation or 'the devil is in the details,'" 15(12):1222-3 (1997).
Stohl et al., *Curr. Dir. Autoimmun.*, "Blysfulness does not equal blissfulness in systemic lupus erythematosus: a therapeutic role for BlyS antogonists," 8:289-304 (2005).
Tesoriero, *Wall Street Journal*, "Drugs in testing show promise for treating lupus," published Jan. 23, 2007, retrieved Dec. 21, 2007 from http://www.post-gazette.com/pf/07023/756127-28.stm.
Thompson et al., *J. Exp. Med.*, "BAFF Binds to the Tumor Necrosis Factor Receptor-like Molecule B Cell Maturation Antigen and Is Important for Maintaining the Peripheral B Cell Population," 192:129-135 (2000).
Thompson et al., *Science*, "BAFF-R, a newly identified TNF receptor that specifically interacts with BAFF," 293(5537):2108-2111 (2001).
Tribouley et al., *Biol. Chem.*, "Characterization of a New member of the TNF Family Expressed on Antigen Presenting Cells," 380:1443-7 (1999).
Vaux et al., *J. Clin. Invest.*, "The Buzz about BAFF," 109:17-18 (2002).
Ware, *J. Exp. Med.*, "April and BAFF connect autoimmunity and cancer," 192:F35-F37 (2000).
Wells, *Biochemistry*, "Additivity of mutational effects in proteins," 29(37):8509-17 (1990).
Wu et al., *J. Biol. Chem.*, "Tumor Necrosis Factor (TNF) Receptor Superfamily Member TACI is a High Affinity Receptor for TNF Family Members APRIL and BlyS," 275:34578-34585 (2000).
Xia et al., *J. Exp. Med.*, "TACI is a TRAF-interacting Receptor for TALL-1, a Tumor Necrosis Factor Family Member involved in B Cell Regulation," 192:137-143 (2000).
Yan et al., *Nature Immunol.*, "Identification of a receptor for BlyS demonstrates a crucial role in humoral immunity," 1:37-41 (2000).
Yu et al., *Nature Immunol.*, "APRIL and TALL-1 and receptors BCMA and TACI: system for regulating humoral immunity," 1:252-256 (2000).
Zhang et al., *J. Immunol.*, "Cutting Edge: A Role for B Lymphocyte Stimulator in Systemic Lupus Erythematosus," 166:6-10 (2001).
Minutes of Oral Proceedings dated Apr. 2, 2007 in Opposition of Biogen, Inc. Patent EP 1146892.
Corixa Corporation's opposition of EP Patent No. 1 141 274 B1. Filed in the European Patent Office on Jun. 6, 2004.
Declaration of Patent Interference No. 105,485 between U.S. Appl. No. 09/589,288 and U.S. Pat. No. 6,869,605.
Eli Lilly and Company's opposition of EP Patent No. 0 939 804 including supporting documents D1-D16. Filed in the European Patent Office on May 17, 2006.
Eli Lilly and Company's Request for Revocation (Claim # HC06CO2687) against European Patent (UK) No. 0 039 804 including supporting documents. Filed in the High Court of Justice, Chancery Division, Patents Court on Jul. 5, 2006.
Genentech's opposition of EP Patent No. 1 141 274 B1. Filed in the European Patent Office on Jun. 10, 2004.

(56) References Cited

OTHER PUBLICATIONS

Human Genome Science's opposition of EP Patent No. 1 141 274 B1. Filed in the European Patent Office on Jun. 7, 2004.
Human Genome Sciences' opposition of EP Patent No. 1 146 892 B1 including Annex A. Filed in the European Patent Office on Sep. 19, 2005.
Human Genome Science Inc.'s Reply filed in the European Patent Office on Sep. 19, 2005 in conjunction with its Opposition of EP Patent No. 1 146 892.
Serono's opposition to Biogen, Inc EP Patent No. 1 146 892. Filed in the European Patent Office on May 21, 2004.
Preliminary Non-Binding Decision of the Opposition Division and Summons to attend Oral Proceedings issued by the European Patent Office on Oct. 2, 2006 in the matter of Human Genome Sciences' and Serono's Opposition of EP 1 146 892.
Serono International SA's opposition of EP Patent No. 1 146 892 B1 with Annexes I and II. Filed in the European Patent Office on Aug. 24, 2005.
Serono International SA's opposition of EP Patent No. 0 939 804 including supporting documents D1-D17. Filed in the European Patent Office on May 17, 2006.
WPI/Derwent Accession No. 2000-572093.
Minutes of the Oral Proceedings before the Opposition Division, issued by the European Patent Office on Apr. 2, 2007 in the matter of Human Genome Sciences' and Serono's Opposition of EP 1 146 892.
ZymoGenetics' opposition of EP Patent No. 0 939 804 including supporting documents D1-D27. Filed in the European Patent Office on May 17, 2006.
Abbas et al., Cellular and Molecular Immunology, W.B. Saunders Company: Philadelphia, pp. 362 and 365 (1991).
Acosta-Rodriguez et al., Eur. J. Immunol., 37:990-1000 (2007).
Alberts, ed., Molecular Biology of the Cell, Second Edition, Garland Publishing, Inc., New York, pp. 117-118 (1989).
Arnett, Arthritis Rheum., "The American Rheumatism Association 1987 revised criteria for the classification of rheumatoid arthritis," 31(3):315-24 (1988).
U.S. Appl. No. 09/226,533, Gross et al.
U.S. Appl. No. 09/589,288, Yu et al.
U.S. Appl. No. 12/135,025, Chevrier et al.
U.S. Appl. No. 12/170,333, Yu et al.
U.S. Appl. No. 60/119,906, Boyle et al.
U.S. Appl. No. 60/132,892, Shu.
U.S. Appl. No. 60/149,378, MacKay et al.
U.S. Appl. No. 60/157,933, Schneider et al.
U.S. Appl. No. 60/166,271, Boyle et al.
U.S. Appl. No. 60/201,012, Shu.
U.S. Appl. No. 60/204,039, Theill.
U.S. Appl. No. 60/214,591, Theill.
U.S. Appl. No. 60/312,808, Gelfanova.
Biogen IDEC's opposition of EP Patent No. 1 141 274 B1. Filed in the European Patent Office on Jun. 10, 2004.
Badr et al., Blood, 111(5):2744-2754 (2008).
Batten et al., "The role of BAFF in Autoimmunity: Is it just a B cell story?" The Midwinter Conference of Immunologists at Asilomar, Pacific Grove, CA (Jan. 22-25, 2005).
Bernstein et al., Cancer Res., 50:1017s-1021s (1990).
Binard et al., Journal of Autoimmunity, 30:63-67 (2008).
Bodmer et al., Trends in Biochemical Sciences, "The molecular architecture of the TNF superfamily," 27:19-26. (2002).
Bosello et al., Int. J. Immunopathol. Pharmacol., 20(1):1-8 (2007).
Brazelton, Current Opinion in Immunology, "Molecular mechanism of action of new xenobiotic immunosuppressive drugs: tacrolimus (FK506), sirolimus (rapamycin), mycophenolate mofetil and lefunomide," 8:710-720 (1996).
Buhlmann et al., J. Clinical Immunology, 16(2) (1996).
Caliceti et al., Bioconjug. Chem., "Biopharmaceutical Properties of Uricase Conjugated to Neutral and Amphiphilic Polymers," 10:638-646 (1999).
Cancro, Immunological Reviews, 202:237-249 (2004).
Carswell et al., Proc. Natl. Acad. Sci. U.S.A., 72(9):3666-3670 (1975).
Cerrutti et al, Immunology and Cell Biology, "Plasmacytoid dendritic cells and the regulation of immunoglobulin heavy chain class switching," 83: 554-562 (2005).
Chang, Blood, "A role for BLyS in this activation of innate immune cells," 108(8):2687-94 (2006).
Chatham et al., "Belimumab (Fully Human Monoclonal Antibody to BLyS) Improved or Stailized Systemic Lupus Erythematosus (SLE) Disease Activity Over 3 Years of Treatment," Poster presented at ACT/ACHP Annual Scientific Meeting, Oct. 24-29, 2008 (San Francisco, CA).
Ciruelo et al., Arthritis and Rheumatism, "Cumulative rate of relapse of lupus nephritis after successful treatment with cyclophosphamide," 39:2028-2034 (1996).
Cohen (Fundamental Immunology, Paul ed. Lippincott-Raven Philadelphia, PA, 1999, chapter 33, pp. 1067-1088.
Couzin, Science, "Magnificent Obsession," 307:1712-1715 (2005).
Cragg et al.,B Cell Trophic Factors and B Cell Antagonism in Autoimmune Disease "The Biology of CD20 and Its Potential as a Target for mAb Therapy," pp. 140-174 (2005).
Cull, Protocols in Molecular Biology, Appendix 2.A.2.5, Supp. 35, John Wiley & Sons (1989).
Cull et al., Proc. Natl. Acad. Sci. USA, "Screening for receptor ligands using large libraries of peptides limited to the C terminus of the las represser," 89:1865-1869 (1992).
Cwirla et al., Proc. Natl. Acad. Sci. USA, "Peptides on phage: A vast library of peptides for identifying ligands," 87:6378-6382 (1990).
Czuczman et al., J. Clin. Oncology, 11(10):2021 (1993).
Davidson and Diamond, New England Journal of Medicine, "Autoimmune Diseases," 345:340-350 (2001).
Davies, Nature Genetics, "The EST express gathers speed," 364:554 (1993).
Delves and Roitt, Encyclopedia of Immunology 2nd ed. Academic Press Inc., pp. 1554-1559. (1998).
Denardo et al., Cancer Res., 50:1014s (1990).
Devlin, Science, "Random Peptide Libraries: A Source of Specific Protein Binding Molecules," 249:404-406 (1990).
Eck et al., J Biol. Chem., 264(29):17595-17605 (1989).
Elgert, Immunology: Understanding the Immune System, Wiley-Liss: New York, pp. 24, 305 and 324-326 (1996).
Falini et al., Blood, 85:1-14 (1995).
Felici, J. Mol. Biol., "Selection of Antibody Ligands from a Large Library of Oligopeptides Expressed on a Multivalent Exposition Vector," 222: 301-310 (1991).
Fell et al., J. Immunol., "Genetic Construction and Characterization of a Fusion Protein Consisting of a Chimeric F(ab') With Specificity for Carcinomas and Human IL-2," 146:2446-2452 (1991).
Fishman et al., Nature, "A new grammar for drug discovery," 437:491-493 (2005).
Fodor, Nature, "Multiplexed biochemical assays with biological chips," 364:555-556 (1993).
Fu et al., Blood, 107(11):4540-4548 (2006).
Furie et al., Arthritis Res. & Therapy, "Biologic activity and safety of belimumab, a neutralizing anti-B-lymphocyte stimulator (BLyS) monoclonal antibody: a phase I trial in patients with systemic lupus erythematosus", 10(5):1-15 (2008).
Gillies et al., Proc. Natl. Acad. Sci. USA, "Antibody-targeted interleukin 2 stimulates T-cell killing of autologous tumor cells," 89:1428-1432 (1992).
Goldblum, Clinical and Experimental Rheumatology, "Therapy of rheumatoid arthritis with mycophenolate mofetil," Supp. 8:S117-119 (1993).
Golub and Green, eds., Immunology A Synthesis, Sinaver Assoc., Inc., p. 134 (1991).
Gras et al., International Immunology, "BCMAp: an integral membrane protein in the Golgi apparatus of human mature B lymphocytes," 7:1093-1106. (1995).
Gross et al., Immunity, "TACI-Ig neutralizes molecules critical for B cell development and autoimmune disease: Impaired B cell maturation in mice lacking BLyS," 15:289-302 (2001).

(56) References Cited

OTHER PUBLICATIONS

Gruss, Blood, "Tumor necrosis factor ligand superfamily; Involvement in the pathology of malignant lymphomas," 85(12):3378-404 (1995).
Gruss, Int. Jour. Clin. Lab. Res., "Regulation of murine B cell growth and differentiation by CD30 ligand," 26:143-159 (1996).
Haberman, Genetic Engineering News, "Strategies to Move Beyond Target Validation," 25(21): pp. 36 (2005).
Hahne et al., J. Exp. Med., "APRIL, a New Ligand of the Tumor Necrosis Factor Family, Stimulates Tumor Cell Growth," 188(6):1185-90 (1998).
Hammarstrom et al., Clin. Exp. Immunol. "Selective IgA deficiency (StgAD) and common variable immunodeficiency (CVID)," 120(2):225-31 (2000).
Han, et al., J. Immunol., 155:556-567 (1995).
Harlow and Lane eds., Antibodies: A Laboratory Manual, Cold Spring Harbor Press, pp. 15 and 567-569 (1988).
He et al., J. Immunol., "Lymphoma B cells evade apoptosis through the TNF family members BAFF/BLyS and APRIL," 172(5):3268-79 (2004).
He et al., J. Immunol., "HIV-1 Envelope Triggers Polyclonal Ig Class Switch Recombination through a CD40-Independent Mechanism Involving BAFF and C-Type Lectin Receptors," 176:3931-3941 (2006).
Hill et al., Molec. Aspects Med., 17:455-509 (1996).
Houghten, Bio/Techniques, "The Use of Synthetic Peptide Combinatorial Libraries for the Identification of Bioactive Peptides," 13: 412-421 (1992).
Huard et al., International Immunology, "BAFF production by antigen-presenting cells provides T cell co-stimulation," 16:467-475 (2004).
Hymowitz et al., J. Biol. Chem., "Structures of APRIL-receptor complexes: like BCMA, TACI employs only a single cysteine-rich domain for high affinity ligand binding," 280:7218-27 (2005), with Tables S1-S4 and Fig. S1 as published in the online version of this article available at http://www.jbc.org.
Hwang et al., J. Mol. Cell Cardiol., "Single Pass Sequencing of a Unidirectional Human Fetal Heart cDNA Library to Discover Novel Genes of the Cardiovascular System," 26:1329-1333 (1994).
Iglesias et al., Allergol. Immunopathol. Review, "Common Variable Immunodeficiency," 29:113-118 (2001).
Janeway and Travers, Immunobiology: The Immune System in Health and Disease, Current Biology Ltd./Garland Publishing, London. pp. 12:1-12:19. (1997).
Janeway and Travers. Immunobiology, The Immune System in Health and Disease, (Current Biology Ltd./Garland Publishing, London), 1:15, 1:16, 5:28 and 11:19 (1994).
Jones et al., Nature, 388:225-228 (1989).
Juweid et al., Cancer Res., 55:5899s (1995).
Kapas and Krueger, Amer. J. Physiology, "Tumor necrosis factor-β induces sleep, fever, and anorexia," 263(3):703-707 (1992).
Kelsoe et al., Nature, 279:333-334 (1979).
Kelsoe et al., J. Exp. Med., 151:289-300 (1980).
Kennell, Prog. Nucleic Acid. Res. Mol. Biol., "Principles and practices of nucleic acid hybridization," 11:259-301 (1971).
Kern, Blood, "Involvement of BAFF and APRIL in the resistance to apoptosis of B.CLL through an autocrine pathway," 103(2):679-88 (2004).
Kessel et al., Clinical and Experimental Immunology, "Increased susceptibility of cord blood B lymphocytes to undergo spontaneous apoptosis," 145:563-570 (2006).
Knox et al., Clin. Cancer Res., 2:457 (1996).
Koller and Smithies, Proc. Natl. Acad. Sci. USA, "Inactivating the (32-microglobulin locus in mouse embryonic stem cells by homologous recombination," 86: 8932-8935 (1989).
Koo et al., FEMS Microbiology Letters, "Cloning of a novel crystal protein gene crylK from Bacillus thuringiensis subsp. Morrisoni," 134:159-164 (1995).
Kreitman, Expert Opn. Biol. Ther., "Recombinant Immunotoxins for the Treatment of Hematological Malignancies," 4(7):1115-1128 (2004).
Krumbholz et al., J. Exp. Med., "BAFF is produced by astrocytes and up-regulated in multiple sclerosis lesions and primary central nervous system lymphoma," 201(2):195-200 (2005).
Mobitech website submitted in UK Revocation suit HC06CO2687.
Declaration of Dr. Penny X. Gilbert filed by Human Genome Sciences in support of HGS EP Patent No. 0 939 804. Filed in the European Patent Office and dated May 8, 2008.
Human Genome Sciences Press Release dated Dec. 1, 1999.
Transcript of Deposition of Dr. Randolph Noelle in Patent Interference 105,485 dated Apr. 5, 2007.
Declaration of Henrik Olsen in support of Yu et al. in Patent Interference 105,485 dated Dec. 16, 2007.
Browning opposition and table of content in Patent Interference 105,485. Filed in the United States Patent Office on Feb. 12, 2007.
Yu Exhibit 1200 submitted during the Deposition of Eleanor Bouffard in Patent Interference 105,485 dated Feb. 28, 2008.
Yu Exhibit 1201 submitted during the Deposition of Eleanor Bouffard in Patent Interference 105,485 dated Feb. 28, 2008.
Transcript of a Teleconference in Patent Interference 105,485 dated Feb. 11, 2008.
Claim Form submitted by Eli Lilly and Company requesting revocation of Human Genome Sciences, Inc EP Patent 0 939 804. Filed in the United Kingdom Patent Office on Jul. 5, 2006.
Human Genome Sciences, Inc Defense of EP Patent 0 939 804 filed in the United Kingdom Patent Office on Aug. 3, 2006.
Application to Amend Claims filed by Human Genome Sciences, Inc during UK Revocation suit HC06CO2687 on Feb. 22, 2007.
Agreed Statement of Facts regarding the IMAGE EST submitted in UK Revocation suit HC06CO2687.
Approved Judgment by Mr Justice Kitchin in UK Revocation suit HC06CO2687 dated Jul. 31, 2008.
Quotations evidencing agreement on the closest prior art, the formulation of the technical problem and its solution by the invention. Filed in the European Patent Office as exhibit D116 in support of Human Genome Sciences' EP Patent No. 0 939 804 on Apr. 13, 2009.
Declaration of Dr. Chih-Hung Lo and Exhibits A to L filed in support of Human Genome Science's EP Patent No. 1 294 769 dated Aug. 19, 2008 and filed in the European Patent Office.
Minutes of the Oral Proceedings before the Opposition Division and the Decision Revoking the European Patent, issued by the European Patent Office on Dec. 3, 2008 in the matter of Eli Lilly and Company's Opposition of EP 0 939 804.
Judgment of Kitchin J. in *Eli Lilly and Company* v *Human Genome Sciences, Inc.* [2008] EWHC 1903 ("the English revocation action").
Transcript of hearing Nov. 8, 2006 in UK Revocation suit HC06CO2687.
Transcript of hearing Nov. 9, 2006 in UK Revocation suit HC06CO2687.
Defendant's civil evidence act notice submitted by Human Genome Sciences in support of Human Genome Sciences in UK Revocation suit HC06CO2687 dated Jun. 1, 2007.
Defendant's civil evidence act notice submitted by Human Genome Sciences in support of Human Genome Sciences in UK Revocation suit HC06CO2687 dated Nov. 29, 2007.
Claimant's civil evidence act notice submitted by Eli Lilly in support of Human Genome Sciences in UK Revocation suit HC06CO2687 dated Jun. 1, 2007.
Defendant's civil evidence act notice submitted by Human Genome Sciences in support of Human Genome Sciences in UK Revocation suit HC06CO2687 dated Dec. 7, 2007.
Claimant's Further Information concerning the statement of opposition submitted by Eli Lilly in UK Revocation suit HC06CO2687 dated May 4, 2007.
Claimant's statement of case relating to SWISS-PROT submitted by Eli Lilly in UK Revocation suit HC06CO2687 dated Nov. 30, 2006.
Claimant's response to defendant's notice of experiments in reply submitted by Eli Lilly in UK Revocation suit HC06CO2687 dated Nov. 30, 2006.
Human Genome Science's response to request to attend oral hearings in UK Revocation suit HC06CO2687 dated Jun. 30, 2004.

(56) References Cited

OTHER PUBLICATIONS

Table of selected passages from EP Patent No. 0 939 804 submitted in UK Revocation suit HC06CO2687.
Second Witness Statement of Mark Hodgson dated Nov. 7, 2007 in support of Eli Lilly in UK Revocation suit HC06CO2687.
First Expert Report of Dr. Randolph Noelle dated Jun. 1, 2007 in support of Human Genome Sciences in UK Revocation suit HC06CO2687.
Second Expert Report of Dr. Randolph Noelle dated Jun. 22, 2007 in support of Human Genome Sciences in UK Revocation suit HC06CO2687.
First Witness Statement of Dr. Penny X. Gilbert dated Nov. 2, 2006 in support of Human Genome Sciences in UK Revocation suit HC06CO2687.
Second Witness Statement of Dr. Penny X. Gilbert dated Nov. 6, 2006 in support of Human Genome Sciences in UK Revocation suit HC06CO2687.
First Expert Report of Dr. Jeremy Saklatvala dated May 25, 2007 in support of Eli Lilly in UK Revocation suit HC06CO2687.
Second Expert Report of Dr. Jeremy Saklatvala dated Jun. 27, 2007 in support of Eli Lilly in UK Revocation suit HC06CO2687.
Third Expert Report of Dr. Jeremy Saklatvala dated Nov. 23, 2007 in support of Eli Lilly in UK Revocation suit HC06CO2687.
Witness Statement of Simon Mark Wright dated Jun. 6, 2007 in support of Human Genome Sciences in UK Revocation suit HC06CO2687.
Witness Statement of Elisabeth Gasteiger dated Jun. 12, 2007 in support of Human Genome Sciences in UK Revocation suit HC06CO2687.
Declaration of Dr. Thi-Sau Migone dated Jul. 12, 2007 in support of Human Genome Sciences in Opposition of EP Patent No. 1141274.
Second Declaration of Carl F. Ware dated Jan. 28, 2008 in support of Browning et al. in Patent Interference 105,485.
Biogen Decision dated Nov. 27, 2007 in Opposition of Patent EP 1146892.
Zymogenetics Interlocutory Decision dated Nov. 30, 2007 in Opposition of Patent EP 1141274.
Zymogenetics Preliminary Opinion dated Mar. 15, 2007 in Opposition of Patent EP 1141274.
Extended European Search Report, European Application No. 07 01 2741.0 dated Feb. 8, 2008.
Grounds of Appeal filed by Merck Serono dated Mar. 27, 2008 in Opposition of Patent EP 1 146 892.
Grounds of Appeal submitted by Human Genome Sciences, Inc. on Apr. 13, 2009 in Appeal Case T 18/09-3.3.08 in support of EP Patent 0939804.
Human Genome Sciences Observations on Oppositions to EP 0939804 dated Apr. 2, 2008.
Auxiliary Requests 1-12 submitted by Human Genome Sciences, Inc. in defense of EP Patent No. 0 939 804 dated May 8, 2008.
Eli Lilly's Submission in Opposition of EP Patent No. 0 939 804 including supporting documents D48-D57. Filed in the European Patent Office on Apr. 2, 2008.
Eli Lilly's Submission in Opposition of EP Patent No. 0 939 804 including supporting documents D98-D112. Filed in the European Patent Office on May 30, 2008.
Serono's Opposition of EP Patent No. 0 939 804 including supporting documents D1-D27. Filed in the European Patent Office on May 18, 2006.
Human Genome Science's Observations on the Oppositions against EP Patent No. 0 939 804 including annexes. Filed in the European Patent Office on Apr. 2, 2008.
Declaration of Dr. Andrew Martin and annexes filed in support of Human Genome Science's EP Patent No. 0 939 804 dated Mar. 26, 2008 and filed in the European Patent Office.
Declaration of Dr. David Cash and annexes filed in support of Human Genome Science's EP Patent No. 0 939 804 dated Mar. 6, 2008 and filed in the European Patent Office.
Declaration of Dr. Randolph Noelle and annexes filed in support of Human Genome Science's EP Patent No. 0 939 804 dated Mar. 23, 2008 and filed in the European Patent Office.
Declaration of Dr. Stuart Farrow and annexes filed in support of Human Genome Science's EP Patent No. 0 939 804 dated Mar. 25, 2008 and filed in the European Patent Office.
Declaration of Dr Garnett Herrel Kelsoe III, filed in support of Human Genome Sciences' EP Patent No. 0 939 804 dated Apr. 12, 2009 and filed in the European Patent Office.
Witness statement of Christa Pange Pennacchio and annexes filed in support of Human Genome Science's EP Patent No. 0 939 804 dated Mar. 25, 2008 and filed in the European Patent Office.
List of documents, dated May 29, 2008 relied upon in Opposition proceedings against Human Genome Science's EP Patent No. 0 939 804.
Human Genome Science's opposition to Biogen, Inc EP Patent No. 1 146 892 with annexes C15-C25. Filed in the European Patent Office on May 10, 2004.
ZymoGenetics' response to the Oppositions against ZymoGenetics EP Patent No. 1 141 274 filed in the European Patent Office on Jun. 6, 2005.
Human Genome Science's reply to ZymoGenetics' response to the Oppositions against ZymoGenetics EP Patent No. 1 141 274 filed in the European Patent Office on Nov. 4, 2005.
Opposition Division's Preliminary Opinion and annex in the Opposition Proceedings against against ZymoGenetics EP Patent No. 1 141 274 filed in the European Patent Office on Mar. 15, 2007.
Second Declaration of Dr. Andrew Martin filed by Human Genome Sciences in support of HGS EP Patent No. 0 939 804. Filed in the European Patent Office and dated May 7, 2008.
HGS Press Release "Human Genome Sciences Reports Phase 2 Results for LYMPHOSTAT-B (Belimumab) in Patients with Rheumatoid Arthritis," dated Nov. 17, 2005.
HGS Press Release "Human Genome Sciences Announces Positive 76-week Results of Phase 2 Clinical Trial of LYMPHOSTAT-B in Systemic Lupus Erythematosus," dated Nov. 14, 2006.
Human Genome Sciences' Press Release dated May 30, 2007.
Alignment of D41 Shu Figure 1B with D1 Gruss and Dower β-sheets. Filed in the European Patent Office as exhibit D146 in support of Human Genome Sciences' EP Patent No. 0 939 804 on Apr. 13, 2009.
Alignment of D10 Schneider Figure 1B with D1 Gruss and Dower β sheets. Filed in the European Patent Office as exhibit D147 in support of Human Genome Sciences' EP Patent No. 0 939 804 on Apr. 13, 2009.
Partial Transcript of Costs Hearing in the English Revocation Action (UK Revocation suit HC06CO2687) dated Oct. 17, 2008.
Requirement for Restriction/Election issued in U.S. Appl. No. 09/932,613, dated Apr. 8, 2003.
Non-Final Rejection issued in U.S. Appl. No. 09/932,613, dated Jul. 14, 2004.
Final Rejection issued in U.S. Appl. No. 09/932,613, dated Apr. 20, 2005.
Requirement for Restriction/Election issued in U.S. Appl. No. 11/232,439, dated Apr. 24, 2007.
Non-Final Rejection issued in U.S. Appl. No. 11/232,439, dated May 28, 2008.
Requirement for Restriction/Election issued in U.S. Appl. No. 09/880,748, dated May 7, 2003.
Examiner Interview Summary issued in U.S. Appl. No. 09/880,748, dated Jun. 2, 2003.
Non-Final Rejection issued in U.S. Appl. No. 09/880,748, dated Sep. 14, 2004.
Final Rejection issued in U.S. Appl. No. 09/880,748, dated May 4, 2005.
Advisory Action issued in U.S. Appl. No. 09/880,748, dated Sep. 28, 2005.
Requirement for Restriction/Election issued in U.S. Appl. No. 10/293,418, dated Mar. 6, 2006.
Non-Final Rejection issued in U.S. Appl. No. 10/293,418, dated Jun. 30, 2006.
Requirement for Restriction/Election issued in U.S. Appl. No. 11/054,515, dated Feb. 15, 2007.

(56) References Cited

OTHER PUBLICATIONS

Requirement for Restriction/Election issued in U.S. Appl. No. 11/054,515, dated Feb. 25, 2008.
Non-Final Rejection issued in U.S. Appl. No. 11/054,515, dated Jul. 3, 2008.
Final Rejection issued in U.S. Appl. No. 11/054,515, dated Feb. 24, 2009.
Requirement for Restriction/Election issued in U.S. Appl. No. 11/266,444, dated Apr. 24, 2007.
Non-Final Rejection issued in U.S. Appl. No. 11/266,444, dated Feb. 28, 2008.
Final Rejection issued in U.S. Appl. No. 11/266,444, dated Dec. 3, 2008.
Advisory Action issued in U.S. Appl. No. 11/266,444, dated Feb. 24, 2009.
Requirement for Restriction/Election issued in U.S. Appl. No. 10/735,865, dated Jul. 12, 2006.
Requirement for Restriction/Election issued in U.S. Appl. No. 10/739,042, dated Jul. 12, 2006.
Requirement for Restriction/Election issued in U.S. Appl. No. 09/589,287, dated Feb. 20, 2001.
Non-Final Rejection issued in U.S. Appl. No. 09/589,287, dated Nov. 6, 2001.
Examiner Interview Summary issued in U.S. Appl. No. 09/589,287, dated Nov. 27, 2001.
Examiner Interview Summary issued in U.S. Appl. No. 09/589,287, dated Dec. 21, 2001.
Notice of Allowance issued in U.S. Appl. No. 09/589,287, dated Dec. 31, 2001.
Requirement for Restriction/Election issued in U.S. Appl. No. 09/588,947, dated Mar. 8, 2001.
Non-Final Rejection issued in U.S. Appl. No. 09/588,947, dated Nov. 26, 2001.
Notice of Allowance issued in U.S. Appl. No. 09/588,947, dated Jul. 15, 2002.
Requirement for Restriction/Election issued in U.S. Appl. No. 09/589,286, dated Dec. 10, 2001.
Non-Final Rejection issued in U.S. Appl. No. 09/589,286, dated Jun. 10, 2002.
Non-Final Rejection issued in U.S. Appl. No. 09/589,286, dated Dec. 4, 2002.
Notice of Allowance issued in U.S. Appl. No. 09/589,286, dated Jun. 3, 2003.
Requirement for Restriction/Election issued in U.S. Appl. No. 09/589,285, dated Feb. 20, 2001.
Non-Final Rejection issued in U.S. Appl. No. 09/589,285, dated Nov. 6, 2001.
Final Rejection issued in U.S. Appl. No. 09/589,285, dated Sep. 6, 2002.
Non-Final Rejection issued in U.S. Appl. No. 09/589,285, dated Oct. 22, 2003.
Notice of Allowance issued in U.S. Appl. No. 09/588,285, dated May 18, 2004.
Requirement for Restriction/Election issued in U.S. Appl. No. 11/377,165, dated Jun. 27, 2008.
Non-Final Rejection issued in U.S. Appl. No. 11/377,165, dated Dec. 3, 2008.
Requirement for Restriction/Election issued in U.S. Appl. No. 11/382,837, dated May 29, 2008.
Non-Final Rejection issued in U.S. Appl. No. 11/382,837, dated Nov. 28, 2008.
Requirement for Restriction/Election issued in U.S. Appl. No. 09/929,493, dated Dec. 16, 2002.
Requirement for Restriction/Election issued in U.S. Appl. No. 10/270,487, dated Jun. 15, 2004.
Non-Final Rejection issued in U.S. Appl. No. 10/270,487, dated Feb. 10, 2005.
Requirement for Restriction/Election issued in U.S. Appl. No. 11/054,539, dated Jan. 9, 2007.
Non-Final Rejection issued in U.S. Appl. No. 11/054,539, dated May 2, 2007.
Final Rejection issued in U.S. Appl. No. 11/054,539, dated Jan. 22, 2008.
Requirement for Restriction/Election issued in U.S. Appl. No. 09/507,968, dated Feb. 14, 2001.
Non-Final Rejection issued in U.S. Appl. No. 09/507,968, dated Nov. 6, 2001.
Examiner Interview Summary issued in U.S. Appl. No. 09/507,968, dated Nov. 27, 2001.
Final Rejection issued in U.S. Appl. No. 09/507,968, dated Jan. 31, 2003.
Advisory Action issued in U.S. Appl. No. 09/507,968, dated Jul. 7, 2003.
Notice of Allowance issued in U.S. Appl. No. 09/507,968, dated Sep. 5, 2003.
Examiner's Amendment issued in U.S. Appl. No. 09/507,968, dated Sep. 22, 2004.
Requirement for Restriction/Election issued in U.S. Appl. No. 09/005,874, dated Nov. 24, 1998.
Non-Final Rejection issued in U.S. Appl. No. 09/005,874, dated Aug. 10, 2000.
Non-Final Rejection issued in U.S. Appl. No. 09/005,874, dated Nov. 22, 2000.
Non-Final Rejection issued in U.S. Appl. No. 09/005,874, dated Jul. 27, 2001.
Non-Final Rejection issued in U.S. Appl. No. 09/005,874, dated Apr. 23, 2002.
Non-Final Rejection issued in U.S. Appl. No. 09/005,874, dated Mar. 27, 2003.
Examiner's Amendment issued in U.S. Appl. No. 09/005,874, dated Nov. 3, 2003.
Notice of Allowance issued in U.S. Appl. No. 09/005,874, dated Nov. 3, 2003.
Requirement for Restriction/Election issued in U.S. Appl. No. 09/255,794, dated Dec. 13, 2000.
Requirement for Restriction/Election issued in U.S. Appl. No. 09/255,794, dated Aug. 27, 2001.
Non-Final Rejection issued in U.S. Appl. No. 09/255,794, dated Feb. 8, 2002.
Examiner Interview Summary issued in U.S. Appl. No. 09/255,794, dated Jul. 2, 2002.
Non-Final Rejection issued in U.S. Appl. No. 09/255,794, dated Oct. 1, 2002.
Notice of Allowance issued in U.S. Appl. No. 09/255,794, dated Aug. 25, 2003.
Requirement for Restriction/Election issued in U.S. Appl. No. 09/589,288, dated Feb. 20, 2001.
Non-Final Rejection issued in U.S. Appl. No. 09/589,288, dated Nov. 6, 2001.
Final Rejection issued in U.S. Appl. No. 09/589,288, dated Aug. 13, 2002.
Non-Final Rejection issued in U.S. Appl. No. 09/589,288, dated Jun. 3, 2003.
Final Rejection issued in U.S. Appl. No. 09/589,288, dated Jun. 3, 2004.
Examiner Interview Summary issued in U.S. Appl. No. 09/589,288, dated Feb. 15, 2006.
Examiner Interview Summary issued in U.S. Appl. No. 09/589,288, dated Jul. 20, 2006.
Interference Decision issued in U.S. Appl. No. 09/589,288, dated Jul. 17, 2008.
Examiner Interview Summary issued in U.S. Appl. No. 09/589,288, dated Apr. 24, 2009.
Requirement for Restriction/Election issued in U.S. Appl. No. 12/170,333, dated May 28, 2009.
Office Communication from EPO in EP Application No. 07109688.7 mailed May 5, 2008 containing Extended European Search Report mailed Sep. 24, 2007.
Response to EP Office Communication in EP Application No. 07109688.7 mailed Nov. 7, 2008.
International Preliminary Report on Patentability issued in PCT/US2007/008021 dated Oct. 9, 2008.

(56) References Cited

OTHER PUBLICATIONS

Requirement for Restriction/Election issued in U.S. Appl. No. 11/543,024, dated Feb. 28, 2007.
Non-Final Rejection issued in U.S. Appl. No. 11/543,024, dated Jul. 31, 2007.
Final Rejection issued in U.S. Appl. No. 11/543,024, dated Mar. 5, 2008.
Final Rejection issued in U.S. Appl. No. 11/232,439, dated May 27, 2009.
Clustal V Alignment of human and mouse TACI filed in Opposition of EP Patent No. 1 141 274 (Filed in the European Patent Office on Jun. 4, 2004).
Further experimental evidence concerning anti-TACI antibodies of EP 1 141 274 B1 Patent Example 18 (Zymogenetics' unpublished data) (Jun. 7, 2005).
Lexikon der Medizin "Hypertension" filed in Opposition of EP Patent No. 1 146 892(Filed in the European Patent Office on Sep. 19, 2005).
Sequence alignment of "Prosite" sequence (D1) and SEQ ID No: 10 of EP 1 141 274 (Feb. 24, 2005).
Table setting out SEQ ID Nos. (provided by Opponent I) (Jun. 4, 2004).
Browning Demonstrative Exhibits submitted by Biogen, Inc. in Patent Interference 105,485 (Jul. 9, 2007).
Browning motion 2 submitted by Biogen, Inc. in Patent Interference 105,485 (Dec. 1, 2006).
Browning motion 3 submitted by Biogen, Inc. in Patent Interference 105,485 (Dec. 1, 2006).
Browning motion 4 submitted by Biogen, Inc. in Patent Interference 105,485 (Dec. 1, 2006).
Browning motion 5 submitted by Biogen, Inc. in Patent Interference 105,485 (Dec. 1, 2006).
Browning motion 6 submitted by Biogen, Inc. in Patent Interference 105,485 (May 7, 2007).
Browning motion 7 submitted by Biogen, Inc. in Patent Interference 105,485 (Jan. 9, 2008).
Browning motion 8 submitted by Biogen, Inc. in Patent Interference 105,485 (Jan. 28, 2008).
Browning motion 9 submitted by Biogen, Inc. in Patent Interference 105,485 (Jan. 28, 2008).
Browning motion 10 submitted by Biogen, Inc. in Patent Interference 105,485 (Jan. 28, 2008).
Browning reply 2 submitted by Biogen, Inc. in Patent Interference 105,485 (Apr. 16, 2007).
Browning reply 3 submitted by Biogen, Inc. in Patent Interference 105,485 (Apr. 16, 2007).
Browning reply 4 submitted by Biogen, Inc. in Patent Interference 105,485 (Apr. 16, 2007).
Browning reply 5 submitted by Biogen, Inc. in Patent Interference 105,485 (Apr. 16, 2007).
Browning reply 6 submitted by Biogen, Inc. in Patent Interference 105,485 (May 29, 2007).
Yu Demonstrative Exhibits submitted by Human Genome Sciences, Inc. in Patent Interference 105,485 (Jul. 13, 2007).
Yu motion 1 submitted by Human Genome Sciences, Inc. in Patent Interference 105,485 (Nov. 16, 2006).
Yu motion 2 submitted by Human Genome Sciences, Inc. in Patent Interference 105,485 (Dec. 1, 2006).
Yu motion 3 submitted by Human Genome Sciences, Inc. in Patent Interference 105,485 (Apr. 30, 2007).
Yu motion 4 submitted by Human Genome Sciences, Inc. in Patent Interference 105,485 (Nov. 28, 2007).
Yu motion 5 submitted by Human Genome Sciences, Inc. in Patent Interference 105,485 (Nov. 28, 2007).
Yu motion 6 submitted by Human Genome Sciences, Inc. in Patent Interference 105,485 (Jan. 9, 2008).
Yu opposition 2 submitted by Human Genome Sciences, Inc. in Patent Interference 105,485 (Feb. 12, 2007).
Yu opposition 3 submitted by Human Genome Sciences, Inc. in Patent Interference 105,485 (Feb. 12, 2007).
Yu opposition 4 submitted by Human Genome Sciences, Inc. in Patent Interference 105,485 (Feb. 12, 2007).
Yu opposition 5 submitted by Human Genome Sciences, Inc. in Patent Interference 105,485 (Feb. 12, 2007).
Yu opposition 6 submitted by Human Genome Sciences, Inc. in Patent Interference 105,485 (May 21, 2007).
Yu opposition 7 submitted by Human Genome Sciences, Inc. in Patent Interference 105,485 (Jan. 14, 2008).
Defendant's Notice of Experiments in Reply submitted by Human Genome Sciences in support of Human Genome Sciences in UK Revocation suit HC06CO2687 (May 8, 2007).
Work up experiments in relation to Defendant's Notice of Experiments in Reply submitted by Human Genome Sciences in support of Human Genome Sciences in UK Revocation suit HC06CO2687 (May 8, 2007).
Claimant's notice of experiments submitted by Eli Lilly against Human Genome Sciences in UK Revocation suit HC06CO2687 (Feb. 23, 2007).
Defendant's response to claimant's notice of experiments submitted by Human Genome Sciences in support of Human Genome Sciences in UK Revocation suit HC06CO2687 (Mar. 16, 2007).
Defendant's conditional application to further amend claim 15 submitted by Human Genome Sciences in UK Revocation suit HC06CO2687 (Jan. 2008).
Claimant's grounds for opposition to further amend claim 15 submitted in UK Revocation suit HC06CO2687 (Dec. 14, 2007).
Correspondence between Human Genome Sciences and the United Kingdom Patent Office submitted by Eli Lilly in UK Revocation suit HC06CO2687 (Feb. 22, 2007).
Defendant's amended response to claimant's request for further information submitted by Human Genome Sciences in UK Revocation suit HC06CO2687 (Apr. 4, 2007).
Defendant's response to claimant's notice to admit submitted in UK Revocation suit HC06CO2687 (Nov. 30, 2006).
Defendant's response to claimant's second request for further information submitted in UK Revocation suit HC06CO2687 (Mar. 30, 2007).
Documents handed up during trial in UK Revocation suit HC06CO2687 (Dec. 2007).
Amended claims submitted by Human Genome Sciences in support of Human Genome Sciences in UK Revocation suit HC06CO2687 (Feb. 22, 2007).
Human Genome Science's Opening Arguments in UK Revocation suit HC06CO2687 (Nov. 29, 2007).
Human Genome Science's Closing Arguments in UK Revocation suit HC06CO2687 (Dec. 20, 2007).
Eli Lilly's Opening Arguments in UK Revocation suit HC06CO2687 (Nov. 28, 2007).
Eli Lilly's Closing Arguments in UK Revocation suit HC06CO2687 (Dec. 2007).
Order Confirming Claimant's Undertaking Not to Infringe submitted in UK Revocation suit HC06CO2687 (Nov. 22, 2006).
Order for Directions submitted in UK Revocation suit HC06CO2687 (Sep. 21, 2006).
Order of Mr Justice Pumfrey submitted in UK Revocation suit HC06CO2687 (Apr. 20, 2007).
Order of Mr Justice Warren submitted in UK Revocation suit HC06CO2687 (May 8, 2007).
Particulars of the Claim submitted in UK Revocation suit HC06CO2687 (Jul. 5, 2006).
Re-reamended grounds of invalidity submitted by Eli Lilly in UK Revocation suit HC06CO2687 (Jun. 28, 2007).
Statement of Opposition submitted by Eli Lilly in UK Revocation suit HC06CO2687 (Apr. 4, 2007).
Defendant Statement of Reasons to amend the claims of EP Patent No. 0 939 804 submitted by Human Genome Sciences in UK Revocation suit HC06CO2687 (Feb. 22, 2007).
Table of relevant scientific papers submitted in UK Revocation suit HC06CO2687 (Dec. 2007).
Table of selected passages from EP Patent No. 0 939 804 submitted in UK Revocation suit HC06CO2687 (Dec. 2007).
BioTherapeutic Overview submitted in UK Revocation suit HC06CO2687 (Sep. 12, 2007).

(56) References Cited

OTHER PUBLICATIONS

Eli Lilly website submitted in UK Revocation suit HC06CO2687 (Sep. 12, 2007).
EMEA 2007 Antibody guidelines submitted in UK Revocation suit HC06CO2687 (Apr. 5, 2007).
Wikipedia page submitted by Eli Lilly in UK Revocation suit HC06CO2687 (Dec. 2007).
Mobitech website submitted in UK Revocation suit HC06CO2687 (Dec. 2007).
Transcript of trial day 1 of UK Revocation suit HC06CO2687 (Dec. 7, 2007).
Transcript of trial day 2 of UK Revocation suit HC06CO2687 (Dec. 10, 2007).
Transcript of trial day 3 of UK Revocation suit HC06CO2687 (Dec. 11, 2007).
Transcript of trial day 4 of UK Revocation suit HC06CO2687 (Dec. 12, 2007).
Transcript of trial day 5 of UK Revocation suit HC06CO2687 (Dec. 13, 2007).
Transcript of trial day 6 of UK Revocation suit HC06CO2687 (Dec. 17, 2007).
Transcript of trial day 7 of UK Revocation suit HC06CO2687 (Dec. 18, 2007).
Transcript of trial day 8 of UK Revocation suit HC06CO2687 (Dec. 19, 2007).
Transcript of trial day 9 of UK Revocation suit HC06CO2687 (Dec. 20, 2007).
Transcript of trial day 10 of UK Revocation suit HC06CO2687 (Dec. 21, 2007).
Transcript of trial day 11 of UK Revocation suit HC06CO2687 (Jan. 11, 2008).
Transcript of trial day 12 of UK Revocation suit HC06CO2687 (Jan. 14, 2008).
Transcript of trial day 13 of UK Revocation suit HC06CO2687 (Jan. 15, 2008).
First Expert Report of Dr. Andrew C.R. Martin in support of Human Genome Sciences in UK Revocation suit HC06CO2687 (Jun. 1, 2007).
Second Expert Report of Dr. Andrew C.R. Martin in support of Human Genome Sciences in UK Revocation suit HC06CO2687 (Jun. 22, 2007).
Human Genome Sciences, Inc Patent in suit as proposed to be amended during UK Revocation suit HC06CO2687 (Dec. 2007).
Agreed Statement of Facts regarding the IMAGE EST submitted in UK Revocation suit HC06CO2687 (Dec. 2007).
*American College of Rheumatology*, "The 1982 Revised Criteria for Classification of Systemic Lupus Erythematosus," retrieved Jun. 10, 2009 from http://www.rheumatology.org/publications/classification/SLE/sle.asp.
Non-Final Rejection issued in U.S. Appl. No. 12/186,404, dated Jun. 21, 2010.
"Classification Criteria for the Diagnosis of Systemic Lupus Erythematosus," retrieved Jul. 22, 2010 from http://medicalcriteria.com/criteria/sle.htm.
Final Rejection issued in U.S. Appl. No. 12/210,134, dated Jul. 21, 2010.
Tan et al., *Arthritis Rheum.*, "Range of antinuclear antibodies in "healthy" individuals," 40(9):1601-1611 (1997).
Sauge-Merle et al., *Eur. J. Biochem.*, "An active ribonucleotide reductase from *Arabidopsis thaliana*: cloning, expression and characterization of the large subunit," 266:62-69 (1999).
Esposito et al., *J. Immunol.*, "Human transaldolase and cross-reactive viral epitopes identified by autoantibodies of multiple sclerosis patients," 163:4027-4032 (1999).
International Search Report issued in PCT Application No. PCT/US01/25850, dated Apr. 1, 2003.
International Search Report issued in PCT Application No. PCT/US01/25891, dated Apr. 2, 2003.
Requirement for Restriction/Election issued in U.S. Appl. No. 09/932,322, dated Jun. 30, 2004.
Non-Final Rejection issued in U.S. Appl. No. 09/932,322, dated Feb. 9, 2005.
Final Rejection issued in U.S. Appl. No. 09/932,322, dated Aug. 24, 2005.
Notice of Allowance issued in U.S. Appl. No. 09/932,322, dated Feb. 8, 2006.
Han et al., "Characterization of Transformation Function of Cottontail Rabbit Papillomavirus E5 and E8 Genes," *Virology*, 251:253-263 (1998).
Non-Final Rejection issued in U.S. Appl. No. 12/135,025, dated Aug. 4, 2010.
Notice of Allowance issued in U.S. Appl. No. 11/054,515, dated Sep. 9, 2010.
Non-Final Rejection issued in U.S. Appl. No. 12/605,202, dated Sep. 20, 2010.
Berenbaum, "Synergy, additivism and antagonism in immunosuppression," *Clin. Exp. Immunol.*, 28:1-18 (1977).
Dooley et al., "Mycophenolate mofetil therapy in lupus nephritis: clinical observations," *J. Am. Soc. Nephrol*, 10:833-839 (1999).
Jonsson et al., "Mycophenolic acid inhibits inosine 5'-monophosphate dehydrogenase and suppresses immunoglobulin and cytokine production of B cells," *Int. Immunopharmacol.*, 3:31-37 (2003).
Koyama et al., "Raised serum APRIL levels in patients with systemic lupus erythematosus," *Ann. Rheum. Dis.* 64:1065-1067 (2005).
Ramanujam et al., "Mechanism of action of transmembrane activator and calcium modulator ligand interactor-Ig in murine systemic lupus erythematosus," *J.Immunol.* 173:3524-3534 (2004).
Stohl et al., "B lymphocyte stimulator protein-associated increase in circulating autoantibody levels may require $CD4^+$ T cells: lessons from HIV-infected patients," *Clin. Immunol.* 104(2):115-122 (2002).
Final Rejection issued in U.S. Appl. No. 12/552,915, dated Sep. 22, 2010.
Notice of Allowance issued in U.S. Appl. No. 12/170,333, dated Oct. 8, 2010.
Extended European Search Report, European Application No. 10156941.6 dated Aug. 16, 2010.
Non-Final Rejection issued in U.S. Appl. No. 12/701,301, dated Oct. 15, 2010.
List of Exhibits filed in Patent Interference 105,652, including the corresponding PTO Form-1449 Doc. No. for each exhibit (2010).
Application File for U.S. Appl. No. 60/225,628 filed on May 28, 2009 in Patent Interference 105,652 (HGS Exhibit 2001).
Application File for U.S. Appl. No. 09/929,493 filed May 28, 2009 in Patent Interference 105,652 (HGS Exhibit 2002).
Application File for U.S. Appl. No. 60/336,726 filed May 28, 2009 in Patent Interference 105,652 (HGS Exhibit 2003).
Application File for U.S. Appl. No. 10/270,487 filed May 28, 2009 in Patent Interference 105,652 (HGS Exhibit 2004).
Application File for U.S. Appl. No. 60/543,261 filed May 28, 2009 in Patent Interference 105,652 (HGS Exhibit 2005).
Application File for U.S. Appl. No. 60/580,387 filed May 28, 2009 in Patent Interference 105,652 (HGS Exhibit 2006).
Helmkamp et al., "High Specific Activity Iodination of γ-Globulin with Iodine-131 Monochloride," *Cancer Res.*, 20:1495-1500 (1960). Filed May 28, 2009 in Patent Interference 105,652 (HGS Exhibit 2010).
Printouts from RDF Technologies, Inc. webpage. Filed May 28, 2009 in Patent Interference 105,652 (HGS Exhibit 2015).
Lyu et al., "The Growth Factor Toxin Construct rGel/BLyS Specifically Targets Tumor Cells Expressing BAFF-R, TACI, and BCMA," AACR #1517 (poster). Filed in Patent Interference 105,652 (HGS Exhibit 2032) (Apr. 1, 2009).
RDF Power of Attorney from inter partes Reexamination No. 95/000,016. Filed May 28, 2009 in Patent Interference 105,652 (HGS Exhibit 2041).
*Chen* v. *Bouchard* Final Decision issued in Patent Interference 103,675. Filed in Patent Interference 105,652 (HGS Exhibit 2043) (May 6, 2009).
Rosenblum Curriculum Vitae. Filed Jun. 30, 2009 in Patent Interference 105,652 (RDF Exhibit 1011).
Memorandum opinion and order issued Jun. 29, 2010 in Patent Interference No. 105,652.

(56) References Cited

OTHER PUBLICATIONS

Judgment on preliminary motions issued Jun. 29, 2010 in Patent Interference No. 105,652.
Technician's précis of notice of the notice of experiments submitted in UK Revocation suit HC06C02687 (Feb. 23, 2007).
van Vollenhoven et al., "Belimumab, a BLyS-Specific Inhibitor, Reduced Corticosteroid Use in Patients With Active SLE: Results From the Phase 3 BLISS-52 and -76 Studies," Poster presented at American College of Rheumatology 2010 Annual Meeting, Nov. 2010.
Petri et al., "Belimumab, a BLyS-Specific Inhibitor, Reduced Disease Activity, Flares, and Prednisone Use in Patients With Seropositive SLE: Combined Efficacy Results From the Phase 3 BLISS-52 and -76 Studies," Poster presented at American College of Rheumatology 2010 Annual Meeting, Nov. 2010.
Wallace et al., "Safety Profile of Belimumab, a BLyS-Specific Inhibitor, in Patients With Active Systemic Lupus Erythematosus (SLE): Pooled Data From Phase 2 and 3 Studies," Poster presented at American College of Rheumatology 2010 Annual Meeting, Nov. 2010.
Stohl et al., "Belimumab, a BLyS-Specific Inhibitor, Significantly Reduced Autoantiboides, Normalized Low Complement, and Reduced Selected B-Cell Populations in Patients With Seropositive Systemic Lupus Erythematosus (SLE): The Phase 3 BLISS Studies," Poster presented at American College of Rheumatology 2010 Annual Meeting, Nov. 2010.
Strand et al., "Belimumab, a BLyS-Specific Inhibitor, Improved Fatigue and SF-36 Physical and Mental Component Summary Scores in Patients With SLE: BLISS-52 and -76 Studies," Poster presented at American College of Rheumatology 2010 Annual Meeting, Nov. 2010.
Manzi et al., "Belimumab, a BLyS-Specific Inhibitor, Reduced Disease Activity Across Multiple Organ Domains: Combined Efficacy Results From the Phase 3 BLISS-52 and BLISS-76 Studies," Oral presentation at American College of Rheumatology 2010 Annual Meeting, Nov. 2010.
Requirement for Restriction/Election issued in U.S. Appl. No. 12/610,128, dated Nov. 29, 2010.
Requirement for Restriction/Election issued in U.S. Appl. No. 12/275,804, dated Dec. 2, 2010.
Non-Final Rejection issued in U.S. Appl. No. 11/054,539, dated Dec. 14, 2010.
Notice of Allowance issued in U.S. Appl. No. 12/552,915, dated Dec. 21, 2010.
Requirement for Restriction/Election issued in U.S. Appl. No. 12/870,394, dated Dec. 30, 2010.
Extended European Search Report, European Application No. 10185178.0 dated Dec. 21, 2010.
Extended European Search Report, European Application No. 10185182.2 dated Dec. 23, 2010.
Extended European Search Report, European Application No. 10185185.5 dated Dec. 23, 2010.
Edwards, *J. Mol. Biol.*, "The Remarkable Flexibility of the Human Antibody Repertoire; Isolation of Over One Thousand Different Antibodies to a Single Protein, BLyS," 334(1): 103-118 (2003).
Requirement for Restriction/Election issued in U.S. Appl. No. 12/870,548, dated Feb. 3, 2011.
Requirement for Restriction/Election issued in U.S. Appl. No. 12/295,572, dated Feb. 18, 2011.
Examiner Interview Summary issued in U.S. Appl. No. 09/589,288, dated Feb. 22, 2011.
Non-Final Rejection issued in U.S. Appl. No. 09/589,288, dated Mar. 2, 2011.
Final Rejection issued in U.S. Appl. No. 12/701,301, dated Apr. 5, 2011.
Notice of Allowance issued in U.S. Appl. No. 12/552,915, dated Apr. 8, 2011.
Non-Final Rejection issued in U.S. Appl. No. 12/275,804, dated Apr. 14, 2011.
Final Rejection issued in U.S. Appl. No. 12/135,025, dated Apr. 13, 2011.
Non-Final Rejection issued in U.S. Appl. No. 12/610,128, dated Apr. 14, 2011.
Requirement for Restriction/Election issued in U.S. Appl. No. 12/952,091, dated Apr. 28, 2011.
Non-Final Rejection issued in U.S. Appl. No. 12/870,394, dated May 4, 2011.
Final Rejection issued in U.S. Appl. No. 12/605,202, dated May 12, 2011.
Notice of Appeal submitted by Human Genome Sciences on Mar. 8, 2010 in UK Supreme Court in support of EP Patent 0939804.
Submission Pursuant to Rule 15 by Joseph Straus on Mar. 19, 2010 in UK Supreme Court case UKSC 2010/0047.
Skeleton Argument for Directions Hearing submitted by Human Genome Sciences on Sep. 30, 2010 in UK Supreme Court case UKSC 2010/0047.
Skeleton Argument for Directions Hearing submitted by Eli Lilly on Sep. 30, 2010 in UK Supreme Court case UKSC 2010/0047.
Appellant's case submitted by Human Genome Sciences on Jun. 13, 2011 in in UK Supreme Court case UKSC 2010/0047.
Vaughan, *Nat. Biotechnol.*, "Human Antibodies with Sub-nanomolar Affinities Isolated from a Large Non-immunized Phage Display Library," 14: 309-314 (1996).
Non-Final Rejection issued in U.S. Appl. No. 12/870,548, dated Jun. 24, 2011.
Non-Final Rejection issued in U.S. Appl. No. 12/295,572, dated Jun. 24, 2011.
Dorner et al., *Arthritis Res. Therapy*, "B cells in autoimmunity," 22: 247-258 (2009).
Jeker et al., *J. Clin. Immunol.*, "Small RNA Regulators of T Cell-Mediated Autoimmunity," 30: 347-357 (2010).
Uthaipibull et al., *J. Mol. Biol.*, "Inhibitory and Blocking Monoclonal Antibody Epitopes on Merozoite Surface Protein 1 of the Malaria Parasite *Plasmodium falciparum*," 307: 1381-1394 (2001).
HGS Press Release "Human Genome Sciences and GlaxoSmith Kline Announce FDA Approval of BENLYSTA® (Belimumab) for Treatment of Systemic Lupus Erythematosus" dated Mar. 9, 2011.
FDA News Release "FDA Approves Benlysta to Treat Lupus" dated Mar. 9, 2011.
Ryan et al., *Adv. Exp. Med. Biol.*, "Targeting of BAFF and APRIL for autoimmunity and oncology," 647: 52-63 (2009).
Elsawa et al., *Blood*, "B-lymphocyte stimulator (BLyS) stimulates immunoglobulin production and malignant B-cell growth in Waldenström macroglobulinemia," 107: 2882-2888 (2006).
Tecchio et al., *Brit. J. Haematol.*, "High serum levels of B-lymphocyte stimulator are associated with clinical-pathological features and outcome in classical Hodgkin lymphoma," 137: 553-559 (2007).
Chiu et al., *Blood*, "The TNF family members BAFF and APRIL play an important role in Hodgkin lymphoma," 106: Abstract 22 (2005).
Chiu et al., *Blood*, "Hodgkin lymphoma cells express TACI and BCMA receptors and generate survival and proliferation signals in response to BAFF and APRIL," 109: 729-739 (2007).
Oki et al., *Haematologica*, "Prognostic significance of serum B-lymphocyte stimulator level in Hodgkin's lymphoma," 92: 269-270 (2007).
Oki et al., *Blood*, "Serum BLyS level as a prognostic marker in patients with lymphoma," 106: Abstract 1926 (2005).
Briones et al., *Exp. Hematol.*, "BLyS and BLyS receptor expression in non-Hodgkin's lymphoma," 30: 135-141 (2002).
Notice of Allowance issued in U.S. Appl. No. 09/589,288, dated Jul. 25, 2011.
Advisory Action issued in U.S. Appl. No. 12/135,025, dated Jul. 29, 2011.
Notice of Allowance issued in U.S. Appl. No. 12/701,301, dated Aug. 5, 2011.
Alignment of BLyS and Eli Lilly's sequences submitted in UK Revocation suit HC06C02687 dated Nov. 29, 2007.
Technician's précis of notice of the notice of experiments submitted in UK Revocation suit HC06C02687.
Application Notice submitted by Human Genome Sciences in support of Human Genome Sciences in UK Revocation suit HC06C02687 dated Nov. 2, 2006.

(56) References Cited

OTHER PUBLICATIONS

International Preliminary Exam Report submitted by Human Genome Sciences in support of Human Genome Sciences in UK Revocation suit HC06CO2687 dated Dec. 20, 1998.
Office communication from European Patent Office submitted by Human Genome Sciences in support of Human Genome Sciences in UK Revocation suit HC06CO2687 dated May 3, 2002.
Human Genome Science's response to Office communication from European Patent Office submitted by Human Genome Sciences in support of Human Genome Sciences in UK Revocation suit HC06CO2687 dated May 30, 2002.
Office communication from European Patent Office submitted by Human Genome Sciences in support of Human Genome Sciences in UK Revocation suit HC06CO2687 dated Jan. 17, 2003.
Human Genome Sciences, Inc response to office communication from European Patent Office submitted by Human Genome Sciences in support of Human Genome Sciences in UK Revocation suit HC06CO2687 dated Jan. 17, 2003.
Office Communication European Patent Office submitted by Human Genome Sciences in support of Human Genome Sciences in UK Revocation suit HC06CO2687 dated Jun. 30, 2004.
Transcript of Examiner Interview dated Oct. 1, 2004 submitted by Human Genome Sciences in support of Human Genome Sciences in UK Revocation suit HC06CO2687.
Human Genome Response to Examiner Interview of Oct. 1, 2004 submitted by Human Genome Sciences in support of Human Genome Sciences in UK Revocation suit HC06CO2687 and dated Oct. 4, 2004.
Office Communication European Patent Office submitted by Human Genome Sciences in support of Human Genome Sciences in UK Revocation suit HC06CO2687 dated Oct. 13, 2004.
Human Genome Sciences, Inc response to office communication from European Patent Office submitted by Human Genome Sciences in support of Human Genome Sciences in UK Revocation suit HC06CO2687 dated Nov. 30, 2004.
Human Genome Sciences amended claims and specification submitted by Human Genome Sciences in support of Human Genome Sciences in UK Revocation suit HC06CO2687 dated Nov. 30, 2004.
Notice of Intent to Grant EP patent No. 0 939 845 submitted by Human Genome Sciences in support of Human Genome Sciences in UK Revocation suit HC06CO2687 dated Jan. 28, 2005.
Human Genome Sciences response to Notice of Intent to Grant submitted by Human Genome Sciences in support of Human Genome Sciences in UK Revocation suit HC06CO2687 dated Jun. 7, 2005.
Kwon et al., J. Biol. Chem., "Identification of a Novel Activation-inducible Protein of the Tumor Necrosis Factor Receptor Superfamily and Its Ligand," 274(10): 6056-61 (1999).
Laabi et al., The EMBO Journal, "A new gene, BCM, on chromosome 16 is fused to the interleukin 2 gene by a t(4;16)(q26;p13) translocation in a malignant T cell lymphoma," 11:3897-3904 (1992).
Laabi et al., Nucleic Acids Research, "The BCMA gene, preferentially expressed during B lymphoid maturation, is bidirectionally transcribed," 22:1147-1154 (1994).
Lam, Nature, "A new type of synthetic peptide library for identifying ligand-binding activity," 354: 82-84 (1991).
Looney, Rheumatology, "B cells as a therapeutic target in autoimmune diseases other than rheumatoid arthritis," 44 (Suppl. 2): ii13-ii17 (2005).
Lyu, Mol. Cancer Ther. "The rGel/BLyS fusion toxin specifically targets malignant B cells expressing the BlyS receptors BAFF-R, TACI, and BCMA," 6(2):460-70 (2007).
MacKay, Curr. Dir. Autoimmun., "The BAFF/APRIL system: an important player in systemic theumatic diseases," 8:243-65 (2005).
MacKay, Semin. Immunol. "The role of the BAFF/APRIL system on T cell function," (5):284-9 (2006).
Madry et al., International Immunology, "The characterization of murine BCMA gene defines it as a new member of the tumor necrosis factor receptor superfamily," 10:1693-1702 (1998).

Malvar et al., Genetics, "The CCR4 Protein from Saccharomyces cervisiae Contains a Leucine-Rich Repeat Region Which Is Required for Its Control of ADH2 Gene Expression," 132:951-962 (1992).
Mariette et al., Annual Rheumatology Discussion, "The Level of BLyS (BAFF) Correlates With the Titre of Autoantibodies in Human Sjogren's Syndrome," 62:168-171 (2003).
Mauri et al., Immunity, "LIGHT, a New member of the TNF Superfamily, and Lymphotoxin a Are Ligands for Herpesvirus Entry Mediator," 8(1): 21-30 (1998).
Melchers, Ann. Rheum. Dis., "Actions of BAFF in B cell maturation and its effects on the development of autoimmune disease," 62 Supp. 2:ii25-27 (2003).
Moore, Clin. Chem., "Genetically engineered antibodies," 35(9):1849-53 (1989).
Moreaux, Blood, "BAFF and APRIL protect myeloma cells from apoptosis induced by interleukin 6 deprivation and dexamethasone," 103(8):3148-57 (2004).
Morens et al., J. Gen. Virol., 68:91-98 (1987).
Morpurgo et al., Appl. Biochem. Biotechnol., "Covalent Modification of Mushroom Tyrosinase with Different Amphiphic Polymers for Pharmaceutical and Biocatalysis Applications," 56:59-72 (1996).
Nakamura et al., Immunol. Lett., "Mechanisms of cellular cytotoxicity mediated by a recombinant antibody-IL2 fusion protein against human melanoma cells," 39: 91-99 (1994).
Nedwin et al., J. Immunol., "Effect of Interleukin 2. Interferon-y, and Mitogens on the Production of Tumor Necrosis Factors α and β," 135(4): 2492-7 (1985).
Ng et al., Journal of Immunology, "B Cell-Activating Factor Belonging to the TNF Family (BAFF)-R is the Principal BAFF Receptor Facilitating BAFF Costimulation of Circulating T and B Cells," 173:807-817 (2004).
Nimmanapalli, Blood, "The growth factor fusion construct containing B-lymphocyte stimulator (BLyS) and the toxin rGel induces apoptosis specifically in BAFF-R-positive CLL cells," 109(6) 2557-64 (2007).
Novak, Blood, "Aberrant expression of B-lymphocyte stimulator by B chronic lymphocytic leukemia cells: a mechanism for survival," 100:2973-9 (2002).
Novak et al., Blood, 103:689-694 (2004).
Novak et al., Blood, "Expression of BlyS and its receptors in B-cell non-Hodgkin lymphoma: correlation with disease activity and patient outcome," 104(8):2247-53 (2004).
Otten, Proc. Natl. Acad. Sci. U.S.A., "Nerve growth factor induces growth and differentiation of human B lymphocytes," 86:10059-63 (1989).
Panayi, G.S., British Journal of Rheumatology, "The Pathogenesis of Rheumatoid Arthritis: From Molecules to the Whole Patient," 32:533-536 (1993).
Patel et al., The Journal of Biological Chemistry, "Engineering an APRIL-specific B cell maturation antigen," 279:16727-16735 (2003).
Peitisch et al., International Immunology, 5(2):233-238 (1993).
Press, O.W. "Malignant Lymphomas, Including Hodgkin's Disease: Diagnosis, Management, and Special Problems," Chapter 9 Kluwer Academic Publishers. ed. B. Dana (1993).
Reed et al., Seminars in Oncology, "Modulating Apoptosis Pathways in Low Grade B-Cell Malignancies Using Biological Response Modifiers," 29:10-24. (2002).
Reth et al., Nature, 290:257-259 (1981).
Rosen et al., J. Clin. Oncol. 5:562 (1987).
Roth, Cell Death Differ., "APRIL, a new member of the tumor necrosis family, modulates death ligand-induced apoptosis," 8:403-410 (2001).
Saxon et al., Immunology, "Long-term administration of 13-cis retinoic acid in common variable immunodeficiency; circulating interleukin-6 levels, B-cell surface molecule display, and in vitro and in vivo B-cell antibody production," 80(3):477-87 (1993).
Scapini et al., J. Exp Med. "G-CSF-stimulated Neutrophils Are a Prominent Source of Functional BLyS," 197(3): 297-302 (2003).
Schaller et al., Microbiology, "Characterization of apxIVA, a new RTX determinant of Actinobacillus pleuropneumoniae," 145 (pt 8):2105-16 (1999).

(56) References Cited

OTHER PUBLICATIONS

Scott et al., Science, "Searching for Peptide Ligands with an Epitope Library," 249: 386-390(1990).
Scott et al., Current Opinion in Immunology, 9:717-722 (1997).
Schneider, Current Opinion in Immunology, 17:282-289 (2005).
Schwartz et al in "Fundamental Immunology", Paul ed Raven Press, NY. NY., pp. 837 (1989).
Sevach (Fundamental Immunology, Paul ed, Lippincott-Raven Philadelphia, PA, chapter 34, pp. 1089-1125 (1999).
Shanebeck, Eur. J. Immunol., "Regulation of murine B-cell growth and differentiation by CD30 ligand," 25(8):2147-53 (1995).
Shoop et al., Proceedings of the Twenty-Seventh Annual Hawaii International Conference on System Sciences, "Automating and Streamlining Inference of Function of Plant ESTs within a Data Analysis System" Extended Abstract (1994).
Smith et al., Principles of Biochemestry: General Aspects, McGraw-Hill Book Company: New York, pp. 194-195 (1983).
Smith et al., Cell, 73:1349-1360 (1993).
Stites and Ten, eds., Basic and Clinical Immunology, Chap. 24, pp. 322-334 (1991).
Suda et al., Cell, "Molecular Cloning and Expression of the Fas Ligand, a Novel Member of the Tumor Necrosis Factor Family," 75(6): 1 169-78 (1993).
Sutherland et al., Pharmacology and Therapeutics, "Targeting BAFF: Immunomodulation for autoimmune diseases and lymphomas," 112:774-786 (2006).
Swindell et al. Internet for the Molecular Biologist, Horizon Scientific Press: Portland, pp. 55-149 (1996).
Tai et al., Cancer Res, "Role of B-Cell-Activating Factor in the Adhesion and Growth of Human Multiple Myeloma Cells in the Bone Marrow Microenvironment," 66(13): 6675-6682 (2006).
Tsokos, G.C., Current Opinion in Rheumatology, "Lymphocytes, cytokines, inflammation, and immune trafficking," 7:376-383 (1995).
Tuma, J. Natl. Cancer Inst., "Phase I Antibody Risks, Trial Safety Examined," 98(14):956-958 (2006).
Van et al., Nature Immunology, "Identification of a receptor for BlyS demonstrates a crucial role in humoral immunity," 1(1):37-41, (2000).
Vandenberghe et al., Biochemistry, "The Primary Structures of the Low-Redox Potential Diheme Cytochromes c from the Phtotrophich Bacteria Rhodobacter sphaeroides and Rhodobacter adriaticus Reveal a New Structural Family of c-Type Cytochromes," vol. 37: pp. 13075-13081 (1998).
Von Bulow and Bram, Science, "NF-AT activation induced by a CAML-interacting member of the tumor necrosis factor receptor superfamily," 278: 138-141 (1997).
Vorbjev et al., Nucleosides & Nucleotides, "Oligonucleotide Conjugated to Linear and Branched High Molecular Weight Polyethylene Glycol as Substrates," 18:2745-2750(1999).
Waldmann, T.A., Nature Medicine, "Immunotherapy: Past, Present and Future," 9:269-277 (2003).
Waldmann et al., Ann. Intern. Med., 116:148 (1992).
Waldschmidt et al., Science, "Long live the Mature B Cell—a BAFFling Mystery Resolved," 293:2012-2013 (2001).
Wallach, "TNF Ligands and TNF/NGF Receptor Families" In Cytokine Reference vol. 1: Ligands, eds. Oppenheim and Feldman, Academic Press, pp. 377-411 (2001).
Ware, Cytokine & Growth Factor Reviews, "The TNF Superfamily," 14:181-184 (2003).
Weinblatt et al., Arthritis and Rheumatism, "Methotrexate in rheumatoid arthritis: A five-year prospective multicenter study," 37:1492-1498 (1994).
Wiley et al., Immunity, "Identification and Characterization of a New Member of the TNF Family that Induces Apoptosis," 3(6): 673-82 (1995).
Williams-Blangero et al., PNAS, "Genes on chromosomes 1 and 13 have significant effects on Ascaris infection," 99(8): 5533-5538 (2002).
Winter et al., Nature, "Man-made antibodies," 349:293-299 (1991).
Wise et al., The Journal of Rheumatology, "Methotrexate in nonrenal lupus and undifferentiated connective tissue disease—a review of 36 patients," 23:1005-1010 (1996).
Ye et al., Eur. J. Immunol., "BAFF binding to T cell-expressed BAFF-R costimulates T cell proliferation and alloresponses," 34(10):2750-9 (2004).
Zganiacz et al., J. Clin. Invest. "TNF-$\alpha$ is a critical negative regulator of type 1 immune activation during intracellular bacterial infection," 113(3):401-413 (2004).
Zhou et al., Blood, "Therapeutic Potential of Antagonizing BLyS for Chronic Lymphocytic Leukemia," 98(11):808A (2001).
Arthritis Rheum., "The American College of Rheumatology Response Criteria for Systemic Lupus Erythematosus Clinical Trials," 50(11):3418-3426 (2004).
"Guideline on Production and Quality Control of Monoclonal Antibodies and Related Substances", issued by European Medicines Agency on Apr. 5, 2007.
CAT News Release "Cambridge Antibody Technology and Human Genome Sciences Form Alliance in Therapeutic Antibodies" dated Aug. 10, 1999.
CAT News Release "CAT and Human Genome Sciences ("HGSI") Create Major Alliance Dedicated to Developing Human Antibody Therapeutics Against Genomics Targets" dated Mar. 1, 2000.
CAT News Release "Cambridge Antibody Technology Group plc ("CAT") Open Offer & International Offering to Raise £100 Million in a New Share Issue" dated Mar. 7, 2000.
CAT News Release "Cambridge Antibody. Technology: Clinical Trials Update" dated Jan. 12, 2004.
CAT News Release "Cambridge Antibody Technology Reports Recent Progress in Licensed Product Candidates" dated Oct. 5, 2005.
HGS Press Release "Cambridge Antibody Technology and Human Genome Sciences Form Alliance in Therapeutic Antibodies" dated Aug. 10, 1999.
HGS Press Release "Human Genome Sciences and Abgenix Enter a Broad Collaboration to Create Fully Human Antibody Therapeutics" dated Dec. 1, 1999.
HGS Press Release "Human Genome Sciences to Initiate Human Clinical Trials of BLyS" dated Jun. 23, 2000.
HGS Press Release "Human Genome Sciences and Medarex Announce Collaboration" dated Jul. 25, 2001.
HGS Press Release "Human Genome Sciences Announces Trial for Treatment of Immunoglobin-A Deficiency" dated Sep. 19, 2001.
International Search Report issued in PCT Application No. PCT/US06/38756, dated Jul. 14, 2008.
International Search Report issued in PCT Application No. PCT/US07/08021, dated Aug. 4, 2008.
Human Genome Sciences Press Release, dated Nov. 1, 2001.
Declaration of Interference 105,485, Paper 1 filed in the United States Patent Office on Aug. 15, 2006.
Order Bd.R 104(c) in Patent Interference 105,485 dated Apr. 19, 2007.
Order Bd.R 104(c) in Patent Interference 105,485 dated Apr. 23, 2007.
Order—Priority times Bd.R. 104(c) in Patent Interference 105,485 dated Apr. 19, 2007.
Decision on Preliminary Motions in Patent Interference 105,485. Filed in the United States Patent Office on Aug. 31, 2007.
Yu Priority Statement in Patent Interference 105,485. Filed in the United States Patent Office on Dec. 1, 2006.
Browning Priority Statement in Patent Interference 105,485. Filed in the United States Patent Office on Dec. 1, 2006.
Browning Amended Priority Statement in Patent Interference 105,485. Filed in the United States Patent Office on Dec. 12, 2006.
Claims involved in Patent Interference 105,485 submitted by Human Genome Sciences. Filed in the United States Patent Office on Aug. 15, 2006.
Browning Notice of Non-filing 135(b) submitted by Biogen, Inc in Patent Interference 105,485. Filed in the United States Patent Office on Nov. 16, 2006.
Browning Observation 1 filed by Biogen, Inc. in Patent Interference 105,485. Filed in the United States Patent Office on Feb. 12, 2007.

(56) References Cited

OTHER PUBLICATIONS

Yu reply and Browning Observation on reply in Patent Interference 105,485. Filed in the United States Patent Office on Apr. 16, 2007 and Apr. 30, 2007.
Re-declaration of Interference in Patent Interference 105,485. Filed in the United States Patent Office on Aug. 31, 2007.
Yu Exhibit List submitted by Human Genome Sciences, Inc in Patent Interference 105,485 as of Nov. 28, 2007.
Declaration of Amy Orr dated Nov. 27, 2007 in support of Yu et al. in Patent Interference 105,485.
Declaration of Biegie Lee dated Nov. 27, 2007 in support of Yu et al. in Patent Interference 105,485.
Declaration of David LaFleur dated Nov. 27, 2007 in support of Yu et al. in Patent Interference 105,485.
Declaration of Ding Liu dated Nov. 27, 2007 in support of Yu et al. in Patent Interference 105,485.
Declaration of Ellie Bouffard dated Nov. 27, 2007 in support of Yu et al. in Patent Interference 105,485.
Marked-up Declaration of Dr. Fritz Melchers dated Jan. 16, 2007 in support of Browning et al. in Patent Interference 105,485.
Declaration of Dr. Guo-Liang Yu dated Nov. 27, 2007 in support of Yu et al. in Patent Interference 105,485.
Declaration of Jeffrey Carrell dated Nov. 27, 2007 in support of Yu et al. in Patent Interference 105,485.
Declaration of Krystyna Pieri dated Nov. 27, 2007 in support of Yu et al. in Patent Interference 105,485.
Declaration of Laurie Brewer dated Nov. 28, 2007 in support of Yu et al. in Patent Interference 105,485.
Marked-up Declaration of Dr. Mark S. Schlissel dated Dec. 1, 2006 in support of Browning et al. in Patent Interference 105,485.
Declaration of Meghan Birkholz dated Nov. 27, 2007 in support of Yu et al. in Patent Interference 105,485.
Declaration of Michael Fannon dated Nov. 27, 2007 in support of Yu et al. in Patent Interference 105,485.
Declaration of Dr. Ornella Belvedere dated Nov. 27, 2007 in support of Yu et al. in Patent Interference 105,485.
Declaration of Dr. Reinhard Ebner dated Nov. 21, 2007 in support of Yu et al. in Patent Interference 105,485.
Declaration of Scott Conklin dated Nov. 26, 2007 in support of Yu et al. in Patent Interference 105,485.
Declaration of William Derrick dated Nov. 28, 2007 in support of Yu et al. in Patent Interference 105,485.
Second Declaration of Dr. Randolph J. Noelle dated Nov. 28, 2007 in support of Yu et al. in Patent Interference 105,485.
Declaration of Dr. David Hilbert dated Nov. 27, 2007 in support of Yu et al. in Patent Interference 105,485.
Declaration of Dr. Paul Moore dated Nov. 26, 2007 in support of Yu et al. in Patent Interference 105,485.
Transcript of Deposition of Dr. Paul Moore in Patent Interference 105,485 dated Jan. 4, 2008.
Transcript of Deposition of Dr. David Hilbert in Patent Interference 105,485 dated Jan. 5, 2008.
Transcript of Deposition of Jeffrey Carrell in Patent Interference 105,485 dated Feb. 12, 2008.
Transcript of Deposition of Krystyna Pieri in Patent Interference 105,485 dated Feb. 12, 2008.
Transcript of Deposition of Dr. Reinhard Ebner in Patent Interference 105,485 dated Feb. 15, 2008.
Transcript of Deposition of Guo-Liang Yu in Patent Interference 105,485 dated Jan. 4, 2008.
Transcript of Deposition of Amy Orr in Patent Interference 105,485 dated Feb. 22, 2008.
Transcript of Deposition of Dr. Randolph Noelle in Patent Interference 105,485 dated Feb. 26, 2008.
Transcript of Deposition of Eleanor Bouffard in Patent Interference 105,485 dated Feb. 28, 2008.

* cited by examiner

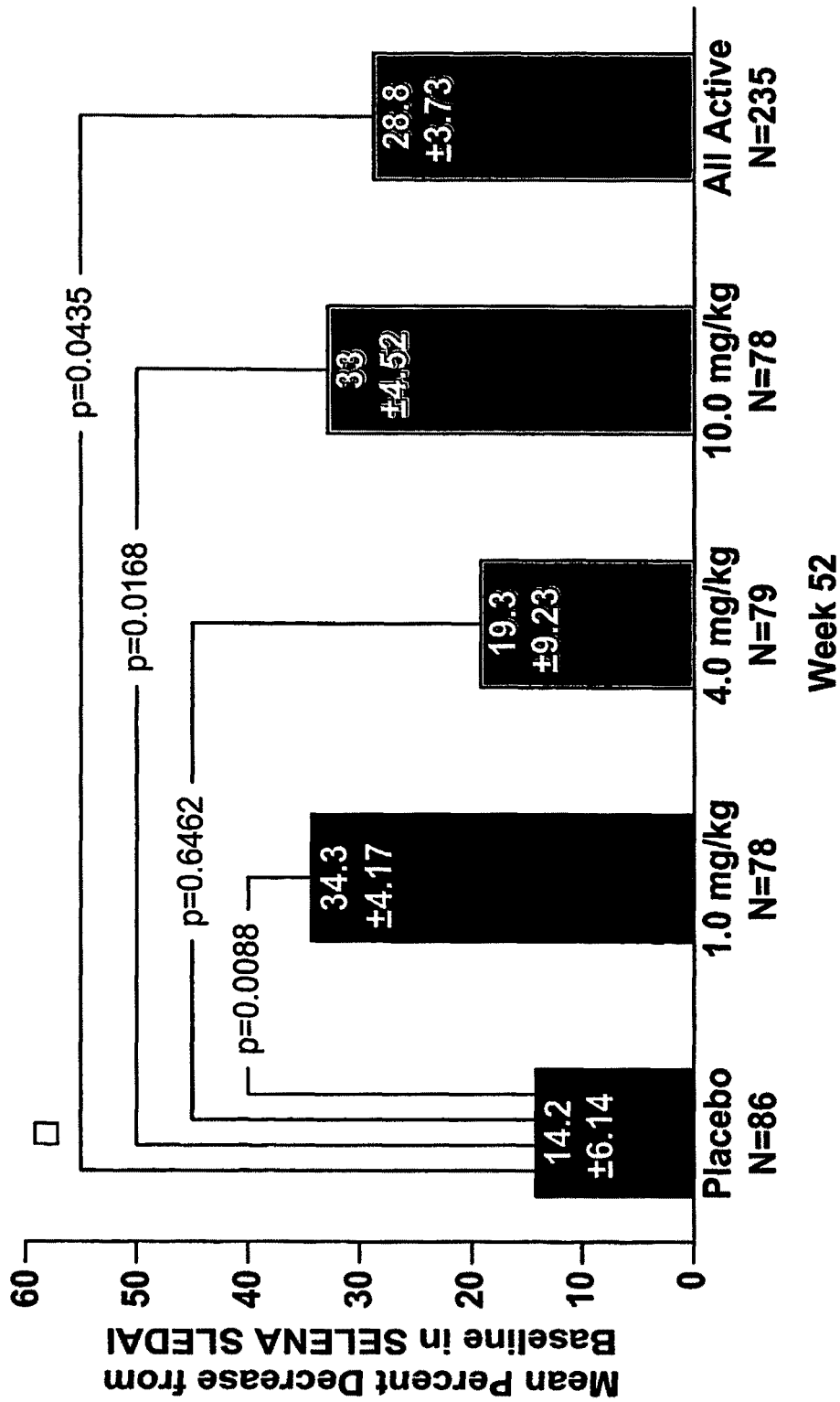

SEQUENCE LISTING

```
<160> NUMBER OF SEQ ID NOS: 28

<210> SEQ ID NO 1
<211> LENGTH: 1100
<212> TYPE: DNA
<213> ORGANISM: Homo sapiens
<220> FEATURE:
<221> NAME/KEY: CDS
<222> LOCATION: (147)..(1001)

<400> SEQUENCE: 1
aaattcagga taactctcct gagggggtgag ccaagccctg ccatgtagtg cacgcaggac        60
atcaacaaac acagataaca ggaaatgatc cattccctgt ggtcacttat tctaaaggcc       120
ccaaccttca aagttcaagt agtgat atg gat gac tcc aca gaa agg gag cag        173
                              Met Asp Asp Ser Thr Glu Arg Glu Gln
                                1               5 tca cgc ctt act tct tgc ctt aag aaa aga gaa gaa atg aaa ctg aag        221
Ser Arg Leu Thr Ser Cys Leu Lys Lys Arg Glu Glu Met Lys Leu Lys
 10              15                  20                  25 gag tgt gtt tcc atc ctc cca cgg aag gaa agc ccc tct gtc cga tcc        269
Glu Cys Val Ser Ile Leu Pro Arg Lys Glu Ser Pro Ser Val Arg Ser
             30                  35                  40 tcc aaa gac gga aag ctg ctg gct gca acc ttg ctg ctg gca ctg ctg        317
Ser Lys Asp Gly Lys Leu Leu Ala Ala Thr Leu Leu Leu Ala Leu Leu
         45                  50                  55 tct tgc tgc ctc acg gtg gtg tct ttc tac cag gtg gcc gcc ctg caa        365
Ser Cys Cys Leu Thr Val Val Ser Phe Tyr Gln Val Ala Ala Leu Gln
     60                  65                  70 ggg gac ctg gcc agc ctc cgg gca gag ctg cag ggc cac cac gcg gag        413
Gly Asp Leu Ala Ser Leu Arg Ala Glu Leu Gln Gly His His Ala Glu
 75                  80                  85 aag ctg cca gca gga gca gga gcc ccc aag gcc ggc ctg gag gaa gct        461
Lys Leu Pro Ala Gly Ala Gly Ala Pro Lys Ala Gly Leu Glu Glu Ala
 90                  95                 100                 105 cca gct gtc acc gcg gga ctg aaa atc ttt gaa cca cca gct cca gga        509
Pro Ala Val Thr Ala Gly Leu Lys Ile Phe Glu Pro Pro Ala Pro Gly
            110                 115                 120 gaa ggc aac tcc agt cag aac agc aga aat aag cgt gcc gtt cag ggt        557
Glu Gly Asn Ser Ser Gln Asn Ser Arg Asn Lys Arg Ala Val Gln Gly
        125                 130                 135 cca gaa gaa aca gtc act caa gac tgc ttg caa ctg att gca gac agt        605
Pro Glu Glu Thr Val Thr Gln Asp Cys Leu Gln Leu Ile Ala Asp Ser
    140                 145                 150 gaa aca cca act ata caa aaa gga tct tac aca ttt gtt cca tgg ctt        653
Glu Thr Pro Thr Ile Gln Lys Gly Ser Tyr Thr Phe Val Pro Trp Leu
155                 160                 165 ctc agc ttt aaa agg gga agt gcc cta gaa gaa aaa gag aat aaa ata        701
Leu Ser Phe Lys Arg Gly Ser Ala Leu Glu Glu Lys Glu Asn Lys Ile
170                 175                 180                 185
```

```
ttg gtc aaa gaa act ggt tac ttt ttt ata tat ggt cag gtt tta tat      749
Leu Val Lys Glu Thr Gly Tyr Phe Phe Ile Tyr Gly Gln Val Leu Tyr
            190                 195                 200 act gat aag acc tac gcc atg gga cat cta att cag agg aag aag gtc      797
Thr Asp Lys Thr Tyr Ala Met Gly His Leu Ile Gln Arg Lys Lys Val
            205                 210                 215 cat gtc ttt ggg gat gaa ttg agt ctg gtg act ttg ttt cga tgt att      845
His Val Phe Gly Asp Glu Leu Ser Leu Val Thr Leu Phe Arg Cys Ile
            220                 225                 230 caa aat atg cct gaa aca cta ccc aat aat tcc tgc tat tca gct ggc      893
Gln Asn Met Pro Glu Thr Leu Pro Asn Asn Ser Cys Tyr Ser Ala Gly
            235                 240                 245 att gca aaa ctg gaa gaa gga gat gaa ctc caa ctt gca ata cca aga      941
Ile Ala Lys Leu Glu Glu Gly Asp Glu Leu Gln Leu Ala Ile Pro Arg
250             255                 260                 265 gaa aat gca caa ata tca ctg gat gga gat gtc aca ttt ttt ggt gca      989
Glu Asn Ala Gln Ile Ser Leu Asp Gly Asp Val Thr Phe Phe Gly Ala
                270                 275                 280 ttg aaa ctg ctg tgacctactt acaccatgtc tgtagctatt ttcctccctt         1041
Leu Lys Leu Leu
            285 tctctgtacc tctaagaaga aagaatctaa ctgaaaatac caaaaaaaaa aaaaaaaaa    1100
```

<210> SEQ ID NO 2
<211> LENGTH: 285
<212> TYPE: PRT
<213> ORGANISM: Homo sapiens

<400> SEQUENCE: 2

```
Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220
```

```
Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
            245                 250                 255

Asp Glu Leu Gln Leu Ala Ile Pro Arg Glu Asn Ala Gln Ile Ser Leu
        260                 265                 270

Asp Gly Asp Val Thr Phe Phe Gly Ala Leu Lys Leu Leu
    275                 280                 285

<210> SEQ ID NO 3
<211> LENGTH: 1717
<212> TYPE: DNA
<213> ORGANISM: Homo sapiens
<220> FEATURE:
<221> NAME/KEY: CDS
<222> LOCATION: (282)..(1034)

<400> SEQUENCE: 3
acctctgtcc ttagagggga ctggaaccta attctcctga gcctgaggga gggtggaggg      60
tctcaagaca acgctgtccc cacgacggag tgccaggagc actaacagta cccttagatt     120
gctttcctcc tccctccttt tttatttca agttcctttt tatttctcct tgcgtaacaa      180
ccttcttccc ttctgcacca ctgcccgtac ccttacccgc gccgccacct ccttgctaca     240
ccactcttga aaccacagct gttggcaggg tcccccagct c atg cca gcc tca tct     296
                                              Met Pro Ala Ser Ser
                                                1               5 cct ttc ttg cta gcc ccc aaa ggg cct cca ggc aac atg ggg ggc cca       344
Pro Phe Leu Leu Ala Pro Lys Gly Pro Pro Gly Asn Met Gly Gly Pro
                10                  15                  20 gtc aga gag ccg gca ctc tca gtt gcc ctc tgg ttg agt tgg ggg gca       392
Val Arg Glu Pro Ala Leu Ser Val Ala Leu Trp Leu Ser Trp Gly Ala
        25                  30                  35 gct ctg ggg gcc gtg gct tgt gcc atg gct ctg ctg acc caa caa aca       440
Ala Leu Gly Ala Val Ala Cys Ala Met Ala Leu Leu Thr Gln Gln Thr
    40                  45                  50 gag ctg cag agc ctc agg aga gag gtg agc cgg ctg cag agg aca gga       488
Glu Leu Gln Ser Leu Arg Arg Glu Val Ser Arg Leu Gln Arg Thr Gly
55                  60                  65 ggc ccc tcc cag aat ggg gaa ggg tat ccc tgg cag agt ctc ccg gag       536
Gly Pro Ser Gln Asn Gly Glu Gly Tyr Pro Trp Gln Ser Leu Pro Glu
70                  75                  80                  85 cag agt tcc gat gcc ctg gaa gcc tgg gag aat ggg gag aga tcc cgg       584
Gln Ser Ser Asp Ala Leu Glu Ala Trp Glu Asn Gly Glu Arg Ser Arg
                90                  95                 100 aaa agg aga gca gtg ctc acc caa aaa cag aag aag cag cac tct gtc       632
Lys Arg Arg Ala Val Leu Thr Gln Lys Gln Lys Lys Gln His Ser Val
            105                 110                 115 ctg cac ctg gtt ccc att aac gcc acc tcc aag gat gac tcc gat gtg       680
Leu His Leu Val Pro Ile Asn Ala Thr Ser Lys Asp Asp Ser Asp Val
        120                 125                 130 aca gag gtg atg tgg caa cca gct ctt agg cgt ggg aga ggc cta cag       728
Thr Glu Val Met Trp Gln Pro Ala Leu Arg Arg Gly Arg Gly Leu Gln
    135                 140                 145 gcc caa gga tat ggt gtc cga atc cag gat gct gga gtt tat ctg ctg       776
Ala Gln Gly Tyr Gly Val Arg Ile Gln Asp Ala Gly Val Tyr Leu Leu
150                 155                 160                 165 tat agc cag gtc ctg ttt caa gac gtg act ttc acc atg ggt cag gtg       824
Tyr Ser Gln Val Leu Phe Gln Asp Val Thr Phe Thr Met Gly Gln Val
                170                 175                 180
```

-continued

```
gtg tct cga gaa ggc caa gga agg cag gag act cta ttc cga tgt ata      872
Val Ser Arg Glu Gly Gln Gly Arg Gln Glu Thr Leu Phe Arg Cys Ile
            185                 190                 195 aga agt atg ccc tcc cac ccg gac cgg gcc tac aac agc tgc tat agc      920
Arg Ser Met Pro Ser His Pro Asp Arg Ala Tyr Asn Ser Cys Tyr Ser
            200                 205                 210 gca ggt gtc ttc cat tta cac caa ggg gat att ctg agt gtc ata att      968
Ala Gly Val Phe His Leu His Gln Gly Asp Ile Leu Ser Val Ile Ile
        215                 220                 225 ccc cgg gca agg gcg aaa ctt aac ctc tct cca cat gga acc ttc ctg     1016
Pro Arg Ala Arg Ala Lys Leu Asn Leu Ser Pro His Gly Thr Phe Leu
230                 235                 240                 245 ggg ttt gtg aaa ctg tga ttgtgttata aaaagtggct cccagcttgg            1064
Gly Phe Val Lys Leu
                250 aagaccaggg tgggtacata ctggagacag ccaagagctg agtatataaa ggagagggaa   1124 tgtgcaggaa cagaggcgtc ttcctgggtt tggctcccg ttcctcactt ttcccttttc    1184 attcccaccc cctagacttt gattttacgg atatcttgct tctgttcccc atggagctcc   1244 gaattcttgc gtgtgtgtag atgagggcg ggggacgggc gccaggcatt gtccagacct    1304 ggtcggggcc cactggaagc atccagaaca gcaccaccat ctagcggccg ctctagagga   1364 tccctcgagg ggcccaagct tacgcgtgca tgcgacgtca tagctctctc cctatagtga   1424 gtcgtattat aagctagctt gggatctttg tgaaggaacc ttacttctgt ggtgtgacat   1484 aattggacaa actacctaca gagatttaaa gctctaaggt aaatataaaa tttttaagtg   1544 tataatgtgt taaactagct gcatatgctt gctgcttgag agtttggctt actgagtatg   1604 attatgaaaa tattatacac aggagctagt gatctatgtt ggttttagat caagccaagg   1664 tcattcaggc ctcagctcaa gctgtcatga tcatatcagc atacaattgt gag          1717
```

<210> SEQ ID NO 4
<211> LENGTH: 250
<212> TYPE: PRT
<213> ORGANISM: Homo sapiens

<400> SEQUENCE: 4

```
Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Arg Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140
```

```
Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 5
<211> LENGTH: 882
<212> TYPE: DNA
<213> ORGANISM: Homo sapiens
<220> FEATURE:
<221> NAME/KEY: CDS
<222> LOCATION: (1)..(882)

<400> SEQUENCE: 5
```

| | | | | | | | | | | | | | | | | |
|---|---|---|---|---|---|---|---|---|---|---|---|---|---|---|---|---|
| atg | agt | ggc | ctg | ggc | cgg | agc | agg | cga | ggt | ggc | cgg | agc | cgt | gtg | gac | 48 |
| Met | Ser | Gly | Leu | Gly | Arg | Ser | Arg | Arg | Gly | Gly | Arg | Ser | Arg | Val | Asp | |
| 1 | | | | 5 | | | | | 10 | | | | | 15 | | |
| cag | gag | gag | cgc | ttt | cca | cag | ggc | ctg | tgg | acg | ggg | gtg | gct | atg | aga | 96 |
| Gln | Glu | Glu | Arg | Phe | Pro | Gln | Gly | Leu | Trp | Thr | Gly | Val | Ala | Met | Arg | |
| | | | 20 | | | | | 25 | | | | | 30 | | | |
| tcc | tgc | ccc | gaa | gag | cag | tac | tgg | gat | cct | ctg | ctg | ggt | acc | tgc | atg | 144 |
| Ser | Cys | Pro | Glu | Glu | Gln | Tyr | Trp | Asp | Pro | Leu | Leu | Gly | Thr | Cys | Met | |
| | | 35 | | | | | 40 | | | | | 45 | | | | |
| tcc | tgc | aaa | acc | att | tgc | aac | cat | cag | agc | cag | cgc | acc | tgt | gca | gcc | 192 |
| Ser | Cys | Lys | Thr | Ile | Cys | Asn | His | Gln | Ser | Gln | Arg | Thr | Cys | Ala | Ala | |
| | 50 | | | | | 55 | | | | | 60 | | | | | |
| ttc | tgc | agg | tca | ctc | agc | tgc | cgc | aag | gag | caa | ggc | aag | ttc | tat | gac | 240 |
| Phe | Cys | Arg | Ser | Leu | Ser | Cys | Arg | Lys | Glu | Gln | Gly | Lys | Phe | Tyr | Asp | |
| 65 | | | | | 70 | | | | | 75 | | | | | 80 | |
| cat | ctc | ctg | agg | gac | tgc | atc | agc | tgt | gcc | tcc | atc | tgt | gga | cag | cac | 288 |
| His | Leu | Leu | Arg | Asp | Cys | Ile | Ser | Cys | Ala | Ser | Ile | Cys | Gly | Gln | His | |
| | | | 85 | | | | | 90 | | | | | 95 | | | |
| cct | aag | caa | tgt | gca | tac | ttc | tgt | gag | aac | aag | ctc | agg | agc | cca | gtg | 336 |
| Pro | Lys | Gln | Cys | Ala | Tyr | Phe | Cys | Glu | Asn | Lys | Leu | Arg | Ser | Pro | Val | |
| | | | 100 | | | | | 105 | | | | | 110 | | | |
| aac | ctt | cca | cca | gag | ctc | agg | aga | cag | cgg | agt | gga | gaa | gtt | gaa | aac | 384 |
| Asn | Leu | Pro | Pro | Glu | Leu | Arg | Arg | Gln | Arg | Ser | Gly | Glu | Val | Glu | Asn | |
| | | 115 | | | | | 120 | | | | | 125 | | | | |
| aat | tca | gac | aac | tcg | gga | agg | tac | caa | gga | ttg | gag | cac | aga | ggc | tca | 432 |
| Asn | Ser | Asp | Asn | Ser | Gly | Arg | Tyr | Gln | Gly | Leu | Glu | His | Arg | Gly | Ser | |
| | 130 | | | | | 135 | | | | | 140 | | | | | |
| gaa | gca | agt | cca | gct | ctc | ccg | ggg | ctg | aag | ctg | agt | gca | gat | cag | gtg | 480 |
| Glu | Ala | Ser | Pro | Ala | Leu | Pro | Gly | Leu | Lys | Leu | Ser | Ala | Asp | Gln | Val | |
| 145 | | | | | 150 | | | | | 155 | | | | | 160 | |
| gcc | ctg | gtc | tac | agc | acg | ctg | ggg | ctc | tgc | ctg | tgt | gcc | gtc | ctc | tgc | 528 |
| Ala | Leu | Val | Tyr | Ser | Thr | Leu | Gly | Leu | Cys | Leu | Cys | Ala | Val | Leu | Cys | |
| | | | 165 | | | | | 170 | | | | | 175 | | | |
| tgc | ttc | ctg | gtg | gcg | gtg | gcc | tgc | ttc | ctc | aag | aag | agg | ggg | gat | ccc | 576 |
| Cys | Phe | Leu | Val | Ala | Val | Ala | Cys | Phe | Leu | Lys | Lys | Arg | Gly | Asp | Pro | |
| | | | 180 | | | | | 185 | | | | | 190 | | | |

```
tgc tcc tgc cag ccc cgc tca agg ccc cgt caa agt ccg gcc aag tct      624
Cys Ser Cys Gln Pro Arg Ser Arg Pro Arg Gln Ser Pro Ala Lys Ser
        195                 200                 205 tcc cag gat cac gcg atg gaa gcc ggc agc cct gtg agc aca tcc ccc      672
Ser Gln Asp His Ala Met Glu Ala Gly Ser Pro Val Ser Thr Ser Pro
210                 215                 220 gag cca gtg gag acc tgc agc ttc tgc ttc cct gag tgc agg gcg ccc      720
Glu Pro Val Glu Thr Cys Ser Phe Cys Phe Pro Glu Cys Arg Ala Pro
225                 230                 235                 240 acg cag gag agc gca gtc acg cct ggg acc ccc gac ccc act tgt gct      768
Thr Gln Glu Ser Ala Val Thr Pro Gly Thr Pro Asp Pro Thr Cys Ala
                245                 250                 255 gga agg tgg ggg tgc cac acc agg acc aca gtc ctg cag cct tgc cca      816
Gly Arg Trp Gly Cys His Thr Arg Thr Thr Val Leu Gln Pro Cys Pro
            260                 265                 270 cac atc cca gac agt ggc ctt ggc att gtg tgt gtg cct gcc cag gag      864
His Ile Pro Asp Ser Gly Leu Gly Ile Val Cys Val Pro Ala Gln Glu
        275                 280                 285 ggg ggc cca ggt gca taa                                              882
Gly Gly Pro Gly Ala
    290
```

<210> SEQ ID NO 6
<211> LENGTH: 293
<212> TYPE: PRT
<213> ORGANISM: Homo sapiens

<400> SEQUENCE: 6

```
Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220
```

```
Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
            245                 250                 255

Gly Arg Trp Gly Cys His Thr Arg Thr Thr Val Leu Gln Pro Cys Pro
        260                 265                 270

His Ile Pro Asp Ser Gly Leu Gly Ile Val Cys Val Pro Ala Gln Glu
    275                 280                 285

Gly Gly Pro Gly Ala
    290

<210> SEQ ID NO 7
<211> LENGTH: 834
<212> TYPE: DNA
<213> ORGANISM: Homo sapiens
<220> FEATURE:
<221> NAME/KEY: CDS
<222> LOCATION: (67)..(621)

<400> SEQUENCE: 7
ttgtaagata ttacttgtcc ttccaggctg ttctttctgt agctcccttg ttttcttttt        60 gtgatc atg ttg cag atg gct ggg cag tgc tcc caa aat gaa tat ttt         108
       Met Leu Gln Met Ala Gly Gln Cys Ser Gln Asn Glu Tyr Phe
       1               5                   10 gac agt ttg ttg cat gct tgc ata cct tgt caa ctt cga tgt tct tct         156
Asp Ser Leu Leu His Ala Cys Ile Pro Cys Gln Leu Arg Cys Ser Ser
15                  20                  25                  30 aat act cct cct cta aca tgt cag cgt tat tgt aat gca agt gtg acc         204
Asn Thr Pro Pro Leu Thr Cys Gln Arg Tyr Cys Asn Ala Ser Val Thr
                35                  40                  45 aat tca gtg aaa gga acg aat gcg att ctc tgg acc tgt ttg gga ctg         252
Asn Ser Val Lys Gly Thr Asn Ala Ile Leu Trp Thr Cys Leu Gly Leu
            50                  55                  60 agc tta ata att tct ttg gca gtt ttc gtg cta atg ttt ttg cta agg         300
Ser Leu Ile Ile Ser Leu Ala Val Phe Val Leu Met Phe Leu Leu Arg
        65                  70                  75 aag ata agc tct gaa cca tta aag gac gag ttt aaa aac aca gga tca         348
Lys Ile Ser Ser Glu Pro Leu Lys Asp Glu Phe Lys Asn Thr Gly Ser
    80                  85                  90 ggt ctc ctg ggc atg gct aac att gac ctg gaa aag agc agg act ggt         396
Gly Leu Leu Gly Met Ala Asn Ile Asp Leu Glu Lys Ser Arg Thr Gly
95                  100                 105                 110 gat gaa att att ctt ccg aga ggc ctc gag tac acg gtg gaa gaa tgc         444
Asp Glu Ile Ile Leu Pro Arg Gly Leu Glu Tyr Thr Val Glu Glu Cys
                115                 120                 125 acc tgt gaa gac tgc atc aag agc aaa ccg aag gtc gac tct gac cat         492
Thr Cys Glu Asp Cys Ile Lys Ser Lys Pro Lys Val Asp Ser Asp His
            130                 135                 140 tgc ttt cca ctc cca gct atg gag gaa ggc gca acc att ctt gtc acc         540
Cys Phe Pro Leu Pro Ala Met Glu Glu Gly Ala Thr Ile Leu Val Thr
        145                 150                 155 acg aaa acg aat gac tat tgc aag agc ctg cca gct gct ttg agt gct         588
Thr Lys Thr Asn Asp Tyr Cys Lys Ser Leu Pro Ala Ala Leu Ser Ala
    160                 165                 170 acg gag ata gag aaa tca att tct gct agg taa ttaaccattt cgactcgagc      641
Thr Glu Ile Glu Lys Ser Ile Ser Ala Arg
175                 180 agtgccactt taaaaatctt ttgtcagaat agatgatgtg tcagatctct ttaggatgac     701 tgtattttc agttgccgat acagcttttt gtcctctaac tgtggaaact ctttatgtta      761
```
gatatatttc tctaggttac tgttgggagc ttaatggtag aaacttcctt ggtttctatg    821
attaaagtct ttt    834

<210> SEQ ID NO 8
<211> LENGTH: 184
<212> TYPE: PRT
<213> ORGANISM: Homo sapiens

<400> SEQUENCE: 8

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 9
<211> LENGTH: 899
<212> TYPE: DNA
<213> ORGANISM: Homo sapiens
<220> FEATURE:
<221> NAME/KEY: CDS
<222> LOCATION: (6)..(560)

<400> SEQUENCE: 9 gcacc atg agg cga ggg ccc cgg agc ctg cgg ggc agg gac gcg cca gcc    50
      Met Arg Arg Gly Pro Arg Ser Leu Arg Gly Arg Asp Ala Pro Ala
      1               5                   10                  15 ccc acg ccc tgc gtc ccg gcc gag tgc ttc gac ctg ctg gtc cgc cac    98
Pro Thr Pro Cys Val Pro Ala Glu Cys Phe Asp Leu Leu Val Arg His
                20                  25                  30 tgc gtg gcc tgc ggg ctc ctg cgc acg ccg cgg ccg aaa ccg gcc ggg    146
Cys Val Ala Cys Gly Leu Leu Arg Thr Pro Arg Pro Lys Pro Ala Gly
            35                  40                  45 gcc agc agc cct gcg ccc agg acg gcg ctg cag ccg cag gag tcg gtg    194
Ala Ser Ser Pro Ala Pro Arg Thr Ala Leu Gln Pro Gln Glu Ser Val
        50                  55                  60 ggc gcg ggg gcc ggc gag gcg gcg ctg ccc ctg ccc ggg ctg ctc ttt    242
Gly Ala Gly Ala Gly Glu Ala Ala Leu Pro Leu Pro Gly Leu Leu Phe
    65                  70                  75

```
ggc gcc ccc gcg ctg ctg ggc ctg gca ctg gtc ctg gcg ctg gtc ctg      290
Gly Ala Pro Ala Leu Leu Gly Leu Ala Leu Val Leu Ala Leu Val Leu
 80              85                  90                  95 gtg ggt ctg gtg agc tgg agg cgg cga cag cgg cgg ctt cgc ggc gcg      338
Val Gly Leu Val Ser Trp Arg Arg Arg Gln Arg Arg Leu Arg Gly Ala
            100                 105                 110 tcc tcc gca gag gcc ccc gac gga gac aag gac gcc cca gag ccc ctg      386
Ser Ser Ala Glu Ala Pro Asp Gly Asp Lys Asp Ala Pro Glu Pro Leu
        115                 120                 125 gac aag gtc atc att ctg tct ccg gga atc tct gat gcc aca gct cct      434
Asp Lys Val Ile Ile Leu Ser Pro Gly Ile Ser Asp Ala Thr Ala Pro
130                 135                 140 gcc tgg cct cct cct ggg gaa gac cca gga acc acc cca cct ggc cac      482
Ala Trp Pro Pro Pro Gly Glu Asp Pro Gly Thr Thr Pro Pro Gly His
    145                 150                 155 agt gtc cct gtg cca gcc aca gag ctg ggc tcc act gaa ctg gtg acc      530
Ser Val Pro Val Pro Ala Thr Glu Leu Gly Ser Thr Glu Leu Val Thr
160                 165                 170                 175 acc aag acg gcc ggc cct gag caa caa tag cagggagccg gcaggaggtg        580
Thr Lys Thr Ala Gly Pro Glu Gln Gln
                180 gcccctgccc tccctctgga cccccagcca ggggcttgga aatcaaattc agctcttcac    640 tccagcatgc acatgccctc tttctgggac caggctaacc ctgcagaagc acagacacta   700 cagaccacag cattcagccc ccatggagtt tggtgtgctt gcctttggct tcagacctca   760 ccatctttga cagcccttga aggtggtagc ccagctcctg ttcctgtgcc ttcaaaaggc   820 tggggcacta tgagtaaaag accgctttta aatggggaa ggcaccatta agccaaaatg    880 aatctgaaaa aagacaaaa                                                 899

<210> SEQ ID NO 10
<211> LENGTH: 184
<212> TYPE: PRT
<213> ORGANISM: Homo sapiens

<400> SEQUENCE: 10

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
                20                  25                  30

Val Ala Cys Gly Leu Leu Arg Thr Pro Arg Pro Lys Pro Ala Gly Ala
            35                  40                  45

Ser Ser Pro Ala Pro Arg Thr Ala Leu Gln Pro Gln Glu Ser Val Gly
        50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Arg Gln Arg Arg Leu Arg Gly Ala Ser
            100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
    130                 135                 140

Trp Pro Pro Pro Gly Glu Asp Pro Gly Thr Thr Pro Pro Gly His Ser
145                 150                 155                 160
```

```
Val Pro Val Pro Ala Thr Glu Leu Gly Ser Thr Glu Leu Val Thr Thr
            165                 170                 175

Lys Thr Ala Gly Pro Glu Gln Gln
            180

<210> SEQ ID NO 11
<211> LENGTH: 585
<212> TYPE: PRT
<213> ORGANISM: Homo sapiens

<400> SEQUENCE: 11

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350
```

```
Tyr Glu Thr Thr Leu Glu Lys Cys Cys Ala Ala Asp Pro His Glu
            355                 360                 365
Cys Tyr Ala Lys Val Phe Asp Glu Phe Lys Pro Leu Val Glu Pro
        370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
            435                 440                 445
Ala Glu Asp Tyr Leu Ser Val Val Leu Asn Gln Leu Cys Val Leu His
        450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 12
<211> LENGTH: 266
<212> TYPE: PRT
<213> ORGANISM: Homo sapiens

<400> SEQUENCE: 12

Met Asp Asp Ser Thr Glu Arg Glu Gln Ser Arg Leu Thr Ser Cys Leu
1               5                   10                  15
Lys Lys Arg Glu Glu Met Lys Leu Lys Glu Cys Val Ser Ile Leu Pro
            20                  25                  30
Arg Lys Glu Ser Pro Ser Val Arg Ser Ser Lys Asp Gly Lys Leu Leu
        35                  40                  45
Ala Ala Thr Leu Leu Leu Ala Leu Leu Ser Cys Cys Leu Thr Val Val
    50                  55                  60
Ser Phe Tyr Gln Val Ala Ala Leu Gln Gly Asp Leu Ala Ser Leu Arg
65                  70                  75                  80
Ala Glu Leu Gln Gly His His Ala Glu Lys Leu Pro Ala Gly Ala Gly
                85                  90                  95
Ala Pro Lys Ala Gly Leu Glu Glu Ala Pro Ala Val Thr Ala Gly Leu
            100                 105                 110
Lys Ile Phe Glu Pro Pro Ala Pro Gly Glu Gly Asn Ser Ser Gln Asn
        115                 120                 125
```

```
Ser Arg Asn Lys Arg Ala Val Gln Gly Pro Glu Glu Thr Gly Ser Tyr
    130                 135                 140

Thr Phe Val Pro Trp Leu Leu Ser Phe Lys Arg Gly Ser Ala Leu Glu
145                 150                 155                 160

Glu Lys Glu Asn Lys Ile Leu Val Lys Glu Thr Gly Tyr Phe Phe Ile
                165                 170                 175

Tyr Gly Gln Val Leu Tyr Thr Asp Lys Thr Tyr Ala Met Gly His Leu
            180                 185                 190

Ile Gln Arg Lys Lys Val His Val Phe Gly Asp Glu Leu Ser Leu Val
            195                 200                 205

Thr Leu Phe Arg Cys Ile Gln Asn Met Pro Glu Thr Leu Pro Asn Asn
210                 215                 220

Ser Cys Tyr Ser Ala Gly Ile Ala Lys Leu Glu Glu Gly Asp Glu Leu
225                 230                 235                 240

Gln Leu Ala Ile Pro Arg Glu Asn Ala Gln Ile Ser Leu Asp Gly Asp
                245                 250                 255

Val Thr Phe Phe Gly Ala Leu Lys Leu Leu
            260                 265

<210> SEQ ID NO 13
<211> LENGTH: 249
<212> TYPE: PRT
<213> ORGANISM: Artificial
<220> FEATURE:
<223> OTHER INFORMATION: I006D08 scFv

<400> SEQUENCE: 13

Gln Val Gln Leu Gln Gln Ser Gly Ala Glu Val Lys Lys Pro Gly Ser
1               5                   10                  15

Ser Val Arg Val Ser Cys Lys Ala Ser Gly Gly Thr Phe Asn Asn Asn
            20                  25                  30

Ala Ile Asn Trp Val Arg Gln Ala Pro Gly Gln Gly Leu Glu Trp Met
        35                  40                  45

Gly Gly Ile Ile Pro Met Phe Gly Thr Ala Lys Tyr Ser Gln Asn Phe
50                  55                  60

Gln Gly Arg Val Ala Ile Thr Ala Asp Glu Ser Thr Ser Thr Ala Ser
65                  70                  75                  80

Met Glu Leu Ser Ser Leu Arg Ser Glu Asp Thr Ala Val Tyr Tyr Cys
                85                  90                  95

Ala Arg Ser Arg Asp Leu Leu Leu Phe Pro His Tyr Gly Met Asp Val
            100                 105                 110

Trp Gly Arg Gly Thr Met Val Thr Val Ser Ser Gly Gly Gly Gly Ser
        115                 120                 125

Gly Gly Gly Gly Ser Gly Gly Gly Ser Ala Phe Ser Ser Glu Leu
    130                 135                 140

Thr Gln Asp Pro Ala Val Ser Val Ala Leu Gly Gln Thr Val Arg Val
145                 150                 155                 160

Thr Cys Gln Gly Asp Ser Leu Arg Ser Tyr Tyr Ala Ser Trp Tyr Gln
                165                 170                 175

Gln Lys Pro Gly Gln Ala Pro Val Leu Val Ile Tyr Gly Lys Asn Asn
            180                 185                 190

Arg Pro Ser Gly Ile Pro Asp Arg Phe Ser Gly Ser Ser Ser Gly Asn
        195                 200                 205

Thr Ala Ser Leu Thr Ile Thr Gly Ala Gln Ala Glu Asp Glu Ala Asp
    210                 215                 220
```

Tyr Tyr Cys Asn Ser Arg Asp Ser Ser Gly Asn His Trp Val Phe Gly
225                 230                 235                 240

Gly Gly Thr Glu Leu Thr Val Leu Gly
            245

<210> SEQ ID NO 14
<211> LENGTH: 251
<212> TYPE: PRT
<213> ORGANISM: Artificial
<220> FEATURE:
<223> OTHER INFORMATION: I050B11 scFv

<400> SEQUENCE: 14

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Ser Asn His
            20                  25                  30

Gly Ile Ser Trp Val Arg Gln Ala Pro Gly Gln Gly Leu Glu Trp Val
        35                  40                  45

Gly Trp Ile Ser Gly His Asp Asp Ser Thr Lys Tyr Ala Gln Lys Phe
    50                  55                  60

Gln Gly Arg Val Thr Met Thr Ala Asp Thr Ser Thr Ser Thr Ala Tyr
65                  70                  75                  80

Ile Glu Leu Arg Ser Leu Lys Ser Asp Asp Thr Ala Val Tyr Tyr Cys
                85                  90                  95

Ala Arg Pro Phe Tyr Asp Thr Leu Thr Ser Tyr Val Phe Gln Tyr Phe
            100                 105                 110

Asp His Trp Gly Gln Gly Thr Met Val Thr Val Ser Ser Gly Gly Gly
        115                 120                 125

Gly Ser Gly Gly Gly Gly Ser Gly Gly Gly Gly Ser Ala Leu Glu Thr
    130                 135                 140

Thr Leu Thr Gln Ser Pro Asp Thr Leu Ser Leu Ser Pro Gly Glu Arg
145                 150                 155                 160

Ala Thr Leu Ser Cys Arg Ala Ser Gln Ser Val Thr Arg Gly Trp Val
                165                 170                 175

Ala Trp Tyr Gln Gln Lys Pro Gly Gln Ala Pro Arg Leu Leu Met Tyr
            180                 185                 190

Gly Thr Ser Arg Arg Ala Thr Gly Val Pro Asp Arg Phe Ser Gly Ser
        195                 200                 205

Glu Ser Gly Thr Asp Phe Thr Leu Thr Ile Ser Arg Leu Glu Pro Glu
    210                 215                 220

Asp Phe Ala Val Tyr Tyr Cys Gln Gln Tyr Ala Thr Ser Pro Arg Thr
225                 230                 235                 240

Phe Gly Gln Gly Thr Arg Leu Glu Ile Lys Arg
                245                 250

<210> SEQ ID NO 15
<211> LENGTH: 250
<212> TYPE: PRT
<213> ORGANISM: Artificial
<220> FEATURE:
<223> OTHER INFORMATION: I050A12 scFv

<400> SEQUENCE: 15

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser His Tyr
            20                  25                  30

-continued

Ala Ile Asn Trp Val Arg Gln Ala Pro Gly Gln Gly Leu Glu Trp Met
            35                  40                  45

Gly Gly Ile Ile Pro Thr Phe Asn Ala Val Lys Tyr Ala Gln Lys Phe
 50                  55                  60

Gln Gly Arg Ala Thr Ile Thr Ala Asp Gly Ser Thr Ser Thr Ala Tyr
 65                  70                  75                  80

Met Glu Leu Asn Ser Leu Arg Ser Glu Asp Thr Ala Val Tyr Tyr Cys
                85                  90                  95

Ala Thr Ala Pro Tyr Asp Leu Leu Thr His Tyr Phe His Tyr Phe Asp
            100                 105                 110

Tyr Trp Gly Gln Gly Thr Met Val Thr Val Ser Gly Gly Gly Gly
            115                 120                 125

Ser Gly Gly Gly Gly Ser Gly Gly Gly Ser Ala Leu Ser Ser Glu
            130                 135                 140

Leu Thr Gln Asp Pro Ala Val Ser Val Thr Leu Gly Gln Thr Val Arg
145                 150                 155                 160

Ile Thr Cys Gln Gly Asp Ser Leu Arg Ser Tyr Tyr Pro Ser Trp Tyr
                165                 170                 175

Gln Gln Lys Pro Gly Gln Ala Pro Val Leu Val Ile Tyr Pro Lys Asn
            180                 185                 190

Ile Arg Pro Ser Gly Ile Pro Asp Arg Phe Ser Gly Ser Ser Ser Gly
            195                 200                 205

Asn Thr Ala Ser Leu Thr Ile Thr Gly Ala Gln Ala Glu Asp Glu Ala
210                 215                 220

Asp Tyr Tyr Cys Asn Ser Arg Ala Ser Ser Gly Asn His Tyr Val Phe
225                 230                 235                 240

Ala Thr Gly Thr Lys Leu Thr Val Leu Gly
                245                 250

<210> SEQ ID NO 16
<211> LENGTH: 251
<212> TYPE: PRT
<213> ORGANISM: Artificial
<220> FEATURE:
<223> OTHER INFORMATION: I050B11-15 scFv

<400> SEQUENCE: 16

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Ser Asn His
            20                  25                  30

Gly Ile Ser Trp Val Arg Gln Ala Pro Gly Gln Gly Leu Glu Trp Val
            35                  40                  45

Gly Trp Ile Ser Gly His Asp Asp Ser Thr Lys Tyr Ala Gln Lys Phe
 50                  55                  60

Gln Gly Arg Val Thr Met Thr Ala Asp Thr Ser Thr Ser Thr Ala Tyr
 65                  70                  75                  80

Ile Glu Leu Arg Ser Leu Lys Ser Asp Asp Thr Ala Val Tyr Tyr Cys
                85                  90                  95

Ala Arg Pro Phe Tyr Asp Thr Leu Thr Ser Tyr Val Phe Gln Val Trp
            100                 105                 110

Val Ala Trp Gly Gln Gly Thr Met Val Thr Val Ser Ser Gly Gly Gly
            115                 120                 125

Gly Ser Gly Gly Gly Gly Ser Gly Gly Gly Ser Ala Leu Glu Thr
            130                 135                 140

```
Thr Leu Thr Gln Ser Pro Asp Thr Leu Ser Leu Ser Pro Gly Glu Arg
145                 150                 155                 160

Ala Thr Leu Ser Cys Arg Ala Ser Gln Ser Val Thr Arg Gly Trp Val
                165                 170                 175

Ala Trp Tyr Gln Gln Lys Pro Gly Gln Ala Pro Arg Leu Leu Met Tyr
            180                 185                 190

Gly Ala Ser Arg Arg Ala Thr Gly Val Pro Asp Arg Phe Ser Gly Ser
        195                 200                 205

Gly Ser Gly Thr Asp Phe Thr Leu Thr Ile Ser Arg Leu Glu Pro Glu
    210                 215                 220

Asp Phe Ala Val Tyr Tyr Cys Gln Gln Tyr Ala Thr Ser Pro Arg Thr
225                 230                 235                 240

Phe Gly Gln Gly Thr Arg Leu Glu Ile Lys Arg
                245                 250

<210> SEQ ID NO 17
<211> LENGTH: 249
<212> TYPE: PRT
<213> ORGANISM: Artificial
<220> FEATURE:
<223> OTHER INFORMATION: I116A01 scFv

<400> SEQUENCE: 17

Gln Val Gln Leu Gln Gln Ser Gly Ala Glu Val Lys Lys Pro Gly Ser
1               5                   10                  15

Ser Val Arg Val Ser Cys Lys Ala Ser Gly Gly Thr Phe Asn Asn Asn
            20                  25                  30

Ala Ile Asn Trp Val Arg Gln Ala Pro Gly Gln Gly Leu Glu Trp Met
        35                  40                  45

Gly Gly Ile Ile Pro Met Phe Gly Thr Ala Lys Tyr Ser Gln Asn Phe
    50                  55                  60

Gln Gly Arg Val Ala Ile Thr Ala Asp Glu Ser Thr Gly Thr Ala Ser
65                  70                  75                  80

Met Glu Leu Ser Ser Leu Arg Ser Glu Asp Thr Ala Val Tyr Tyr Cys
                85                  90                  95

Ala Arg Ser Arg Asp Leu Leu Leu Phe Pro His His Ala Leu Ser Pro
            100                 105                 110

Trp Gly Arg Gly Thr Met Val Thr Val Ser Ser Gly Gly Gly Gly Ser
        115                 120                 125

Gly Gly Gly Gly Ser Gly Gly Gly Ser Ala Phe Ser Ser Glu Leu
    130                 135                 140

Thr Gln Asp Pro Ala Val Ser Val Ala Leu Gly Gln Thr Val Arg Val
145                 150                 155                 160

Thr Cys Gln Gly Asp Ser Leu Arg Ser Tyr Tyr Ala Ser Trp Tyr Gln
                165                 170                 175

Gln Lys Pro Gly Gln Ala Pro Val Leu Val Ile Tyr Gly Lys Asn Asn
            180                 185                 190

Arg Pro Ser Gly Ile Pro Asp Arg Phe Ser Gly Ser Ser Gly Asn
        195                 200                 205

Thr Ala Ser Leu Thr Ile Thr Gly Ala Gln Ala Glu Asp Glu Ala Asp
    210                 215                 220

Tyr Tyr Cys Ser Ser Arg Asp Ser Ser Gly Asn His Trp Val Phe Gly
225                 230                 235                 240

Gly Gly Thr Glu Leu Thr Val Leu Gly
                245
```

```
<210> SEQ ID NO 18
<211> LENGTH: 250
<212> TYPE: PRT
<213> ORGANISM: Artificial
<220> FEATURE:
<223> OTHER INFORMATION: I026C04-K scFv

<400> SEQUENCE: 18

Gln Val Gln Leu Val Gln Ser Gly Ala Glu Val Lys Lys Pro Gly Ser
1               5                   10                  15

Ser Val Lys Val Ser Cys Arg Ala Ser Gly Gly Ser Phe Asn Lys His
            20                  25                  30

Ala Ile Ser Trp Val Arg Gln Ala Pro Gly Arg Gly Leu Glu Trp Met
        35                  40                  45

Gly Gly Ile Leu Pro Met Tyr Gly Thr Ala Asn Tyr Ala Gln Lys Phe
    50                  55                  60

Gln Gly Arg Val Thr Ile Thr Ala Asp Lys Leu Thr Asn Thr Val Tyr
65                  70                  75                  80

Met Asp Leu Ser Arg Leu Arg Tyr Glu Asp Thr Ala Val Tyr Tyr Cys
                85                  90                  95

Ala Arg Glu Leu Gly Leu Ser Ile Val Gly Ala Thr Gly Ala Leu
            100                 105                 110

Asp Met Trp Gly Lys Gly Thr Leu Val Thr Val Ser Ser Gly Gly Gly
        115                 120                 125

Gly Ser Gly Gly Gly Gly Ser Gly Gly Gly Gly Ser Ala Gln Ser Val
    130                 135                 140

Leu Thr Gln Pro Pro Ser Val Ser Ala Ala Pro Gly Gln Lys Val Thr
145                 150                 155                 160

Ile Ser Cys Ser Gly Ser Ser Asn Ile Gly Asn Asn Tyr Val Ser
                165                 170                 175

Trp Tyr Gln Gln Ile Pro Gly Thr Ala Pro Lys Leu Leu Ile Tyr Glu
            180                 185                 190

Asn Asn Lys Arg Pro Ser Gly Ile Pro Asp Arg Phe Ser Gly Ser Lys
        195                 200                 205

Ser Gly Ala Ser Ala Thr Leu Asp Ile Thr Gly Leu Gln Thr Gly Asp
    210                 215                 220

Glu Ala Asp Tyr Tyr Cys Gly Thr Trp His Ser Ser Gln Val Val Phe
225                 230                 235                 240

Gly Gly Gly Thr Lys Leu Thr Val Leu Gly
                245                 250

<210> SEQ ID NO 19
<211> LENGTH: 120
<212> TYPE: PRT
<213> ORGANISM: Mus musculus

<400> SEQUENCE: 19

Gln Val Gln Leu Gln Gln Ser Gly Ala Glu Leu Ala Arg Pro Gly Ala
1               5                   10                  15

Ser Val Lys Met Ser Cys Arg Ala Ser Gly Tyr Thr Phe Thr Thr Tyr
            20                  25                  30

Thr Met His Trp Val Lys Gln Arg Pro Gly Gln Gly Leu Glu Trp Ile
        35                  40                  45

Gly Tyr Ile Ile Pro Arg Asn Thr Tyr Thr Thr Phe Asn Gln Lys Phe
    50                  55                  60
```

```
Lys Asn Lys Ala Thr Leu Thr Ala Asp Lys Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg His Tyr Gly Gly Gly Tyr Trp Phe Phe Asp Val Trp Gly Ala
            100                 105                 110

Gly Thr Thr Val Thr Val Ser Ser
            115                 120

<210> SEQ ID NO 20
<211> LENGTH: 113
<212> TYPE: PRT
<213> ORGANISM: Mus musculus

<400> SEQUENCE: 20

Glu Leu Val Met Thr Gln Thr Pro Ala Ser Leu Ala Val Ser Leu Gly
  1               5                  10                  15

Gln Arg Ala Thr Ile Ser Cys Arg Gly Ser Glu Ser Val Asp Ser Tyr
                 20                  25                  30

Gly Asn Ser Phe Met His Trp Tyr Gln Gln Lys Pro Gly Gln Pro Pro
             35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Tyr
 65                  70                  75                  80

Pro Val Glu Ala Asp Asp Val Ala Thr Tyr Tyr Cys Gln Gln Ser Asn
                 85                  90                  95

Asp Asp Pro Met Tyr Thr Phe Gly Gly Gly Thr Lys Leu Glu Ile Lys
            100                 105                 110

Arg

<210> SEQ ID NO 21
<211> LENGTH: 123
<212> TYPE: PRT
<213> ORGANISM: Homo sapiens

<400> SEQUENCE: 21

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Tyr Tyr Asp Ile Leu Thr Gly Tyr Tyr Tyr Tyr Phe Asp Tyr
            100                 105                 110

Trp Gly Gln Gly Thr Leu Val Thr Val Ser Ser
            115                 120

<210> SEQ ID NO 22
<211> LENGTH: 109
<212> TYPE: PRT
```

<213> ORGANISM: Homo sapiens

<400> SEQUENCE: 22

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Ser Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys Arg Thr
            100                 105
```

<210> SEQ ID NO 23
<211> LENGTH: 293
<212> TYPE: PRT
<213> ORGANISM: Artificial
<220> FEATURE:
<223> OTHER INFORMATION: Neutrokine-alpha inhibitory peptibody

<400> SEQUENCE: 23

```
Met Leu Pro Gly Cys Lys Trp Asp Leu Leu Ile Lys Gln Trp Val Cys
1               5                   10                  15

Asp Pro Leu Gly Ser Gly Ser Ala Thr Gly Gly Ser Gly Ser Thr Ala
            20                  25                  30

Ser Ser Gly Ser Gly Ser Ala Thr His Met Leu Pro Gly Cys Lys Trp
        35                  40                  45

Asp Leu Leu Ile Lys Gln Trp Val Cys Asp Pro Leu Gly Gly Gly Gly
    50                  55                  60

Gly Val Asp Lys Thr His Thr Cys Pro Pro Cys Pro Ala Pro Glu Leu
65                  70                  75                  80

Leu Gly Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Lys Phe Asn Trp Tyr Val Asp Gly Val
        115                 120                 125

Glu Val His Asn Ala Lys Thr Lys Pro Arg Glu Glu Gln Tyr Asn Ser
130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175

Pro Ile Glu Lys Thr Ile Ser Lys Ala Lys Gly Gln Pro Arg Glu Pro
            180                 185                 190

Gln Val Tyr Thr Leu Pro Pro Ser Arg Asp Glu Leu Thr Lys Asn Gln
        195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240
```

```
Pro Pro Val Leu Asp Ser Asp Gly Ser Phe Phe Leu Tyr Ser Lys Leu
            245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
            275                 280                 285

Leu Ser Pro Gly Lys
        290

<210> SEQ ID NO 24
<211> LENGTH: 293
<212> TYPE: PRT
<213> ORGANISM: Artificial
<220> FEATURE:
<223> OTHER INFORMATION: Neutrokine-alpha inhibitory peptibody

<400> SEQUENCE: 24

Met Phe His Asp Cys Lys Trp Asp Leu Leu Thr Lys Gln Trp Val Cys
1               5                   10                  15

His Gly Leu Gly Ser Gly Ser Ala Thr Gly Gly Ser Gly Ser Thr Ala
            20                  25                  30

Ser Ser Gly Ser Gly Ser Ala Thr His Met Phe His Asp Cys Lys Trp
            35                  40                  45

Asp Leu Leu Thr Lys Gln Trp Val Cys His Gly Leu Gly Gly Gly Gly
    50                  55                  60

Gly Val Asp Lys Thr His Thr Cys Pro Pro Cys Pro Ala Pro Glu Leu
65                  70                  75                  80

Leu Gly Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Lys Phe Asn Trp Tyr Val Asp Gly Val
        115                 120                 125

Glu Val His Asn Ala Lys Thr Lys Pro Arg Glu Glu Gln Tyr Asn Ser
    130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175

Pro Ile Glu Lys Thr Ile Ser Lys Ala Lys Gly Gln Pro Arg Glu Pro
            180                 185                 190

Gln Val Tyr Thr Leu Pro Pro Ser Arg Asp Glu Leu Thr Lys Asn Gln
        195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly Lys
    290
```

<210> SEQ ID NO 25
<211> LENGTH: 18
<212> TYPE: PRT
<213> ORGANISM: Artificial
<220> FEATURE:
<223> OTHER INFORMATION: Neutrokine-alpha binding peptide

<400> SEQUENCE: 25

```
Gly Gln Met Gly Trp Arg Trp Asp Pro Leu Thr Lys Met Trp Leu Gly
1               5                   10                  15

Thr Ser
```

<210> SEQ ID NO 26
<211> LENGTH: 70
<212> TYPE: PRT
<213> ORGANISM: Artificial
<220> FEATURE:
<223> OTHER INFORMATION: Amino acids 1-70 of BAFF-R (SEQ ID NO:10) with V20N & L27P amino acid substitutions

<400> SEQUENCE: 26

```
Met Arg Arg Gly Pro Arg Ser Leu Arg Gly Arg Asp Ala Pro Ala Pro
1               5                   10                  15

Thr Pro Cys Asn Pro Ala Glu Cys Phe Asp Pro Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60

Ala Gly Ala Gly Glu Ala
65                  70
```

<210> SEQ ID NO 27
<211> LENGTH: 17
<212> TYPE: PRT
<213> ORGANISM: Homo sapiens
<220> FEATURE:
<221> NAME/KEY: SIGNAL
<222> LOCATION: (1)..(17)

<400> SEQUENCE: 27

```
Met Leu Gln Asn Ser Ala Val Leu Leu Leu Leu Val Ile Ser Ala Ser
1               5                   10                  15

Ala
```

<210> SEQ ID NO 28
<211> LENGTH: 22
<212> TYPE: PRT
<213> ORGANISM: Artificial
<220> FEATURE:
<223> OTHER INFORMATION: consensus signal sequence
<220> FEATURE:
<221> NAME/KEY: SIGNAL
<222> LOCATION: (1)..(22)

<400> SEQUENCE: 28

```
Met Pro Thr Trp Ala Trp Trp Leu Phe Leu Val Leu Leu Leu Ala Leu
1               5                   10                  15

Trp Ala Pro Ala Arg Gly
            20
```

METHODS AND COMPOSITIONS FOR USE IN TREATMENT OF PATIENTS WITH AUTOANTIBODY POSITIVE DISEASE

RELATED APPLICATIONS

This patent application is a continuation-in-part of copending U.S. patent application Ser. No. 11/543,024, filed Oct. 5, 2006. This patent application claims the benefit of U.S. Provisional Application No. 60/929,109, filed Jun. 13, 2007. U.S. patent application Ser. No. 11/543,024 claims the benefit of U.S. Provisional Application No. 60/725,625, filed Oct. 13, 2005, and U.S. Provisional Application No. 60/735,967, filed Nov. 14, 2005, and U.S. Provisional Application No. 60/776,664, filed Feb. 27, 2006, and U.S. Provisional Application No. 60/781,387, filed Mar. 13, 2006, and U.S. Provisional Application No. 60/787,557, filed Mar. 31, 2006, and U.S. Provisional Application No. 60/797,360, filed May 4, 2006, and U.S. Provisional Application No. 60/814,870, filed Jun. 20, 2006, and U.S. Provisional Application No. 60/815,558, filed Jun. 22, 2006, and U.S. Provisional Application No. 60/815,827, filed Jun. 23, 2006, and U.S. Provisional Application No. 60/834,150, filed Jul. 31, 2006, and U.S. Provisional Application No. 60/725,626, filed Oct. 13, 2005, and U.S. Provisional Application No. 60/735,988, filed Nov. 14, 2005, and U.S. Provisional Application No. 60/776,665, filed Feb. 27, 2006, and U.S. Provisional Application No. 60/797,351, filed May 4, 2006, and U.S. Provisional Application No. 60/814,869, filed Jun. 20, 2006, and U.S. Provisional Application No. 60/815,559, filed Jun. 22, 2006, and U.S. Provisional Application No. 60/834,152, filed Jul. 31, 2006, and U.S. Provisional Application No. 60/725,627, filed Oct. 13, 2005, and U.S. Provisional Application No. 60/735,964, filed Nov. 14, 2005, and U.S. Provisional Application No. 60/776,658, filed Feb. 27, 2006, and U.S. Provisional Application No. 60/725,629, filed Oct. 13, 2005, and U.S. Provisional Application No. 60/735,963, filed Nov. 14, 2005, and U.S. Provisional Application No. 60/776,660, filed Feb. 27, 2006, and U.S. Provisional Application No. 60/725,628, filed Oct. 13, 2005, and U.S. Provisional Application No. 60/735,987, filed Nov. 14, 2005, and U.S. Provisional Application No. 60/776,659, filed Feb. 27, 2006.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 65,178 Byte ASCII (Text) file named "703129_SEQUENCE_LISTING.TXT."

BACKGROUND OF THE INVENTION

Neutrokine-alpha protein (SEQ ID NO:2) is a member of the TNF family of ligands that shares amino acid sequence identity to APRIL (28.7%, SEQ ID NO:4), TNFα (16.2%), and lymphotoxin-α (LTα) (14.1%) (Moore, et al., (1999) Science 285:260-263). Neutrokine-alpha is known in the scientific and patent literature under many names, including B lymphocyte Stimulator (BLyS), B cell activating factor (BAFF), TNF- and ApoL-related leukocyte expressed ligand-1 (TALL-1). (Moore, et al., (1999) Science 285:260-263; Schneider et al., (1999) J. Exp. Med. 189:1747-1756; and Khare et al., (2000) Proc. Natl. Acad. Sci. 97:3370-3375). The official nomenclature for Neutrokine-alpha is Tumor Necrosis Factor (ligand) Super Family member 13B (TNFSF13b). The full length Neutrokine-alpha gene encodes a 285 amino acid polypeptide that has a transmembrane spanning domain between amino acids 47 and 73 preceded by a non-hydrophobic sequence characteristic of type II membrane bound proteins. Like other members of the TNF family, Neutrokine-alpha functions as a trimeric protein. Upon expression of Neutrokine-alpha at the surface of the cell, the extracellular domain is cleaved off at amino acid 134 to release a biologically active trimer.

Neutrokine-alpha is known to bind to three different receptors from the Tumor Necrosis Factor Receptor Super Family. These are transmembrane activator and CAML interactor (TACI, GenBank accession number AAC51790, SEQ ID NO:6), B cell activating factor receptor, B-cell maturation antigen (BCMA, GenBank accession number NP_001183 SEQ ID NO:8) and (BAFF-R, GenBank Accession Number NP_443177 SEQ ID NO:10). (Gross, et al., (2000) Nature 404:995-999; Thompson et al., (2001) Science 293:2108-2111; and Yan et al., (2000) Nature Immunol. 1:252-256) Expression of the receptors is largely restricted to B lymphocytes (Moore, et al., (1999) Science 285:260-263). The bulk of Neutrokine-alpha's effects are believed to be mediated by BAFF-R because of marked defects in the B cell compartments of mice deficient in Neutrokine-alpha expression or BAFF-R expression that are not apparent in TACI or BCMA deficient mice. (Schieman, et al., (2001) Science 292:2111-2114; Gross et al., (2001) Immunity 15:289-302; and Yan et al., (2000) Nature Immunol. 1:252-256).

When Neutrokine-alpha protein was assayed in in vitro and in vivo, it was shown that Neutrokine-alpha promotes B cell proliferation, differentiation and survival. Additionally, Neutrokine-alpha was shown to have some effect on T cells as well. (MacKay et al., (1999) J. Exp. Med. 190:1697-1710; Huard et al., (2001) J. Immunol. 167:6225-6231; Huard et al., (2004) Int. Immunol. 16:467-475; Ng et al., (2004) J. Immunol. 173:807-817). Mice that were engineered to transgenically overexpress Neutrokine-alpha had increased numbers of peripheral B cells and increased serum immunoglobulin concentrations. Additionally, Neutrokine-alpha transgenic mice presented with an autoimmune phenotype akin to that seen in human systemic lupus erythematosus including the development of autoantibodies and symptoms associated with glomerulonephritis. (Moore, et al., (1999) Science 285:260-263; MacKay, et al., (1999) J. Exp. Med. 192:129-135). Later studies showed that levels of Neutrokine-alpha in serum and/or synovial fluid were also upregulated in patients with autoimmune diseases such as systemic lupus erythematosus, rheumatoid arthritis and Sjogren's Syndrome. (Cheema et al., (2001) Arthritis Rheum. 44:1313-1319; Groom et al., (2002) J. Clin. Invest. 109:59-68; Mariette et al., (2003) Ann. Rheum. Dis 62:168-171). Accordingly, there is widespread belief in the scientific community that antagonists of Neutrokine-alpha have therapeutic potential in the treatment of autoimmune diseases.

Systemic lupus erythematosus (SLE or "lupus") is an autoimmune disease whose symptoms are extremely heterogeneous. The current standard for diagnosing a patient with SLE contains 11 criteria: (1) malar "butterfly" rash, (2) discoid rash, (3) photosensitivity, (4) oral ulcers, (5) arthritis, (6) serositis, (7) renal disorder, (8) neurologic disorder, (9) hematologic disorder, (10) immunologic disorder, and (11) presence of anti-nuclear antibody. These criteria are explained in more detail in Tan et al., (1982) Arthritis Rheum. 25:1271-1277; and Hochberg et al., Arthritis Rheum. (1997) 40:1725, which are hereby incorporated by reference in their entirety. A person that has any 4 of these eleven criteria can be diagnosed with SLE. Accordingly, individuals having a clinical diagnosis of SLE may have non-overlapping symptoms. Moreover, many of the symptoms of lupus overlap with symptoms in other diseases. For instance, rheumatoid arthritis, polymyositis-dermatomyositis, systemic sclerosis (or scleroderma), Sjogren's syndrome and various forms of vasculitis share symptoms with lupus including one or more of the following characteristics, the presence of autoantibodies, including anti-nuclear antibodies and anti-dsDNA antibodies, joint pain and swelling and skin rashes, and organ involvement. Thus, in practice, it is often difficult to correctly diagnose lupus patients and patients with other similar disease. Additional factors that lead to difficulty in diagnosing lupus disease include the fact that the disease does not develop rapidly; rather, patients gradually accumulate symptoms over time. Additionally, SLE is a disease with variable activity within a patient. Sometimes the disease is quiescent, while at other times patients experience an increase in the number and/or severity of their symptoms, in a "flare" episode. Finally, there is no one laboratory test that will definitively diagnose lupus. Accordingly, there is a need in the art to be able to define subsets of lupus patients with particular symptoms and to make correlations between those subsets of patients and treatments that are more likely to benefit patients in those subsets.

The present application identifies particular subgroups of patients with autoimmune disease that are more likely to benefit from treatment with immunomodulatory agents.

SUMMARY OF THE INVENTION

In a phase 2 clinical trial, it was found that treatment of lupus patients with an antibody that neutralizes Neutrokine-alpha protein, given as an IV infusion on days 0, 14, 28 and then every four weeks until week 52, significantly ameliorated symptoms associated with lupus in the subset of patients having an ANA titer of 1:80 or greater, and/or greater than or equal to 30 IU/mL of anti-dsDNA antibodies in his/her blood plasma or serum (see Example 1). Surprisingly, statistically significant improvements in clinical endpoints measuring disease activity (such as reduction in SELENA SLEDAI score, explained in more detail below) were only obtained in a subset of the patients, as opposed to the entire patient population enrolled in the clinical trial. Thus, the present invention relates to the identification of subgroups of patients that are more likely to respond to treatment with an immunomodulatory agent such as an antagonist of Neutrokine-alpha.

Accordingly, in one embodiment, the present invention provides a method of treating a patient that has an ANA titer of 1:80 or greater and/or greater than or equal to 30 IU/mL of anti-dsDNA antibodies in his/her blood plasma or serum comprising administering a therapeutically effective amount of an immunomodulatory agent. Immunomodulatory agents are described in more detail below. In a specific embodiment, the immunomodulatory agent is an antagonist of Neutrokine-alpha, including but not limited to an anti-Neutrokine-alpha antibody or antigen-binding fragment thereof, a Neutrokine-alpha receptor protein or fragment or variant thereof, an antibody that binds a Neutrokine-alpha receptor or antigen binding fragment thereof, a Neutrokine-alpha binding peptide or polypeptide, a Neutrokine-alpha and/or APRIL polypeptide variant (e.g., a dominant negative form of Neutrokine-alpha and/or APRIL). Additional antagonists of Neutrokine-alpha include small molecule antagonists of Neutrokine-alpha, Neutrokine-alpha peptide mimetics, antisense RNAs and short interfering RNAs (siRNAs) that target Neutrokine-alpha, antisense RNAs and short interfering RNAs (siRNAs) that target APRIL, antisense RNAs and short interfering RNAs (siRNAs) that target receptors for Neutrokine-alpha and/or receptors for APRIL. Neutrokine-alpha receptors include, e.g., transmembrane activator and CAML interactor (TACI, GenBank accession number AAC51790, SEQ ID NO:6), B cell activating factor receptor, B-cell maturation antigen (BCMA, GenBank accession number NP_001183 SEQ ID NO:8) and (BAFF-R, GenBank Accession Number NP_443177 SEQ ID NO:10).

In another embodiment, the present invention provides a method of treating a patient with an autoimmune disease that has an ANA titer of 1:80 or greater and/or greater than or equal to 30 IU/mL of anti-dsDNA antibodies in his/her blood plasma or serum comprising administering a therapeutically effective amount of an immunomodulatory agent. Examples of autoimmune disease in which one may identify patients with an ANA titer of 1:80 or greater and/or greater than or equal to 30 IU/mL of anti-dsDNA antibodies in his/her blood plasma or serum include, but are not limited to, systemic lupus erythematosus (SLE), rheumatoid arthritis, Sjögren's syndrome, scleroderma, polymyositis-dermatomyositis, Felty's syndrome, mixed connective tissue disease, Raynaud's syndrome, juvenile chronic arthritis, glomerulonephritis, idiopathic thrombocytopenia purpura and IgA nephropathy.

In a specific embodiment, the invention provides a method of treating a patient with Sjögren's Syndrome that has an ANA titer of 1:80 or greater and/or greater than or equal to 30 IU/mL of anti-dsDNA antibodies in his/her blood plasma or serum comprising administering a therapeutically effective amount of an immunomodulatory agent. In another specific embodiment, the invention provides a method of treating a patient with Sjögren's Syndrome that has an ANA titer of 1:80 or greater and/or greater than or equal to 30 IU/mL of anti-dsDNA antibodies in his/her blood plasma or serum comprising administering a therapeutically effective amount of an antagonist of Neutrokine-alpha.

In a specific embodiment, the invention provides a method of treating a patient with rheumatoid arthritis that has an ANA titer of 1:80 or greater and/or greater than or equal to 30 IU/mL of anti-dsDNA antibodies in his/her blood plasma or serum comprising administering a therapeutically effective amount of an immunomodulatory agent. In another specific embodiment, the invention provides a method of treating a patient with rheumatoid arthritis that has an ANA titer of 1:80 or greater and/or greater than or equal to 30 IU/mL of anti-dsDNA antibodies in his/her blood plasma or serum comprising administering a therapeutically effective amount of an antagonist of Neutrokine-alpha.

In a specific embodiment, the invention provides a method of treating a patient with systemic lupus erythematosus (SLE) that has an ANA titer of 1:80 or greater and/or greater than or equal to 30 IU/mL of anti-dsDNA antibodies in his/her blood plasma or serum comprising administering a therapeutically effective amount of an immunomodulatory agent. In another specific embodiment, the invention provides a method of treating a patient with systemic lupus erythematosus (SLE) that has an ANA titer of 1:80 or greater and/or greater than or equal to 30 IU/mL of anti-dsDNA antibodies in his/her blood plasma or serum comprising administering a therapeutically effective amount of an antagonist of Neutrokine-alpha. In a specific embodiment, the lupus patient will have a clinical diagnosis of SLE according to the American College of Rheumatology (ACR) criteria (See, for example, Tan et al., Arthritis Rheum. 25:1271-7, (1982); and Hochberg et al., Arthritis Rheum. 40:1725, (1997), which are hereby incorporated by reference in their entirety).

The present invention also provides a method of treating a patient comprising making a determination, prior to administration of an immunomodulatory agent, that the patient has an ANA titer of 1:80 or greater and/or greater than or equal to 30 IU/mL of anti-dsDNA antibodies in his/her blood plasma or serum. The present invention also provides a method of treating a patient comprising making a determination, prior to administration of an antagonist of Neutrokine-alpha, that the patient has an ANA titer of 1:80 or greater and/or greater than or equal to 30 IU/mL of anti-dsDNA antibodies in his/her blood plasma or serum.

In other embodiments, the invention provides a method of treating a lupus patient comprising making a determination, prior to administration of an immunomodulatory agent, that the lupus patient has one or more of the following characteristics: a clinical diagnosis of SLE according to the American College of Rheumatology (ACR) criteria (see, for example, Tan et al., Arthritis Rheum. 25:1271-7, (1982); and Hochberg et al., Arthritis Rheum. 40:1725, (1997)); a SELENA SLE-DAI score ≥6; depressed C4 complement levels in his/her blood plasma or serum; depressed C3 complement levels in his/her blood plasma or serum; an ANA titer of 1:80 or greater; greater than or equal to 30 IU/mL of anti-dsDNA antibodies in his/her blood plasma or serum; is receiving≥7.5 milligrams/day of prednisone or other corticosteroid for treatment of lupus-related symptoms; and/or is receiving or had previously received immunosuppressant therapy for treatment of lupus-related symptoms. In a specific embodiment, the determination is made by a medical practitioner on the basis of an evaluation of the patient's medical record. In another specific embodiment, the determination is made by a medical practitioner on the basis of laboratory test results. In a specific embodiment the determination is made by a medical practitioner on the basis of laboratory test results obtained since the patient's last medical treatment (including medical treatments with immunomodulatory agents) for lupus, if any, and prior to commencing medical treatment comprising administering a therapeutically effective amount of an immunomodulatory agent (including an antagonist of Neutrokine-alpha) as described herein.

In another embodiment, the present invention provides a method of reducing the frequency and/or quantity of corticosteroid administered to a patient that has an ANA titer of 1:80 or greater and/or greater than or equal to 30 IU/mL of anti-dsDNA antibodies in his/her blood plasma or serum comprising administering a therapeutically effective amount of an immunomodulatory agent.

In a specific embodiment, the invention provides a method of reducing the frequency and/or quantity of corticosteroid administered to a patient with Sjögren's Syndrome that has an ANA titer of 1:80 or greater and/or greater than or equal to 30 IU/mL of anti-dsDNA antibodies in his/her blood plasma or serum comprising administering a therapeutically effective amount of an immunomodulatory agent. In another specific embodiment, the invention provides a method of reducing the frequency and/or quantity of corticosteroid administered to a patient with Sjögren's Syndrome that has an ANA titer of 1:80 or greater and/or greater than or equal to 30 IU/mL of anti-dsDNA antibodies in his/her blood plasma or serum comprising administering a therapeutically effective amount of an antagonist of Neutrokine-alpha.

In a specific embodiment, the invention provides a method of reducing the frequency and/or quantity of corticosteroid administered to a patient with rheumatoid arthritis that has an ANA titer of 1:80 or greater and/or greater than or equal to 30 IU/mL of anti-dsDNA antibodies in his/her blood plasma or serum comprising administering a therapeutically effective amount of an immunomodulatory agent. In another specific embodiment, the invention provides a method of reducing the frequency and/or quantity of corticosteroid administered to a patient with rheumatoid arthritis that has an ANA titer of 1:80 or greater and/or greater than or equal to 30 IU/mL of anti-dsDNA antibodies in his/her blood plasma or serum comprising administering a therapeutically effective amount of an antagonist of Neutrokine-alpha.

In a specific embodiment, the invention provides a method of reducing the frequency and/or quantity of corticosteroid administered to a patient with systemic lupus erythematosus (SLE) that has an ANA titer of 1:80 or greater and/or greater than or equal to 30 IU/mL of anti-dsDNA antibodies in his/her blood plasma or serum comprising administering a therapeutically effective amount of an immunomodulatory agent. In another specific embodiment, the invention provides a method of reducing the frequency and/or quantity of corticosteroid administered to a patient with systemic lupus erythematosus (SLE) that has an ANA titer of 1:80 or greater and/or greater than or equal to 30 IU/mL of anti-dsDNA antibodies in his/her blood plasma or serum comprising administering a therapeutically effective amount of an antagonist of Neutrokine-alpha. In a specific embodiment, the lupus patient will have a clinical diagnosis of SLE according to the American College of Rheumatology (ACR) criteria (See, for example, Tan et al., Arthritis Rheum. 25:1271-7, (1982); and Hochberg et al., Arthritis Rheum. 40:1725, (1997), which are hereby incorporated by reference in their entirety).

In a further embodiment, the invention provides a method of reducing the quantity of corticosteroid administered to a patient that has an ANA titer of 1:80 or greater and/or greater than or equal to 30 IU/mL of anti-dsDNA antibodies in his/her blood plasma or serum is reduced by at least 25% to ≤7.5 milligrams/day. In a specific embodiment, the corticosteroid is selected from the group consisting of prednisone, prednisolone, hydrocortisone, methylprednisolone and dexamethasone. In a further specific embodiment, the corticosteroid is prednisone. In another embodiment, a method of reducing the frequency and/or quantity of corticosteroid administered to a patient with an autoimmune disease comprising administering a therapeutically effective amount of an anti-Neutrokine-alpha antibody is provided.

In another phase 2 clinical trial (Example 3) in which rheumatoid arthritis patients received treatment with an antibody that neutralizes Neutrokine-alpha protein, given as an IV infusion on days 0, 14, 28 and then every four weeks until week 24, treatment was more likely to ameliorate symptoms associated with rheumatoid arthritis in patients that had a DAS28 score greater than 5.1, patients that had not previously received anti-TNF therapy, and/or patients that had rheumatoid factor in his/her blood plasma and/or serum prior to commencing treatment with the antibody that neutralizes Neutrokine-alpha protein. Additional subgroups or rheumatoid arthritis patients that appeared to be more likely to respond to treatment with the antibody that neutralizes Neutrokine-alpha protein included male patients, patients that had anti-CCP (cyclic citrullinated peptide) antibodies in his/her blood plasma and/or serum, patients that received methotrexate concomitantly with the antibody that neutralizes Neutrokine-alpha protein, patients that had previously failed treatment with methotrexate, and/or patients that had previously failed methotrexate therapy and at least one other DMARD therapy.

In another embodiment, the invention provides a method of determining if a lupus patient is responding to medical treatment comprising determining the patient's SELENA SLE-DAI, BILAG and PGA score prior to administration of a medical treatment; administering the medical treatment; and determining the patient's SELENA SLEDAI, BILAG and PGA score following the administration of the medical treatment. In this method, the patient will be considered as having responded to medical treatment if: the patient's SELENA SLEDAI score determined following the administration of the medical treatment is 4 or more points less than the SELENA SLEDAI score prior to the administration of the medical treatment; the patient's BILAG index score determined following the administration of the medical treatment does not include a new BILAG A organ domain score or 2 new BILAG B organ domain scores compared to the BILAG score determined prior to the administration of the medical treatment, and the PGA score determined following the administration of the medical treatment is <0.3 point higher than the PGA score determined prior to the administration of the medical treatment.

Accordingly, in one embodiment, the invention provides a method of treating a rheumatoid arthritis patient comprising making a determination, prior to administration of an immunomodulatory agent, that the rheumatoid arthritis patient has one or more of the following characteristics: the patient has not previously received anti-TNF therapy, e.g., Infliximab (also known as Remicade™ Centocor, Inc.), adalimumab (Humira® from Abbott Laboratories) or etanercept (Enbrel®); the patient has rheumatoid factor in his/her blood plasma and/or serum; the patient has measurable anti-CCP (cyclic citrullinated peptide) antibodies in his/her blood plasma and/or serum; the patient has an elevated CRP (C reactive protein) level in his/her blood plasma and/or serum; the patient previously failed treatment with one or more disease-modifying antirheumatic drugs; that patient has a high modified disease activity score (DAS28); the patient has swollen and tender joints; the patient suffers from morning stiffness; the patient has an increased erythrocyte sedimentation rate (ESR) and/or the patient is male.

In another embodiment, the invention provides an aqueous pharmaceutical formulation comprising a therapeutically effective amount of an antibody, a buffer in an amount from about 5 mM to about 50 mM, NaCl in an amount from about 150 mM to about 500 mM, a surfactant in an amount from about 0.003% to about 0.05%, with a pH from about 5.5 to about 6.5. In a specific embodiment, the antibody in the above described formulation is an antibody having an IgG1/lambda isotype. In a further embodiment, the antibody in the above-described formulation is a human antibody having an IgG1/lambda isotype, the buffer in the above-described formulation is 10 mM histidine or sodium citrate, the surfactant in the above-described formulation is polysorbate 80 in an amount of 0.01% w/v, the NaCl in the above-described formulation is present in a concentration of about 150 mM and the formulation has a pH of 6.0. In other specific embodiments, the above-described formulations are stable at a temperature of about 2-8° C. for at least one year. In another embodiment, the antibody in the above-described formulation is present in an amount of 100 mg/ml.

In a specific embodiment, the invention provides an aqueous pharmaceutical formulation comprising 100 mg/ml IgG1/λ antibody, 0.74 mg/ml L-histidine, 1.1 mg/ml L-histidine monohydrochloride, 8.8 mg/ml NaCl and 0.1 mg/ml polysorbate 80 and wherein the formulation has a pH of 6.0.

BRIEF DESCRIPTION OF THE FIGURES

The following drawings are illustrative of embodiments of the invention and are not meant to limit the scope of the invention as encompassed by the claims.

FIG. 1 shows the mean percent decrease in SELENA SLEDAI at week 52 in patients that had an ANA titer of 1:80 or greater, and/or greater than or equal to 30 IU/mL of anti-dsDNA antibodies at baseline. The P-values were determined using a t-test.

DEFINITIONS

In one aspect, the present invention is directed broadly to methods of treating a patient with autoantibody positive disease by administering a therapeutically effective amount of an immunomodulatory agent. A patient with autoantibody positive disease is a patient that has detectable autoantibody titers in one or more biological fluid samples such as blood plasma or serum or synovial fluid.

Herein, reference to an "immunomodulatory agent" is a reference to the general class of pharmaceutical compounds that can stimulate or inhibit the immune system. The working examples herein describe the successful use of an antagonistic anti-Neutrokine-alpha antibody in the treatment of a subgroup of lupus patients. Thus, the term "immunomodulatory agent" is specifically intended to cover pharmaceutical compounds or molecules that can act as an antagonist of Neutrokine-alpha. Antagonists of Neutrokine-alpha include, but are not limited to, compositions comprising an anti-Neutrokine-alpha antibody or antigen-binding fragments thereof, Neutrokine-alpha receptor proteins or fragments or variants thereof, an antibody that binds a Neutrokine-alpha receptor or antigen binding fragment thereof and Neutrokine-alpha binding peptide or polypeptides. Neutrokine-alpha receptors include, e.g., transmembrane activator and CAML interactor (TACI, GenBank accession number AAC51790), BAFF-R (GenBank Accession Number NP_443177) and B-cell maturation antigen (BCMA, GenBank accession number NP_001183). Particularly useful forms of the Neutrokine-alpha receptors include soluble forms of the extracellular domains. Neutrokine-alpha-receptors or fragments or variants thereof and Neutrokine-alpha binding polypeptides may be used as fusion proteins, e.g., Fc or human serum albumin (HSA) fusion proteins. Additional antagonists of Neutrokine-alpha include small molecule antagonists of Neutrokine-alpha, Neutrokine-alpha peptide mimetics, Neutrokine-alpha and/or APRIL polypeptide variants (e.g., dominant negative forms of Neutrokine-alpha and or APRIL). Such Neutrokine-alpha and/or APRIL polypeptide variants may antagonize Neutrokine-alpha function, for example, by interfering with Neutrokine-alpha and/or APRIL homo- or hetero-multimerization. Alternatively, Neutrokine-alpha and/or APRIL polypeptide variants will prevent polypeptides comprising them from binding to and/or signaling through Neutrokine-alpha-receptors such as TACI, BCMA and BAFF-R. Additional antagonists of Neutrokine-alpha include small molecule antagonists of Neutrokine-alpha, Neutrokine-alpha peptide mimetics, antisense RNAs and short interfering RNAs (siRNAs) that target Neutrokine-alpha, antisense RNAs and short interfering RNAs (siRNAs) that target APRIL, antisense RNAs and short interfering RNAs (siRNAs) that target receptors for Neutrokine-alpha and/or receptors for APRIL. Antagonists of Neutrokine-alpha are described in more detail below.

It is believed that the anti-Neutrokine-alpha antibody works by reducing B cell numbers and/or B cell activity, such as immunoglobulin secretion. Thus, the term "immunomodulatory agent" is also specifically intended to cover B cell modulatory agents and in particular pharmaceutical molecules and compounds that directly or indirectly inhibit or reduce B cell activity (e.g., B cell proliferation, differentiation, survival or immunoglobulin secretion) and or B cell number. In a specific embodiment, a B cell modulatory agent that can be used in conjunction with the methods of the present invention is an agent that reduces the activity or number of total B cells, activated B cells, naïve B cells, memory B cells, plasma B cells, and plasmacytoid B cells, CD19+ B cells and/or CD20+ B cells.

The immune system is a complex network of interacting cells and cytokines. For example, antigen presenting cells (APCs, such as macrophages and dendritic cells) and T cells, specifically CD4+ T helper (Th) cells, play a role in activating B cells to proliferate and secrete antibodies (including autoantibodies in certain disease settings). Thus, it is possible to inhibit B cell activity by reducing or inhibiting APC or Th cell numbers or activity. Likewise, it is known that there are different types of immune response such as Th1 and Th2 responses. Immunomodulatory agents that may be used in the methods of the invention may promote one type of immune response over another and thereby have beneficial effects in the treatment of patients with autoantibody positive disease. Accordingly, in its broadest sense, the term "immunomodulatory agent" is specifically intended to cover pharmaceutical molecules or compounds that stimulate or inhibit the activity or quantity of one or more cells, cell surface molecules (e.g., cell surface signaling molecules) and/or cytokines of the immune system, including cells, cell surface molecules (e.g., cell surface signaling molecules) and cytokines that are part of the innate and/or adaptive immune system. Cells of the immune system include, but are not limited to B cells, T cells, dendritic cells, monocytes, macrophages, neutrophils, eosinophils, basophils, mast cells, and natural killer (NK) cells. Cell surface molecules on the surface of cells of the immune system that may be stimulated or inhibited by an immunomodulatory agent include, but are not limited to the CD antigens such as CD20. Cytokines important in the immune system include, but are not limited to, members of the TNF ligand superfamily, including but not limited to Neutrokine-alpha, APRIL and CD40L.

DETAILED DESCRIPTION

In a phase II clinical trial in systemic lupus erythematosus patients, applicants found that treatment of lupus patients with an antibody that neutralizes Neutrokine-alpha protein, given as an IV infusion on days 0, 14, 28 and then every four weeks until week 52, significantly ameliorated symptoms associated with lupus in patients having an ANA titer of 1:80 or greater, and/or greater than or equal to 30 IU/mL of anti-dsDNA antibodies in his/her blood plasma or serum (see Example 1).

Accordingly, a specific embodiment of the present invention provides a method of treating a patient with systemic lupus erythematosus that has an ANA titer of ≥1:80 and/or greater than or equal to 30 IU/mL of anti-dsDNA antibodies in his/her blood plasma or serum with an antibody antagonist of Neutrokine-alpha. One of skill in the art would readily understand however, that antibody molecules are but one of a variety of molecules that can act as antagonists of Neutrokine-alpha. Thus, another specific embodiment of the present invention provides a method of treating a patient with systemic lupus erythematosus that has an ANA titer of ≥1:80 and/or greater than or equal to 30 IU/mL of anti-dsDNA antibodies in his/her blood plasma or serum with an antagonist of Neutrokine-alpha.

Antagonists of Neutrokine-alpha include, but are not limited to, compositions comprising an anti-Neutrokine-alpha antibody or antigen-binding fragments thereof, Neutrokine-alpha receptor proteins or fragments or variants thereof, an antibody that binds a Neutrokine-alpha receptor or antigen binding fragment thereof, or Neutrokine-alpha binding peptide or polypeptides. Neutrokine-alpha receptors include, e.g., transmembrane activator and CAML interactor (TACI, GenBank accession number AAC51790), BAFF-R (GenBank Accession Number NP_443177) and B-cell maturation antigen (BCMA, GenBank accession number NP_001183. Particularly useful forms of the Neutrokine-alpha receptors include soluble forms of the extracellular domains capable of binding Neutrokine-alpha. Neutrokine-alpha-receptors or fragments or variants thereof and Neutrokine-alpha binding polypeptides may be used as fusion proteins, e.g., Fc or human serum albumin (HSA) fusion proteins. In a specific embodiment a Neutrokine-alpha antagonist is a TACI-Fc protein. One example of a TACI-Fc protein is amino acids 1-154 of SEQ ID NO:6 fused to the Fc region of an IgG1 immunoglobulin molecule. In a specific embodiment a Neutrokine-alpha antagonist is a BAFF-R-Fc protein. One example of a BAFF-R-Fc protein is amino acids 1-70 of SEQ ID NO:10 fused to the Fc region of an IgG1 immunoglobulin molecule. Optionally, amino acid 20 (valine) in BAFF-R is substituted with asparagine and amino acid 27 (leucine) in BAFF-R is substituted with proline. SEQ ID NO:26 shows amino acids 1-70 of BAFF-R with these two amino acid changes.

Additional antagonists of Neutrokine-alpha include small molecule antagonists of Neutrokine-alpha, Neutrokine-alpha peptide mimetics, Neutrokine-alpha and/or APRIL polypeptide variants (e.g., dominant negative forms of Neutrokine-alpha and or APRIL). Such Neutrokine-alpha and/or APRIL polypeptide variants may antagonize Neutrokine-alpha function, for example, by interfering with Neutrokine-alpha and/ or APRIL homo- or hetero-multimerization. In a specific embodiment a Neutrokine-alpha antagonist is Neutrokine-alpha protein fragment or variant that function as a dominant negative. Alternatively, Neutrokine-alpha and/or APRIL polypeptide variants will prevent polypeptides comprising them from binding to and/or signaling through Neutrokine-alpha-receptors such as TACI, BCMA and BAFF-R. Additional antagonists of Neutrokine-alpha include small molecule antagonists of Neutrokine-alpha, Neutrokine-alpha peptide mimetics, antisense RNAs and short interfering RNAs (siRNAs) that target Neutrokine-alpha, antisense RNAs and short interfering RNAs (siRNAs) that target APRIL, antisense RNAs and short interfering RNAs (siRNAs) that target receptors for Neutrokine-alpha and/or receptors for APRIL. Antagonists of Neutrokine-alpha are described in more detail below.

Similarly, one of skill in the art would appreciate that other immunomodulatory agents, including in particular, molecules that can modulate B cell activities or numbers, may be useful in the present invention. In specific embodiments, a B cell modulatory agent that can be used in conjunction with the methods of the present invention is an agent that directly or indirectly inhibits or reduces B cell activity (e.g., B cell proliferation, differentiation, survival or immunoglobulin secretion) and or B cell number. In another embodiment, B cell modulatory agents that can be used in conjunction with the methods of the present invention are agents that reduce the activity or number of total B cells, activated B cells, naïve B cells, memory B cells, plasma B cells, and plasmacytoid B cells, CD19+ B cells and/or CD20+ B cells. Immunodulatory and B cell modulatory molecules that may be used in the present invention are known to those of skill in the art and are described in more detail below.

In another embodiment, the invention provides a method of treating a patient that falls within the subset of systemic lupus erythematosus patients that have "active" systemic lupus erythematosus (SLE or "lupus") disease comprising administering a therapeutically effective amount of an antibody antagonist of Neutrokine-alpha. In specific embodiments, the invention provides a method of treating a patient that has previously been diagnosed with lupus and has active lupus, comprising administering a therapeutically effective amount of an antibody antagonist of Neutrokine-alpha. The invention provides a method of treating a patient that falls within the subset of systemic lupus erythematosus patients that have active systemic lupus erythematosus (SLE or "lupus") disease comprising making a determination the patient has "active lupus" prior to administering a therapeutically effective amount of an antibody antagonist of Neutrokine-alpha. In specific embodiments, the invention provides a method of treating a patient that has previously been diagnosed with lupus and has active lupus, comprising making a determination the patient was previously diagnosed with lupus and has active lupus prior to administering a therapeutically effective amount of an antibody antagonist of Neutrokine-alpha.

In another embodiment, the invention provides a method of treating a patient that falls within the subset of systemic lupus erythematosus patients that have "active" systemic lupus erythematosus (SLE or "lupus") disease comprising administering a therapeutically effective amount of an antagonist of Neutrokine-alpha or other immunomodulatory agent known in the art and/or described herein. In specific embodiments, the invention provides a method of treating a patient that has previously been diagnosed with lupus and has active lupus, comprising administering a therapeutically effective amount of an antagonist of Neutrokine-alpha or other immunomodulatory agent known in the art and/or described herein. The invention provides a method of treating a patient that falls within the subset of systemic lupus erythematosus patients that have active systemic lupus erythematosus disease comprising making a determination the patient has "active lupus" prior to administering a therapeutically effective amount of an antagonist of Neutrokine-alpha or other immunomodulatory agent known in the art and/or described herein. In specific embodiments, the invention provides a method of treating a patient that has previously been diagnosed with lupus and has active lupus, comprising making a determination the patient was previously diagnosed with lupus and has active lupus prior to administering a therapeutically effective amount of an antagonist of Neutrokine-alpha or other immunomodulatory agent known in the art and/or described herein.

In specific embodiments, a patient with active lupus is defined as a patient having a clinical diagnosis of SLE according to the American College of Rheumatology (ACR) criteria (See, for example, Tan et al., Arthritis Rheum. 25:1271-7, (1982); and Hochberg et al., Arthritis Rheum. 40:1725, (1997), which are hereby incorporated by reference in their entirety).

In specific embodiments, a patient with active lupus is defined as a patient having a SELENA SLEDAI score ≥4. SELENA SLEDAI stands for Systemic Lupus Erythematosus Disease Activity Index, as modified by the Safety of Estrogen in Lupus Erythematosus National Assessment trial. SELENA SLEDAI scores are routinely determined by clinicians/physicians using techniques and methodologies known in the art, see, for example, Bombardier, et al., Arthritis Rheum. June; 35(6):630-40, 1992; and Strand, et al., J Rheumatol. February; 26(2):490-7, 1999, which are hereby incorporated by reference in their entirety. Briefly, a SELENA SLEDAI score is determined by considering SLE disease activity in 24 categories spread across 9 organ systems. Disease in some organ systems scores is weighted more heavily than disease in other organ systems. In particular, central nervous system and vascular SLE disease activity measures, if present, are assigned 8 points, renal and musculoskeletal SLE disease activity measures, if present, are assigned 4 points, serosal, dermal and immunologic SLE disease activity measures, if present, are assigned 2 points, and constitutional and hematologic SLE disease activity measures, if present, are assigned 1 point. The maximum theoretical SELENA SLEDAI score is 105, but in practice, few patients have scores greater than 45.

In the standard SELENA SLEDAI scoring system, 4 points are assigned if a subject has a new onset or recent increase in proteinuria greater than 0.5 grams/24 hours. In other words, if the proteinuria value obtained in one 24 hour urine sample is more than 0.5 g greater than the value determined for the patient's immediate prior 24 hour urine sample, 4 points will be assigned for proteinuria on the SELENA SLEDAI scale. This is commonly described as an increase or new onset of proteinuria of ">0.5 g/24 hours." Thus, a under the standard SELENA SLEDAI scoring system, a subject that is assigned 4 points at baseline for proteinuria will have an improving SELENA SLEDAI at a subsequent visit as long as proteinuria value in the current 24 hour urine sample is not more than 0.5 g greater than the proteinuria value determined for the patient's immediate prior 24 hour urine sample. In other words, the patient will have 4 points deducted from their total score even in the face of stable proteinuria or increases in proteinuria≤0.5 g/24 hours. A modification to the SELENA SLEDAI proteinuria scoring rules is described in Example 2. In Example 2, the proteinuria scoring is modified so that 4 points continue to be assigned unless proteinuria determined for the present 24 hour urine sample is more than 0.5 grams lower than the proteinuria value determined for that patient's immediate prior 24 hour urine sample. Further, if there is a new onset of proteinuria or an increase in proteinuria that is >0.5 g/24 hours, 4 points are assigned. Herein, when the SELENA SLEDAI scale is referred to, scoring for proteinuria may be done according to the standard SELENA SLEDAI scale. Preferably, scoring for proteinuria in the determination of a patient's SELENA SLEDAI score is performed according to the proteinuria scoring system described in Example 2.

In other specific embodiments, a patient with active lupus is defined as a patient having a SELENA SLEDAI score ≥5. In additional specific embodiments, a patient with active lupus is defined as a patient having a SELENA SLEDAI score ≥6. In further specific embodiments, a patient with active lupus is defined as a patient having a SELENA SLEDAI score ≥7. In additional specific embodiments, a patient with active lupus is defined as a patient having a SELENA SLEDAI score ≥8. In other specific embodiments, a patient with active lupus is defined as a patient having a SELENA SLEDAI score ≥9. In other specific embodiments, a patient with active lupus is defined as a patient having a SELENA SLEDAI score ≥10. In additional specific embodiments, a patient with active lupus is defined as a patient having a SELENA SLEDAI score ≥11. In additional specific embodiments, a patient with active lupus is defined as a patient having a SELENA SLEDAI score ≥12.

In other embodiments, a patient with active lupus is defined as a patient that has anti-dsDNA antibodies in his/her blood plasma or serum. Anti-dsDNA antibody titers, concentrations or levels can be routinely determined by clinicians/physicians using techniques and methodologies known in the art. One example assay for determining anti-dsDNA antibody titers, concentrations or levels is an enzyme-linked immunosorbent assay (ELISA) based on the specific binding of anti-dsDNA antibodies to immobilized dsDNA, see, for example, Halbert, et al., J Lab Clin Med. 97:97-111, (1981). Another example assay for determining anti-dsDNA antibody titers, concentrations or levels is an indirect immunofluorescence assay based on the specific binding of anti-dsDNA antibodies to the dsDNA of a *Crithidia luciliae* cell, see, for example, Whiteside, et al., Am J Clin Pathol. 72:829-35, (1979). Yet another example assay for determining anti-dsDNA antibody titers, concentrations or levels is the Farr assay based on the specific binding of anti-dsDNA antibodies to radiolabeled dsDNA, followed by precipitation of anti-dsDNA antibody-radiolabeled dsDNA complexes, see for example, Davis, et al., Am J Clin Pathol., 67:374-8, (1977). In specific embodiments, a patient with active lupus is defined as a patient that has greater than or equal to 30 International Units/mL of anti-dsDNA antibodies in his/her blood plasma or serum, wherein an International Unit (IU) is based on the World Heath Organization anti-dsDNA antibody reference preparation, see, for example, Feltkamp, et al., Ann. Rheum. Dis., 47:740-746, (1988). Each of the references referred to in this paragraph is herein incorporated by reference in its entirety.

In an additional specific embodiment, a patient with active lupus is defined as a patient that has greater than or equal to 40 IU/mL of anti-dsDNA antibodies in his/her blood plasma or serum. In an additional specific embodiment, a patient with active lupus is defined as a patient that has greater than or equal to 50 IU/mL of anti-dsDNA antibodies in his/her blood plasma or serum. In an additional specific embodiment, a patient with active lupus is defined as a patient that has greater than or equal to 60 IU/mL of anti-dsDNA antibodies in his/her blood plasma or serum In an additional specific embodiment, a patient with active lupus is defined as a patient that has greater than or equal to 75 IU/mL of anti-dsDNA antibodies in his/her blood plasma or serum In an additional specific embodiment, a patient with active lupus is defined as a patient that has greater than or equal to 100 IU/mL of anti-dsDNA antibodies in his/her blood plasma or serum In an additional specific embodiment, a patient with active lupus is defined as a patient that has greater than or equal to 125 IU/mL of anti-dsDNA antibodies in his/her blood plasma or serum In an additional specific embodiment, a patient with active lupus is defined as a patient that has greater than or equal to 150 IU/mL of anti-dsDNA antibodies in his/her blood plasma or serum In an additional specific embodiment, a patient with active lupus is defined as a patient that has greater than or equal to 200 IU/mL of anti-dsDNA antibodies in his/her blood plasma or serum In an additional specific embodiment, a patient with active lupus is defined as a patient that has greater than or equal to 300 IU/mL of anti-dsDNA antibodies in his/her blood plasma or serum.

In other embodiments, a patient with active lupus is defined as a patient that has antinuclear antibodies (ANA+) in his/her blood plasma or serum. Antinuclear antibody titer can be routinely determined by clinicians/physicians using techniques and methodologies known in the art. One example assay for determining antinuclear antibody titer is an indirect immunofluorescence assay based on the specific binding of antinuclear antibodies to HEp-2 human epithelial cells, see, for example, Osborn, et al., Arthritis Rheum., 27:1286-9, (1984). In another example assay, antinuclear antibodies concentrations or levels can be determined by using an ELISA based on the specific binding of ANA to immobilized ANA antigens, for example, dsDNA, Ro/SS-A, La/SS-B, Sm, RNP, see, for example, Fenger, et al., Clin Chem., 50:2141-7, (2004). ANA tests are further described in Kavanaugh et al., *Archives of Pathology & Laboratory Medicine* (2000) 124: 71-81 and Greidinger, E L and Hoffman, R W, *Laboratory Medicine* (2003) 34:113-117. Each of the references referred to in this paragraph is herein incorporated by reference in its entirety.

In preferred specific embodiments, a patient with active lupus is defined as a patient that has an ANA titer of 1:80 or greater (i.e., a positive ANA test is obtained when the dilution factor of the patient's blood plasma or serum is 80 or greater). Titers of 1:160, 1:320 and 1:640, for example, are greater than a titer of 1:80.) In other preferred embodiments, a patient with active lupus is defined as a patient that has an ANA titer of 1:160 or greater. In an additional preferred embodiment, a patient with active lupus is defined as a patient that has an ANA titer of 1:320 or greater. In an additional preferred embodiment, a patient with active lupus is defined as a patient that has an ANA titer of 1:640 or greater. In a specific embodiment the ANA titer is measured using indirect immunofluorescence on HEp-2 cells. In another specific embodiment the ANA titer is measured using an anti-dsDNA ELISA assay.

In other embodiments, a patient with active lupus is defined as a patient that has detectable autoantibodies, including but not limited to anti-Ro/SS-A antibodies, anti-La/SS-B antibodies, anti-RNP antibodies, anti-cardiolipin (anti-phospholipid), anti-dsDNA antibodies, anti-Sm antibodies. Autoantibody titers, concentrations or levels can be routinely determined by clinicians/physicians using techniques and methodologies known in the art.

In other embodiments, a patient with active lupus is defined as a patient that has depressed C3 and/or C4 complement levels in his/her blood plasma or serum. One of skill in the art understands that the normal level of C3 and/or C4 may vary depending on the assay used to measure C3 and/or C4. Accordingly, a normal level of plasma or serum C3 complement may be from about 90 milligrams/deciliter to about 180 milligrams/deciliter. In other specific embodiments, a normal level of plasma or serum C3 complement may also range from about 88 milligrams/deciliter to about 206 milligrams/deciliter or from about 88 milligrams/deciliter to about 252 milligrams/deciliter. A normal level of plasma or serum C4 complement may be from about 16 milligrams/deciliter to about 47 milligrams/deciliter. In other specific embodiments, a normal level of plasma or serum C4 complement may also range from about 12 milligrams/deciliter to about 72 milligrams/deciliter or from about 13 milligrams/deciliter to about 75 milligrams/deciliter. In specific embodiments, a depressed level of plasma or serum C3 complement is defined as less than 90 milligrams/deciliter. In specific embodiments, a depressed level of plasma or serum C3 complement is defined as less than 88 milligrams/deciliter. In specific embodiments, a depressed level of plasma or serum C3 complement is defined as less than 85 milligrams/deciliter. In specific embodiments, a depressed level of plasma or serum C3 complement is defined as less than 80 milligrams/deciliter. In specific embodiments, a depressed level of plasma or serum C3 complement is defined as less than 75 milligrams/deciliter. In specific embodiments, a depressed level of plasma or serum C4 complement is defined as less than 16 milligrams/deciliter. In specific embodiments, a depressed level of plasma or serum C4 complement is defined as less than 15 milligrams/deciliter. In specific embodiments, a depressed level of plasma or serum C4 complement is defined as less than 14 milligrams/deciliter. In specific embodiments, a depressed level of plasma or serum C4 complement is defined as less than 13 milligrams/deciliter. In specific embodiments, a depressed level of plasma or serum C4 complement is defined as less than 12 milligrams/deciliter. In specific embodiments, a depressed level of plasma or serum C4 complement is defined as less than 11 milligrams/deciliter. In specific embodiments, a depressed level of plasma or serum C4 complement is defined as less than 10 milligrams/deciliter. In specific embodiments, a depressed level of plasma or serum C4 complement is defined as less than 9 milligrams/deciliter. Complement levels can be routinely determined by clinicians/physicians using techniques and methodologies known in the art, e.g., using a radial immunodiffusion assay.

In other embodiments, a patient with active lupus is defined as a patient that has any one or more of the following characteristics: a clinical diagnosis of SLE according to the American College of Rheumatology (ACR) criteria (see, for example, Tan et al., Arthritis Rheum. 25:1271-7, (1982); and Hochberg et al., Arthritis Rheum. 40:1725, (1997)); a SELENA SLEDAI score ≥6; depressed C4 complement levels in his/her blood plasma or serum; depressed C3 complement levels in his/her blood plasma or serum; an ANA titer of 1:80 or greater; greater than or equal to 30 IU/mL of anti-dsDNA antibodies in his/her blood plasma or serum; is receiving ≥7.5 milligrams/day of prednisone or other corticosteroid for treatment of lupus-related symptoms; and/or is receiving or had previously received immunosuppressant therapy for treatment of lupus-related symptoms.

In other embodiments, a patient with active lupus is defined as a patient that has any one or more of the following characteristics: a clinical diagnosis of SLE according to the American College of Rheumatology (ACR) criteria; a SELENA SLEDAI score ≥8; depressed C4 complement levels in his/her blood plasma or serum; depressed C3 complement levels in his/her blood plasma or serum; an ANA titer of 1:80 or greater; greater than or equal to 30 IU/mL of anti-dsDNA antibodies in his/her blood plasma or serum; is receiving up to 40 milligrams/day of prednisone or other corticosteroid for treatment of lupus-related symptoms; and/or is receiving or had previously received immunosuppressant therapy for treatment of lupus-related symptoms.

Multiple disease activity indices are well known to clinicians/physicians in the art and can be used to measure the extent of rheumatic disease activity, such as SLE disease activity (see, for example, Strand, et al., J Rheumatol., 26:490-7, (1999)). In one embodiment, the SELENA SLEDAI is used as a disease activity index (DAI) (see, for example, Bombardier, et al., Arthritis Rheum. 35:630-40, (1992)). In another embodiment, the SLE Flare Index is used as a DAI (see, for example, Petri, et al., Lupus, 8:685-91, (1999)). In a further embodiment, the Systemic Lupus International Collaborating Clinics/American College of Rheumatology Damage Index (SLICC/ACR) is used as a DAI (see, for example, Gladman, et al., Arthritis Rheum., 39:363-9, (1996)). In another embodiment the Physician's Global assessment (PGA) is used as a DAI, The PGA is a visual analogue scale with a range from 0 to 3 where 0 is no disease activity, 1 is mild disease activity, 2 is moderate disease activity and 3 is severe disease activity, is used as a DAI. In yet another embodiment, The Medical Outcomes Survey Short Form 36 (SF-36) is used as a DAI. The SF-36 is a generic health-related quality of life (HRQOL) instrument that has been shown to reflect the impact of SLE on all domains of HRQOL in observational cohort studies, as well as randomized trials (Cook, et al., J. Rheumatol., 27:1892-1895, (2000); Thumboo, et al., J Rheumatol., 26:97-102, (1999); Thumboo, et al., J Rheumatol., 27:1414-1420, (2000); Ware J E, et al., Med Care, 30:473-483, (1992); Smolen J S, et al., J Rheumatol., 26:504-507, (1999); Gladman, et al., Lupus, 5:190-195, (1996); Alonso J, et al., Qual Life Res., 13:283-298, 2004; and Gladman et al, J Rheumatol., 27:377-9, (1995), each of which is incorporated by reference herein in its entirety).

In a further embodiment, the EQ-5D (also known as the EuroQol instrument) is used as a DAI. The EQ-5D is a generic health-related quality of life measure. It is intended to be a simple, self-administered questionnaire that not only contains a descriptive health state classification system but also is capable of generating a composite score or index reflecting the preference value associated with a given health state. The EQ-5D descriptive system consists of five dimensions: mobility, self-care, usual activities, pain/discomfort, and anxiety/depression. Each dimension has three levels, reflecting "no health problems," "moderate health problems," and "extreme health problems" (see, for example, Health Policy. 1990 December; 16(3):199-208, which is incorporated herein by reference).

In a further embodiment, the Functional Assessment for Chronic Illness Therapy-Fatigue (FACIT-F) subscale of the Functional Assessment of Chronic Illness Therapy (FACIT) Measurement System is used as a DAI. The FACIT-F subscale is a 27-item compilation of general questions divided into four primary QOL domains: Physical Well-Being, Social/Family Well-Being, Emotional Well-Being, and Functional Well-Being. This measurement tool gathers patient feedback about energy level, listlessness and the ability to start or finish activities (see, for example, Yellen, S. B., et al., Journal of Pain and Symptom Management, 13:63-74, (1997); Cella, D., et al., 94(2):528-538, (2002); and Cella, D., et al., Journal of Pain & Symptom Management, 24 (6):547-561, (2002), each of which is incorporated by reference herein in its entirety).

In a further embodiment, the Disease Activity Score (DAS28) is used as a DAI. DAS28 is a standard tool used by rheumatologists for assessment of rheumatic disease activity. This measurement tool calculates an index score based upon assessment of: the number of joints tender to the touch (TEN), the number of swollen joints (SW), the erythrocyte sedimentation rate (ESR), and the patient assessment of disease activity (VAS; mm) (see, for example, Van der Heijde D. M. F. M., et al., J. Rheumatol, 20:579-8, (1993); Prevoo M. L. L., et al., Arthritis Rheum, 38:44-8, (1995), each of which is incorporated by reference herein in its entirety).

In a further embodiment, the British Isles Lupus Assessment Group (BILAG) is used as a DAI (see, for example, Isenberg, et al., Rheumatology, 44:902-6, (2005); Gordon, et al., Rheumatology, 42(11):1372-9, (2003); Isenberg, et al., Lupus, 9(9):651-4, (2000); Hay et al., Q J Med., 86:447-58, (1993); and the BLIPS™ Version 3.0 Software program users guide, released Apr. 4, 2004, ADS-Limathon Ltd, each of which is incorporated by reference herein in its entirety). The BILAG index comprises 8 body organs/systems known to be affected in lupus and scores each depending on whether the clinical features are new, worse, the same or improving compared to the previous measurement. For each of the 8 body organs/systems, the severity of the SLE disease manifestation is an A, B, C, D or E score with A being the most severe (see, for example, Hay, ibid). The BILAG index provides a composite score to assess disease severity and effectiveness of treatment. This composite score adds contributions across each of the 8 body organs/systems affected in lupus. Using BILAG or other measures known in the art, treatment may be targeted to lupus patients with disease manifestation in specific subsets of organs/systems.

Accordingly, in a specific embodiment, a lupus patient that is being or has been treated with an immunomodulatory agent known in the art and/or described herein is considered to be responding/have responded to treatment if the patient has achieved a reduction in their SELENA SLEDAI score. In a specific embodiment, a lupus patient that is being or has been treated with an immunomodulatory agent known in the art and/or described herein is considered to be responding/have responded to treatment if the patient has achieved a reduction in their SELENA SLEDAI score compared to the same patient's baseline SELENA SLEDAI score, the SELENA SLEDAI score determined prior to that patient's commencing of treatment with the immunomodulatory agent. In a specific embodiment, a lupus patient that is being or has been treated with an immunomodulatory agent known in the art and/or described herein is considered to be responding/have responded to treatment if the patient has achieved at least a four point reduction in their SELENA SLEDAI score. In a specific embodiment, a lupus patient that is being or has been treated with an immunomodulatory agent known in the art and/or described herein is considered to be responding/have responded to treatment if the patient has achieved at least a four point reduction in their SELENA SLEDAI score compared to the same patient's baseline SELENA SLEDAI score, the SELENA SLEDAI score determined just prior to that patient's commencing of treatment with the immunomodulatory agent.

In another specific embodiment, a lupus patient that is being or has been treated with an immunomodulatory agent known in the art and/or described herein is considered to be responding/have responded to treatment if the patient has not experienced a worsening of disease activity as determined by the Physician's Global Assessment (PGA). In a specific embodiment, the patient has not experienced a worsening of disease activity if the PGA score has decreased, remained stable or increased by less than 0.3 points. In a specific embodiment, the patient has not experienced a worsening of disease activity if the PGA score has decreased, remained stable or increased by less than 0.3 points from same patient's baseline PGA score, the PGA score determined just prior to that patient's commencing of treatment with the immunomodulatory agent.

In another specific embodiment, a lupus patient that is being or has been treated with an immunomodulatory agent known in the art and/or described herein is considered to be responding/have responded to treatment if the patient has not experienced a worsening of disease activity as determined by the British Isles Lupus Assessment Group (BILAG) disease activity index. In a specific embodiment, the patient has not experienced a worsening of disease activity if the patient has not gained a new BILAG A organ domain score or has not gained 2 new BILAG B organ domain scores. In a specific embodiment, the patient has not experienced a worsening of disease activity if the patient has not gained a new BILAG A organ domain score or has not gained 2 new BILAG B organ domain scores since the patient's baseline BILAG assessment, the BILAG assessment determined just prior to that patient's commencing of treatment with the immunomodulatory agent.

In another specific embodiment, a lupus patient that is being or has been treated with an immunomodulatory agent known in the art and/or described herein is considered to be responding/have responded to treatment if the patient has achieved a reduction in their SELENA SLEDAI score, has not had a substantial worsening of their PGA score, and has not experienced a worsening of disease activity as determined by the British Isles Lupus Assessment Group (BILAG) disease activity index, compared to their baseline SELENA SLEDAI score, PGA score and BILAG assessment, respectively. In a specific embodiment, a lupus patient that is being or has been treated with an immunomodulatory agent is considered to be responding/have responded to treatment if the patient has achieved at least a 4 point reduction in their SELENA SLEDAI score, has not had more than a 0.30 point increase in their PGA score and has not gained a new BILAG A organ domain score or has not gained 2 new BILAG B organ domain scores, compared to their baseline SELENA SLEDAI score, PGA score and BILAG assessment, respectively.

In another specific embodiment, a lupus patient that is being or has been treated with an immunomodulatory agent known in the art and/or described herein is considered to be responding/have responded to treatment if the patient's prednisone dose has been reduced. In another specific embodiment, a lupus patient that is being or has been treated with an immunomodulatory agent known in the art and/or described herein is considered to be responding/have responded to treatment if the patient's prednisone dose has been reduced compared to the patient's baseline prednisone dose, the prednisone dose the patient was taking just prior to that patient's commencing of treatment with the immunomodulatory agent. In another specific embodiment, a lupus patient that is being or has been treated with an immunomodulatory agent known in the art and/or described herein is considered to be responding/have responded to treatment if the patient's prednisone dose has been reduced by at least 25%. In another specific embodiment, a lupus patient that is being or has been treated with an immunomodulatory agent known in the art and/or described herein is considered to be responding/have responded to treatment if the patient's prednisone dose has been reduced by at least 25% to less than or equal to 7.5 mg/day. In another specific embodiment, a lupus patient that is being or has been treated with an immunomodulatory agent known in the art and/or described herein is considered to be responding/have responded to treatment if the patient's prednisone dose has been reduced by at least 25% from the patient's baseline prednisone dose to less than or equal to 7.5 mg/day. In another specific embodiment, a lupus patient that is being or has been treated with an immunomodulatory agent known in the art and/or described herein is considered to be responding/have responded to treatment if the patient's prednisone dose has been reduced by at least 50%. In another specific embodiment, a lupus patient that is being or has been treated with an immunomodulatory agent known in the art and/or described herein is considered to be responding/have responded to treatment if the patient's prednisone dose has been reduced by at least 50% to less than or equal to 7.5 mg/day. In another specific embodiment, a lupus patient that is being or has been treated with an immunomodulatory agent known in the art and/or described herein is considered to be responding/have responded to treatment if the patient's prednisone dose has been reduced by at least 50% from the patient's baseline prednisone dose to less than or equal to 7.5 mg/day.

Other measures can be used to measure the quality of a lupus patient's response to treatment. In a specific embodiment, a lupus patient that is being or has been treated with an immunomodulatory agent known in the art and/or described herein is considered to be responding/have responded to treatment if the patient has an improved SF-36 Health Survey Score. In another specific embodiment, a lupus patient that is being or has been treated with an immunomodulatory agent known in the art and/or described herein is considered to be responding/have responded to treatment if the patient has an improved SF-36 Health Survey Score compared to the patient's baseline SF-36 Health Survey Score.

In a specific embodiment, a lupus patient that is being or has been treated with an immunomodulatory agent known in the art and/or described herein is considered to be responding/ have responded to treatment if the patient has an improved EQ-5D score. In another specific embodiment, a lupus patient that is being or has been treated with an immunomodulatory agent known in the art and/or described herein is considered to be responding/have responded to treatment if the patient has an improved EQ-5D score compared to the patient's baseline EQ-5D score.

In a specific embodiment, a lupus patient that is being or has been treated with an immunomodulatory agent known in the art and/or described herein is considered to be responding/have responded to treatment if the patient demonstrates reduced fatigue as shown by the patient's FACIT-F score. In another specific embodiment, a lupus patient that is being or has been treated with an immunomodulatory agent known in the art and/or described herein is considered to be responding/have responded to treatment if the patient demonstrates reduced fatigue as shown by the patient's FACIT-F score compared to the patient's baseline FACIT-F score.

In a specific embodiment, a lupus patient that is being or has been treated with an immunomodulatory agent known in the art and/or described herein is considered to be responding/have responded to treatment if the patient has an improved DAS28 score. In another specific embodiment, a lupus patient that is being or has been treated with an immunomodulatory agent known in the art and/or described herein is considered to be responding/have responded to treatment if the patient has an improved DAS28 score compared to the patient's baseline DAS28 score.

In another specific embodiment, a lupus patient that is being or has been treated with an immunomodulatory agent known in the art and/or described herein is considered to be responding/have responded to treatment if the patient has a decreased frequency and/or duration of flares. In another specific embodiment, a lupus patient that is being or has been treated with an immunomodulatory agent known in the art and/or described herein is considered to be responding/have responded to treatment if the patient has a decreased frequency and/or duration of flares compared to the frequency and/or duration of flares prior to treatment with the immunomodulatory agent. In another specific embodiment, a lupus patient that is being or has been treated with an immunomodulatory agent known in the art and/or described herein is considered to be responding/have responded to treatment if the patient has a decreased severity of flares. In another specific embodiment, a lupus patient that is being or has been treated with an immunomodulatory agent known in the art and/or described herein is considered to be responding/have responded to treatment if the patient has a decreased severity of flares compared to the severity of flares prior to treatment with the immunomodulatory agent. The SLE flare index assesses the frequency and severity of exacerbations in lupus symptoms (flares). Flares are categorized as "mild or moderate" or "severe". Mild or moderate flares involve one or more of the following: change in SELENA SLEDAI score of 3 points or more; new/worse discoid, photosensitive, profundus, cutaneous vasculitis or bullous lupus; nasopharyngeal ulcers; pleuritis; pericarditis; arthritis; fever (SLE); increase in prednisone, but not to more than 0.5 mg/kg/day; added NSAID or Plaquenil for disease activity; and greater than 1.0 increase in PGA score, but not to more than 2.5. Severe flares involve one or more of the following: change in SELENA SLEDAI score to greater than 12; new/worse CNS-SLE; vasculitis; nephritis; myositis; Plt <60,000; heme anemia (<7% or decrease in Hb >3%); doubling of Prednisone dosage; increase in Prednisone to more than 0.5 mg/kg/day; prescription of Cytoxan; prescription of Azathioprine; prescription of Methotrexate; hospitalization (SLE) and increase in PGA score to more than 2.5. In another specific embodiment, a lupus patient that is being or has been treated with an immunomodulatory agent known in the art and/or described herein is considered to be responding/have responded to treatment if the patient has a decreased frequency and/or severity of flares as measured by the SLE flare index. In another specific embodiment, a lupus patient that is being or has been treated with an immunomodulatory agent known in the art and/or described herein is considered to be responding/have responded to treatment if the patient has a decreased frequency and/or severity of flares as measured the SLE flare index compared to the patient's previous flare frequency and/or severity. In another specific embodiment, a lupus patient that is being or has been treated with an immunomodulatory agent known in the art and/or described herein is considered to be responding/have responded to treatment if the patient has a decreased frequency and/or severity of flares as measured by a modified version of the SLE flare index. In another specific embodiment, a lupus patient that is being or has been treated with an immunomodulatory agent known in the art and/or described herein is considered to be responding/have responded to treatment if the patient has a decreased frequency and/or severity of flares as measured by a modified version of the SLE flare index compared to the patient's previous flare frequency and/or severity. The modified version of the SLE flare index excludes severe flares triggered by SELENA SLEDAI score change alone.

Accordingly, in a specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof. Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has achieved a reduction in his/her SELENA SLEDAI score. In a specific embodiment, a lupus patient that is being or has been treated with an antagonist of Neutrokine-alpha is considered to be responding/have responded to treatment if the patient has achieved a reduction in his/her SELENA SLEDAI score compared to the same patient's baseline SELENA SLEDAI score, the SELENA SLEDAI score determined just prior to that patient's commencing of treatment with the antagonist of Neutrokine-alpha. In a specific embodiment, a lupus patient that is being or has been treated with an antagonist of Neutrokine-alpha is considered to be responding/have responded to treatment if the patient has achieved at least a four point reduction in his/her SELENA SLEDAI score. In a specific embodiment, a lupus patient that is being or has been treated with an antagonist of Neutrokine-alpha is considered to be responding/have responded to treatment if the patient has achieved at least a four point reduction in his/her SELENA SLEDAI score compared to the same patient's baseline SELENA SLEDAI score, the SELENA SLEDAI score determined just prior to that patient's commencing of treatment with the antagonist of Neutrokine-alpha. In a specific embodiment, a Neutrokine-alpha antagonist is an anti-Neutrokine-alpha antibody. In a specific embodiment, a Neutrokine-alpha antagonist is a TACI-Fc protein. In a specific embodiment, a Neutrokine-alpha antagonist is a BAFF-R-Fc protein. In a specific embodiment, a Neutrokine-alpha antagonist is an anti-Neutrokine-alpha peptibody. In a specific embodiment, a Neutrokine-alpha antagonist is Neutrokine-alpha protein fragment or variant that functions as a dominant negative.

In another specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has not experienced a worsening of disease activity as determined by the Physician's Global Assessment (PGA). In a specific embodiment, the patient has not experienced a worsening of disease activity if the PGA score has decreased, remained stable or increased by less than 0.3 points. In a specific embodiment, the patient has not experienced a worsening of disease activity if the PGA score has decreased, remained stable or increased by less than 0.3 points from same patient's baseline PGA score, the PGA score determined just prior to that patient's commencing of treatment with the antagonist of Neutrokine-alpha. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In another specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has not experienced a worsening of disease activity as determined by the British Isles Lupus Assessment Group (BILAG) disease activity index. In a specific embodiment, the patient has not experienced a worsening of disease activity if the patient has not gained a new BILAG A organ domain score or has not gained 2 new BILAG B organ domain scores. In a specific embodiment, the patient has not experienced a worsening of disease activity if the patient has not gained a new BILAG A organ domain score or has not gained 2 new BILAG B organ domain scores since the patient's baseline BILAG assessment, the BILAG score determined just prior to that patient's commencing of treatment with the antagonist of Neutrokine-alpha. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In another specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has achieved a reduction in his/her SELENA SLEDAI score, has not had a substantial worsening of his/her PGA score, and has not experienced a worsening of disease activity as determined by the British Isles Lupus Assessment Group (BILAG) disease activity index, compared to his/her baseline SELENA SLEDAI score, PGA score and BILAG score, respectively. In a specific embodiment, a lupus patient that is being or has been treated with an antagonist of Neutrokine-alpha is considered to be responding/have responded to treatment if the patient has achieved at least a 4 point reduction in his/her SELENA SLEDAI score, has not had more than a 0.30 point increase in his/her PGA score and has not gained a new BILAG A organ domain score or has not gained 2 new BILAG B organ domain scores, compared to his/her baseline SELENA SLEDAI score, PGA score and BILAG score, respectively. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In another specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient's prednisone dose has been reduced. In another specific embodiment, a lupus patient that is being or has been treated with an antagonist of Neutrokine-alpha is considered to be responding/have responded to treatment if the patient's prednisone dose has been reduced compared to the patient's baseline prednisone dose, the prednisone dose the patient was taking just prior to that patient's commencing of treatment with the antagonist of Neutrokine-alpha. In another specific embodiment, a lupus patient that is being or has been treated with an antagonist of Neutrokine-alpha is considered to be responding/have responded to treatment if the patient's prednisone dose has been reduced by at least 25%. In another specific embodiment, a lupus patient that is being or has been treated with an antagonist of Neutrokine-alpha is considered to be responding/have responded to treatment if the patient's prednisone dose has been reduced by at least 25% to less than or equal to 7.5 mg/day. In another specific embodiment, a lupus patient that is being or has been treated with an antagonist of Neutrokine-alpha is considered to be responding/have responded to treatment if the patient's prednisone dose has been reduced by at least 25% from the patient's baseline prednisone dose to less than or equal to 7.5 mg/day. In another specific embodiment, a lupus patient that is being or has been treated with an antagonist of Neutrokine-alpha is considered to be responding/have responded to treatment if the patient's prednisone dose has been reduced by at least 50%. In another specific embodiment, a lupus patient that is being or has been treated with an antagonist of Neutrokine-alpha is considered to be responding/have responded to treatment if the patient's prednisone dose has been reduced by at least 50% to less than or equal to 7.5 mg/day. In another specific embodiment, a lupus patient that is being or has been treated with an antagonist of Neutrokine-alpha is considered to be responding/have responded to treatment if the patient's prednisone dose has been reduced by at least 50% from the patient's baseline prednisone dose to less than or equal to 7.5 mg/day. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

Other measures can be used to measure the quality of a lupus patient's response to treatment. In a specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has an improved SF-36 Health Survey Score. In another specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has an improved SF-36 Health Survey Score compared to the patient's baseline SF-36 Health Survey Score. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In a specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has an improved EQ-5D score. In another specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has an improved EQ-5D score compared to the patient's baseline EQ-5D score. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In a specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient demonstrates reduced fatigue as shown by the patient's FACIT-F score. In another specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient demonstrates reduced fatigue as shown by the patient's FACIT-F score compared to the patient's baseline FACIT-F score. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In a specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has an improved DAS28 score. In another specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has an improved DAS28 score compared to the patient's baseline DAS28 score. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In another specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has a decreased frequency and/or duration of flares. In another specific embodiment, a lupus patient that is being or has been treated with an antagonist of Neutrokine-alpha is considered to be responding/have responded to treatment if the patient has a decreased frequency and/or duration of flares compared to the frequency and/or duration of flares prior to treatment with the antagonist of Neutrokine-alpha. In another specific embodiment, a lupus patient that is being or has been treated with an antagonist of Neutrokine-alpha is considered to be responding/have responded to treatment if the patient has a decreased severity of flares. In another specific embodiment, a lupus patient that is being or has been treated with an antagonist of Neutrokine-alpha is considered to be responding/have responded to treatment if the patient has a decreased severity of flares compared to the severity of flares prior to treatment with the antagonist of Neutrokine-alpha. The SLE flare index assesses the frequency and severity of exacerbations in lupus symptoms (flares). Flares are categorized as "mild or moderate" or "severe". Mild or moderate flares involve one or more of the following: change in SELENA SLEDAI score of 3 points or more; new/worse discoid, photosensitive, profundus, cutaneous vasculitis or bullous lupus; nasopharyngeal ulcers; pleuritis; pericarditis; arthritis; fever (SLE); increase in Prednisone, but not to more than 0.5 mg/kg/day; added NSAID or Plaquenil for disease activity; and greater than 1.0 increase in PGA score, but not to more than 2.5. Severe flares involve one or more of the following: change in SELENA SLEDAI score to greater than 12; new/worse CNS-SLE; vasculitis; nephritis; myositis; Plt <60,000; heme anemia (<7% or decrease in Hb >3%); doubling of Prednisone dosage; increase in Prednisone to more than 0.5 mg/kg/day; prescription of Cytoxan; prescription of Azathioprine; prescription of Methotrexate; hospitalization (SLE) and increase in PGA score to more than 2.5. In another specific embodiment, a lupus patient that is being or has been treated with an antagonist of Neutrokine-alpha is considered to be responding/have responded to treatment if the patient has a decreased frequency and/or severity of flares as measured by the SLE flare index. In another specific embodiment, a lupus patient that is being or has been treated with an antagonist of Neutrokine-alpha is considered to be responding/have responded to treatment if the patient has a decreased frequency and/or severity of flares as measured the SLE flare index compared to the frequency and/or severity of flares prior to treatment with the antagonist of Neutrokine-alpha. In another specific embodiment, a lupus patient that is being or has been treated with an antagonist of Neutrokine-alpha is considered to be responding/have responded to treatment if the patient has a decreased frequency and/or severity of flares as measured by a modified version of the SLE flare index. In another specific embodiment, a lupus patient that is being or has been treated with an antagonist of Neutrokine-alpha is considered to be responding/have responded to treatment if the patient has a decreased frequency and/or severity of flares as measured by a modified version of the SLE flare index compared to the frequency and/or severity of flares prior to treatment with the antagonist of Neutrokine-alpha. The modified version of the SLE flare index excludes severe flares triggered by SELENA SLEDAI score change alone. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

The above described disease activity indices (e.g., SELENA SLEDAI, PGA, BILAG, SLE flare index, SF-36 Health Survey Score, EQ-5D, FACIT-F, DAS28) may be used to evaluate the status of a lupus patient individually or in combination. Improvements in a patient's health as measured by these disease activity indices may also be assessed at a time following commencement of treatment with an antagonist of Neutrokine-alpha or other immunomodulatory agent known in the art and/or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, in relation to one or more of the patient's previous disease activity index score measurements. Additionally, in a specific embodiment, a lupus patient that is being or has been treated with an antagonist of Neutrokine-alpha or other immunomodulatory agent is considered to be responding/have responded to treatment if the patient maintains an improved disease activity score relative to a previous measurement. In a specific embodiment, one or more disease activity index scores are assessed prior to beginning treatment with an antagonist of Neutrokine-alpha or other immunomodulatory agent at 1, 2, 3, 4, 5, 6 7, 8, 9, 10, 11, or 12 weeks, months and/or years following commencement of treatment with the an antagonist of Neutrokine-alpha or other immunomodulatory agent. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In a specific embodiment, a lupus patient with disease manifestation in one or more organs/systems is treated with an antagonist of Neutrokine-alpha and/or other immunomodulatory agent known in the art and/or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. In specific embodiments, a lupus patient with disease manifestation in one or more internal organ systems, with or without involvement of mucocutaneous and/or musculoskeletal systems, is treated with an antagonist of Neutrokine-alpha and/or other immunomodulatory agent known in the art and/or described herein. In specific embodiments, a lupus patient with disease manifestation in one or more internal organ systems, without involvement of mucocutaneous and/or musculoskeletal systems, is treated with an antagonist of Neutrokine-alpha and/or other immunomodulatory agent known in the art and/or described herein. In lupus, disease manifestations involving the mucocutaneous and/or musculoskeletal systems include, but are not limited to: discoid rash, malar rash, or other skin eruption, mucosal ulceration, panniculitis, cutaneous vasculitis, cutaneous thrombosis, digital infarcts, digital thrombosis, alopecia, peri-ungual erythema, chilblains, splinter hemorrhages, myositis, polyarthritis, arthritis, tendonitis, arthralgia and myalgia. In lupus, internal organ systems that may be affected by lupus, include, but are not limited to, the nervous system, the circulatory system, the respiratory system, the urinary/excretory system, the digestive system, and the eyes. Lupus disease manifestation in the nervous system include, but are not limited to aseptic meningitis, cerebral vasculitis, demyelinating syndrome, myelopathy, acute confusional state, psychosis, acute inflammatory demyelinating polyradiculoneuropathy, mononeuropathy, cranial neuropathy, plexopathy, polyneuropathy, seizure disorder, status epilepticus, cerebrovascular disease not due to vasculitis, cognitive dysfunction, movement disorder, autonomic disorder, cerebellar ataxia, headache, migraine, mood disorder and anxiety disorder. Lupus disease manifestations in the circulatory system include, but are not limited to myocarditis, cardiac failure, arrhythmia, new valvular dysfunction, serositis, cardiac tamponade, pleural effusion with dyspnoea, pulmonary hemorrhage, pulmonary vasculitis, interstitial alveolitis, interstitial pneumonitis, shrinking lung syndrome, aortitis and coronary vasculitis. Lupus disease manifestations in the digestive system include, but are not limited to peritonitis, abdominal serositis, ascites, lupus enteritris, lupus colitis, malabsorption, protein losing enteropathy, hepatitis, intestinal pseudo-obstruction, acute cholecystitis and acute pancreatitis. Lupus disease manifestations associated with the eye include, but are not limited to orbital inflammation, keratitis, anterior uveitis, posterior uveitis, retinal vasculitis, episcleritis, scleritis, retinal/choroidal vaso-occlusive disease, cutoid bodies, optic neuritis and anterior ischemic optic neuropathy.

A patient's response to treatment with an antagonist of Neutrokine-alpha or other immunomodulatory agent known in the art and/or described herein, including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, may also be monitored by assessing biomarkers at one or more intervals after commencing treatment and comparing the patient's biomarker assessment with the patient's baseline and/or a previous measurement for the same biomarker(s). Biomarkers that may be assessed include, but are not limited to, immunoglobulin levels (e.g., total serum immunoglobulin, as well as serum IgM, IgG, IgA, and/or IgE levels), autoantibody levels (e.g., anti-dsDNA antibody, anti-CCP antibody, anti-Ro/SS-A antibody, anti-La/SS-B antibody, anti-RNP antibody, anti-cardiolipin (anti-phospholipid) antibody and anti-Sm antibody levels as well as ANA titer), B cell numbers (e.g., total B cell numbers, activated B cell numbers, naïve B cell numbers, memory B cell numbers, plasma B cell numbers, and plasmacytoid B cell numbers, total CD19+ B cells and/or CD20+ B cells), C4 complement level, C3 complement level. In a specific embodiment, biomarker measurements are assessed prior to beginning treatment with an antagonist of Neutrokine-alpha or other immunomodulatory agent and/or at 1, 2, 3, 4, 5, 6 7, 8, 9, 10, 11, or 12 weeks, months and/or years following commencement of treatment with the antagonist of Neutrokine-alpha or other immunomodulatory agent. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In a specific embodiment, a lupus patient that is being or has been treated with an antagonist of Neutrokine-alpha or other immunomodulatory agent known in the art and/or described herein, including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has a decreased level of immunoglobulin (e.g., total serum immunoglobulin, as well as serum IgM, IgG, IgA, and/or IgE levels) compared to the patient's baseline measurement of immunoglobulin. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. In a specific embodiment, a lupus patient that is being or has been treated with an antagonist of Neutrokine-alpha or other immunomodulatory agent is considered to be responding/have responded to treatment if the patient has a decreased level of immunoglobulin (e.g., total serum immunoglobulin, as well as serum IgM, IgG, IgA, and/or IgE levels) compared to one or more of the patient's previous measurements of immunoglobulin. In a specific embodiment, a lupus patient that is being or has been treated with an antagonist of Neutrokine-alpha or other immunomodulatory agent is considered to be responding/have responded to treatment if the patient maintains a decreased level of immunoglobulin (e.g., total serum immunoglobulin, as well as serum IgM, IgG, IgA, and/or IgE levels) compared to one or more of the patient's previous measurements of immunoglobulin. In a specific embodiment, a lupus patient that is being or has been treated with an antagonist of Neutrokine-alpha or other immunomodulatory agent is considered to be responding/have responded to treatment if the patient achieves a normal level of immunoglobulin (e.g., total serum immunoglobulin, as well as serum IgM, IgG, IgA, and/or IgE levels).

In a specific embodiment, a lupus patient that is being or has been treated with an antagonist of Neutrokine-alpha including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has a decreased level of autoantibody (e.g., anti-dsDNA antibody, anti-CCP antibody, anti-Ro/SS-A antibody, anti-La/SS-B antibody, anti-RNP antibody, anti-cardiolipin (anti-phospholipid) antibody and anti-Sm antibody levels as well as ANA titer) compared to the patient's baseline measurement of autoantibody. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. In a specific embodiment, a lupus patient that is being or has been treated with an antagonist of Neutrokine-alpha or other immunomodulatory agent is considered to be responding/have responded to treatment if the patient has a decreased level of autoantibody (e.g., anti-dsDNA antibody, anti-CCP antibody, anti-Ro/SS-A antibody, anti-La/SS-B antibody, anti-RNP antibody, anti-cardiolipin (anti-phospholipid) antibody and anti-Sm antibody levels as well as ANA titer) compared to one or more of the patient's previous measurements of autoantibody. In a specific embodiment, a lupus patient that is being or has been treated with an antagonist of Neutrokine-alpha or other immunomodulatory agent is considered to be responding/have responded to treatment if the patient maintains a decreased level of autoantibody (e.g., anti-dsDNA antibody, anti-CCP antibody, anti-Ro/SS-A antibody, anti-La/SS-B antibody, anti-RNP antibody, anti-cardiolipin (anti-phospholipid) antibody and anti-Sm antibody levels as well as ANA titer) compared to one or more of the patient's previous measurements of autoantibody. In a specific embodiment, a lupus patient that is being or has been treated with an antagonist of Neutrokine-alpha or other immunomodulatory agent is considered to be responding/have responded to treatment if the patient achieves a normal level of autoantibody (e.g., anti-dsDNA antibody, anti-CCP antibody, anti-Ro/SS-A antibody, anti-La/SS-B antibody, anti-RNP antibody, anti-cardiolipin (anti-phospholipid) antibody and anti-Sm antibody levels as well as ANA titer). In a specific embodiment, autoantibodies of the IgG isotype are measured.

In a specific embodiment, a lupus patient that is being or has been treated with an antagonist of Neutrokine-alpha or other immunomodulatory agent including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has a decreased number of B cells (e.g., total B cell numbers, activated B cell numbers, naïve B cell numbers, plasma B cell numbers, and plasmacytoid B cell numbers, total CD19+ B cell numbers and/or CD20+ B cell numbers) compared to the patient's baseline measurement of B cell number. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. In a specific embodiment, a lupus patient that is being or has been treated with an antagonist of Neutrokine-alpha or other immunomodulatory agent is considered to be responding/have responded to treatment if the patient has a decreased number of B cells (e.g., total B cell numbers, activated B cell numbers, naïve B cell numbers, plasma B cell numbers, and plasmacytoid B cell numbers, total CD19+ B cell numbers and/or CD20+ B cell numbers) compared to one or more of the patient's previous measurements of B cell number. In a specific embodiment, a lupus patient that is being or has been treated with an antagonist of Neutrokine-alpha or other immunomodulatory agent is considered to be responding/have responded to treatment if the patient maintains a decreased number of B cells (e.g., total B cell numbers, activated B cell numbers, naïve B cell numbers, plasma B cell numbers, and plasmacytoid B cell numbers, total CD19+ B cell numbers and/or CD20+ B cell numbers) compared to one or more of the patient's previous measurements of B cell number. In a specific embodiment, a lupus patient that is being or has been treated with an antagonist of Neutrokine-alpha or other immunomodulatory agent is considered to be responding/have responded to treatment if the patient achieves a normal number of B cells (e.g., total B cell numbers, activated B cell numbers, naïve B cell numbers, plasma B cell numbers, and plasmacytoid B cell numbers, total CD19+ B cell numbers and/or CD20+ B cell numbers).

In a specific embodiment, a lupus patient that is being or has been treated with an antagonist of Neutrokine-alpha or other immunomodulatory agent known in the art and/or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has an increased serum complement factor C4 level compared to the patient's baseline measurement of C4. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. In a specific embodiment, a lupus patient that is being or has been treated with an antagonist of Neutrokine-alpha or other immunomodulatory agent is considered to be responding/have responded to treatment if the patient has an increased level of C4 compared to one or more of the patient's previous measurements of C4. In a specific embodiment, a lupus patient that is being or has been treated with an antagonist of Neutrokine-alpha or other immunomodulatory agent is considered to be responding/have responded to treatment if the patient maintains an increased level of C4 compared to one or more of the patient's previous measurements of C4. In a specific embodiment, a lupus patient that is being or has been treated with an antagonist of Neutrokine-alpha or other immunomodulatory agent is considered to be responding/have responded to treatment if the patient achieves a normal level of C4.

In a specific embodiment, a lupus patient that is being or has been treated with an antagonist of Neutrokine-alpha or other immunomodulatory agent known in the art and/or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has an increased serum complement factor C3 level compared to the patient's baseline measurement of C3. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. In a specific embodiment, a lupus patient that is being or has been treated with an antagonist of Neutrokine-alpha or other immunomodulatory agent is considered to be responding/have responded to treatment if the patient has an increased level of C3 compared to one or more of the patient's previous measurements of C3. In a specific embodiment, a lupus patient that is being or has been treated with an antagonist of Neutrokine-alpha or other immunomodulatory agent is considered to be responding/have responded to treatment if the patient maintains an increased level of C3 compared to one or more of the patient's previous measurements of C3. In a specific embodiment, a lupus patient that is being or has been treated with an antagonist of Neutrokine-alpha or other immunomodulatory agent is considered to be responding/have responded to treatment if the patient achieves a normal level of C3.

In specific embodiments, the invention provides a method of treating a patient that has previously been treated with one or more immunosuppressants comprising administering a therapeutically effective amount of an antagonist of Neutrokine-alpha or other immunomodulatory agent known in the art and/or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL. In specific embodiments, the invention provides a method of treating a patient that has previously been diagnosed with systemic lupus erythematosus (lupus) and has previously been treated with one or more immunosuppressants comprising administering a therapeutically effective amount of an antagonist of Neutrokine-alpha or other immunomodulatory agent. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. In specific embodiments, the immunosuppressant the patient was previously treated with is azathioprine (e.g., IMURAN™), cyclophosphamide (e.g., Cytoxan®, Neosar®, CTX), a calcineurin inhibitor, for example, FK506, tacrolimus or cyclosporine (e.g., PROGRAF®) and/or CELLCEPT® (mycophenolate motefil, of which the active metabolite is mycophenolic acid).

Most current therapies for lupus and other autoimmune diseases utilize medications that non-specifically block various inflammatory pathways. Perhaps the most dangerous medications used in this therapy are corticosteroids. While corticosteroids such as prednisone are essential in controlling disease manifestations, they also have numerous adverse effects on patient health such as, global immunosuppression leading to infection, osteoporosis leading to fractures, and atherosclerosis leading to early onset heart attacks and strokes. In a clinical trial, applicants found that treatment with an antibody that neutralizes Neutrokine-alpha protein, given as an IV infusion on days 0, 14, 28 and then every four weeks until week 52, was effective in reducing the dosage of the corticosteroid prednisone which was necessary to ameliorate disease manifestations in lupus patients. Specifically, treatment with the anti-Neutrokine-alpha antibody appeared to be associated with reduced prednisone use during the last three months of the treatment period. In patients that had an ANA titer of 1:80 or greater, and/or greater than or equal to 30 IU/mL of anti-dsDNA at baseline, a greater percentage of subjects receiving the anti-Neutrokine-alpha antibody had their prednisone dose reduced, while conversely a greater number of subjects receiving placebo treatment had increases to a prednisone dose greater than 7.5 mg/day.

Accordingly, in one embodiment, the invention provides a method of reducing the frequency of corticosteroid treatments and/or the quantity of corticosteroid administered to a patient comprising administering a therapeutically effective amount of an antagonist of Neutrokine-alpha or other immunomodulatory agent known in the art and/or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL. In specific embodiments, the corticosteroid is prednisone, prednisolone, hydrocortisone, methylprednisolone or dexamethasone. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. In a specific embodiment, the patient in whom corticosteroid therapy is reduced is a patient suffering from inflammation. In another specific embodiment, the patient in whom corticosteroid therapy is reduced is a patient suffering from an autoimmune disease, including but not limited to, rheumatoid arthritis, lupus, Sjogren's syndrome or other autoimmune disease, such as one listed herein.

Accordingly, in a specific embodiment, the invention provides a method of reducing the frequency of corticosteroid treatments and/or the quantity of corticosteroid administered to a systemic lupus erythematosus (lupus) patient comprising administering a therapeutically effective amount of an antagonist of Neutrokine-alpha or other immunomodulatory agent known in the art and/or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL. In another specific embodiment, the invention provides a method of reducing the frequency of prednisone treatments and/or the quantity of prednisone administered to a systemic lupus erythematosus (lupus) patient comprising administering a therapeutically effective amount of an antagonist of Neutrokine-alpha or other immunomodulatory agent including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL. In this context "therapeutically effective amount" refers to an amount that reduces the corticosteroid necessary to alleviate disease manifestations for which corticosteroids are typically prescribed. These manifestations are well known by clinicians/physicians, as are the methodologies for determining antibody/composition amount effective in reducing the severity of these manifestations. In preferred embodiments, the dosage of the antibody of the invention administered to a patient is 0.1 mg/kg to 100 mg/kg of the patient's body weight. More preferably, the dosage administered to a patient is between 0.1 mg/kg and 20 mg/kg of the patient's body weight. In the most preferred embodiments, the dose administered to a patient is 1, 4, 10, or 20 mg/kg.

In a specific embodiment, the amount of corticosteroid (e.g., prednisone) administered to a patient is lowered from a previously higher dose to ≤80 milligrams/day while the same patient is concomitantly on a treatment regimen comprising administration of an antagonist of Neutrokine-alpha or other immunomodulatory agent known in the art or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL. In a specific embodiment, the amount of corticosteroid (e.g., prednisone) administered to a patient is lowered from a previously higher dose to ≤40 milligrams/day while the same patient is concomitantly on a treatment regimen comprising administration of an antagonist of Neutrokine-alpha or other immunomodulatory agent. In a specific embodiment, the amount of corticosteroid (e.g., prednisone) administered to a patient is lowered from a previously higher dose to less than 20 milligrams/day while the same patient is concomitantly on a treatment regimen comprising administration of an antagonist of Neutrokine-alpha or other immunomodulatory agent. In a specific embodiment, the amount of corticosteroid (e.g., prednisone) administered to a patient is lowered from a previously higher dose to ≤10 milligrams/day while the same patient is concomitantly on a treatment regimen comprising administration of an antagonist of Neutrokine-alpha or other immunomodulatory agent. In a specific embodiment, the amount of corticosteroid (e.g., prednisone) administered to a patient is lowered from a previously higher dose to ≤8 milligrams/day while the same patient is concomitantly on a treatment regimen comprising administration of an antagonist of Neutrokine-alpha or other immunomodulatory agent. In a specific embodiment, the amount of corticosteroid (e.g., prednisone) administered to a patient is lowered from a previously higher dose to ≤6 milligrams/day while the same patient is concomitantly on a treatment regimen comprising administration of an antagonist of Neutrokine-alpha or other immunomodulatory agent. In a specific embodiment, the amount of corticosteroid (e.g., prednisone) administered to a patient is lowered from a previously higher dose to ≤4 milligrams/day while the same patient is concomitantly on a treatment regimen comprising administration of an antagonist of Neutrokine-alpha or other immunomodulatory agent. In a specific embodiment, the amount of corticosteroid (e.g., prednisone) administered to a patient is lowered from a previously higher dose to ≤2 milligrams/day while the same patient is concomitantly on a treatment regimen comprising administration of an antagonist of Neutrokine-alpha or other immunomodulatory agent. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In a specific embodiment, the amount of corticosteroid (e.g., prednisone) administered to a patient is lowered from a previously higher dose to ≤7.5 milligrams/day while the same patient is concomitantly on a treatment regimen comprising administration of an antagonist of Neutrokine-alpha or other immunomodulatory agent known in the art and/or described herein. In a specific embodiment, the amount of corticosteroid (e.g., prednisone) administered to a patient is ultimately lowered by at least 25% while the patient is concomitantly on a treatment regimen comprising administration of an antagonist of Neutrokine-alpha or other immunomodulatory agent compared to the dose of prednisone the patient was taking prior to beginning the treatment regimen comprising administration of an antagonist of Neutrokine-alpha or other immunomodulatory agent. In a specific embodiment, the amount of corticosteroid (e.g., prednisone) administered to a patient is ultimately lowered by at least 50% while the patient is concomitantly on a treatment regimen comprising administration of an antagonist of Neutrokine-alpha or other immunomodulatory agent compared to the dose of prednisone the patient was taking prior to beginning the treatment regimen comprising administration of an antagonist of Neutrokine-alpha or other immunomodulatory agent. In a specific embodiment, the amount of corticosteroid (e.g., prednisone) administered to a patient is ultimately lowered by at least 25% to ≤7.5 milligrams/day while the patient is concomitantly on a treatment regimen comprising administration of an antagonist of Neutrokine-alpha or other immunomodulatory agent compared to the dose of prednisone the patient was taking prior to beginning the treatment regimen comprising administration of an antagonist of Neutrokine-alpha or other immunomodulatory agent. In a specific embodiment, the amount of corticosteroid (e.g., prednisone) administered to a patient is ultimately lowered by at least 50% to ≤7.5 milligrams/day while the patient is concomitantly on a treatment regimen comprising administration of an antagonist of Neutrokine-alpha or other immunomodulatory agent compared to the dose of prednisone the patient was taking prior to beginning the treatment regimen comprising administration of an antagonist of Neutrokine-alpha or other immunomodulatory agent. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In a specific embodiment, a patient is taken off, either temporarily or permanently, corticosteroid (e.g., prednisone) therapy while the same patient is concomitantly on a treatment regimen comprising administration of an antagonist of Neutrokine-alpha or other immunomodulatory agent. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In specific embodiments, antagonists of Neutrokine-alpha or other immunomodulatory agents known in the art and/or described herein are used to treat patients with clinical diagnosis of rheumatoid arthritis (RA). In specific embodiments, the rheumatoid arthritis patient treated will not have a B cell malignancy. Moreover, the rheumatoid arthritis patient is optionally further treated with any one or more agents employed for treating RA such as salicylate; nonsteroidal anti-inflammatory drugs such as indomethacin, phenylbutazone, phenylacetic acid derivatives (e.g., ibuprofen and fenoprofen), naphthalene acetic acids (naproxen), pyrroleal-kanoic acid (tometin), indoleacetic acids (sulindac), halogenated anthranilic acid (meclofenamate sodium), piroxicam, zomepirac and diflunisal; antimalarials such as chloroquine; gold salts; penicillamine; or immunosuppressive agents such as methotrexate or corticosteroids in dosages known for such drugs or reduced dosages. Preferably however, the rheumatoid arthritis patient is only treated with the antagonist of Neutrokine-alpha or other immunomodulatory agent known in the art and/or described herein. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. Such immunomodulatory agents are administered to the RA patient according to a dosing schedule as described infra, which may be readily determined by one of ordinary skill in the art. The primary response is determined by the Paulus index (Paulus et al. Arthritis Rheum. 33:477-484 (1990)), i.e., improvement in morning stiffness, number of painful and inflamed joints, erythrocyte sedimentation (ESR), and at least a 2-point improvement on a 5-point scale of disease severity assessed by patient and by physician. Administration of antagonist of Neutrokine-alpha or other immunomodulatory agent known in the art and/or described herein will alleviate one or more of the symptoms of RA in the patient treated as described above.

In a phase 2 clinical trial (Example 3) in which rheumatoid arthritis patients received treatment an antibody that neutralizes Neutrokine-alpha protein, given as an IV infusion on days 0, 14, 28 and then every four weeks until week 24, treatment was more likely to ameliorate symptoms associated with rheumatoid arthritis in patients that had a DAS28 score greater than 5.1, patients that had not previously received anti-TNF therapy, and/or patients that had rheumatoid factor in his/her blood plasma and/or serum prior to commencing treatment with the antibody that neutralizes Neutrokine-alpha protein. Additional subgroups that appeared to be more likely to respond to treatment with the antibody that neutralizes Neutrokine-alpha protein included male patients, patients that had anti-CCP (cyclic citrullinated peptide) antibodies in his/her blood plasma and/or serum, patients that received methotrexate concomitantly with the antibody that neutralizes Neutrokine-alpha protein, patients that had previously failed treatment with methotrexate, and/or patients that had previously failed methotrexate therapy and at least one other DMARD therapy.

Accordingly, the invention provides for a method of treating a rheumatoid arthritis patient with antagonist of Neutrokine-alpha or other immunomodulatory agent known in the art and/or described herein, wherein said rheumatoid arthritis patient has any one or more of the following characteristics: the patient has not previously received anti-TNF therapy, e.g., Infliximab (also known as Remicade™ Centocor, Inc.), adalimumab (Humira® from Abbott Laboratories) or etanercept (Enbrel®); the patient has rheumatoid factor in his/her blood plasma and/or serum; the patient has measurable anti-CCP (cyclic citrullinated peptide) antibodies in his/her blood plasma and/or serum; the patient has an elevated CRP (C reactive protein) level in his/her blood plasma and/or serum; the patient previously failed treatment with one or more disease-modifying antirheumatic drugs; that patient has a high modified disease activity score (DAS28); the patient has swollen and tender joints; the patient suffers from morning stiffness; the patient has an increased erythrocyte sedimentation rate (ESR) and/or the patient is male. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. In specific embodiments, the rheumatoid arthritis patient has equal to or greater than 12 IU/ml of rheumatoid factor in his/her blood plasma and/or serum. In specific embodiments, elevated CRP level are defined as at least 1.5 milligrams per liter. In specific embodiments, an elevated CRP level is defined as at least 5 milligrams per liter. In specific embodiments, an elevated CRP level is defined as at least 6 milligrams per liter. In specific embodiments, an elevated CRP level is defined as at least 9 milligrams per liter. In specific embodiments, an elevated CRP level is defined as at least 10 milligrams per liter. In specific embodiments, an elevated CRP level is defined as at least 20 milligrams per liter. In specific embodiments, the rheumatoid arthritis patient has equal to or greater than 10 units of anti-CCP antibody in his/her blood plasma and/or serum. In specific embodiments, the rheumatoid arthritis patient has equal to or greater than 20 units of anti-CCP antibody in his/her blood plasma and/or serum. In specific embodiments, the patient previously failed treatment with one or more DMARDs, including but not limited to methotrexate, aminoquinolone, sulfasalazine, and leflunomide. In specific embodiments, the patient previously failed treatment with methotrexate. In specific embodiments, the patient has a DAS28 score greater than 5.1. In specific embodiments, the patient has at least 6 swollen joints and at least 8 tender joints. In specific embodiments, the patient has an ESR greater than 28 mm/hours. In specific embodiments, the patient suffers from morning stiffness for at least 45 minutes. In specific embodiments, the patient suffers from morning stiffness for at least an hour. In specific embodiments, the patient suffers from morning stiffness for at least an hour and a half. In specific embodiments, the patient suffers from morning stiffness for at least 2 hours. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

Accordingly, the invention provides for a method of treating a rheumatoid arthritis patient with an antagonist of Neutrokine-alpha or other immunomodulatory agent known in the art and/or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, wherein said rheumatoid arthritis patient has any one or more of the following characteristics: the patient has not previously received anti-TNF therapy, e.g., Infliximab (also known as Remicade™ Centocor, Inc.), adalimumab (Humira® from Abbott Laboratories) or etanercept (Enbrel®); the patient has rheumatoid factor in his/her blood plasma and/or serum; the patient has measurable anti-CCP (cyclic citrullinated peptide) antibodies in his/her blood plasma and/or serum; the patient has an elevated CRP (C reactive protein) level in his/her blood plasma and/or serum; the patient previously failed treatment with one or more disease-modifying antirheumatic drugs; that patient has a high modified disease activity score (DAS28); the patient has swollen and tender joints; the patient suffers from morning stiffness; the patient has an increased erythrocyte sedimentation rate (ESR) and/or the patient is male. In specific embodiments, the rheumatoid arthritis patient has equal to or greater than 12 IU/ml of rheumatoid factor in his/her blood plasma and/or serum. In specific embodiments, elevated CRP level are defined as at least 1.5 milligrams per liter. In specific embodiments, an elevated CRP level is defined as at least 5 milligrams per liter. In specific embodiments, an elevated CRP level is defined as at least 6 milligrams per liter. In specific embodiments, an elevated CRP level is defined as at least 9 milligrams per liter. In specific embodiments, an elevated CRP level is defined as at least 10 milligrams per liter. In specific embodiments, an elevated CRP level is defined as at least 20 milligrams per liter. In specific embodiments, the rheumatoid arthritis patient has equal to or greater than 10 units of anti-CCP antibody in his/her blood plasma and/or serum. In specific embodiments, the rheumatoid arthritis patient has equal to or greater than 20 units of anti-CCP antibody in his/her blood plasma and/or serum. In specific embodiments, the patient previously failed treatment with one or more DMARDs, including but not limited to methotrexate, aminoquinolone, sulfasalazine, and leflunomide. In specific embodiments, the patient previously failed treatment with methotrexate. In specific embodiments, the patient has a DAS28 score greater than 5.1. In specific embodiments, the patient has at least 6 swollen joints and at least 8 tender joints. In specific embodiments, the patient has an ESR greater than 28 mm/hours. In specific embodiments, the patient suffers from morning stiffness for at least 45 minutes. In specific embodiments, the patient suffers from morning stiffness for at least an hour. In specific embodiments, the patient suffers from morning stiffness for at least an hour and a half. In specific embodiments, the patient suffers from morning stiffness for at least 2 hours.

In another specific embodiment, a rheumatoid arthritis patient that is being or has been treated with an antagonist of Neutrokine-alpha or other immunomodulatory agent known in the art and/or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has achieved an ACR20 Response. The ACR20 is an index developed by the American College of Rheumatology (ACR) to assess patient response to treatment for rheumatoid arthritis. An ACR20 response is defined as at least a 20% reduction in tender joint count and swollen joint count, in addition to an improvement of at least 20% on three of five other assessments of symptoms or disease manifestations (i.e., patient pain assessment, patient global assessment, physician global assessment, patient self-assessed disability, acute-phase reactant [ESR or CRP]). In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In another specific embodiment, a rheumatoid arthritis patient that is being or has been treated with an antagonist of Neutrokine-alpha or other immunomodulatory agent known in the art and/or described herein including but not limited to, an anti-Neutrokine-alpha antibody or antigen-binding fragment thereof, a Neutrokine-alpha receptor protein or fragment or variant thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has achieved an ACR50 Response. The ACR50 is an index developed by the American College of Rheumatology (ACR) to assess patient response to treatment for rheumatoid arthritis. An ACR50 response is defined as at least a 50% reduction in tender joint count and swollen joint count, in addition to an improvement of at least 50% on three of five other assessments of symptoms or disease manifestations (i.e., patient pain assessment, patient global assessment, physician global assessment, patient self-assessed disability, acute-phase reactant [ESR or CRP]). In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

In another specific embodiment, a rheumatoid arthritis patient that is being or has been treated with an antagonist of Neutrokine-alpha or other immunomodulatory agent known in the art and/or described herein including but not limited to, an anti-Neutrokine-alpha antibody or antigen-binding fragment thereof, a Neutrokine-alpha receptor protein (e.g., TACI, BCMA or BAFF-R) or fragment or variant thereof, an anti-Neutrokine-alpha receptor (e.g., TACI, BCMA or BAFF-R) antibody or antigen-binding fragment thereof, Neutrokine-alpha binding polypeptides, Neutrokine-alpha and/or APRIL polypeptide variants, and antisense or siRNAs that target Neutrokine-alpha, APRIL, TACI, BCMA, BAFF-R or other receptor for Neutrokine-alpha and/or APRIL, is considered to be responding/have responded to treatment if the patient has achieved an ACR70 Response. The ACR70 is an index developed by the American College of Rheumatology (ACR) to assess patient response to treatment for rheumatoid arthritis. An ACR70 response is defined as at least a 70% reduction in tender joint count and swollen joint count, in addition to an improvement of at least 70% on three of five other assessments of symptoms or disease manifestations (i.e., patient pain assessment, patient global assessment, physician global assessment, patient self-assessed disability, acute-phase reactant [ESR or CRP]). In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative.

Immunomodulatory Agents

The present invention provides a method of treating a patient that has an ANA titer of 1:80 or greater and/or greater than or equal to 30 IU/mL of anti-dsDNA antibodies in his/her blood plasma or serum with an immunomodulatory agent. The meaning of "immunomodulatory agent" when used herein is discussed supra. In a specific embodiment, the immunomodulatory agent is an antagonist of Neutrokine-alpha. By "antagonist", it is meant agents capable of inhibiting or counteracting the in vitro and/or in vivo functional and/or biological actions of Neutrokine-alpha (e.g., stimulation of differentiation, proliferation, and/or survival of B cells; stimulation of Ig production by B-cells; and binding to a Neutrokine-alpha receptor. This inhibition may occur with or without direct physical contact between the antagonist and the Neutrokine-alpha polypeptide (e.g., the antagonist may modulate an upstream effector of Neutrokine-alpha activity in order to reduce said activity). Assays for testing the ability of Neutrokine-alpha antagonists to inhibit B cell activity are described herein. Neutrokine-alpha antagonists include, but are not limited to, an anti-Neutrokine-alpha antibody or antigen-binding fragment thereof, a Neutrokine-alpha receptor protein or fragment or variant thereof, an antibody that binds a Neutrokine-alpha receptor or antigen binding fragment thereof, a Neutrokine-alpha binding peptide or polypeptide, a Neutrokine-alpha and/or APRIL polypeptide variant (e.g., a dominant negative form of Neutrokine-alpha and/or APRIL). Additional antagonists of Neutrokine-alpha include small molecule antagonists of Neutrokine-alpha, Neutrokine-alpha peptide mimetics, antisense RNAs and short interfering RNAs (siRNAs) that target Neutrokine-alpha, antisense RNAs and short interfering RNAs (siRNAs) that target APRIL, antisense RNAs and short interfering RNAs (siRNAs) that target receptors for Neutrokine-alpha and/or receptors for APRIL. Each of these are described in more detail below.

Neutrokine-Alpha Antagonists

A. Neutrokine-Alpha and APRIL Polypeptides

In a specific embodiment, the Neutrokine-alpha antagonist for use in the methods of the present invention is a Neutrokine-alpha or APRIL polypeptide, fragment or variant. Neutrokine-alpha polypeptides, APRIL polypeptides and fragments and variants thereof are described in more detail below. Neutrokine-alpha protein (SEQ ID NO:2) is a member of the TNF family of ligands that shares amino acid sequence identity to APRIL (SEQ ID NO:4; GenBank Accession No. AF046888; PCT International Publication Number WO97/33902; Hahne, M., et al., J Exp Med. (1998) 188(6):1185-90), TNFα, and lymphotoxin-α (LTα) (Moore, et al., 1999). The full length Neutrokine-alpha gene encodes a 285 amino acid polypeptide that has an intracellular domain between residues 1 and 46, a transmembrane spanning domain between residues 47 and 73 preceded by a non-hydrophobic sequence characteristic of type II membrane bound proteins, and an extracellular domain between residues 74 and 285. Like other members of the TNF family, Neutrokine-alpha functions as a trimeric protein. Upon expression of Neutrokine-alpha at the surface of the cell, the extracellular domain is cleaved at amino acid 134 to release a biologically active trimer. Structural characterization reveals that while the TNF-family ligands demonstrate sequence diversity, they show high structural homology. The Neutrokine-alpha protein, like other members of the TNF-family of ligands, is a 2 layered β-sandwich that forms a TNF-like jellyroll form. The Neutrokine-alpha protein is similar to the other TNF-family ligands in overall structure and dimensions. However, the receptor binding region of Neutrokine-alpha is a more pronounced groove than that observed for other cytokines (Oren, et al., (2002) Nature Structural Biology 9:288-292). Neutrokine-alpha polypeptides are described in more detail in, for example, International Publication Numbers WO98/18921, WO00/50597, WO02/1820, and WO03/033658 each of which are herein incorporated by reference in there entireties.

As described above, Neutrokine-alpha polypeptides function to stimulate B-cell proliferation, differentiation, survival, and Ig secretion. Thus, one would not expect to use the native form of Neutrokine-alpha in the methods of the present invention. However, the Neutrokine-alpha native form may be used as a targeting agent to bring other agents that can inhibit B-cell activity (e.g., cytotoxic moieties or proteins) in proximity with a B-cell (See, for example, Example 12 and 13 of WO00/033658, wherein radiolabelled Neutrokine-alpha is used to target and kill cells expressing Neutrokine-alpha receptors which are predominantly B-cell in origin.) Alternatively, fragments or variants of Neutrokine-alpha which bind to one or more Neutrokine-alpha receptors but do not induce signalling may be used as a Neutrokine-alpha antagonist. Neutrokine-alpha fragments or variants which affect the ability of Neutrokine-alpha to form or maintain stable homotrimers or heterotrimers may also be used as a Neutrokine-alpha antagonist in the methods of the invention. Thus, Neutrokine-alpha polypeptides that may be used in the methods of the present invention include polypeptide fragments or variants of the Neutrokine-alpha protein of SEQ ID NO:2. The polypeptide fragments or variants may be "free-standing," or comprised within a larger polypeptide of which the fragment forms a part or region, most preferably as a single continuous region. In specific embodiments, Neutrokine-alpha polypeptides that may be used in the methods of the invention encompass polypeptide fragments comprising, or alternatively consisting of, the predicted extracellular domain of Neutrokine-alpha (amino acid residues 73-285 of SEQ ID NO:2) and the soluble fragment of Neutrokine-alpha (amino acid residues 134-285 of SEQ ID NO:2). In another embodiment, the polypeptide fragments or variants that may be used in the methods of the invention comprise, or alternatively, consist of, a polypeptide fragment or variant at least 80%, 85%, 90%, 92%, 95%, 96%, 97%, 98% or 99% identical to the polypeptide fragments of native Neutrokine-alpha described above.

In another embodiment, Neutrokine-alpha polypeptide variants that may be used in the methods of the present invention include peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993), incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and even improved characteristics.

APRIL (SEQ ID NO:4) is a member of the TNF family of ligands that shares amino acid sequence identity to Neutrokine-alpha (SEQ ID NO:2; GenBank Accession No. NM_006573; Moore, et al., (1999) Science 285:260-263; Schneider et al., (1999) J. Exp. Med. 189:1747-1756; and Khare et al., (2000) Proc. Natl. Acad Sci. 97:3370-3375), TNFα, and lymphotoxin-α (LTα) (Moore, et al., 1999). The full length APRIL gene encodes a 250 amino acid polypeptide that has an intracellular domain between residues 1 and 28, a transmembrane spanning domain between residues 29 and 49, and an extracellular domain between residues 50 and 250. Like other members of the TNF family, APRIL functions as a trimeric protein. Upon expression of APRIL at the surface of the cell, the extracellular domain is cleaved at amino acid 105 to release a biologically active trimer.

In a specific embodiment, a APRIL polypeptide that may be used in the methods of the present invention includes polypeptide fragments or variants of the APRIL protein of SEQ ID NO:4. The polypeptide fragments may be "free-standing," or comprised within a larger polypeptide of which the fragment forms a part or region, most preferably as a single continuous region. In specific embodiments, APRIL polypeptides that may be used in the methods of the invention encompass polypeptide fragments comprising, or alternatively consisting of, the predicted extracellular domain of APRIL (amino acid residues 50-250 of SEQ ID NO:4) and the soluble fragment of APRIL (amino acid residues 105-250 of SEQ ID NO:4). In another embodiment, the polypeptide fragments or variants that may be used in the methods of the invention comprise, or alternatively, consist of, a polypeptide fragment or variant at least 80%, 85%, 90%, 92%, 95%, 96%, 97%, 98% or 99% identical to the polypeptide fragments of native APRIL described above.

In another embodiment, APRIL polypeptide variants that may be used in the methods of the present invention include peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993), incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and even improved characteristics.

The Neutrokine-alpha and APRIL polypeptides that may be used in the methods of the invention may be expressed or synthesized in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating Neutrokine-alpha or APRIL polynucleotides and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

A preferred Neutrokine-alpha or APRIL fusion protein that may be used in the methods of the invention comprises a heterologous region from immunoglobulin that is useful to stabilize and purify proteins. For example, EP-A-O 464 533 (Canadian counterpart 2045869) and WO00/024782 disclose fusion proteins comprising various portions of constant region of immunoglobulin molecules together with another human protein or part thereof. Neutrokine-alpha immunoglobulin fusion proteins have been described in, for example, Yu, et al., (2000) Nat Immunol 1:252-256, herein incorporated by reference in its entirety. APRIL immunoglobulin fusion proteins have been described in, for example, PCT Publication WO01/087977, herein incorporated by reference in its entirety. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5 has been fused with Fc portions for the purpose of high-throughput screening assays to identify antagonists of hIL-5. See, D. Bennett et al., J. Molecular Recognition 8:52-58 (1995) and K. Johanson et al., J. Biol. Chem. 270:9459-9471 (1995).

As one of skill in the art will appreciate, and as discussed above, the Neutrokine-alpha and APRIL polypeptides can be fused to other polypeptide sequences. For example, the Neutrokine-alpha polypeptides that may be used in the methods of the current invention may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides.

Such fusion proteins may facilitate purification, may extend shelf-life and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995).

Human serum albumin (HSA, or HA), a protein of 585 amino acids in its mature form (SEQ ID NO:11), is responsible for a significant proportion of the osmotic pressure of serum and also functions as a carrier of endogenous and exogenous ligands. At present, HA for clinical use is produced by extraction from human blood. The production of recombinant HA (rHA) in microorganisms has been disclosed in EP 330 451 and EP 361 991.

The role of albumin as a carrier molecule and its inert nature are desirable properties for use as a carrier and transporter of polypeptides in vivo. The use of albumin as a component of an albumin fusion protein as a carrier for various proteins has been suggested in WO 93/15199, WO 93/15200, and EP 413 622. The use of N-terminal fragments of HA for fusions to polypeptides has also been proposed (EP 399 666). Fusion of albumin to a Therapeutic protein may be achieved by genetic manipulation, such that the DNA coding for HA, or a fragment thereof, is joined to the DNA coding for the Therapeutic protein. A suitable host is then transformed or transfected with the fused nucleotide sequences, so arranged on a suitable plasmid as to express a fusion polypeptide. The expression may be effected in vitro from, for example, prokaryotic or eukaryotic cells, or in vivo e.g., from a transgenic organism.

An albumin fusion protein that may be used in methods of the present invention comprises at least a fragment or variant of a Neutrokine-alpha polypeptide and at least a fragment or variant of human serum albumin, which are associated with one another, preferably by genetic fusion (i.e., the albumin fusion protein is generated by translation of a nucleic acid in which a polynucleotide encoding all or a portion of Neutrokine-alpha is joined in-frame with a polynucleotide encoding all or a portion of albumin) or chemical conjugation to one another. The Neutrokine-alpha polypeptide and albumin protein, once part of the albumin fusion protein, may be referred to as a "portion", "region" or "moiety" of the albumin fusion protein (e.g., a "Neutrokine-alpha portion" or an "albumin protein portion").

In one embodiment, an albumin fusion protein that may be used in the methods of the invention comprises, or alternatively consists of, a Neutrokine-alpha polypeptide and a serum albumin protein. In other embodiments, an albumin fusion protein that may be used in the methods of the invention comprises, or alternatively consists of, a fragment of Neutrokine-alpha and a serum albumin protein. In other embodiments, an albumin fusion protein that may be used in the methods of the invention comprises, or alternatively consists of, a variant of Neutrokine-alpha and a serum albumin protein In preferred embodiments, the serum albumin protein component of the albumin fusion protein is the mature portion of serum albumin.

In further embodiments, an albumin fusion protein that may be used in the methods of the invention comprises, or alternatively consists of, a Neutrokine-alpha polypeptide and a biologically active and/or therapeutically active fragment of serum albumin. In further embodiments, an albumin fusion protein that may be used in the methods of the invention comprises, or alternatively consists of, a Neutrokine-alpha polypeptide and a biologically active and/or therapeutically active variant of serum albumin. In preferred embodiments, the Neutrokine-alpha portion of the albumin fusion protein is the full-length Neutrokine-alpha polypeptide. In a further preferred embodiment, the Neutrokine-alpha protein portion of the albumin fusion protein is the mature, soluble domain of the Neutrokine-alpha polypeptide.

In further embodiments, an albumin fusion protein that may be used in the methods of the invention comprises, or alternatively consists of, a fragment or variant of Neutrokine-alpha and a biologically active and/or therapeutically active fragment or variant of serum albumin. In preferred embodiments, the invention provides an albumin fusion protein comprising, or alternatively consisting of, the mature portion of the Neutrokine-alpha polypeptide and the mature portion of serum albumin. (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, Neutrokine-alpha polypeptides (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment Neutrokine-alpha polypeptides (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Neutrokine-alpha polypeptides (including fragments or variants thereof) may be fused to either the N- or C-terminal end of the heterologous protein (e.g., immunoglobulin Fc polypeptide or human serum albumin polypeptide).

In preferred embodiments, the human serum albumin protein used in the albumin fusion proteins that may be used in the methods of the invention contains one or both of the following sets of point mutations with reference to SEQ ID NO:11: Leu-407 to Ala, Leu-408 to Val, Val-409 to Ala, and Arg-410 to Ala; or Arg-410 to A, Lys-413 to Gln, and Lys-414 to Gln (see, e.g., International Publication No. WO95/23857, hereby incorporated in its entirety by reference herein). In even more preferred embodiments, albumin fusion proteins that may be used in the methods of the invention that contain one or both of above-described sets of point mutations have improved stability/resistance to yeast Yap3p proteolytic cleavage, allowing increased production of recombinant albumin fusion proteins expressed in yeast host cells.

Preferably, the albumin fusion protein that may be used in the methods of the invention comprises HA as the N-terminal portion, and Neutrokine-alpha polypeptide as the C-terminal portion. Alternatively, an albumin fusion protein comprising HA as the C-terminal portion, and Neutrokine-alpha polypeptide as the N-terminal portion may also be used.

In other embodiments, the albumin fusion protein that may be used in methods of the invention has a Neutrokine-alpha polypeptide fused to both the N-terminus and the C-terminus of albumin. In a specific embodiment, the Neutrokine-alpha polypeptides fused at the N- and C-termini are the same. In another embodiment, the Neutrokine-alpha polypeptides fused at the N- and C-termini are different Neutrokine-alpha polypeptides. In another embodiment, a Neutrokine-alpha polypeptide is fused at either the N- or C-terminus of albumin, and a heterologous polypeptide is fused at the remaining terminus.

Additionally, the albumin fusion proteins that may be used in the methods of the invention may include a linker peptide between the fused portions to provide greater physical separation between the moieties. The linker peptide may consist of amino acids such that it is flexible or more rigid.

Generally, the albumin fusion proteins that may be used in the methods of the invention may have one HA-derived region and one Neutrokine-alpha region. Multiple regions of each protein, however, may be used to make an albumin fusion protein that may be used in the methods of the invention. Similarly, more than one protein may be used to make an albumin fusion protein that may be used in the methods of the invention. For instance, a protein may be fused to both the N- and C-terminal ends of the HA. In such a configuration, the protein portions may be the same or different protein molecules. The structure of bifunctional albumin fusion proteins may be represented as: X-HA-Y or Y-HA-X.

In a specific embodiment, Neutrokine-alpha protein or fragment or variant thereof that may be used in the methods of the invention may be conjugated to a cytotoxin (e.g., a cytostatic or cytocidal agent). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In another embodiment, a Neutrokine-alpha protein or fragment or variant thereof that may be used in the methods of the invention may be conjugated to a toxin.

By "toxin" is meant one or more compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium.

In an additional example, the APRIL polypeptides that may be used in the methods of the current invention may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876, 969, issued Mar. 2, 1999, EP Patent 0 413 622, and U.S. Pat. No. 5,766,883, issued Jun. 16, 1998, herein incorporated by reference in their entirety)), resulting in chimeric polypeptides.

Such fusion proteins may facilitate purification, may extend shelf-life and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995).

An albumin fusion protein that may be used in methods of the present invention comprises at least a fragment or variant of an APRIL polypeptide and at least a fragment or variant of human serum albumin, which are associated with one another, preferably by genetic fusion (i.e., the albumin fusion protein is generated by translation of a nucleic acid in which a polynucleotide encoding all or a portion of APRIL is joined in-frame with a polynucleotide encoding all or a portion of albumin) or chemical conjugation to one another. The APRIL polypeptide and albumin protein, once part of the albumin fusion protein, may be referred to as a "portion", "region" or "moiety" of the albumin fusion protein (e.g., an "APRIL portion" or an "albumin protein portion").

In one embodiment, an albumin fusion protein that may be used in the methods of the invention comprises, or alternatively consists of, an APRIL polypeptide and a serum albumin protein. In other embodiments, an albumin fusion protein that may be used in the methods of the invention comprises, or alternatively consists of, a fragment of APRIL and a serum albumin protein. In other embodiments, an albumin fusion protein that may be used in the methods of the invention comprises, or alternatively consists of, a variant of APRIL and a serum albumin protein In preferred embodiments, the serum albumin protein component of the albumin fusion protein is the mature portion of serum albumin.

In further embodiments, an albumin fusion protein that may be used in the methods of the invention comprises, or alternatively consists of, an APRIL polypeptide and a biologically active and/or therapeutically active fragment of serum albumin. In further embodiments, an albumin fusion protein that may be used in the methods of the invention comprises, or alternatively consists of, an APRIL polypeptide and a biologically active and/or therapeutically active variant of serum albumin. In preferred embodiments, the APRIL portion of the albumin fusion protein is the full-length APRIL polypeptide. In a further preferred embodiment, the APRIL portion of the albumin fusion protein is the mature, soluble domain of the APRIL polypeptide.

In further embodiments, an albumin fusion protein that may be used in the methods of the invention comprises, or alternatively consists of, a fragment or variant of APRIL and a biologically active and/or therapeutically active fragment or variant of serum albumin. In preferred embodiments, the invention provides an albumin fusion protein comprising, or alternatively consisting of, the mature portion of the APRIL polypeptide and the mature portion of serum albumin.

In further embodiments, an albumin fusion protein that may be used in the methods of the invention comprises, or alternatively consists of, a fragment or variant of APRIL and a biologically active and/or therapeutically active fragment or variant of serum albumin. In preferred embodiments, the invention provides an albumin fusion protein comprising, or alternatively consisting of, the mature portion of the APRIL polypeptide and the mature portion of serum albumin. (including but not limited to recombinant human serum albumin or fragments or variants thereof (see, e.g., U.S. Pat. No. 5,876, 969, issued Mar. 2, 1999, EP Patent 0 413 622, and U.S. Pat. No. 5,766,883, issued Jun. 16, 1998, herein incorporated by reference in their entirety)). In a preferred embodiment, APRIL polypeptides (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment APRIL polypeptides (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. APRIL polypeptides (including fragments or variants thereof) may be fused to either the N- or C-terminal end of the heterologous protein (e.g., immunoglobulin Fc polypeptide or human serum albumin polypeptide).

In preferred embodiments, the human serum albumin protein used in the albumin fusion proteins that may be used in the methods of the invention contains one or both of the following sets of point mutations with reference to SEQ ID NO:11: Leu-407 to Ala, Leu-408 to Val, Val-409 to Ala, and Arg-410 to Ala; or Arg-410 to A, Lys-413 to Gln, and Lys-414 to Gln (see, e.g., International Publication No. WO95/23857, hereby incorporated in its entirety by reference herein). In even more preferred embodiments, albumin fusion proteins that may be used in the methods of the invention that contain one or both of above-described sets of point mutations have improved stability/resistance to yeast Yap3p proteolytic cleavage, allowing increased production of recombinant albumin fusion proteins expressed in yeast host cells.

Preferably, the albumin fusion protein that may be used in the methods of the invention comprises HA as the N-terminal portion, and APRIL polypeptide as the C-terminal portion. Alternatively, an albumin fusion protein comprising HA as the C-terminal portion, and APRIL polypeptide as the N-terminal portion may also be used.

In other embodiments, the albumin fusion protein that may be used in methods of the invention has an APRIL polypeptide fused to both the N-terminus and the C-terminus of albumin. In a specific embodiment, the APRIL polypeptides fused at the N- and C-termini are the same. In another embodiment, the APRIL polypeptides fused at the N- and C-termini are different APRIL polypeptides. In another embodiment, a APRIL polypeptide is fused at either the N- or C-terminus of albumin, and a heterologous polypeptide is fused at the remaining terminus.

Additionally, the albumin fusion proteins that may be used in the methods of the invention may include a linker peptide between the fused portions to provide greater physical separation between the moieties. The linker peptide may consist of amino acids such that it is flexible or more rigid.

Generally, the albumin fusion proteins that may be used in the methods of the invention may have one HA-derived region and one APRIL region. Multiple regions of each protein, however, may be used to make an albumin fusion protein that may be used in the methods of the invention. Similarly, more than one protein may be used to make an albumin fusion protein that may be used in the methods of the invention. For instance, a protein may be fused to both the N- and C-terminal ends of the HA. In such a configuration, the protein portions may be the same or different protein molecules. The structure of bifunctional albumin fusion proteins may be represented as: X-HA-Y or Y-HA-X.

In a specific embodiment, an APRIL protein or fragment or variant thereof that may be used in the methods of the invention may be conjugated to a cytotoxin (e.g., a cytostatic or cytocidal agent). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In another embodiment, an APRIL protein or fragment or variant thereof that may be used in the methods of the invention may be conjugated to a toxin.

By "toxin" is meant one or more compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium.

Protein engineering may be employed to alter the characteristics of Neutrokine-alpha and APRIL polypeptides to generate polypeptides that may be used in the methods of the invention. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity, decreased activity or increased stability. In addition, they may be purified in higher yields and show better solubility than the corresponding natural polypeptide, at least under certain purification and storage conditions. For instance, for many proteins, including the extracellular domain or the mature form(s) of a secreted protein, it is known in the art that one or more amino acids may be deleted from the N-terminus or C-terminus without substantial loss of biological function. For instance, Ron et al., J. Biol. Chem., 268:2984-2988 (1993) reported modified KGF proteins that had heparin binding activity even if 3, 8, or 27 amino-terminal amino acid residues were missing.

The Neutrokine-alpha and APRIL polypeptides that may be used in the methods of the present invention may be monomers or multimers (i.e., dimers, trimers, tetramers and higher multimers). In specific embodiments, the Neutrokine-alpha and APRIL polypeptides that may be used in the methods of the invention may be homomers or heteromers. A Neutrokine-alpha homomer, refers to a multimer containing only Neutrokine-alpha polypeptides (including Neutrokine-alpha fragments, variants, and fusion proteins, as described herein). These homomers may contain Neutrokine-alpha polypeptides having identical or different amino acid sequences. In specific embodiments, the Neutrokine-alpha polypeptide that may be used in the methods of the present invention are Neutrokine-alpha homodimers (e.g., containing two Neutrokine-alpha polypeptides having identical or different amino acid sequences) or are Neutrokine-alpha homotrimers (e.g., containing three Neutrokine-alpha polypeptides having identical or different amino acid sequences). In a preferred embodiment, the Neutrokine-alpha polypeptides that may be used in the methods of the invention are homotrimers of Neutrokine-alpha. In additional embodiments, the Neutrokine-alpha polypeptide that may be used in the methods of the invention is at least a homodimer, at least a homotrimer, or at least a homotetramer. An APRIL homomer, refers to a multimer containing only APRIL polypeptides (including APRIL fragments, variants, and fusion proteins, as described herein). These homomers may contain APRIL polypeptides having identical or different amino acid sequences. In specific embodiments, the APRIL polypeptide that may be used in the methods of the present invention are APRIL homodimers (e.g., containing two APRIL polypeptides having identical or different amino acid sequences) or are APRIL homotrimers (e.g., containing three APRIL polypeptides having identical or different amino acid sequences). In a preferred embodiment, the APRIL polypeptides that may be used in the methods of the invention are homotrimers of APRIL. In additional embodiments, the APRIL polypeptide that may be used in the methods of the invention is at least a homodimer, at least a homotrimer, or at least a homotetramer.

Heteromeric Neutrokine-alpha refers to a multimer containing heterologous polypeptides (i.e., polypeptides of a different protein) in addition to Neutrokine-alpha polypeptides. In a specific embodiment, the Neutrokine-alpha polypeptide that may be used in the methods of the invention is a heterodimer, a heterotrimer, or a heterotetramer. In additional embodiments, the Neutrokine-alpha polypeptide that may be used in the methods of the invention is a multimer which is at least a heterodimer, at least a heterotrimer, or at least a heterotetramer. Heteromeric APRIL refers to a multimer containing heterologous polypeptides (i.e., polypeptides of a different protein) in addition to APRIL polypeptides. In a specific embodiment, the APRIL polypeptide that may be used in the methods of the invention is a heterodimer, a heterotrimer, or a heterotetramer. In additional embodiments, the APRIL polypeptide that may be used in the methods of the invention is a multimer which is at least a heterodimer, at least a heterotrimer, or at least a heterotetramer. In additional embodiments, the Neutrokine-alpha polypeptide that may be used in the methods of the invention is a heterotrimer comprising both Neutrokine-alpha polypeptides and APRIL polypeptides or fragments or variants thereof. In additional embodiments, the Neutrokine-alpha polypeptide that may be used in the methods of the invention is a heterotrimer comprising one Neutrokine-alpha polypeptide (including fragments or variants) and two APRIL polypeptides (including fragments or variants). In additional embodiments, the Neutrokine-alpha polypeptide that may be used in the methods of the invention is a heterotrimer comprising two Neutrokine-alpha polypeptides (including fragments or variants) and one APRIL polypeptide (including fragments or variants).

In additional embodiments, the Neutrokine-alpha polypeptides that may be used in the methods of the invention are homomeric, especially homotrimeric, Neutrokine-alpha polypeptides, wherein the individual protein components of the multimers comprise, or alternatively, consist of the mature form of Neutrokine-alpha (e.g., amino acids residues 134-285 of SEQ ID NO:2) or fragments or variants thereof. In other specific embodiments, the Neutrokine-alpha polypeptides that may be used in the methods of the invention are heteromeric, especially heterotrimeric, Neutrokine-alpha polypeptides such as a heterotrimer containing two Neutrokine-alpha polypeptides and one APRIL polypeptide or a heterotrimer containing one Neutrokine-alpha polypeptide and two APRIL polypeptides, and wherein the individual protein components of the Neutrokine-alpha heteromer comprise, or alternatively, consist of either the mature extracellular soluble portion of Neutrokine-alpha (e.g., amino acids residues 134-285 of SEQ ID NO:2) or fragments or variants thereof, or the mature extracellular soluble portion APRIL (e.g., amino acid residues 105-250 of SEQ ID NO:4) or fragments or variants thereof.

In additional embodiments, the APRIL polypeptides that may be used in the methods of the invention are homomeric, especially homotrimeric, APRIL polypeptides, wherein the individual protein components of the multimers comprise, or alternatively, consist of the mature form of APRIL (e.g., amino acids residues 105-250 of SEQ ID NO:4) or fragments or variants thereof. In other specific embodiments, the APRIL polypeptides that may be used in the methods of the invention are heteromeric, especially heterotrimeric, APRIL polypeptides such as a heterotrimer containing two APRIL polypeptides and one Neutrokine-alpha polypeptide or a heterotrimer containing one APRIL polypeptide and two Neutrokine-alpha polypeptides, and wherein the individual protein components of the APRIL heteromer comprise, or alternatively, consist of either the mature extracellular soluble portion of APRIL (e.g., amino acid residues 105-250 of SEQ ID NO:4) or fragments or variants thereof, or the mature extracellular soluble portion of Neutrokine-alpha (e.g., amino acids residues 134-285 of SEQ ID NO:2) or fragments or variants thereof.

Multimers that may be used in the methods of the invention may be the result of hydrophobic, hydrophilic, ionic and/or covalent associations and/or may be indirectly linked, by for example, liposome formation. Thus, in one embodiment, multimers, such as, for example, homodimers or homotrimers, are formed when the polypeptides contact one another in solution. In another embodiment, heteromultimers, such as, for example, heterotrimers or heterotetramers, are formed when the polypeptides contact one another in solution. In other embodiments, multimers are formed by covalent associations with and/or between the Neutrokine-alpha polypeptides. In other embodiments, multimers are formed by covalent associations with and/or between the APRIL polypeptides. Such covalent associations may involve one or more amino acid residues contained in the polypeptide sequence (e.g., that recited in SEQ ID NO:2 for Neutrokine-alpha or that recited in SEQ ID NO:4 for APRIL). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a Neutrokine-alpha or APRIL fusion protein (see, e.g., U.S. Pat. No. 5,478,925). In a specific example, the covalent associations are between the heterologous sequence contained in a Neutrokine-alpha-Fc fusion protein (as described herein). In a specific example, the covalent associations are between the heterologous sequence contained in an APRIL-Fc fusion protein (as described herein). In another specific example, covalent associations in the fusion proteins that may be used in the methods of the invention are between heterologous polypeptide sequence from another TNF family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more Neutrokine-alpha polypeptides and/or APRIL polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple Neutrokine-alpha polypeptides and/or APRIL polypeptides separated by peptide linkers may be produced using conventional recombinant DNA technology.

In a specific embodiment, a Neutrokine-alpha antagonist that may be used in the methods of the invention is a dominant negative form of Neutrokine-alpha and/or APRIL. In particular, variants of Neutrokine-alpha and/or APRIL, including dominant negative forms, have been described in, for example, International Patent Publication numbers WO06/

034106, WO05/113598, WO04/089982, WO04/081043 and WO03/057856 and US Patent Publication numbers US20060014248, US20050221443, US20050130892, US20050048626, US2005003480 and US20030166559. Each of the aforementioned references is herein incorporated by reference in its entirety. Such Neutrokine-alpha and/or APRIL polypeptide variants may antagonize Neutrokine-alpha function, for example, by interfering with Neutrokine-alpha and/or APRIL homo- or hetero-multimerization. Alternatively, Neutrokine-alpha and/or APRIL polypeptide variants may prevent polypeptides comprising them from binding to and/or signaling through Neutrokine alpha-receptors such as TACI, BCMA and BAFF-R.

In another embodiment, the Neutrokine-alpha antagonist is the Neutorkine-alpha protein mutant described in Gao et al., (2006) *Biotechnol. Lett.* 28:1649-54, which is herein incorporated by reference in its entirety.

In another embodiment, the Neutrokine-alpha antagonist that may be used in the methods of the invention is Δ BAFF (SEQ ID NO:12).

B. Anti-Neutrokine-Alpha Antibodies

In a specific embodiment, the Neutrokine-alpha antagonist is an anti-Neutrokine-alpha antibody or antigen-binding fragment thereof. Anti-Neutrokine-alpha antibodies and fragments thereof have been described in, for example, PCT Publications WO01/087977, WO03/016468, WO01/60397, WO02/02641 and WO03/55979; US Publication Nos. 2005/0070694 and 2005/0255532; and Cao et al., (2005) *Immunol Lett* 101:87-94; Ch' en et al., (2005) *Cell Immunol* 236:78-85; Liu et al., (2005) *Acta Biochim Biophys Sin (Shanghai)* 37:415-420; Schneider et al., (1999) *J Exp Med* 189:1747-1756; Sun et al., (2006) *Hybridoma* 25:80-85; Sun et al., (2006) *Hybridoma* 25:238-242; and are described in more detail below. Each of the aforementioned references is herein incorporated by reference in its entirety.

The term "antibody," as used herein, refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. Examples of molecules which are described by the term "antibody" in this application include, but are not limited to: single chain Fvs (scFvs), Fab fragments, Fab' fragments, F(ab')$_2$, disulfide linked Fvs (sdFvs), Fvs, and fragments comprising or alternatively consisting of, either a VL or a VH domain. The term "single chain Fv" or "scFv" as used herein refers to a polypeptide comprising a VL domain of antibody linked to a VH domain of an antibody. Antibodies that immunospecifically bind to a particular antigen (e.g. Neutrokine-alpha) may have cross-reactivity with other antigens. Preferably, antibodies that immunospecifically bind to a particular antigen do not cross-react with other antigens. Antibodies that immunospecifically bind to a particular antigen can be identified, for example, by immunoassays or other techniques known to those of skill in the art, e.g., the immunoassays described in U.S. Patent Application No. 60/834,152, filed Jul. 31, 2006, which is hereby incorporated by reference in its entirety.

Antibodies that may be used in the methods of the present invention include, but are not limited to, monoclonal, multi-specific, human or chimeric antibodies, single chain antibodies, Fab fragments, F(ab') fragments, antiidiotypic (anti-Id) antibodies, and epitope-binding fragments of any of the above. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule.

Antibodies that may be used in the methods of the present invention may also include multimeric forms of antibodies. For example, antibodies that may be used in the methods of the present invention may take the form of antibody dimers, trimers, or higher-order multimers of monomeric immunoglobulin molecules. Dimers of whole immunoglobulin molecules or of F(ab')$_2$ fragments are tetravalent, whereas dimers of Fab fragments or scFv molecules are bivalent. Individual monomers within an antibody multimer may be identical or different, i.e., they may be heteromeric or homomeric antibody multimers. For example, individual antibodies within a multimer may have the same or different binding specificities. Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., *Proceedings of the National Academy of Sciences USA* (1997) 94:7509-7514, which is hereby incorporated by reference in its entirety. Antibody homodimers can be converted to Fab'2 homodimers through digestion with pepsin. Another way to form antibody homodimers is through the use of the autophilic T15 peptide described in Zhao and Kohler, *The Journal of Immunology* (2002) 25:396-404, which is hereby incorporated by reference in its entirety.

Alternatively, antibodies can be made to multimerize through recombinant DNA techniques. IgM and IgA naturally form antibody multimers through the interaction with the J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) *Clinical Immunology* 101:21-31. and Frigerio et al., (2000) *Plant Physiology* 123:1483-94., both of which are hereby incorporated by reference in their entireties.) ScFv dimers can also be formed through recombinant techniques known in the art; an example of the construction of scFv dimers is given in Goel et al., (2000) *Cancer Research* 60:6964-6971 which is hereby incorporated by reference in its entirety. Antibody multimers may be purified using any suitable method known in the art, including, but not limited to, size exclusion chromatography.

Unless otherwise defined in the specification, specific binding or immunospecific binding by an antibody means that the antibody binds the target antigen but does not significantly bind to (i.e., cross react with) proteins other than the target antigen, such as other proteins in the same family of proteins (e.g., other TNF family ligands). An antibody that binds a target antigen and does not cross-react with other proteins is not necessarily an antibody that does not bind said other proteins in all conditions; rather, the target antigen-specific antibody preferentially binds the target antigen compared to its ability to bind said other proteins such that it will be suitable for use in at least one type of assay or treatment, i.e., give low background levels or result in no unreasonable adverse effects in treatment. It is well known that the portion of a protein bound by an antibody is known as the epitope. An epitope may either be linear (i.e., comprised of sequential amino acids residues in a protein sequences) or conformational (i.e., comprised of one or more amino acid residues that are not contiguous in the primary structure of the protein but that are brought together by the secondary, tertiary or quaternary structure of a protein). Given that target antigen-specific antibodies bind to epitopes of the target antigen, an antibody that specifically binds the target antigen may or may not bind fragments of the target antigen and/or variants of the target antigen (e.g., proteins that are at least 90% identical to the target antigen) depending on the presence or absence of the epitope bound by a given target antigen-specific antibody in the target antigen fragment or variant. Likewise, target antigen-specific antibodies may bind species orthologues of the target antigen (including fragments thereof) depending on the presence or absence of the epitope recognized by the antibody in the orthologue. Additionally, target antigen-specific antibodies may bind modified forms of the target antigen, for example, target antigen fusion proteins. In such a case when antibodies bind target antigen fusion proteins, the antibody must make binding contact with the target antigen moiety of the fusion protein in order for the binding to be specific. Antibodies that specifically bind to any particular target antigen can be identified, for example, by immunoassays or other techniques known to those of skill in the art, e.g., the immunoassays described in U.S. Patent Application No. 60/834, 152, filed Jul. 31, 2006, which is hereby incorporated by reference in its entirety.

Antibodies that may be used in the methods of the present invention may be "specific" for Neutrokine-alpha, but it is not a requirement. Anti-Neutrokine-alpha antibodies that may be used in the methods of the invention may be described or specified in terms of their cross-reactivity. Antibodies that do not bind any other analog, ortholog, or homolog of a Neutrokine-alpha polypeptide may be used in the methods of the invention. In a specific embodiment, antibodies that may be used in the methods of the invention cross react with APRIL. In specific embodiments, antibodies that may be used in the methods of the invention cross-react with murine, rat and/or rabbit homologs of human proteins and the corresponding epitopes thereof.

In a specific embodiment, antibodies that bind to a Neutrokine-alpha polypeptide, polypeptide fragment, or variant of SEQ ID NO:2, and/or an Neutrokine-alpha epitope (as determined by immunoassays well known in the art for assaying specific antibody-antigen binding) may be used in the methods of the invention. In a specific embodiment, antibodies that may be used in the methods of the invention may bind Neutrokine-alpha polypeptides fused to other polypeptide sequences. For example, Neutrokine-alpha polypeptides may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876, 969, issued Mar. 2, 1999, EP Patent 0 413 622, and U.S. Pat. No. 5,766,883, issued Jun. 16, 1998, herein incorporated by reference in their entirety)), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995).

In another embodiment, antibodies that may be used in the methods of the invention bind mutant Neutrokine-alpha polypeptides that have been generated by random mutagenesis of a polynucleotide encoding the Neutrokine-alpha polypeptide, by error-prone PCR, random nucleotide insertion or other methods prior to recombination. In another embodiment, antibodies that may be used in the methods of the invention bind one or more components, motifs, sections, parts, domains, fragments, etc., of Neutrokine-alpha recombined with one or more components, motifs, sections, parts, domains, fragments, etc. of one or more heterologous molecules. In preferred embodiments, the heterologous molecules are, for example, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II (International Publication No. WO 97/34911), APRIL (J. Exp. Med. 188(6):1185-1190), endokine-alpha (International Publication No. WO 98/07880), OPG, OX40, and nerve growth factor (NGF), and soluble forms of Fas, CD30, CD27, CD40 and 4 IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), TR12, CAD, and v-FLIP. In further embodiments, the heterologous molecules are any member of the TNF family.

In specific embodiments, antibodies that may be used in the methods of the invention bind homomeric, especially homotrimeric, Neutrokine-alpha polypeptides. In other specific embodiments, antibodies that may be used in the methods of the invention bind heteromeric, especially heterotrimeric, Neutrokine-alpha polypeptides such as a heterotrimer containing two Neutrokine-alpha polypeptides and one APRIL polypeptide or a heterotrimer containing one Neutrokine-alpha polypeptide and two APRIL polypeptides. In a specific embodiment, the antibodies that may be used in the methods of the invention bind homomeric, especially homotrimeric, Neutrokine-alpha polypeptides, wherein the individual protein components of the multimers consist of the mature form of Neutrokine-alpha (e.g., amino acids residues 134-285 of SEQ ID NO:2). In other specific embodiments, antibodies that may be used in the methods of the invention bind heteromeric, especially heterotrimeric, Neutrokine-alpha polypeptides such as a heterotrimer containing two Neutrokine-alpha polypeptides and one APRIL polypeptide or a heterotrimer containing one Neutrokine-alpha polypeptide and two APRIL polypeptides, and wherein the individual protein components of the Neutrokine-alpha heteromer consist of either the mature extracellular soluble portion of Neutrokine-alpha (e.g., amino acids residues 134-285 of SEQ ID NO:2) or the mature extracellular soluble portion APRIL (e.g., amino acid residues 105-250 of SEQ ID NO:4).

In specific embodiments, the antibodies that may be used in the methods of the invention bind conformational epitopes of a Neutrokine-alpha monomeric protein. In specific embodiments, the antibodies that may be used in the methods of the invention bind conformational epitopes of a Neutrokine-alpha multimeric, especially trimeric, protein. In other embodiments, antibodies that may be used in the methods of the invention bind conformational epitopes that arise from the juxtaposition of Neutrokine-alpha with a heterologous polypeptide, such as might be present when Neutrokine-alpha forms heterotrimers (e.g., with APRIL polypeptides), or in fusion proteins between Neutrokine-alpha and a heterologous polypeptide.

Antibodies that may be used in the methods of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-id antibodies to anti-Neutrokine-alpha antibodies), and epitope-binding fragments of any of the above. In preferred embodiments, the immunoglobulin is an IgG1 or an IgG4 isotype. Immunoglobulins may have both a heavy and light chain. An array of IgG, IgE, IgM, IgD, IgA, and IgY heavy chains may be paired with a light chain of the kappa or lambda forms.

In a specific embodiment, the antibodies that may be used in the methods of the invention are Neutrokine-alpha-binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. Neutrokine-alpha-binding antibody fragments, including single-chain antibodies, may comprise the variable region(s) alone or in combination with the entirety or a portion of the following: hinge region, CH1, CH2, and CH3 domains. In a specific embodiment, Neutrokine-alpha-binding fragments that may be used in the methods of the invention comprise any combination of variable region(s) with a hinge region, CH1, CH2, and CH3 domains. The antibodies that may be used in the methods of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati et al, the contents of which are herein incorporated by reference in its entirety.

The antibodies that may be used in the methods of the invention may be monospecific, bispecific, trispecific or of greater multispecificity. Multispecific antibodies may be specific for different epitopes of a Neutrokine-alpha polypeptide or may be specific for both a Neutrokine-alpha polypeptide as well as for a heterologous epitope, such as a heterologous polypeptide or solid support material. See, e.g., PCT publications WO 93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies that may be used in the methods of the invention may be described or specified in terms of their binding affinity to a Neutrokine-alpha polypeptide. In specific embodiments, antibodies that may be used in the methods of the invention bind Neutrokine-alpha polypeptides, or fragments or variants thereof, with a dissociation constant or $K_D$ of less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, or $10^{-12}$ M. In a specific embodiment, antibodies that may be used in the methods of the invention bind Neutrokine-alpha polypeptides with a dissociation constant or $K_D$ that is within any one of the ranges that are between each of the individual recited values.

Neutrokine-alpha antibodies which disrupt the receptor/ligand interactions with Neutrokine-alpha polypeptides either partially or fully may be used in the methods of the invention. Also included are Neutrokine-alpha-specific antibodies which do not prevent ligand binding but prevent receptor activation. Receptor activation (i.e., signaling) may be determined by techniques described herein or otherwise known in the art. For example, receptor activation can be determined by detecting activation of the transcription factors NF-AT, AP-1, MAPK8/JNK and/or NF-kappaB (including the noncanonical NF-kappaB signaling pathway) using techniques known in the art, and/or the phosphorylation (e.g., tyrosine or serine/threonine) of the receptor or its substrate by immunoprecipitation followed by western blot analysis.

The above Neutrokine-alpha antibodies can be made using methods known in the art. See, e.g., PCT publication WO 96/40281; U.S. Pat. No. 5,811,097; Deng et al., Blood 92(6): 1981-1988 (1998); Chen et al., Cancer Res. 58(16):3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272 (17):11295-11301 (1997); Taryman et al., Neuron 14(4):755-762 (1995); Muller et al., Structure 6(9):1153-1167 (1998); Bartunek et al., Cytokine 8(1):14-20 (1996) (which are all incorporated by reference herein in their entireties).

In a specific embodiment, Neutrokine-alpha antibodies (including molecules comprising, or alternatively consisting of, antibody fragments or variants thereof) that may be used in the methods of the invention specifically bind to Neutrokine-alpha or a fragment or variant of Neutrokine-alpha. In particular, antibodies such as, for example, single chain Fvs (scFvs) having an amino acid sequence of any one of SEQ ID NOS:13-18, as referred to in Table 1 may be used in the methods of the invention.

TABLE 1 scFvs that Immunospecifically Bind to Neutrokine-alpha

| Clone ID | scFv SEQ ID NO | AAs of VL | AAs of VL CDR1 | AAs of VL CDR2 | AAs of VL CDR3 | AAs of VH | AAs of VH CDR1 | AAs of VH CDR2 | AAs of VH CDR3 |
|---|---|---|---|---|---|---|---|---|---|
| I006D08 | 13 | 141-249 | 163-173 | 189-195 | 228-238 | 1-123 | 26-35 | 50-66 | 99-112 |
| I050B11 | 14 | 143-251 | 166-177 | 193-199 | 232-240 | 1-125 | 26-35 | 50-66 | 99-114 |

TABLE 1-continued scFvs that Immunospecifically Bind to Neutrokine-alpha

| Clone ID | scFv SEQ ID NO | AAs of VL | AAs of VL CDR1 | AAs of VL CDR2 | AAs of VL CDR3 | AAs of VH | AAs of VH CDR1 | AAs of VH CDR2 | AAs of VH CDR3 |
|---|---|---|---|---|---|---|---|---|---|
| I050A12 | 15 | 142-250 | 164-174 | 190-196 | 229-239 | 1-124 | 26-35 | 50-66 | 99-113 |
| I050B11-15 | 16 | 143-251 | 166-177 | 193-199 | 232-240 | 1-125 | 26-35 | 50-66 | 99-114 |
| I116A01 | 17 | 141-249 | 163-173 | 189-195 | 228-238 | 1-123 | 26-35 | 50-66 | 99-112 |
| I026C04-K | 18 | 142-250 | 164-176 | 192-198 | 231-239 | 1-125 | 26-35 | 50-66 | 99-114 |

In one embodiment of the present invention, antibodies that may be used in the methods of the invention bind to Neutrokine-alpha and comprise a polypeptide having the amino acid sequence of any one of the VH domains referred to in Table 1 and/or any one of the VL domains referred to in Table 1. In preferred embodiments, antibodies that may be used in the methods of the invention comprise the amino acid sequence of a VH domain and VL domain from the same scFv referred to in Table 1. In alternative embodiments, antibodies that may be used in the methods of the invention comprise the amino acid sequence of a VH domain and VL domain from different scFvs referred to in Table 1. In another embodiment, antibodies that may be used in the methods of the invention specifically bind to Neutrokine-alpha and comprise a polypeptide having the amino acid sequence of any one, two, three, or more of the VH CDRs referred to in Table 1 and/or any one, two, three, or more of the VL CDRs referred to in Table 1. In preferred embodiments, antibodies that may be used in the methods of the invention comprise the amino acid sequence of a VH CDR and VL CDR from the same scFv referred to in Table 1. In alternative embodiments, antibodies that may be used in the methods of the invention comprise the amino acid sequence of a VH CDR and VL CDR from different scFvs referred to in Table 1. Molecules comprising, or alternatively consisting of, antibody fragments or variants of the scFvs referred to in Table 1 that immunospecifically bind to Neutrokine-alpha may also be used in the methods of the invention.

In a specific embodiment, an anti-Neutrokine-alpha antibody that may be used in the methods of the invention comprises the VH and VL domains of SEQ ID NO:13, as described in Table 1. In another specific embodiment, an antibody that may be used in the methods of the present invention comprises the VHCDR1, VHCDR2, VHCDR3 and VL CDR1, VLCDR2 and VLCDR3 regions of SEQ ID NO:13, as described in Table 1.

In a specific embodiment, an anti-Neutrokine-alpha antibody that may be used in the methods of the invention comprises the VH and VL domains of SEQ ID NO:14, as described in Table 1. In another specific embodiment, an antibody that may be used in the methods of the present invention comprises the VHCDR1, VHCDR2, VHCDR3 and VL CDR1, VLCDR2 and VLCDR3 regions of SEQ ID NO:13, as described in Table 1.

In a specific embodiment, an anti-Neutrokine-alpha antibody that may be used in the methods of the invention comprises the VH and VL domains of SEQ ID NO:13, as described in Table 1. In another specific embodiment, an antibody that may be used in the methods of the present invention comprises the VHCDR1, VHCDR2, VHCDR3 and VL CDR1, VLCDR2 and VLCDR3 regions of SEQ ID NO:14, as described in Table 1.

In a specific embodiment, an anti-Neutrokine-alpha antibody that may be used in the methods of the invention comprises the VH and VL domains of SEQ ID NO:15, as described in Table 1. In another specific embodiment, an antibody that may be used in the methods of the present invention comprises the VHCDR1, VHCDR2, VHCDR3 and VL CDR1, VLCDR2 and VLCDR3 regions of SEQ ID NO:15, as described in Table 1.

In a specific embodiment, an anti-Neutrokine-alpha antibody that may be used in the methods of the invention comprises the VH and VL domains of SEQ ID NO:16, as described in Table 1. In another specific embodiment, an antibody that may be used in the methods of the present invention comprises the VHCDR1, VHCDR2, VHCDR3 and VL CDR1, VLCDR2 and VLCDR3 regions of SEQ ID NO:16, as described in Table 1.

In a specific embodiment, an anti-Neutrokine-alpha antibody that may be used in the methods of the invention comprises the VH and VL domains of SEQ ID NO:17, as described in Table 1. In another specific embodiment, an antibody that may be used in the methods of the present invention comprises the VHCDR1, VHCDR2, VHCDR3 and VL CDR1, VLCDR2 and VLCDR3 regions of SEQ ID NO:17, as described in Table 1.

In a specific embodiment, an anti-Neutrokine-alpha antibody that may be used in the methods of the invention comprises the VH and VL domains of SEQ ID NO:18, as described in Table 1. In another specific embodiment, an antibody that may be used in the methods of the present invention comprises the VHCDR1, VHCDR2, VHCDR3 and VL CDR1, VLCDR2 and VLCDR3 regions of SEQ ID NO:18, as described in Table 1.

In a specific embodiment, an anti-Neutrokine-alpha antibody that may be used in the methods of the invention comprises the VH and VL domains of 15C10, a neutralizing anti-Neutrokine-alpha antibody which is described in, for example, US patent publication No. 20050186637. The amino acid sequence of the VH domain of 15C10 is given in SEQ ID NO:19. The amino acid sequence of the VL domain is given in VH domain of 15C10 is given in SEQ ID NO:20. In a specific embodiment, an anti-Neutrokine-alpha antibody that may be used in the methods of the invention is an antigen binding fragment or variant of 15C10. In a specific embodiment, an antibody that may be used in the methods of the present invention is an humanized version of 15C10. In another specific embodiment, an antibody that may be used in the methods of the present invention comprises the VHCDR1, VHCDR2, VHCDR3 and VL CDR1, VLCDR2 and VLCDR3 regions of 15C10.

In another specific embodiment, an anti-Neutrokine-alpha antibody that may be used in the methods of the invention comprises the VH and VL domains of the 4A5-3.1.1-B4 anti-Neutrokine-alpha antibody described in International Patent Publication Number WO03/0164468, which is herein incorporated by reference in its entirety. Neutrokine-alpha is referred to as hTNFSF13b in WO03/0164468. The amino acid sequence of the VH domain of 4A5-3.1.1-B4 is given in SEQ ID NO:21. The amino acid sequence of the VL domain is given in VH domain of 4A5-3.1.1-B4 is given in SEQ ID NO:22. In a specific embodiment, an anti-Neutrokine-alpha antibody that may be used in the methods of the invention is an antigen binding fragment or variant of 4A5-3.1.1-B4. In another specific embodiment, an antibody that may be used in the methods of the present invention comprises the VHCDR1, VHCDR2, VHCDR3 and VL CDR1, VLCDR2 and VLCDR3 regions of 4A5-3.1.1-B4.

In a specific embodiment, Neutrokine-alpha antibodies that may be used in the methods of the invention specifically bind to native Neutrokine-alpha polypeptide expressed from a cell.

C. Neutrokine-Alpha Binding Polypeptides

In a specific embodiment, the Neutrokine-alpha antagonist is a Neutrokine-alpha binding peptide or polypeptide. Neutrokine-alpha binding peptides or polypeptides have been described in, for example International Patent Publication numbers WO05/005462, WO05/000351, WO02/092620, WO02/16412, WO02/02641 and WO02/16411 and US Patent Publication numbers US2006135430, US2006084608, US2003194743, US20030195156 and US2003091565, each of which is herein incorporated by reference in its entirety. Neutrokine-alpha binding peptides or polypeptides have been described in, for example Sun et al., (2006) *Biochem. Biophys. Res. Commun.* 346:1158-1162 which is herein incorporated by reference in its entirety. Neutrokine-alpha binding peptides that may be used in the methods of the present invention include short polypeptides identified from random peptide sequences displayed by fusion with coat proteins of filamentous phage. For discussion of phage display peptide library technology see, for example, Scott et al. (1990), Science 249: 386; Devlin et al. (1990), Science 249: 404; U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference in its entirety). Phage expressing the peptides are isolated by successive rounds of affinity purification against an immobilized Neutrokine-alpha target peptide followed by repropagation. The candidates with the highest binding to Neutrokine-alpha can be sequenced to determine the identity of each binding peptide. Each identified Neutrokine-alpha binding peptide may then be attached to a "vehicle" to generate a further Neutrokine-alpha binding peptide for use in the methods of the present experiment. The term "vehicle" refers to a molecule that prevents degradation and/or increases half-life, reduces toxicity, reduces immunogenicity, or increases biological activity of a Neutrokine-alpha binding peptide. Exemplary vehicles include an Fc domain and variants thereof (a "Peptibody" which is preferred); a linear polymer (e.g., polyethylene glycol (PEG), including 5 kD, 20 kD, and 30 kD PEG, polylysine, dextran, etc.); a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published Oct. 28, 1993); a lipid; a cholesterol group (such as a steroid); a carbohydrate or oligosaccharide (e.g., dextran); any natural or synthetic protein, polypeptide or peptide that binds to a salvage receptor; albumin, including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety); and a leucine zipper domain, and other such proteins and protein fragments. Neutrokine-alpha binding polypeptides that may be used in the methods of the invention require the presence of at least one vehicle attached to the peptide through the N-terminus, C-terminus or a sidechain of one of the amino acid residues. Multiple vehicles may also be used; e.g., Fc's at each terminus or an Fc at a terminus and a PEG group at the other terminus or a sidechain. For Neutrokine-alpha binding peptides an Fc domain is the preferred vehicle. The Fc domain may be fused to the N or C termini of the peptides or at both the N and C termini. Fusion to the N terminus is preferred.

As noted above, Fc variants are suitable vehicles for Neutrokine-alpha binding peptides that may be used in the methods of the invention. A native Fc may be extensively modified to form an Fc variant, provided binding to the salvage receptor is maintained; see, for example WO 97/34631 and WO 96/32478. In such Fc variants, one may remove one or more sites of a native Fc that provide structural features or functional activity not required by the Neutrokine-alpha binding peptides that may be used in the methods of the invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). Even when cysteine residues are removed, the single chain Fc domains can still form a dimeric Fc domain that is held together non-covalently.

2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionine residue, especially when the molecule is expressed recombinantly in a bacterial cell such as *E. coli*.

3. A portion of the N-terminus of a native Fc is removed to prevent N-terminal heterogeneity when expressed in a selected host cell. For this purpose, one may delete any of the first 20 amino acid residues at the N-terminus.

4. One or more glycosylation sites are removed. Residues that are typically glycosylated (e.g., asparagine) may confer cytolytic response. Such residues may be deleted or substituted with unglycosylated residues (e.g., alanine).

5. Sites involved in interaction with complement, such as the C1q binding site, are removed. For example, one may delete or substitute the EKK sequence of human IgG1. Complement recruitment may not be advantageous for the molecules that may be used in the methods of the invention and so may be avoided with such an Fc variant.

6. Sites are removed that affect binding to Fc receptors other than a salvage receptor. A native Fc may have sites for interaction with certain white blood cells that are not required for the Neutrokine-alpha binding peptide fusion molecules that may be used in the methods of the invention and so may be removed.

7. The ADCC site is removed. ADCC sites are known in the art; see, for example, Molec. Immunol. 29 (5): 633-9 (1992) with regard to ADCC sites in IgG1. These sites, as well, are not required for the fusion molecules that may be used in the methods of the invention and so may be removed.

8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

An alternative vehicle for Neutrokine-alpha binding peptides that may be used in the methods of the invention would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277. Peptides could also be selected by phage display or RNA-peptide screening for binding to the salvage receptor. Such salvage receptor-binding compounds are also included within the meaning of "vehicle" and may be used in the for Neutrokine-alpha binding peptides that may be used in the methods of the invention. Such vehicles should be selected for increased half-life (e.g., by avoiding sequences recognized by proteases) and decreased immunogenicity (e.g., by favoring non-immunogenic sequences, as discovered in antibody humanization).

As noted above, polymer vehicles may also be used in Neutrokine-alpha binding peptides that may be used in the methods of the invention. Various means for attaching chemical moieties useful as vehicles are currently available, see, e.g., Patent Cooperation Treaty ("PCT") International Publication No. WO 96/11953, herein incorporated by reference in its entirety. This PCT publication discloses, among other things, the selective attachment of water soluble polymers to the N-terminus of proteins.

In a specific embodiment, a preferred polymer vehicle is polyethylene glycol (PEG). The PEG group may be of any convenient molecular weight and may be linear or branched. The average molecular weight of the PEG will preferably range from about 2 kiloDalton ("kD") to about 100 kD, more preferably from about 5 kD to about 50 kD, most preferably from about 5 kD to about 10 kD. The PEG groups will generally be attached to the for Neutrokine-alpha binding peptides that may be used in the methods of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for Neutrokine-alpha binding peptides that may be used in the methods of the invention. Dextrans are polysaccharide polymers comprised of individual subunits of glucose predominantly linked by $\alpha 1$-6 linkages. The dextran itself is available in many molecular weight ranges, and is readily available in molecular weights from about 1 kD to about 70 kD. Dextran is a suitable water soluble polymer for use in Neutrokine-alpha binding peptides that may be used in the methods of the invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference in its entirety. Dextran of about 1 kD to about 20 kD is preferred when dextran is used as a vehicle in accordance with the present invention.

In a specific embodiment, Neutrokine-alpha binding peptides that may be used in the methods of the invention optionally include a "linker". When present, its chemical structure is not critical, since it serves primarily as a spacer. The linker is preferably made up of amino acids linked together by peptide bonds. Thus, in preferred embodiments, the linker is made up of from 1 to 30 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly $(Gly)_4$, $(Gly)_5$), poly(Gly-Ala), and polyalanines. Preferred linkers are amino acid linkers comprising greater than 5 amino acids, with suitable linkers having up to about 500 amino acids selected from glycine, alanine, proline, asparagine, glutamine, lysine, threonine, serine or aspartate. Linkers of about 20 to 50 amino acids are most preferred.

Non-peptide linkers are also useful for Neutrokine-alpha binding peptides that may be used in the methods of the invention. For example, alkyl linkers such as —NH—$(CH_2)_n$—C(O)—, wherein n=2-20 could be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc.

In preferred embodiments, the Neutrokine-alpha binding peptides that may be used in the methods of the invention include the amino acid sequence of SEQ ID NO:23, the amino acid sequence of SEQ ID NO:24 or the amino acid sequence of SEQ ID NO:25. In a particularly preferred embodiment, the Neutrokine-alpha binding peptide that may be used in the methods of the invention is the amino acid sequence of SEQ ID NO:23 (AMG 623; AGP3 peptibody).

Neutrokine-Alpha Receptors

In a specific embodiment, the Neutrokine-alpha antagonist is a Neutrokine-alpha receptor protein or fragment or variant thereof. Neutrokine-alpha receptors include, e.g., transmembrane activator and CAML interactor (TACI, GenBank accession number AAC51790, SEQ ID NO:6), B cell activating factor receptor (BAFF-R, GenBank Accession Number NP_443177 SEQ ID NO:10), and B-cell maturation antigen (BCMA, GenBank accession number NP_001183 SEQ ID NO:8). Neutrokine-alpha receptor proteins, fragments and variants thereof, as well as antibodies there to have been described in, for example, PCT Publications WO03/014294, WO02/066516, WO02/024909 WO03/014294, WO03/024991, WO02/094852 and WO04/011611 and U.S. Patent Publication Nos. US20030148445, US20030099990, US2005070689, US2005043516 and US2003012783, and are described in more detail below. Each of the aforementioned references is herein incorporated by reference in its entirety.

D. Neutrokine-Alpha Receptors, TACI

TACI polypeptides, such as those described below, act as Neutrokine-alpha and/or APRIL antagonists and may also be used in the methods of the present invention. TACI, also known as TR17, is a protein of 293 amino acid residues (SEQ ID NO:6), with a deduced molecular weight of about 31.8 kDa. A nucleotide sequence of a cDNA that encodes TACI is given in SEQ ID NO:5. Predicted amino acids from about 1 to about 165 constitute the extracellular domain (SEQ ID NO:6); amino acids from about 166 to about 186 constitute the transmembrane domain (SEQ ID NO:6); and amino acids from about 187 to about 293 constitute the intracellular domain (SEQ ID NO:6).

Accordingly, in one embodiment, a TACI protein that may be used in the methods of the present invention is an isolated polypeptide comprising, or alternatively, consisting of the amino acid sequence of SEQ ID NO:6, or a polypeptide comprising, or alternatively, consisting of a portion of SEQ ID NO:6, such as for example, the TACI extracellular domain (comprising amino acids 1 to 165 of SEQ ID NO:6) and/or the TACI cysteine rich domain (comprising amino acids 33 to 104 of SEQ ID NO:6); as well as polypeptides which are at least 80% identical, more preferably at least 90% or 95% identical, still more preferably at least 96%, 97%, 98%, 99% or 100% identical to the polypeptides described above.

In another embodiment, a TACI protein that may be used in the methods of the present invention is an isolated polypeptide comprising amino acids 1 to 154 of SEQ ID NO:6 as well as polypeptides which are at least 80% identical, more preferably at least 90% or 95% identical, still more preferably at least 96%, 97%, 98%, 99% or 100% identical to the polypeptides described above.

By a polypeptide having an amino acid sequence at least, for example, 95% "identical" to a reference amino acid sequence of a TACI polypeptide is intended that the amino acid sequence of the polypeptide is identical to the reference sequence except that the polypeptide sequence may include up to five amino acid alterations per each 100 amino acids of the reference amino acid of the TACI receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptide fragments of TACI include polypeptides comprising or alternatively, consisting of: an amino acid sequence contained in SEQ ID NO:6. Polypeptide fragments may be "free-standing," or comprised within a larger polypeptide of which the fragment forms a part or region, most preferably as a single continuous region. In additional embodiments, the polypeptide fragments comprise, or alternatively consist of, one or more TACI domains. Preferred polypeptide fragments include a member selected from the group: (a) a polypeptide comprising or alternatively, consisting of, the TACI extracellular domain (predicted to constitute amino acid residues from about 1 to about 165 of SEQ ID NO:6); (b) a polypeptide comprising or alternatively, consisting of, a TACI cysteine rich domain (predicted to constitute amino acid residues from about 33 to about 104 of SEQ ID NO:6); (c) a polypeptide comprising or alternatively, consisting of, the TACI transmembrane domain (predicted to constitute amino acid residues from about 166 to about 186 of SEQ ID NO:6); (d) a polypeptide comprising or alternatively, consisting of, the TACI intracellular domain (predicted to constitute amino acid residues from about 187 to about 293 of SEQ ID NO:6); or (e) any combination of polypeptides (a)-(d).

It is believed that the extracellular cysteine rich motifs of TACI are important for interactions between TACI and its ligands, Neutrokine-alpha and APRIL. Accordingly, in preferred embodiments, TACI polypeptide fragments that may be used in the methods of the present invention comprise, or alternatively consist of amino acid residues 33 to 66 and/or 70 to 104 of SEQ ID NO:6. In a specific embodiment the TACI polypeptides that may be used in the methods of the present invention comprise, or alternatively consist of one or both of the extracellular cysteine rich motifs (residues 33 to 66 and residues 70 to 104 of SEQ ID NO:6). Proteins comprising or alternatively consisting of a polypeptide sequence which is at least 80%, 90%, 95%, 96%, 97%, 98% or 99% identical to the polypeptide sequences of one or both of these cysteine rich motifs are also preferred.

Other fragments of the TACI protein that may be used in the methods of the invention are fragments characterized by structural or functional attributes of TACI. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) TACI (SEQ ID NO:6) as is discussed in U.S. Pat. No. 6,969,519. Certain preferred regions include, but are not limited to, Garnier-Robson predicted alpha-regions, beta-regions, turn-regions, and coil-regions; Chou-Fasman predicted alpha-regions, beta-regions, and turn-regions; Kyte-Doolittle predicted hydrophilic; Hopp-Woods predicted hydrophobic regions; Eisenberg alpha and beta amphipathic regions; Emini surface-forming regions; and Jameson-Wolf high antigenic index regions, as predicted using the default parameters of these computer programs.

The TACI polypeptide for use in the methods of the invention may be expressed in a modified form, such as a fusion protein (comprising the polypeptide joined via a peptide bond to a heterologous protein sequence (of a different protein)), and may include not only secretion signals but also additional heterologous functional regions. Alternatively, such a fusion protein can be made by protein synthetic techniques, e.g., by use of a peptide synthesizer. Thus, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

A preferred TACI fusion protein that may be used in the methods of the invention comprises a heterologous region from immunoglobulin that is useful to solubilize proteins. For example, EP-A-O 464 533 (Canadian counterpart 2045869)

and WO00/024782 disclose fusion proteins comprising various portions of constant region of immunoglobin molecules together with another human protein or part thereof. TACI immunoglobulin fusion proteins have been described in, for example, PCT Publications WO01/60397, WO01/81417, WO01/087977, and WO02/94852; U.S. Publication Nos. US2003103986 and US2006034852 and Gross, et al., (2000) *Nature* 404:995-999 and Yu, et al., (2000) *Nat Immunol* 1:252-256, herein incorporated by reference in their entirety. In many cases, the Fc part in a fusion protein is thoroughly advantageous for use in therapy and diagnosis and thus results, for example, in improved pharmacokinetic properties (EP-A 0232 262). On the other hand, for some uses, it would be desirable to be able to delete the Fc part after the fusion protein has been expressed, detected and purified in the advantageous manner described. This is the case when the Fc portion proves to be a hindrance to use in therapy and diagnosis, for example, when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., Journal of Molecular Recognition 8:52-58 (1995) and K. Johanson et al., The Journal of Biological Chemistry 270:16: 9459-9471 (1995). In a specific embodiment, the TACI-Fc fusion protein that may be used in the methods of the invention is Atacicept (TACI-Ig).

As one of skill in the art will appreciate, and as discussed above, the TACI polypeptides can be fused to other polypeptide sequences. For example, the TACI polypeptides may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876, 969, issued Mar. 2, 1999, EP Patent 0 413 622, and U.S. Pat. No. 5,766,883, issued Jun. 16, 1998, herein incorporated by reference in their entirety)) resulting in chimeric polypeptides.

Such fusion proteins may facilitate purification, may extend shelf-life and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995).

An albumin fusion protein that may be used in methods of the present invention comprises at least a fragment or variant of a TACI polypeptide and at least a fragment or variant of human serum albumin, which are associated with one another, preferably by genetic fusion (i.e., the albumin fusion protein is generated by translation of a nucleic acid in which a polynucleotide encoding all or a portion of TACI is joined in-frame with a polynucleotide encoding all or a portion of albumin) or chemical conjugation to one another. The TACI polypeptide and albumin protein, once part of the albumin fusion protein, may be referred to as a "portion", "region" or "moiety" of the albumin fusion protein (e.g., a "TACI portion" or an "albumin protein portion").

In one embodiment, an albumin fusion protein that may be used in the methods of the invention comprises, or alternatively consists of, a TACI polypeptide and a serum albumin protein. In other embodiments, an albumin fusion protein that may be used in the methods of the invention comprises, or alternatively consists of, a fragment of TACI and a serum albumin protein. In other embodiments, an albumin fusion protein that may be used in the methods of the invention comprises, or alternatively consists of, a variant of TACI and a serum albumin protein In preferred embodiments, the serum albumin protein component of the albumin fusion protein is the mature portion of serum albumin.

In further embodiments, an albumin fusion protein that may be used in the methods of the invention comprises, or alternatively consists of, a TACI polypeptide and a biologically active and/or therapeutically active fragment of serum albumin. In further embodiments, an albumin fusion protein that may be used in the methods of the invention comprises, or alternatively consists of, a TACI polypeptide and a biologically active and/or therapeutically active variant of serum albumin. In preferred embodiments, the TACI portion of the albumin fusion protein is the full-length TACI polypeptide. In a further preferred embodiment, the TACI portion of the albumin fusion protein is the mature, soluble domain of the TACI polypeptide.

In further embodiments, an albumin fusion protein that may be used in the methods of the invention comprises, or alternatively consists of, a fragment or variant of TACI and a biologically active and/or therapeutically active fragment or variant of serum albumin. In preferred embodiments, the invention provides an albumin fusion protein comprising, or alternatively consisting of, the mature portion of the TACI polypeptide and the mature portion of serum albumin.

In further embodiments, an albumin fusion protein that may be used in the methods of the invention comprises, or alternatively consists of, a fragment or variant of TACI and a biologically active and/or therapeutically active fragment or variant of serum albumin. In preferred embodiments, the invention provides an albumin fusion protein comprising, or alternatively consisting of, the mature portion of the TACI polypeptide and the mature portion of serum albumin. (including but not limited to recombinant human serum albumin or fragments or variants thereof (see, e.g., U.S. Pat. No. 5,876, 969, issued Mar. 2, 1999, EP Patent 0 413 622, and U.S. Pat. No. 5,766,883, issued Jun. 16, 1998, herein incorporated by reference in their entirety)). In a preferred embodiment, TACI polypeptides (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment TACI polypeptides (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. TACI polypeptides (including fragments or variants thereof) may be fused to either the N- or C-terminal end of the heterologous protein (e.g., immunoglobulin Fc polypeptide or human serum albumin polypeptide).

In preferred embodiments, the human serum albumin protein used in the albumin fusion proteins that may be used in the methods of the invention contains one or both of the following sets of point mutations with reference to SEQ ID NO:11: Leu-407 to Ala, Leu-408 to Val, Val-409 to Ala, and Arg-410 to Ala; or Arg-410 to A, Lys-413 to Gln, and Lys-414 to Gln (see, e.g., International Publication No. WO95/23857, hereby incorporated in its entirety by reference herein). In even more preferred embodiments, albumin fusion proteins that may be used in the methods of the invention that contain one or both of above-described sets of point mutations have improved stability/resistance to yeast Yap3p proteolytic cleavage, allowing increased production of recombinant albumin fusion proteins expressed in yeast host cells.

Preferably, the albumin fusion protein that may be used in the methods of the invention comprises HA as the N-terminal portion, and TACI polypeptide as the C-terminal portion. Alternatively, an albumin fusion protein comprising HA as the C-terminal portion, and TACI polypeptide as the N-terminal portion may also be used.

In other embodiments, the albumin fusion protein that may be used in methods of the invention has a TACI polypeptide fused to both the N-terminus and the C-terminus of albumin. In a specific embodiment, the TACI polypeptides fused at the N- and C-termini are the same. In another embodiment, the TACI polypeptides fused at the N- and C-termini are different TACI polypeptides. In another embodiment, a TACI polypeptide is fused at either the N- or C-terminus of albumin, and a heterologous polypeptide is fused at the remaining terminus.

Additionally, the albumin fusion proteins that may be used in the methods of the invention may include a linker peptide between the fused portions to provide greater physical separation between the moieties. The linker peptide may consist of amino acids such that it is flexible or more rigid.

Generally, the albumin fusion proteins that may be used in the methods of the invention may have one HA-derived region and one TACI region. Multiple regions of each protein, however, may be used to make an albumin fusion protein that may be used in the methods of the invention. Similarly, more than one protein may be used to make an albumin fusion protein that may be used in the methods of the invention. For instance, a protein may be fused to both the N- and C-terminal ends of the HA. In such a configuration, the protein portions may be the same or different protein molecules. The structure of bifunctional albumin fusion proteins may be represented as: X-HA-Y or Y-HA-X.

In a specific embodiment a TACI protein or fragment or variant thereof that may be used in the methods of the invention may be conjugated to a cytotoxin (e.g., a cytostatic or cytocidal agent). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In another embodiment, a TACI protein or fragment or variant thereof that may be used in the methods of the invention may be conjugated to a toxin.

By "toxin" is meant one or more compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium.

To improve or alter the characteristics of TACI polypeptides that may be used in the methods of the invention, protein engineering may be employed. Recombinant DNA technology known to those skilled in the art can be used to create novel mutant proteins or "muteins including single or multiple amino acid substitutions, deletions, additions or fusion proteins". Such modified polypeptides can show, e.g., enhanced activity or increased stability. In addition, they may be purified in higher yields and show better solubility than the corresponding natural polypeptide, at least under certain purification and storage conditions.

The TACI proteins that may be used in the methods of the invention may be in monomers or multimers (i.e., dimers, trimers, tetramers, and higher multimers). In specific embodiments, the polypeptides of the invention are monomers, dimers, trimers or tetramers. In additional embodiments, the multimers of the invention are at least dimers, at least trimers, or at least tetramers. Certain members of the TNF family of proteins are believed to exist in trimeric form (Beutler and Huffel, Science 264:667, 1994; Banner et al., Cell 73:431, 1993). Thus, trimeric TACI may offer the advantage of enhanced biological activity.

In specific embodiments, the multimers may be homomers or heteromers. As used herein, the term homomer, refers to a multimer containing only TACI proteins (including TACI fragments, variants, and fusion proteins, as described herein). These homomers may contain TACI proteins having identical or different polypeptide sequences. In a specific embodiment, a homomer is a multimer containing only TACI proteins having an identical polypeptide sequence. In another specific embodiment, a homomer is a multimer containing TACI proteins having different polypeptide sequences.

As used herein, the term heteromer refers to a multimer containing heterologous proteins (i.e., proteins containing only polypeptide sequences that do not correspond to a polypeptide sequences encoded by the TACI gene) in addition to the TACI proteins. Multimers may be the result of hydrophobic, hydrophilic, ionic and/or covalent associations and/or may be indirectly linked, by for example, liposome formation. Thus, in one embodiment, multimers, such as, for example, homodimers, homotrimers, heterotrimers or heterotetramers, are formed when the proteins contact one another in solution. In other embodiments, multimers are formed by covalent associations with and/or between the TACI proteins. Such covalent associations may involve one or more amino acid residues contained in the polypeptide sequence of the protein. In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation.

Alternatively, such covalent associations may involve one or more amino acid residues contained in the heterologous polypeptide sequence in a TACI fusion protein. In one example, covalent associations are between the heterologous sequence contained in a fusion protein (see, e.g., U.S. Pat. No. 5,478,925, the contents of which are herein incorporated by reference in its entirety). In a specific example, the covalent associations are between the heterologous sequence contained in a TACI-Fc fusion protein (as described herein). In another specific example, covalent associations of fusion proteins are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more TACI polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple TACI polypeptides separated by peptide linkers may be produced using conventional recombinant DNA technology.

In a specific embodiment, antibodies that bind to a TACI polypeptide, a polypeptide fragment, a variant of SEQ ID NO:6, and/or an TACI polypeptide epitope (as determined by immunoassays well known in the art for assaying specific antibody-antigen binding) may be used in the methods of the invention. Anti-TACI antibodies and fragments thereof have been described in, for example, PCT Publications WO04/011611, WO01/087977, WO01/60397, and WO02/66516; U.S. Patent Publication US2005043516 and US2003012783; and Ch'en, et al., (2005) *Cell Immunol* 236:78-85 and Liu, et al., (2003) *Xi Bao Yu Fen Zi Mian Yi Xue Za Zhi* 19:168-169. Each of the aforementioned references is herein incorporated by reference in its entirety. Antibodies include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to anti-TACI antibodies), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. In specific embodiments, the immunoglobulin molecules are IgG1. In other specific embodiments, the immunoglobulin molecules are IgG4.

TACI binding antibody fragments that may be used in the methods of the invention include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included are antigen-binding fragments also comprising any combination of variable region(s) with a hinge region, CH1, CH2, and CH3 domains. The antibodies may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati et al, the contents of which are herein incorporated by reference in its entirety.

Anti-TACI antibodies that may be used in the methods of the invention may be monospecific, bispecific, trispecific or of greater multispecificity. Multispecific antibodies may be specific for different epitopes of a TACI polypeptide or may be specific for both a TACI polypeptide as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992), the contents of which are herein incorporated by reference in their entirety.

TACI Antibodies may be described or specified in terms of their cross-reactivity. Antibodies that do not bind any other analog, ortholog, or homolog of a TACI polypeptide may be used in the methods of the invention. In specific embodiments, TACI antibodies cross-react with murine, rat and/or rabbit homologs of human TACI proteins and the corresponding epitopes thereof. In a specific embodiment, an anti-TACI antibody that may be used in the methods of the invention binds not only to TACI, but also binds to BCMA and BAFF-R.

TACI antibodies that may be used in the methods of the invention may also be described or specified in terms of their binding affinity to a TACI polypeptide. Preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-12}$ M, or $10^{-12}$ M.

TACI antibodies that may be used in the methods of the invention may act as agonists or antagonists of the TACI polypeptides. For example, TACI antibodies which disrupt the receptor/ligand interactions with the TACI polypeptides either partially or fully are included. Also included are receptor-specific antibodies which do not prevent ligand binding but prevent receptor activation. Receptor activation (i.e., signaling) may be determined by techniques described herein or otherwise known in the art. For example, receptor activation can be determined by detecting activation of the transcription factors NF-AT, AP-1, and/or NF-kappaB using techniques known in the art, and/or the phosphorylation (e.g., tyrosine or serine/threonine) of the receptor or its substrate by immunoprecipitation followed by western blot analysis.

In a specific embodiment, receptor-specific TACI antibodies which both prevent ligand binding and receptor activation as well as TACI antibodies that recognize the receptor-ligand complex, and, preferably, do not specifically recognize the unbound receptor or the unbound ligand may be used in the methods of the invention. The above TACI antibodies can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167

(1998); Bartunek et al., Cytokine 8(1):14-20 (1996) (which are all incorporated by reference herein in their entireties).

E. Neutrokine-Alpha Receptor, BCMA

BCMA polypeptides, such as those described below, act as Neutrokine-alpha and/or APRIL antagonists and may also be used in the methods of the present invention. BCMA, also known as TR18, is a protein of 184 amino acid residues (SEQ ID NO:8), with a deduced molecular weight of about 20.1 kDa A nucleotide sequence of a cDNA that encodes BCMA is given in SEQ ID NO:7. Predicted amino acids from about 1 to about 54 constitute the extracellular domain (SEQ ID NO:8); amino acids from about 55 to about 80 constitute the transmembrane domain (SEQ ID NO:8); and amino acids from about 81 to about 184 constitute the intracellular domain (SEQ ID NO:8).

Accordingly, in one embodiment, a BCMA protein that may be used in the methods of the present invention is an isolated polypeptide comprising, or alternatively, consisting of the amino acid sequence of SEQ ID NO:8, or a polypeptide comprising, or alternatively, consisting of a portion of SEQ ID NO:8, such as for example, the BCMA extracellular domain (comprising amino acids 1 to 54 of SEQ ID NO:8) and/or the BCMA cysteine rich domain (comprising amino acids 8 to 41 of SEQ ID NO:8); as well as polypeptides which are at least 80% identical, more preferably at least 90% or 95% identical, still more preferably at least 96%, 97%, 98%, 99% or 100% identical to the polypeptides described above.

By a polypeptide having an amino acid sequence at least, for example, 95% "identical" to a reference amino acid sequence of a BCMA polypeptide is intended that the amino acid sequence of the polypeptide is identical to the reference sequence except that the polypeptide sequence may include up to five amino acid alterations per each 100 amino acids of the reference amino acid of the BCMA receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptide fragments of BCMA include polypeptides comprising or alternatively, consisting of: an amino acid sequence contained in SEQ ID NO:8. Polypeptide fragments may be "free-standing," or comprised within a larger polypeptide of which the fragment forms a part or region, most preferably as a single continuous region. In additional embodiments, the polypeptide fragments comprise, or alternatively consist of, one or more BCMA domains. Preferred polypeptide fragments include a member selected from the group: (a) a polypeptide comprising or alternatively, consisting of, the BCMA extracellular domain (predicted to constitute amino acid residues from about 1 to about 54 of SEQ ID NO:8); (b) a polypeptide comprising or alternatively, consisting of, a BCMA cysteine rich domain (predicted to constitute amino acid residues from about 8 to about 41 of SEQ ID NO:8); (c) a polypeptide comprising or alternatively, consisting of, the BCMA transmembrane domain (predicted to constitute amino acid residues from about 55 to about 80 of SEQ ID NO:8); (d) a polypeptide comprising or alternatively, consisting of, the BCMA intracellular domain (predicted to constitute amino acid residues from about 81 to about 184 of SEQ ID NO:8); or (e) any combination of polypeptides (a)-(d).

It is believed that the extracellular cysteine rich motif of BCMA is important for interactions between BCMA and its ligands, Neutrokine-alpha and APRIL. Accordingly, in preferred embodiments, BCMA polypeptide fragments that may be used in the methods of the present invention comprise, or alternatively consist of, the amino acid sequence of amino acid residues 8 to 41 of SEQ ID NO:8. Proteins comprising or alternatively consisting of a polypeptide sequence which is at least 80%, 90%, 95%, 96%, 97%, 98% or 99% identical to the polypeptide sequences of the cysteine rich motif are also preferred.

Other fragments of the BCMA protein that may be used in the methods of the invention are fragments characterized by structural or functional attributes of BCMA. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) BCMA (SEQ ID NO:8) as is discussed in U.S. patent application Ser. No. 10/786,176. Certain preferred regions include, but are not limited to, Garnier-Robson predicted alpha-regions, beta-regions, turn-regions, and coil-regions; Chou-Fasman predicted alpha-regions, beta-regions, and turn-regions; Kyte-Doolittle predicted hydrophilic; Hopp-Woods predicted hydrophobic regions; Eisenberg alpha and beta amphipathic regions; Emini surface-forming regions; and Jameson-Wolf high antigenic index regions, as predicted using the default parameters of these computer programs.

The BCMA polypeptide for use in the methods of the invention may be expressed in a modified form, such as a fusion protein (comprising the polypeptide joined via a peptide bond to a heterologous protein sequence (of a different protein)), and may include not only secretion signals but also additional heterologous functional regions. Alternatively, such a fusion protein can be made by protein synthetic techniques, e.g., by use of a peptide synthesizer. Thus, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

A preferred BCMA fusion protein that may be used in the methods of the invention comprises a heterologous region from immunoglobulin that is useful to solubilize proteins. For example, EP-A-O 464 533 (Canadian counterpart 2045869) and WO00/024782 disclose fusion proteins comprising various portions of constant region of immunoglobin molecules together with another human protein or part thereof. BCMA immunoglobulin fusion proteins have been described in, for example, PCT Publications WO01/087977, WO01/60397, and WO01/24811 and Gross, et al., (2000) *Nature* 404:995-999, Thompson, et al., (2000) *J Exp Med* 192:129-135, and Yu, et al., (2000) *Nat Immunol* 1:252-256, herein incorporated by reference in their entirety. In many cases, the Fc part in a fusion protein is thoroughly advantageous for use in therapy and diagnosis and thus results, for example, in improved pharmacokinetic properties (EP-A 0232 262). On the other hand, for some uses, it would be desirable to be able to delete the Fc part after the fusion protein has been expressed, detected and purified in the advantageous manner described. This is the case when the Fc portion proves to be a hindrance to use in therapy and diagnosis, for example, when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., Journal of Molecular Recognition 8:52-58 (1995) and K. Johanson et al., The Journal of Biological Chemistry 270:16:9459-9471 (1995).

As one of skill in the art will appreciate, and as discussed above, the BCMA polypeptides can be fused to other polypeptide sequences. For example, the BCMA polypeptides may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)) resulting in chimeric polypeptides.

Such fusion proteins may facilitate purification, may extend shelf-life and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995).

An albumin fusion protein that may be used in methods of the present invention comprises at least a fragment or variant of a BCMA polypeptide and at least a fragment or variant of human serum albumin, which are associated with one another, preferably by genetic fusion (i.e., the albumin fusion protein is generated by translation of a nucleic acid in which a polynucleotide encoding all or a portion of BCMA is joined in-frame with a polynucleotide encoding all or a portion of albumin) or chemical conjugation to one another. The BCMA polypeptide and albumin protein, once part of the albumin fusion protein, may be referred to as a "portion", "region" or "moiety" of the albumin fusion protein (e.g., a "BCMA portion" or an "albumin protein portion").

In one embodiment, an albumin fusion protein that may be used in the methods of the invention comprises, or alternatively consists of, a BCMA polypeptide and a serum albumin protein. In other embodiments, an albumin fusion protein that may be used in the methods of the invention comprises, or alternatively consists of, a fragment of BCMA and a serum albumin protein. In other embodiments, an albumin fusion protein that may be used in the methods of the invention comprises, or alternatively consists of, a variant of BCMA and a serum albumin protein In preferred embodiments, the serum albumin protein component of the albumin fusion protein is the mature portion of serum albumin.

In further embodiments, an albumin fusion protein that may be used in the methods of the invention comprises, or alternatively consists of, a BCMA polypeptide and a biologically active and/or therapeutically active fragment of serum albumin. In further embodiments, an albumin fusion protein that may be used in the methods of the invention comprises, or alternatively consists of, a BCMA polypeptide and a biologically active and/or therapeutically active variant of serum albumin. In preferred embodiments, the BCMA portion of the albumin fusion protein is the full-length BCMA polypeptide. In a further preferred embodiment, the BCMA portion of the albumin fusion protein is the mature, soluble domain of the BCMA polypeptide.

In further embodiments, an albumin fusion protein that may be used in the methods of the invention comprises, or alternatively consists of, a fragment or variant of BCMA and a biologically active and/or therapeutically active fragment or variant of serum albumin. In preferred embodiments, the invention provides an albumin fusion protein comprising, or alternatively consisting of, the mature portion of the BCMA polypeptide and the mature portion of serum albumin.

In further embodiments, an albumin fusion protein that may be used in the methods of the invention comprises, or alternatively consists of, a fragment or variant of BCMA and a biologically active and/or therapeutically active fragment or variant of serum albumin. In preferred embodiments, the invention provides an albumin fusion protein comprising, or alternatively consisting of, the mature portion of the BCMA polypeptide and the mature portion of serum albumin. (including but not limited to recombinant human serum albumin or fragments or variants thereof (see, e.g., U.S. Pat. No. 5,876, 969, issued Mar. 2, 1999, EP Patent 0 413 622, and U.S. Pat. No. 5,766,883, issued Jun. 16, 1998, herein incorporated by reference in their entirety)). In a preferred embodiment, BCMA polypeptides (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment BCMA polypeptides (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. BCMA polypeptides (including fragments or variants thereof) may be fused to either the N- or C-terminal end of the heterologous protein (e.g., immunoglobulin Fc polypeptide or human serum albumin polypeptide).

In preferred embodiments, the human serum albumin protein used in the albumin fusion proteins that may be used in the methods of the invention contains one or both of the following sets of point mutations with reference to SEQ ID NO:11: Leu-407 to Ala, Leu-408 to Val, Val-409 to Ala, and Arg-410 to Ala; or Arg-410 to A, Lys-413 to Gln, and Lys-414 to Gln (see, e.g., International Publication No. WO95/23857, hereby incorporated in its entirety by reference herein). In even more preferred embodiments, albumin fusion proteins that may be used in the methods of the invention that contain one or both of above-described sets of point mutations have improved stability/resistance to yeast Yap3p proteolytic cleavage, allowing increased production of recombinant albumin fusion proteins expressed in yeast host cells.

Preferably, the albumin fusion protein that may be used in the methods of the invention comprises HA as the N-terminal portion, and BCMA polypeptide as the C-terminal portion. Alternatively, an albumin fusion protein comprising HA as the C-terminal portion, and BCMA polypeptide as the N-terminal portion may also be used.

In other embodiments, the albumin fusion protein that may be used in methods of the invention has a BCMA polypeptide fused to both the N-terminus and the C-terminus of albumin. In a specific embodiment, the BCMA polypeptides fused at the N- and C-termini are the same. In another embodiment, the BCMA polypeptides fused at the N- and C-termini are different BCMA polypeptides. In another embodiment, a BCMA polypeptide is fused at either the N- or C-terminus of albumin, and a heterologous polypeptide is fused at the remaining terminus.

Additionally, the albumin fusion proteins that may be used in the methods of the invention may include a linker peptide between the fused portions to provide greater physical separation between the moieties. The linker peptide may consist of amino acids such that it is flexible or more rigid.

Generally, the albumin fusion proteins that may be used in the methods of the invention may have one HA-derived region and one BCMA region. Multiple regions of each protein, however, may be used to make an albumin fusion protein that may be used in the methods of the invention. Similarly, more than one protein may be used to make an albumin fusion protein that may be used in the methods of the invention. For instance, a protein may be fused to both the N- and C-terminal ends of the HA. In such a configuration, the protein portions may be the same or different protein molecules. The structure of bifunctional albumin fusion proteins may be represented as: X-HA-Y or Y-HA-X.

In a specific embodiment, a BCMA protein or fragment or variant thereof that may be used in the methods of the invention may be conjugated to a cytotoxin (e.g., a cytostatic or cytocidal agent). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In another embodiment, a BCMA protein or fragment or variant thereof that may be used in the methods of the invention may be conjugated to a toxin.

By "toxin" is meant one or more compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium.

To improve or alter the characteristics of BCMA polypeptides that may be used in the methods of the invention, protein engineering may be employed. Recombinant DNA technology known to those skilled in the art can be used to create novel mutant proteins or "muteins including single or multiple amino acid substitutions, deletions, additions or fusion proteins". Such modified polypeptides can show, e.g., enhanced activity or increased stability. In addition, they may be purified in higher yields and show better solubility than the corresponding natural polypeptide, at least under certain purification and storage conditions. In yet another embodiment of the invention, the BCMA polypeptide mutant can be a "dominant negative." To this end, defective BCMA polypeptides, such as, for example, mutants lacking all or a portion of the TNF-conserved domain, can be used to diminish the activity of BCMA. The non-functional BCMA polypeptides will assemble to form a receptor (e.g., multimer) that may be capable of binding, but which is incapable of inducing signal transduction.

The BCMA proteins that may be used in the methods of the invention may be in monomers or multimers (i.e., dimers, trimers, tetramers, and higher multimers). In specific embodiments, the polypeptides of the invention are monomers, dimers, trimers or tetramers. In additional embodiments, the multimers of the invention are at least dimers, at least trimers, or at least tetramers. Certain members of the TNF family of proteins are believed to exist in trimeric form (Beutler and Huffel, Science 264:667, 1994; Banner et al., Cell 73:431, 1993). Thus, trimeric BCMA may offer the advantage of enhanced biological activity.

In specific embodiments, the multimers may be homomers or heteromers. As used herein, the term homomer, refers to a multimer containing only BCMA proteins (including BCMA fragments, variants, and fusion proteins, as described herein). These homomers may contain BCMA proteins having identical or different polypeptide sequences. In a specific embodiment, a homomer is a multimer containing only BCMA proteins having an identical polypeptide sequence. In another specific embodiment, a homomer is a multimer containing BCMA proteins having different polypeptide sequences.

As used herein, the term heteromer refers to a multimer containing heterologous proteins (i.e., proteins containing only polypeptide sequences that do not correspond to a polypeptide sequences encoded by the BCMA gene) in addition to the BCMA proteins. Multimers may be the result of hydrophobic, hydrophilic, ionic and/or covalent associations and/or may be indirectly linked, by for example, liposome formation. Thus, in one embodiment, multimers, such as, for example, homodimers, homotrimers, heterotrimers or heterotetramers, are formed when the proteins contact one another in solution. In other embodiments, multimers are formed by covalent associations with and/or between the BCMA proteins. Such covalent associations may involve one or more amino acid residues contained in the polypeptide sequence of the protein. In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation.

Alternatively, such covalent associations may involve one or more amino acid residues contained in the heterologous polypeptide sequence in a BCMA fusion protein. In one example, covalent associations are between the heterologous sequence contained in a fusion protein (see, e.g., U.S. Pat. No. 5,478,925, the contents of which are herein incorporated by reference in its entirety). In a specific example, the covalent associations are between the heterologous sequence contained in a BCMA-Fc fusion protein (as described herein). In another specific example, covalent associations of fusion proteins are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more BCMA polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple BCMA polypeptides separated by peptide linkers may be produced using conventional recombinant DNA technology.

In a specific embodiment, antibodies that bind to a BCMA polypeptide, a polypeptide fragment, a variant of SEQ ID NO:8, and/or an BCMA polypeptide epitope (as determined by immunoassays well known in the art for assaying specific antibody-antigen binding) may be used in the methods of the invention. Anti-BCMA antibodies and fragments thereof have been described in, for example, PCT Publications WO01/087977, WO01/60397, and WO02/66516 and Ch' en, et al., (2005) *Cell Immunol* 236:78-85. Each of the aforementioned references is herein incorporated by reference in its entirety. Antibodies include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to anti-BCMA antibodies), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. In specific embodiments, the immunoglobulin molecules are IgG1. In other specific embodiments, the immunoglobulin molecules are IgG4.

BCMA binding antibody fragments that may be used in the methods of the invention include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included are antigen-binding fragments also comprising any combination of variable region(s) with a hinge region, CH1, CH2, and CH3 domains. The antibodies may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati et al, the contents of which are herein incorporated by reference in its entirety.

Anti-BCMA antibodies that may be used in the methods of the invention may be monospecific, bispecific, trispecific or of greater multispecificity. Multispecific antibodies may be specific for different epitopes of a BCMA polypeptide or may be specific for both a BCMA polypeptide as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992), the contents of which are herein incorporated by reference in their entirety.

BCMA Antibodies may be described or specified in terms of their cross-reactivity. Antibodies that do not bind any other analog, ortholog, or homolog of a BCMA polypeptide may be used in the methods of the invention. In specific embodiments, BCMA antibodies cross-react with murine, rat and/or rabbit homologs of human BCMA proteins and the corresponding epitopes thereof. In a specific embodiment, an anti-BCMA antibody that may be used in the methods of the invention binds not only to BCMA, but also binds to TACI and BAFF-R.

BCMA antibodies that may be used in the methods of the invention may also be described or specified in terms of their binding affinity to a BCMA polypeptide. Preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-12}$ M, or $10^{-12}$ M.

BCMA antibodies that may be used in the methods of the invention may act as agonists or antagonists of the BCMA polypeptides. For example, BCMA antibodies which disrupt the receptor/ligand interactions with the BCMA polypeptides either partially or fully are included. Also included are receptor-specific antibodies which do not prevent ligand binding but prevent receptor activation. Receptor activation (i.e., signaling) may be determined by techniques described herein or otherwise known in the art. For example, receptor activation can be determined by detecting activation of the transcription factors NF-AT, AP-1, and/or NF-kappaB using techniques known in the art, and/or the phosphorylation (e.g., tyrosine or serine/threonine) of the receptor or its substrate by immunoprecipitation followed by western blot analysis.

In a specific embodiment, receptor-specific BCMA antibodies which both prevent ligand binding and receptor activation as well as BCMA antibodies that recognize the receptor-ligand complex, and, preferably, do not specifically recognize the unbound receptor or the unbound ligand may be used in the methods of the invention. The above BCMA antibodies can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4):1786-1794 (1998); Zhu et al., Cancer Res. 58(15): 3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4):755-762 (1995); Muller et al., Structure 6(9):

1153-1167 (1998); Bartunek et al., Cytokine 8(1):14-20 (1996) (which are all incorporated by reference herein in their entireties).

F. Neutrokine-Alpha Receptor, BAFF-R

BAFF-R polypeptides, such as those described below, act as Neutrokine-alpha and/or APRIL antagonists and may also be used in the methods of the present invention. BAFF-R, also known as TR21, is a protein of 184 amino acid residues (SEQ ID NO:10), with a deduced molecular weight of about 18.9 kDa A nucleotide sequence of a cDNA that encodes BAFF-R is given in SEQ ID NO:9. Predicted amino acids from about 1 to about 81 constitute the extracellular domain (SEQ ID NO:10); amino acids from about 82 to about 101 constitute the transmembrane domain (SEQ ID NO:10); and amino acids from about 102 to about 184 constitute the intracellular domain (SEQ ID NO:10).

Accordingly, in one embodiment, a BAFF-R protein that may be used in the methods of the present invention is an isolated polypeptide comprising, or alternatively, consisting of the amino acid sequence of SEQ ID NO:10, or a polypeptide comprising, or alternatively, consisting of a portion of SEQ ID NO:10, such as for example, the BAFF-R extracellular domain (comprising amino acids 1 to 81 of SEQ ID NO:10) and/or the BAFF-R cysteine rich domain (comprising amino acids 19 to 35 of SEQ ID NO:10); as well as polypeptides which are at least 80% identical, more preferably at least 90% or 95% identical, still more preferably at least 96%, 97%, 98%, 99% or 100% identical to the polypeptides described above.

In another embodiment, a BAFF-R protein that may be used in the methods of the present invention is an isolated polypeptide comprising amino acids 1 to 70 of SEQ ID NO:10 and/or the amino acid sequence of SEQ ID NO:26. SEQ ID NO:26 shows amino acids 1-70 of BAFF-R wherein amino acid 20 (valine) in BAFF-R is substituted with asparagine and amino acid 27 (leucine) in BAFF-R is substituted with proline. In another embodiment, a BAFF-R protein that may be used in the methods of the present invention is an isolated polypeptide comprising amino acids 2 to 70 of SEQ ID NO:26. Polypeptides which are at least 80% identical, more preferably at least 90% or 95% identical, still more preferably at least 96%, 97%, 98%, 99% or 100% identical to the polypeptides described above may also be used in the methods of the present invention.

By a polypeptide having an amino acid sequence at least, for example, 95% "identical" to a reference amino acid sequence of a BAFF-R polypeptide is intended that the amino acid sequence of the polypeptide is identical to the reference sequence except that the polypeptide sequence may include up to five amino acid alterations per each 100 amino acids of the reference amino acid of the BAFF-R receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptide fragments of BAFF-R include polypeptides comprising or alternatively, consisting of: an amino acid sequence contained in SEQ ID NO:10. Polypeptide fragments may be "free-standing," or comprised within a larger polypeptide of which the fragment forms a part or region, most preferably as a single continuous region. In additional embodiments, the polypeptide fragments comprise, or alternatively consist of, one or more BAFF-R domains. Preferred polypeptide fragments include a member selected from the group: (a) a polypeptide comprising or alternatively, consisting of, the BAFF-R extracellular domain (predicted to constitute amino acid residues from about 1 to about 81 of SEQ ID NO:10); (b) a polypeptide comprising or alternatively, consisting of, a BAFF-R cysteine rich domain (predicted to constitute amino acid residues from about 19 to about 35 of SEQ ID NO:10); (c) a polypeptide comprising or alternatively, consisting of, the BAFF-R transmembrane domain (predicted to constitute amino acid residues from about 82 to about 101 of SEQ ID NO:10); (d) a polypeptide comprising or alternatively, consisting of, the BAFF-R intracellular domain (predicted to constitute amino acid residues from about 102 to about 184 of SEQ ID NO:10); or (e) any combination of polypeptides (a)-(d).

It is believed that the extracellular cysteine rich motif of BAFF-R is important for interactions between BAFF-R and its ligands, Neutrokine-alpha and APRIL. Accordingly, in preferred embodiments, BAFF-R polypeptide fragments that may be used in the methods of the present invention comprise, or alternatively consist of, the amino acid sequence of amino acid residues 19 to 35 of SEQ ID NO:10. Proteins comprising or alternatively consisting of a polypeptide sequence which is at least 80%, 90%, 95%, 96%, 97%, 98% or 99% identical to the polypeptide sequences of the cysteine rich motif are also preferred.

Other fragments of the BAFF-R protein that may be used in the methods of the invention are fragments characterized by structural or functional attributes of BAFF-R. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) BAFF-R (SEQ ID NO:10) as is discussed in U.S. Pat. No. 7,112,410. Certain preferred regions include, but are not limited to, Garnier-Robson predicted alpha-regions, beta-regions, turn-regions, and coil-regions; Chou-Fasman predicted alpha-regions, beta-regions, and turn-regions; Kyte-Doolittle predicted hydrophilic; Hopp-Woods predicted hydrophobic regions; Eisenberg alpha and beta amphipathic regions; Emini surface-forming regions; and Jameson-Wolf high antigenic index regions, as predicted using the default parameters of these computer programs.

The BAFF-R polypeptide for use in the methods of the invention may be expressed in a modified form, such as a fusion protein (comprising the polypeptide joined via a peptide bond to a heterologous protein sequence (of a different protein)), and may include not only secretion signals but also additional heterologous functional regions. Alternatively, such a fusion protein can be made by protein synthetic techniques, e.g., by use of a peptide synthesizer. Thus, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

A preferred BAFF-R fusion protein that may be used in the methods of the invention comprises a heterologous region from immunoglobulin that is useful to solubilize proteins. For example, EP-A-O 464 533 (Canadian counterpart 2045869) and WO0/0024782 disclose fusion proteins comprising various portions of constant region of immunoglobin molecules together with another human protein or part thereof. BAFF-R immunoglobulin fusion proteins have been described in, for example, Pelletier, et al., (2003) *J Biol Chem* 278:33127-33133 and Carter, et al., (2005) *Arthritis Rheum* 52:3943-3954, herein incorporated by reference in their entirety. In many cases, the Fc part in a fusion protein is thoroughly advantageous for use in therapy and diagnosis and thus results, for example, in improved pharmacokinetic properties (EP-A 0232 262). On the other hand, for some uses, it would be desirable to be able to delete the Fc part after the fusion protein has been expressed, detected and purified in the advantageous manner described. This is the case when the Fc portion proves to be a hindrance to use in therapy and diagnosis, for example, when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., Journal of Molecular Recognition 8:52-58 (1995) and K. Johanson et al., The Journal of Biological Chemistry 270:16: 9459-9471 (1995). In a specific embodiment, the BAFF-R-Fc fusion protein that may be used in the methods of the invention is BR3-Fc.

As one of skill in the art will appreciate, and as discussed above, the BAFF-R polypeptides can be fused to other polypeptide sequences. For example, the BAFF-R polypeptides may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)) resulting in chimeric polypeptides.

Such fusion proteins may facilitate purification, may extend shelf-life and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995).

One example of a BAFF-R-Fc protein is amino acids 1-70 of SEQ ID NO:10 fused to the Fc region of an IgG1 immunoglobulin molecule. Optionally, amino acid 20 (valine) in BAFF-R is substituted with asparagine and amino acid 27 (leucine) in BAFF-R is substituted with proline. SEQ ID NO:26 shows amino acids 1-70 of BAFF-R with these two amino acid changes.

An albumin fusion protein that may be used in methods of the present invention comprises at least a fragment or variant of a BAFF-R polypeptide and at least a fragment or variant of human serum albumin, which are associated with one another, preferably by genetic fusion (i.e., the albumin fusion protein is generated by translation of a nucleic acid in which a polynucleotide encoding all or a portion of BAFF-R is joined in-frame with a polynucleotide encoding all or a portion of albumin) or chemical conjugation to one another. The BAFF-R polypeptide and albumin protein, once part of the albumin fusion protein, may be referred to as a "portion", "region" or "moiety" of the albumin fusion protein (e.g., a "BAFF-R portion" or an "albumin protein portion").

In one embodiment, an albumin fusion protein that may be used in the methods of the invention comprises, or alternatively consists of, a BAFF-R polypeptide and a serum albumin protein. In other embodiments, an albumin fusion protein that may be used in the methods of the invention comprises, or alternatively consists of, a fragment of BAFF-R and a serum albumin protein. In other embodiments, an albumin fusion protein that may be used in the methods of the invention comprises, or alternatively consists of, a variant of BAFF-R and a serum albumin protein In preferred embodiments, the serum albumin protein component of the albumin fusion protein is the mature portion of serum albumin.

In further embodiments, an albumin fusion protein that may be used in the methods of the invention comprises, or alternatively consists of, a BAFF-R polypeptide and a biologically active and/or therapeutically active fragment of serum albumin. In further embodiments, an albumin fusion protein that may be used in the methods of the invention comprises, or alternatively consists of, a BAFF-R polypeptide and a biologically active and/or therapeutically active variant of serum albumin. In preferred embodiments, the BAFF-R portion of the albumin fusion protein is the full-length BAFF-R polypeptide. In a further preferred embodiment, the BAFF-R portion of the albumin fusion protein is the mature, soluble domain of the BAFF-R polypeptide.

In further embodiments, an albumin fusion protein that may be used in the methods of the invention comprises, or alternatively consists of, a fragment or variant of BAFF-R and a biologically active and/or therapeutically active fragment or variant of serum albumin. In preferred embodiments, the invention provides an albumin fusion protein comprising, or alternatively consisting of, the mature portion of the BAFF-R polypeptide and the mature portion of serum albumin.

In further embodiments, an albumin fusion protein that may be used in the methods of the invention comprises, or alternatively consists of, a fragment or variant of BAFF-R and a biologically active and/or therapeutically active fragment or variant of serum albumin. In preferred embodiments, the invention provides an albumin fusion protein comprising, or alternatively consisting of, the mature portion of the BAFF-R polypeptide and the mature portion of serum albumin. (including but not limited to recombinant human serum albumin or fragments or variants thereof (see, e.g., U.S. Pat. No. 5,876, 969, issued Mar. 2, 1999, EP Patent 0 413 622, and U.S. Pat. No. 5,766,883, issued Jun. 16, 1998, herein incorporated by reference in their entirety)). In a preferred embodiment, BAFF-R polypeptides (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment BAFF-R polypeptides (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. BAFF-R polypeptides (including fragments or variants thereof) may be fused to either the N- or C-terminal end of the heterologous protein (e.g., immunoglobulin Fc polypeptide or human serum albumin polypeptide).

In preferred embodiments, the human serum albumin protein used in the albumin fusion proteins that may be used in the methods of the invention contains one or both of the following sets of point mutations with reference to SEQ ID NO:11: Leu-407 to Ala, Leu-408 to Val, Val-409 to Ala, and Arg-410 to Ala; or Arg-410 to A, Lys-413 to Gln, and Lys-414 to Gln (see, e.g., International Publication No. WO95/23857, hereby incorporated in its entirety by reference herein). In even more preferred embodiments, albumin fusion proteins that may be used in the methods of the invention that contain one or both of above-described sets of point mutations have improved stability/resistance to yeast Yap3p proteolytic cleavage, allowing increased production of recombinant albumin fusion proteins expressed in yeast host cells.

Preferably, the albumin fusion protein that may be used in the methods of the invention comprises HA as the N-terminal portion, and BAFF-R polypeptide as the C-terminal portion. Alternatively, an albumin fusion protein comprising HA as the C-terminal portion, and BAFF-R polypeptide as the N-terminal portion may also be used.

In other embodiments, the albumin fusion protein that may be used in methods of the invention has a BAFF-R polypeptide fused to both the N-terminus and the C-terminus of albumin. In a specific embodiment, the BAFF-R polypeptides fused at the N- and C-termini are the same. In another embodiment, the BAFF-R polypeptides fused at the N- and C-termini are different BAFF-R polypeptides. In another embodiment, a BAFF-R polypeptide is fused at either the N- or C-terminus of albumin, and a heterologous polypeptide is fused at the remaining terminus.

Additionally, the albumin fusion proteins that may be used in the methods of the invention may include a linker peptide between the fused portions to provide greater physical separation between the moieties. The linker peptide may consist of amino acids such that it is flexible or more rigid.

Generally, the albumin fusion proteins that may be used in the methods of the invention may have one HA-derived region and one BAFF-R region. Multiple regions of each protein, however, may be used to make an albumin fusion protein that may be used in the methods of the invention. Similarly, more than one protein may be used to make an albumin fusion protein that may be used in the methods of the invention. For instance, a protein may be fused to both the N- and C-terminal ends of the HA. In such a configuration, the protein portions may be the same or different protein molecules. The structure of bifunctional albumin fusion proteins may be represented as: X-HA-Y or Y-HA-X.

In a specific embodiment, a BAFF-R protein or fragment or variant thereof that may be used in the methods of the invention may be conjugated to a cytotoxin (e.g., a cytostatic or cytocidal agent). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In another embodiment, a BAFF-R protein or fragment or variant thereof that may be used in the methods of the invention may be conjugated to a toxin.

By "toxin" is meant one or more compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium.

To improve or alter the characteristics of BAFF-R polypeptides that may be used in the methods of the invention, protein engineering may be employed. Recombinant DNA technology known to those skilled in the art can be used to create novel mutant proteins or "muteins including single or multiple amino acid substitutions, deletions, additions or fusion proteins". Such modified polypeptides can show, e.g., enhanced activity or increased stability. In addition, they may be purified in higher yields and show better solubility than the corresponding natural polypeptide, at least under certain purification and storage conditions. In yet another embodiment of the invention, the BAFF-R polypeptide mutant can be a "dominant negative." To this end, defective BAFF-R polypeptides, such as, for example, mutants lacking all or a portion of the TNF-conserved domain, can be used to diminish the activity of BAFF-R. The non-functional BAFF-R polypeptides will assemble to form a receptor (e.g., multimer) that may be capable of binding, but which is incapable of inducing signal transduction.

The BAFF-R proteins that may be used in the methods of the invention may be in monomers or multimers (i.e., dimers, trimers, tetramers, and higher multimers). In specific embodiments, the polypeptides of the invention are monomers, dimers, trimers or tetramers. In additional embodiments, the multimers of the invention are at least dimers, at least trimers, or at least tetramers. Certain members of the TNF family of proteins are believed to exist in trimeric form (Beutler and Huffel, Science 264:667, 1994; Banner et al., Cell 73:431, 1993). Thus, trimeric BAFF-R may offer the advantage of enhanced biological activity.

In specific embodiments, the multimers may be homomers or heteromers. As used herein, the term homomer, refers to a multimer containing only BAFF-R proteins (including BAFF-R fragments, variants, and fusion proteins, as described herein). These homomers may contain BAFF-R proteins having identical or different polypeptide sequences. In a specific embodiment, a homomer is a multimer containing only BAFF-R proteins having an identical polypeptide sequence. In another specific embodiment, a homomer is a multimer containing BAFF-R proteins having different polypeptide sequences.

As used herein, the term heteromer refers to a multimer containing heterologous proteins (i.e., proteins containing only polypeptide sequences that do not correspond to a polypeptide sequences encoded by the BAFF-R gene) in addition to the BAFF-R proteins. Multimers may be the result of hydrophobic, hydrophilic, ionic and/or covalent associations and/or may be indirectly linked, by for example, liposome formation. Thus, in one embodiment, multimers, such as, for example, homodimers, homotrimers, heterotrimers or heterotetramers, are formed when the proteins contact one another in solution. In other embodiments, multimers are formed by covalent associations with and/or between the BAFF-R proteins. Such covalent associations may involve one or more amino acid residues contained in the polypeptide sequence of the protein. In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation.

Alternatively, such covalent associations may involve one or more amino acid residues contained in the heterologous polypeptide sequence in a BAFF-R fusion protein. In one example, covalent associations are between the heterologous sequence contained in a fusion protein (see, e.g., U.S. Pat. No. 5,478,925, the contents of which are herein incorporated by reference in its entirety). In a specific example, the covalent associations are between the heterologous sequence contained in a BAFF-R-Fc fusion protein (as described herein). In another specific example, covalent associations of fusion proteins are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more BAFF-R polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple BAFF-R polypeptides separated by peptide linkers may be produced using conventional recombinant DNA technology.

In a specific embodiment, antibodies that bind to a BAFF-R polypeptide, a polypeptide fragment, a variant of SEQ ID NO:10, and/or an BAFF-R polypeptide epitope (as determined by immunoassays well known in the art for assaying specific antibody-antigen binding) may be used in the methods of the invention. Anti-BAFF-R antibodies and fragments thereof have been described in, for example, Lee, et al., (2006) *Synthetic anti-BR3 antibodies that mimic BAFF binding and target both human and murine B cells Blood* (Blood First Edition Paper, prepublished online Jul. 13, 2006) Vol. 0, No. 2006, pp. 200603011, Ch' en, et al., (2005) *Cell Immunol* 236:78-85, Nakamura, et al., (2005) *Virchows Arch* 447:53-60, and Carter, et al., (2005) *Arthritis Rheum* 52:3943-3954. Each of the aforementioned references is herein incorporated by reference in its entirety. Antibodies include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to anti-BAFF-R antibodies), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. In specific embodiments, the immunoglobulin molecules are IgG1. In other specific embodiments, the immunoglobulin molecules are IgG4.

BAFF-R binding antibody fragments that may be used in the methods of the invention include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included are antigen-binding fragments also comprising any combination of variable region(s) with a hinge region, CH1, CH2, and CH3 domains. The antibodies may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati et al, the contents of which are herein incorporated by reference in its entirety.

Anti-BAFF-R antibodies that may be used in the methods of the invention may be monospecific, bispecific, trispecific or of greater multispecificity. Multispecific antibodies may be specific for different epitopes of a BAFF-R polypeptide or may be specific for both a BAFF-R polypeptide as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992), the contents of which are herein incorporated by reference in their entirety.

BAFF-R Antibodies may be described or specified in terms of their cross-reactivity. Antibodies that do not bind any other analog, ortholog, or homolog of a BAFF-R polypeptide may be used in the methods of the invention. In specific embodiments, BAFF-R antibodies cross-react with murine, rat and/or rabbit homologs of human BAFF-R proteins and the corresponding epitopes thereof. In a specific embodiment, an anti-BAFF-R antibody that may be used in the methods of the invention binds not only to BAFF-R, but also binds to TACI and BCMA.

BAFF-R antibodies that may be used in the methods of the invention may also be described or specified in terms of their binding affinity to a BAFF-R polypeptide. Preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-12}$ M, or $10^{-12}$ M.

BAFF-R antibodies that may be used in the methods of the invention may act as agonists or antagonists of the BAFF-R polypeptides. For example, BAFF-R antibodies which disrupt the receptor/ligand interactions with the BAFF-R polypeptides either partially or fully are included. Also included are receptor-specific antibodies which do not prevent ligand binding but prevent receptor activation. Receptor activation (i.e., signaling) may be determined by techniques described herein or otherwise known in the art. For example, receptor activation can be determined by detecting activation of the transcription factors NF-AT, AP-1, and/or NF-kappaB using techniques known in the art, and/or the phosphorylation (e.g., tyrosine or serine/threonine) of the receptor or its substrate by immunoprecipitation followed by western blot analysis.

In a specific embodiment, receptor-specific BAFF-R antibodies which both prevent ligand binding and receptor activation as well as BAFF-R antibodies that recognize the receptor-ligand complex, and, preferably, do not specifically recognize the unbound receptor or the unbound ligand may be used in the methods of the invention. The above BAFF-R antibodies can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4):1786-1794 (1998); Zhu et al., Cancer Res. 58(15): 3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4):755-762 (1995); Muller et al., Structure 6(9): 1153-1167 (1998); Bartunek et al., Cytokine 8(1):14-20 (1996) (which are all incorporated by reference herein in their entireties).

G. Anti-APRIL Antibodies

In a specific embodiment, the Neutrokine-alpha antagonist is an anti-APRIL antibody or antigen-binding fragment thereof. Anti-APRIL antibodies and fragments thereof have been described in, for example, PCT Publications WO01/087977, WO99/12965, WO01/60397, and WO02/094192; U.S. Pat. No. 6,506,882; U.S. Patent Publication No. 2003/0166864, filed Oct. 11, 2002; and Ch' en, et al., (2005) Cell Immunol 236:78-85; and are described in more detail below. Each of the aforementioned references is herein incorporated by reference in its entirety.

In a specific embodiment, antibodies that bind to a APRIL polypeptide, polypeptide fragment, or variant of SEQ ID NO:4, and/or an APRIL epitope (as determined by immunoassays well known in the art for assaying specific antibody-antigen binding) may be used in the methods of the invention. In a specific embodiment, antibodies that may be used in the methods of the invention may bind APRIL polypeptides fused to other polypeptide sequences. For example, APRIL polypeptides may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995).

In specific embodiments, antibodies that may be used in the methods of the invention bind homomeric, especially homotrimeric, APRIL polypeptides. In other specific embodiments, antibodies that may be used in the methods of the invention bind heteromeric, especially heterotrimeric, APRIL polypeptides such as a heterotrimer containing two APRIL polypeptides and one Neutrokine-alpha polypeptide or a heterotrimer containing one APRIL polypeptide and two Neutrokine-alpha polypeptides. In a specific embodiment, the antibodies that may be used in the methods of the invention bind homomeric, especially homotrimeric, APRIL polypeptides, wherein the individual protein components of the multimers consist of the mature form of APRIL (e.g., amino acids residues 105-250 of SEQ ID NO:4). In other specific embodiments, antibodies that may be used in the methods of the invention bind heteromeric, especially heterotrimeric, APRIL polypeptides such as a heterotrimer containing two APRIL polypeptides and one Neutrokine-alpha polypeptide or a heterotrimer containing one APRIL polypeptide and two Neutrokine-alpha polypeptides, and wherein the individual protein components of the APRIL heteromer consist of either the mature extracellular soluble portion of APRIL (e.g., amino acids residues 105-250 of SEQ ID NO:4) or the mature extracellular soluble portion Neutrokine-alpha (e.g., amino acid residues 134-285 of SEQ ID NO:2).

In specific embodiments, the antibodies that may be used in the methods of the invention bind conformational epitopes of a APRIL monomeric protein. In specific embodiments, the antibodies that may be used in the methods of the invention bind conformational epitopes of a APRIL multimeric, especially trimeric, protein. In other embodiments, antibodies that may be used in the methods of the invention bind conformational epitopes that arise from the juxtaposition of APRIL with a heterologous polypeptide, such as might be present when APRIL forms heterotrimers (e.g., with Neutrokine-alpha polypeptides), or in fusion proteins between APRIL and a heterologous polypeptide.

Antibodies that may be used in the methods of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-id antibodies to anti-APRIL antibodies), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In preferred embodiments, the immunoglobulin is an IgG1 or an IgG4 isotype. Immunoglobulins may have both a heavy and light chain. An array of IgG, IgE, IgM, IgD, IgA, and IgY heavy chains may be paired with a light chain of the kappa or lambda forms.

In a specific embodiment, the antibodies that may be used in the methods of the invention are APRIL-binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. APRIL-binding antibody fragments, including single-chain antibodies, may comprise the variable region(s) alone or in combination with the entirety or a portion of the following: hinge region, CH1, CH2, and CH3 domains. In a specific embodiment, APRIL-binding fragments that may be used in the methods of the invention comprise any combination of variable region(s) with a hinge region, CH1, CH2, and CH3 domains. The antibodies that may be used in the methods of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati et al, the contents of which are herein incorporated by reference in its entirety.

The antibodies that may be used in the methods of the invention may be monospecific, bispecific, trispecific or of greater multispecificity. Multispecific antibodies may be specific for different epitopes of a APRIL polypeptide or may be specific for both a APRIL polypeptide as well as for a heterologous epitope, such as a heterologous polypeptide or solid support material. See, e.g., PCT publications WO 93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Anti-APRIL antibodies that may be used in the methods of the invention may be described or specified in terms of their cross-reactivity. Antibodies that do not bind any other analog, ortholog, or homolog of a APRIL polypeptide may be used in the methods of the invention. In a specific embodiment, antibodies that may be used in the methods of the invention cross react with Neutrokine-alpha. In specific embodiments, antibodies that may be used in the methods of the invention cross-react with murine, rat and/or rabbit homologs of human proteins and the corresponding epitopes thereof.

Antibodies that may be used in the methods of the invention may also be described or specified in terms of their binding affinity to a APRIL polypeptide. In specific embodiments, antibodies that may be used in the methods of the invention bind APRIL polypeptides, or fragments or variants thereof, with a dissociation constant or $K_D$ of less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, or $10^{-12}$ M. In a specific embodiment, antibodies that may be used in the methods of the invention bind APRIL polypeptides with a dissociation constant or $K_D$ that is within any one of the ranges that are between each of the individual recited values.

For example, APRIL antibodies which disrupt the receptor/ligand interactions with APRIL polypeptides either partially or fully are included. Also included are APRIL-specific antibodies which do not prevent ligand binding but prevent receptor activation. Receptor activation (i.e., signaling) may be determined by techniques described herein or otherwise known in the art. For example, receptor activation can be determined by detecting activation of the transcription factors NF-AT, AP-1, and/or NF-kappaB using techniques known in the art, and/or the phosphorylation (e.g., tyrosine or serine/threonine) of the receptor or its substrate by immunoprecipitation followed by western blot analysis.

In a specific embodiment, APRIL-specific antibodies which both prevent ligand binding and receptor activation as well as antibodies that recognize the receptor-ligand complex, and, preferably, do not specifically recognize the unbound receptor or the unbound ligand may be used in the methods of the invention. In a specific embodiment, neutralizing antibodies which bind the ligand and prevent binding of the ligand to the receptor, as well as antibodies which bind the ligand, thereby preventing receptor activation, but do not prevent the ligand from binding the receptor may be used in the methods of the invention. The above APRIL antibodies can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

H. APRIL Binding Polypeptides

In a specific embodiment, the Neutrokine-alpha antagonist is an APRIL binding peptide or polypeptide. APRIL binding peptides or polypeptides have been described in, for example International Patent Publication numbers WO01/87977, WO01/87979 and US Patent Publication numbers US2002081296 and US2002086018, each of which is herein incorporated by reference in its entirety. APRIL binding peptides that may be used in the methods of the present invention include short polypeptides identified from random peptide sequences displayed by fusion with coat proteins of filamentous phage. For discussion of phage display peptide library technology see, for example, Scott et al. (1990), Science 249: 386; Devlin et al. (1990), Science 249: 404; U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference in its entirety). Phage expressing the peptides are isolated by successive rounds of affinity purification against an immobilized APRIL target peptide followed by repropagation. The candidates with the highest binding to APRIL can be sequenced to determine the identity of each binding peptide. Each identified APRIL binding peptide may then be attached to a "vehicle" to generate a further APRIL binding peptide for use in the methods of the present experiment. The term "vehicle" refers to a molecule that prevents degradation and/or increases half-life, reduces toxicity, reduces immunogenicity, or increases biological activity of an APRIL binding peptide. Exemplary vehicles include an Fc domain and variants thereof (a "Peptibody" which is preferred); a linear polymer (e.g., polyethylene glycol (PEG), including 5 kD, 20 kD, and 30 kD PEG, polylysine, dextran, etc.); a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published Oct. 28, 1993); a lipid; a cholesterol group (such as a steroid); a carbohydrate or oligosaccharide (e.g., dextran); any natural or synthetic protein, polypeptide or peptide that binds to a salvage receptor; albumin, including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety); and a leucine zipper domain, and other such proteins and protein fragments. APRIL binding polypeptides that may be used in the methods of the invention require the presence of at least one vehicle attached to the peptide through the N-terminus, C-terminus or a sidechain of one of the amino acid residues. Multiple vehicles may also be used; e.g., Fc's at each terminus or an Fc at a terminus and a PEG group at the other terminus or a sidechain. For APRIL binding peptides an Fc domain is the preferred vehicle. The Fc domain may be fused to the N or C termini of the peptides or at both the N and C termini. Fusion to the N terminus is preferred.

As noted above, Fc variants are suitable vehicles for APRIL binding peptides that may be used in the methods of the invention. A native Fc may be extensively modified to form an Fc variant, provided binding to the salvage receptor is maintained; see, for example WO 97/34631 and WO 96/32478. In such Fc variants, one may remove one or more sites of a native Fc that provide structural features or functional activity not required by the APRIL binding peptides that may be used in the methods of the invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). Even when cysteine residues are removed, the single chain Fc domains can still form a dimeric Fc domain that is held together non-covalently.

2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionine residue, especially when the molecule is expressed recombinantly in a bacterial cell such as *E. coli*.

3. A portion of the N-terminus of a native Fc is removed to prevent N-terminal heterogeneity when expressed in a selected host cell. For this purpose, one may delete any of the first 20 amino acid residues at the N-terminus.

4. One or more glycosylation sites are removed. Residues that are typically glycosylated (e.g., asparagine) may confer cytolytic response. Such residues may be deleted or substituted with unglycosylated residues (e.g., alanine).

5. Sites involved in interaction with complement, such as the C1q binding site, are removed. For example, one may delete or substitute the EKK sequence of human IgG1. Complement recruitment may not be advantageous for the molecules that may be used in the methods of the invention and so may be avoided with such an Fc variant.

6. Sites are removed that affect binding to Fc receptors other than a salvage receptor. A native Fc may have sites for interaction with certain white blood cells that are not required for the Neutrokine-alpha binding peptide fusion molecules that may be used in the methods of the invention and so may be removed.

7. The ADCC site is removed. ADCC sites are known in the art; see, for example, Molec. Immunol. 29 (5): 633-9 (1992) with regard to ADCC sites in IgG1. These sites, as well, are not required for the fusion molecules that may be used in the methods of the invention and so may be removed.

8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

An alternative vehicle for APRIL binding peptides that may be used in the methods of the invention would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277. Peptides could also be selected by phage display or RNA-peptide screening for binding to the salvage receptor. Such salvage receptor-binding compounds are also included within the meaning of "vehicle" and may be used in the for APRIL binding peptides that may be used in the methods of the invention. Such vehicles should be selected for increased half-life (e.g., by avoiding sequences recognized by proteases) and decreased immunogenicity (e.g., by favoring non-immunogenic sequences, as discovered in antibody humanization).

As noted above, polymer vehicles may also be used in APRIL binding peptides that may be used in the methods of the invention. Various means for attaching chemical moieties useful as vehicles are currently available, see, e.g., Patent Cooperation Treaty ("PCT") International Publication No. WO 96/11953, herein incorporated by reference in its entirety. This PCT publication discloses, among other things, the selective attachment of water soluble polymers to the N-terminus of proteins.

In a specific embodiment, a preferred polymer vehicle is polyethylene glycol (PEG). The PEG group may be of any convenient molecular weight and may be linear or branched. The average molecular weight of the PEG will preferably range from about 2 kiloDalton ("kD") to about 100 kD, more preferably from about 5 kD to about 50 kD, most preferably from about 5 kD to about 10 kD. The PEG groups will generally be attached to the APRIL binding peptides that may be used in the methods of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for APRIL binding peptides that may be used in the methods of the invention. Dextrans are polysaccharide polymers comprised of individual subunits of glucose predominantly linked by α1-6 linkages. The dextran itself is available in many molecular weight ranges, and is readily available in molecular weights from about 1 kD to about 70 kD. Dextran is a suitable water soluble polymer for use in APRIL binding peptides that may be used in the methods of the invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference in its entirety. Dextran of about 1 kD to about 20 kD is preferred when dextran is used as a vehicle in accordance with the present invention.

In a specific embodiment, APRIL binding peptides that may be used in the methods of the invention optionally include a "linker". When present, its chemical structure is not critical, since it serves primarily as a spacer. The linker is preferably made up of amino acids linked together by peptide bonds. Thus, in preferred embodiments, the linker is made up of from 1 to 30 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly $(Gly)_4$, $(Gly)_5$), poly(Gly-Ala), and polyalanines. Preferred linkers are amino acid linkers comprising greater than 5 amino acids, with suitable linkers having up to about 500 amino acids selected from glycine, alanine, proline, asparagine, glutamine, lysine, threonine, serine or aspartate. Linkers of about 20 to 50 amino acids are most preferred.

Non-peptide linkers are also useful for APRIL binding peptides that may be used in the methods of the invention. For example, alkyl linkers such as —NH—$(CH_2)_n$—C(O)—, wherein n=2-20 could be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc.

I. Antisense and siRNAs

In a specific embodiment, the Neutrokine-alpha antagonist is an antisense RNA, catalytic RNA (ribozyme) or short interfering RNA (siRNA) that targets Neutrokine-alpha, APRIL or receptors for Neutrokine-alpha (e.g., TACI, BCMA and BAFF-R). In a specific embodiment, antisense molecules directed against Neutrokine-alpha, APRIL, TACI, BCMA or BAFF-R may be used in the methods of the invention. Antisense technology can be used to control gene expression through antisense DNA or RNA or through triple-helix formation. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the extracellular domain of the polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of Neutrokine-alpha, APRIL, TACI, BCMA or BAFF-R. The antisense RNA oligonucleotide hybridizes to the mRNA in vivo and blocks translation of the mRNA molecule into Neutrokine-alpha, APRIL, TACI, BCMA or BAFF-R polypeptide. The oligonucleotides described above can also be delivered to cells such that the antisense RNA or DNA may be expressed in vivo to inhibit production of Neutrokine-alpha, APRIL, TACI, BCMA or BAFF-R.

In one embodiment, the Neutrokine-alpha, APRIL, TACI, BCMA or BAFF-R antisense nucleic acid that may be used in the methods of the invention is produced intracellularly by transcription from an exogenous sequence. For example, a vector or a portion thereof, is transcribed, producing an antisense nucleic acid (RNA) that may be used in the methods of the invention. Such a vector would contain a sequence encoding the Neutrokine-alpha, APRIL, TACI, BCMA or BAFF-R antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding Neutrokine-alpha, APRIL, TACI, BCMA or BAFF-R, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304-310 (1981), the promoter contained in the 3' long terminal repeat of Rous sarcoma virus (Yamamoto et al., Cell 22:787-797 (1980), the herpes thymidine promoter (Wagner et al., Proc. Natl. Acad. Sci. U.S.A. 78:1441-1445 (1981), the regulatory sequences of the metallothionein gene (Brinster, et al., Nature 296:39-42 (1982)), etc.

The antisense nucleic acids that may be used in the methods of the invention comprise a sequence complementary to at least a portion of an RNA transcript of a Neutrokine-alpha, APRIL, TACI, BCMA or BAFF-R gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded Neutrokine-alpha, APRIL, TACI, BCMA or BAFF-R antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a Neutrokine-alpha, APRIL, TACI, BCMA or BAFF-R RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-335. Thus, oligonucleotides complementary to either the 5'- or 3'-non-translated, non-coding regions of Neutrokine-alpha (SEQ ID NO:1), APRIL (SEQ ID NO:3), TACI (SEQ ID NO:5), BCMA (SEQ ID NO:7) or BAFF-R (SEQ ID NO:9), could be used in an antisense approach to inhibit translation of endogenous Neutrokine-alpha, APRIL, TACI, BCMA or BAFF-R mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with methods of the invention. Whether designed to hybridize to the 5'-, 3'- or coding region of Neutrokine-alpha, APRIL, TACI, BCMA or BAFF-R mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides that may be used in the methods of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., Proc. Natl. Acad. Sci. 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., BioTechniques 6:958-976 (1988)) or intercalating agents. (See, e.g., Zon, Pharm. Res. 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide that may be used in the methods of the invention may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide that may be used in the methods of the invention may also comprise at least one modified sugar moiety selected from the group including, but not limited to, arabinose, 2-fluoroarabinose, xylulose, and hexose.

In yet another embodiment, the antisense oligonucleotide that may be used in the methods of the invention comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide that may be used in the methods of the invention is an alpha-anomeric oligonucleotide. An alpha-anomeric oligonucleotide forms specific double-stranded hybrids with complementary RNA in which, contrary to the usual beta-units, the strands run parallel to each other (Gautier et al., Nucl. Acids Res. 15:6625-6641 (1987)). The oligonucleotide is a 2-O-methylribonucleotide (Inoue et al., Nucl. Acids Res. 15:6131-6148 (1987)), or a chimeric RNA-DNA analogue (Inoue et al., FEBS Lett. 215:327-330 (1997)).

Polynucleotides that may be used in the methods of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448-7451 (1988)), etc.

While antisense nucleotides complementary to the Neutrokine-alpha, APRIL, TACI, BCMA or BAFF-R coding region sequence could be used, those complementary to the transcribed untranslated region are most preferred for use in the methods of the invention.

In a specific embodiment, Neutrokine-alpha antagonists that may be used in the methods of the invention also include a catalytic RNA, or a ribozyme (See, e.g., PCT International Publication WO 90/11364, published Oct. 4, 1990; Sarver et al, Science 247:1222-1225 (1990) directed against Neutrokine-alpha, APRIL, TACI, BCMA or BAFF-R. While ribozymes that cleave mRNA at site specific recognition sequences can be used to destroy Neutrokine-alpha, APRIL, TACI, BCMA or BAFF-R mRNAs, the use of hammerhead ribozymes is preferred for use in the methods of the invention. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of Neutrokine-alpha, APRIL, TACI, BCMA or BAFF-R. Preferably, the ribozyme is engineered so that the cleavage recognition site is located near the 5' end of the Neutrokine-alpha, APRIL, TACI, BCMA or BAFF-R mRNA; i.e., to increase efficiency and minimize the intracellular accumulation of non-functional mRNA transcripts.

As in the antisense approach, the ribozymes that may be used in the methods of the invention can be composed of modified oligonucleotides (e.g., for improved stability, targeting, etc.) and should be delivered to cells which express Neutrokine-alpha, APRIL, TACI, BCMA or BAFF-R in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous Neutrokine-alpha, APRIL, TACI, BCMA or BAFF-R messages and inhibit translation. Since ribozymes unlike antisense molecules, are catalytic, a lower intracellular concentration is required for efficiency.

In a specific embodiment, short interfering RNA directed against Neutrokine-alpha, APRIL, TACI, BCMA or BAFF-R may be used in the methods of the invention. siRNA technology can be used to control gene expression through induction of the cells RNA-induced silencing complex (RISC). siRNA techniques are discussed, for example, in Hamilton A J and Baulcombe D C. Science. 1999 Oct. 29; 286(5441):950-2; Elbashir S M, et al. Nature. 2001 May 24; 411(6836):494-8 and Hanon, Gregory J. and Rossi, John J. Nature 431, 371-378 (2004). The methods are based on the introduction of short double stranded RNA (generally 20-25 nucleotides) into a cell. The doublestranded RNA is unwound and each strand separated. A single strand of the RNA is then incorporated into the RISC. The RISC then directs sequence specific mRNA cleavage, resulting in translational repression. For example, the coding portion of a polynucleotide that encodes a Neutrokine-alpha, APRIL, TACI, BCMA or BAFF-R polypeptide may be used to design a siRNA oligonucleotide of about 20 to 25 nucleotides in length. A DNA oligonucleotide is designed with the appropriate 20-25 nucleotide fragment, a spacer of approximately 9 nucleotides, and the reverse complement of the chosen nucleotide fragment. The RNA transcript produced from this construct would be expected to fold on itself to form a hairpin loop. Delivery of the hairpin loop RNA to the cell results in processing by the Rnase, Dicer to yield the short double stranded siRNA. Incorporation of a strand of this siRNA into the RISC effector complex results in cleavage of mRNA targeted by the siRNA in order to inhibit production of Neutrokine-alpha, APRIL, TACI, BCMA or BAFF-R.

In one embodiment, the Neutrokine-alpha, APRIL, TACI, BCMA or BAFF-R siRNA nucleic acid that may be used in the methods of the invention is produced intracellularly by transcription from an exogenous sequence. For example, a vector or a portion thereof, is transcribed, producing an siRNA that may be used in the methods of the invention. Such a vector would contain a sequence encoding the Neutrokine-alpha, APRIL, TACI, BCMA or BAFF-R siRNA nucleic acid. Such vectors can be constructed by recombinant DNA technology methods standard in the art. Vectors can be plasmid, viral, or others known in the art, used for replication and expression in vertebrate cells. Transcription of the sequence encoding the Neutrokine-alpha, APRIL, TACI, BCMA or BAFF-R siRNA is typically carried out using a RNA polymerase III promoter (e.g., U6 or H1), which usually direct the transcription of small nuclear RNAs (snRNAs).

B-Cell Modulators

In addition to receptors for Neutrokine-alpha and APRIL, B lymphocytes express a variety of cell surface molecules that function to inform B-cells about the extracellular microenvironment and act as transmembrane signals to positively and negatively regulate B-cell function and survival. Among these receptors, CD19, CD20 and CD22 have been identified as promising targets for therapeutic intervention.

CD20 is an integral membrane protein that acts in a complex as a calcium channel. Inhibitors of the CD20 calcium channel disrupt $Ca^{2+}$ homeostasis and cell cycle progression. In a specific embodiment, an anti-CD20 antibody may be used in the methods of the present invention. In a preferred embodiment, the anti-CD20 antibody that may be used in the methods of the invention is Rituxan® (rituximab). In another preferred embodiment, the anti-CD20 antibody that may be used in the methods of the invention is TRU-015. In another preferred embodiment, the anti-CD20 antibody that may be used in the methods of the invention is ocrelizumab (PRO70769). In another preferred embodiment, the anti-CD20 antibody that may be used in the methods of the invention is IMMU-106. In another preferred embodiment, the anti-CD20 antibody that may be used in the methods of the invention is HuMax-CD20.

CD22 is a member of the single family of sialic acid binding proteins found in a variety of cells, including B lymphocytes. The interaction of CD22 with a variety of cis and trans carbohydrate ligands results in regulation of various aspects of B-cell development, proliferation and activation. In a specific embodiment, an anti-CD22 antibody may be used in the methods of the present invention. In a preferred embodiment, the anti-CD22 antibody that may be used in the methods of the invention is epratuzumab.

Other Immunomodulatory Agents

In a specific embodiment, the methods of the present invention may be practiced with one or more of the following drugs: CellCept (mycophenolate mofetil; MMF), Orencia (abatacept; CTLA4-Ig), Riquent™ (abetimus sodium; LJP 394), Prestara™ (praserone), Edratide (TV-4710), Actemra® (tocilizumab; atlizumab), VX-702, TRX 1, IPP-201101, ABR-215757, sphingosine-1-phosphate-1 (SIP1) agonist, HuMax-Inflam™ (MDX 018), MEDI-545 (MDX-1103/1333), RhuDex®, Deoxyspergualin, ENBREL™ (Etanercept), anti-TNF antibody, anti-interferon-alpha antibody.

Patient Populations

As described herein, data from a clinical trial in which lupus patients were treated with an antibody that neutralizes Neutrokine-alpha protein, significantly ameliorated symptoms associated with lupus in patients having an ANA titer of 1:80 or greater, and/or greater than or equal to 30 IU/mL of anti-dsDNA (Example 1). Surprisingly, statistically significant improvements in clinical endpoints measuring disease activity (such as reduction in SELENA SLEDAI score, explained in more detail below) were only obtained in a subset of the patients, as opposed to the entire patient population enrolled in the clinical trial. Thus, the present invention relates to the identification of subgroups of patients that are more likely to respond to treatment with an immunomodulatory agent such as an antagonist of Neutrokine-alpha.

Additionally, as described herein, systemic lupus erythematosus (SLE) is an extremely heterogeneous disease that is difficult to correctly diagnose due to the broad nature of symptoms that a patient may have and the fact that many of the symptoms associated with lupus are also seen in a number of other autoimmune diseases. Thus, one embodiment of the present invention provides a method of treating a patient that has an ANA titer of 1:80 or greater, and/or greater than or equal to 30 IU/mL of anti-dsDNA antibodies in their blood plasma or serum comprising administering a therapeutically effective amount of an antagonist of Neutrokine-alpha or other immunomodulatory agent known in the art and/or described herein irrespective of the disease diagnosis. Another embodiment of the present invention provides a method of treating a patient that has an ANA titer of 1:80 or greater, and/or greater than or equal to 30 IU/mL of anti-dsDNA antibodies in their blood plasma or serum comprising administering a therapeutically effective amount an antagonist of Neutrokine-alpha or other immunomodulatory agent known in the art and/or described herein irrespective of the disease diagnosis, and further comprising making a determination that the patient has an ANA titer of 1:80 or greater, and/or greater than or equal to 30 IU/mL of anti-dsDNA antibodies in their blood plasma or serum, prior to administering the immunomodulatory agent.

In further embodiments, the patient that has an ANA titer of 1:80 or greater, and/or greater than or equal to 30 IU/mL of anti-dsDNA antibodies in their blood plasma or serum has an autoimmune disease that is not SLE. In further embodiments, the patient that has an ANA titer of 1:80 or greater, and/or greater than or equal to 30 IU/mL of anti-dsDNA antibodies in their blood plasma or serum has rheumatoid arthritis. In further embodiments, the patient that has an ANA titer of 1:80 or greater, and/or greater than or equal to 30 IU/mL of anti-dsDNA antibodies in their blood plasma or serum has Sjögren's syndrome. In further embodiments, the patient that has an ANA titer of 1:80 or greater, and/or greater than or equal to 30 IU/mL of anti-dsDNA antibodies in their blood plasma or serum has scleroderma. In further embodiments, the patient that has an ANA titer of 1:80 or greater, and/or greater than or equal to 30 IU/mL of anti-dsDNA antibodies in their blood plasma or serum has polymyositis-dermatomyositis. In further embodiments, the patient that has an ANA titer of 1:80 or greater, and/or greater than or equal to 30 IU/mL of anti-dsDNA antibodies in their blood plasma or serum has Felty's syndrome. In further embodiments, the patient that has an ANA titer of 1:80 or greater, and/or greater than or equal to 30 IU/mL of anti-dsDNA antibodies in their blood plasma or serum has mixed connective tissue disease. In further embodiments, the patient that has an ANA titer of 1:80 or greater, and/or greater than or equal to 30 IU/mL of anti-dsDNA antibodies in their blood plasma or serum has Raynaud's syndrome. In further embodiments, the patient that has an ANA titer of 1:80 or greater, and/or greater than or equal to 30 IU/mL of anti-dsDNA antibodies in their blood plasma or serum has juvenile chronic arthritis.

Moreover, it is noted that in both the phase 2 clinical trials using an antibody that neutralizes Neutrokine-alpha protein to treat patients with systemic lupus erythematosus and rheumatoid arthritis (See, Examples 1 and 3) it was observed that patients with autoantibody positive disease at baseline were more likely to respond to treatment. As described herein, SLE patients that had an ANA titer of 1:80 or greater, and/or greater than or equal to 30 IU/mL of anti-dsDNA at baseline showed a stronger response as a group than SLE patients whose ANA titer was less than 1:80 and whose level of anti-dsDNA antibody was less than 30 IU/mL. Similarly, in rheumatoid arthritis, it was observed that patients that were positive for rheumatoid factor [RF] or anti-cyclic citrullinated peptide [CCP] antibodies at baseline showed a stronger response as a group than rheumatoid arthritis patients that were not positive for rheumatoid factor [RF] or anti-cyclic citrullinated peptide [CCP] antibodies at baseline.

Thus, in another aspect of the present invention, there is provided a method of treating a patient that is positive for rheumatoid factor [RF] and/or anti-cyclic citrullinated peptide [CCP] antibodies at baseline, comprising administering a therapeutically effective amount of an antagonist of Neutrokine-alpha or other immunomodulatory agent known in the art an/or described herein irrespective of the disease diagnosis. Another embodiment of the present invention provides a method of treating a patient that that is positive for rheumatoid factor [RF] and/or anti-cyclic citrullinated peptide [CCP] antibodies at baseline comprising administering a therapeutically effective amount an antagonist of Neutrokine-alpha or other immunomodulatory agent known in the art an/or described herein irrespective of the disease diagnosis, and further comprising making a determination that the patient that is positive for rheumatoid factor [RF] and/or anti-cyclic citrullinated peptide [CCP] antibodies at baseline, prior to administering the immunomodulatory agent. In specific embodiments, a patient is considered to be positive for rheumatoid factor if they have ≥12 IU/ml of rheumatoid factor in his/her blood plasma and/or serum. In specific embodiments, a patient is considered to be positive for anti-CCP antibody if the patient has ≥10 units of anti-CCP antibody in his/her blood plasma and/or serum.

In a further aspect of the present invention, there is provided a method of treating a patient that is autoantibody positive at baseline, comprising administering a therapeutically effective amount of an antagonist of Neutrokine-alpha or other immunomodulatory agent known in the art an/or described herein irrespective of the disease diagnosis. Another embodiment of the present invention provides a method of treating a patient is autoantibody positive at baseline comprising administering a therapeutically effective amount an antagonist of Neutrokine-alpha or other immunomodulatory agent known in the art an/or described herein irrespective of the disease diagnosis, and further comprising making a determination that the patient that is autoantibody positive at baseline, prior to administering the immunomodulatory agent.

Making Immunomodulatory Agents

Methods of making and/or isolating immunomodulatory agents that can be used in the present invention are known to those of skill in the relevant arts. Below, methods available for making immunomodulatory agents that are proteinaceous in nature (e.g., anti-Neutrokine-alpha antibodies, Neutrokine-alpha binding peptides and polypeptides, Neutrokine-alpha receptor proteins as well as fragments and variants of the aforementioned polypeptides) are briefly reviewed.

In one embodiment, a polynucleotide encoding an immunomodulatory protein is inserted in a vector (e.g., a cloning or expression vector). The vector may be, for example, a phage, plasmid, viral or retroviral vector. Retroviral vectors may be replication competent or replication defective. In the latter case, viral propagation generally will occur only in complementing host cells. The polynucleotides encoding an immunomodulatory protein may be joined to a vector containing a selectable marker for propagation in a host. Introduction of the vector construct into the host cell can be effected by techniques known in the art which include, but are not limited to, calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, for example, stabilization or simplified purification of expressed recombinant product.

In one embodiment, the polynucleotide encoding an immunomodulatory protein is operatively associated with an appropriate heterologous regulatory element (e.g., promoter or enhancer), such as, the phage lambda PL promoter, the *E. coli* lac, trp, phoA, and tac promoters, the SV40 early and late promoters and promoters of retroviral LTRs, to name a few. Other suitable promoters will be known to the skilled artisan.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293 and Bowes melanoma cells; and plant cells. Appropriate culture mediums and conditions for the above-described host cells are known in the art.

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed. Selection of appropriate vectors and promoters for expression in a host cell is a well-known procedure and the requisite techniques for expression vector construction, introduction of the vector into the host and expression in the host are routine skills in the art.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium*, and various species within the genera *Pseudomonas, Streptomyces*, and *Staphylococcus*, although others may also be employed as a matter of choice. As a representative, but nonlimiting example, useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed. Among vectors preferred for use in bacteria include pHE4-5 (ATCC Accession No. 209311; and variations thereof), pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Preferred expression vectors for use in yeast systems include, but are not limited to, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, pPIC9K, and PAO815 (all available from Invitrogen, Carlsbad, Calif.). Among preferred eukaryotic vectors are pWLNEO, pSV2CAT, pOG44, pXT1 and pSG available from Stratagene; and pSVK3, pBPV, pMSG and pSVL (available from Pharmacia). Other suitable vectors will be readily apparent to the skilled artisan.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

In one embodiment, the yeast *Pichia pastoris* is used to express Neutrokine-alpha protein in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111-21 (1985); Koutz, P. J, et al., Yeast 5:167-77 (1989); Tschopp, J. F., et al., Nucl. Acids Res. 15:3859-76 (1987). Thus, a heterologous coding sequence under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a immunomodulatory protein or portion thereof as set forth herein, in a *Pichea* yeast system essentially as described in "*Pichia* Protocols: Methods in Molecular Biology," D. R. Higgins and J. Cregg, eds. The Humana Press, Totowa, N.J., 1998. This expression vector allows expression and secretion of an immunomodulatory protein by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In one embodiment, high-level expression of a heterologous coding sequence may be achieved by cloning the heterologous polynucleotide of the invention into an expression vector such as, for example, pGAPZ or pGAPZalpha, and growing the yeast culture in the absence of methanol.

Transcription of the DNA encoding immunomodulatory proteins by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Various mammalian cell culture systems can also be employed to express recombinant protein. Examples of mammalian expression systems include the COS-7 lines of monkey kidney fibroblasts, described by Gluzman (Cell 23:175 (1981)), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

In a specific embodiment, constructs designed to express a portion of an immunomodulatory protein, such as the extracellular domains of the Neutrokine-alpha receptors, (e.g., TACI, BCMA and BAFF-R) are used. One of skill in the art would be able to use the polynucleotide and polypeptide sequences provided as SEQ ID NO:5 and SEQ ID NO:6, respectively, SEQ ID NO:7 and SEQ ID NO:8, respectively, or SEQ ID NO:9 and SEQ ID NO:10, respectively, to design polynucleotide primers to generate such an expression construct.

Host cell are used to express the polynucleotides encoding an immunomodulatory protein. Such host cells include primary, secondary, and immortalized host cells of vertebrate origin, particularly mammalian origin. In some cases, the host cells will have been engineered to delete or replace endogenous genetic material (e.g., Neutrokine-alpha coding sequence), and/or to include genetic material (e.g., heterologous polynucleotide sequences). In some instance, the host cell is modified so as to promote and/or alter expression of the endogenous polynucleotide encoding the immunomodulatory protein. For example, techniques known in the art may be used to operably associate heterologous control regions (e.g., promoter and/or enhancer) and endogenous polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

The host cells described herein can be used in a conventional manner to produce the immunomodulatory protein. Alternatively, cell-free translation systems can also be employed to produce an immunomodulatory polypeptide using RNAs derived from the DNA constructs of the present invention.

The frame AUG as required may be expressed or synthesized in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides encoding the immunomodulatory protein and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer.

Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

In one embodiment, a polynucleotide encoding an immunomodulatory protein may be fused to signal sequences which will direct the localization of an immunomodulatory protein to particular compartments of a prokaryotic or eukaryotic cell and/or direct the secretion of the immunomodulatory protein from a prokaryotic or eukaryotic cell. For example, in E. coli, one may wish to direct the expression of the protein to the periplasmic space. Examples of signal sequences or proteins (or fragments thereof) to which the polypeptides of the invention may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic E. coli heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, polynucleotides encoding an immunomodulatory protein may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that may be fused to an immunomodulatory protein in order to direct its secretion in mammalian cells include, but are not limited to, the MPIF-1 signal sequence (amino acids 1-21 of GenBank Accession number AAB51134), the stanniocalcin signal sequence (MLQNSAVLLLLVISASA, SEQ ID NO:27), and a consensus signal sequence (MPTWAWWLFLVLLLALWAPARG, SEQ ID NO:28). A suitable signal sequence that may be used in conjunction with baculoviral expression systems is the gp67 signal sequence, (amino acids 1-19 of GenBank Accession Number AAA72759).

A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5 has been fused with Fc portions for the purpose of high-throughput screening assays to identify antagonists of hIL-5. See, D. Bennett et al., J.

Molecular Recognition 8:52-58 (1995) and K. Johanson et al., J. Biol. Chem. 270:9459-9471 (1995).

Immunomodulatory proteins that may be used in the methods of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the immunomodulatory proteins may be glycosylated or may be non-glycosylated. In addition, immunomodulatory proteins may also include an initial modified methionine residue, in some cases as a result of host-mediated processes.

Immunomodulatory proteins that may be used in the methods of the present invention can be chemically synthesized using techniques known in the art (e.g., see Creighton, 1983, Proteins: Structures and Molecular Principles, W.H. Freeman & Co., N.Y., and Hunkapiller, M., et al., 1984, Nature 310: 105-111). For example, a peptide corresponding to a fragment of an immunomodulatory protein can be synthesized by use of a peptide synthesizer. Furthermore, if desired, nonclassical amino acids or chemical amino acid analogs can be introduced as a substitution or addition into the polynucleotide sequence encoding the immunomodulatory protein. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

Immunomodulatory proteins that may be used in the methods of the present invention may be differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational modifications include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, radioisotopic or affinity label to allow for detection and isolation of the protein.

Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, $^{213}Bi$, or other radioisotopes such as, for example, iodine ($^{131}I$, $^{125}I$, $^{123}I$, $^{121}I$), carbon ($^{14}C$), sulfur ($^{35}S$), tritium ($^{3}H$), indium ($^{115m}In$, $^{113m}In$, $^{112}In$, $^{111}In$), and technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{14}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, and $^{117}Tin$.

In specific embodiments, immunomodulatory proteins that may be used in the methods of the present invention may be labeled with Europium. For example, immunomodulatory proteins (e.g., antagonists of Neutrokine-alpha) may be labelled with Europium using the DELFIA Eu-labeling kit (catalog#1244-302, Perkin Elmer Life Sciences, Boston, Mass.) following manufacturer's instructions.

In specific embodiments, immunomodulatory proteins (e.g., are attached to macrocyclic chelators useful for conjugating radiometal ions, including but not limited to, $^{111}In$, $^{177}Lu$, $^{90}Y$, $^{166}Ho$, and $^{153}Sm$, to polypeptides. In a preferred embodiment, the radiometal ion associated with the macrocyclic chelators attached to an immunomodulatory protein is $^{111}In$. In another preferred embodiment, the radiometal ion associated with the macrocyclic chelator attached to an immunomodulatory protein is $^{90}Y$. In specific embodiments, the macrocyclic chelator is 1,4,7,10-tetraazacyclododecane-N,N',N",N"'-tetraacetic acid (DOTA). In other specific embodiments, the DOTA is attached to an immunomodulatory protein via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art could readily adapt the method disclosed therein in order to conjugate chelating agents to other polypeptides.

In one embodiment, an immunomodulatory protein that may be used in the methods of the present invention may be labeled with biotin.

Chemically modified derivatives of immunomodulatory proteins which may provide additional advantages such as increased solubility, stability and in vivo or in vitro circulating time of the polypeptide, or decreased immunogenicity (see U.S. Pat. No. 4,179,337) may also be used in the methods of the present invention. The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monomethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoroethane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., Crit. Rev. Thera. Drug Carrier Sys. 9:249-304 (1992).

Immunomodulatory proteins that may be used in the methods of the present invention can be recovered and purified by known methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Formulations and Administration

The invention provides methods of treatment, inhibition and prophylaxis by administration to a subject of an effective amount of a pharmaceutical composition comprising an immunomodulatory agent, such as an antagonist of Neutrokine-alpha. In a specific embodiment, the Neutrokine-alpha antagonist is an anti-Neutrokine-alpha antibody. In a specific embodiment, the Neutrokine-alpha antagonist is a TACI-Fc protein. In a specific embodiment, the Neutrokine-alpha antagonist is a BAFF-R-Fc protein. In a specific embodiment, the Neutrokine-alpha antagonist is an anti-Neutrokine-alpha peptibody. In a specific embodiment, the Neutrokine-alpha antagonist is Neutrokine-alpha protein fragment or variant that functions as a dominant negative. In a preferred embodiment, the immunomodulatory agent is substantially purified (e.g., substantially free from substances that limit its effect or produce undesired side effects). The subject is preferably an animal, including but not limited to animals such as cows, pigs, horses, chickens, cats, dogs, etc., and is preferably a mammal, and most preferably human.

An immunomodulatory agent will be formulated and dosed in a fashion consistent with good medical practice, taking into account the clinical condition of the individual patient (especially the side effects of treatment with the immunomodulatory agent alone), the site of delivery of the composition containing the immunomodulatory agent, the method of administration, the scheduling of administration, and other factors known to practitioners. The "therapeutically effective amount" of an immunomodulatory agent for purposes herein is thus determined by such considerations.

Various delivery systems are known and can be used to administer a pharmaceutical composition comprising an immunomodulatory agent, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. A pharmaceutical composition comprising an immunomodulatory agent may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical composition comprising an immunomodulatory agent into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, the present invention is directed to pharmaceutical formulations of therapeutic agents (e.g., immunomodulatory agents known in the art and/or described herein). In particular, the present invention is directed to pharmaceutical formulations of therapeutic agents that are proteinacious in nature (e.g., proteins and antibodies). A pharmaceutical formulation of the invention contains pharmaceutically acceptable excipients. In general, a pharmaceutical formulation of the invention is formulated such that a therapeutic agent retains its physical, chemical and biological activity. A pharmaceutical formulation of the invention may be stored at suitable temperatures. For example, a pharmaceutical formulation of the invention may be stored at 2-8° C., at −40° C., or at −80° C. In a specific embodiment, a stable formulation is one in which less than about 1% aggregation of the therapeutic agent is observed over 2 years, less than about 1% oxidation of the therapeutic agent is observed over 2 years, and/or less than about 4% deamidation of the therapeutic agent is observed over 2 years. The amount of therapeutic agent present in a pharmaceutical formulation of the invention is determined, for example, by taking into account the desired dose volumes and mode(s) of administration. In one embodiment of the invention, the concentration of a therapeutic agent in a pharmaceutical formulation of the invention is about 1-160 mg/ml, about 10-155 mg/ml, about 20-150 mg/ml, about 30-145 mg/ml, about 40-140 mg/ml, about 50-135 mg/ml, about 60-130 mg/ml, about 70-125 mg/ml, about 80-120 mg/ml, about 90-115 mg/ml, about 95-110 mg/ml, about 100-105 mg/ml, or about 100 mg/ml. Ranges intermediate to the above recited concentrations, e.g., about 11-154 mg/ml, are also intended to be part of the invention. For example, ranges of values using a combination of any of the above recited values as upper and/or lower limits are intended to be included. In this context "about" includes the particularly recited ranges, and ranges that are larger or smaller by several (5, 4, 3, 2, or 1) mg/ml, at the upper and/or lower limits of the range.

Aqueous pharmaceutical formulations of the invention comprise a pH-buffered solution. In one embodiment of the invention, the buffer used in pharmaceutical formulations of the invention has a pH ranging from about 5 to about 7. In a preferred embodiment, the buffer used in pharmaceutical formulations of the invention has a pH ranging from about 5.5 to about 6.5. In another preferred embodiment, the buffer used in pharmaceutical formulations of the invention has a pH ranging from about 5.8 to about 6.2. In another preferred embodiment, the buffer used in pharmaceutical formulations of the invention has a pH of about 6.0. Ranges intermediate to the above recited pH's are also intended to be part of the invention. For example, ranges of values using a combination of any of the above recited values as upper and/or lower limits are intended to be included. In this context "about" includes the particularly recited ranges, and ranges that are larger or smaller by 0.5, 0.4, 0.3, 0.2, or 0.1 pH units, at the upper and/or lower limits of the range. Examples of buffers that will control the pH within preferred ranges include acetate (e.g., sodium acetate), succinate (such as sodium succinate), gluconate, histidine, citrate, Tris, phosphate, glycylglycine and other organic acid buffers. Additional exemplary buffers are those which are pharmaceutically acceptable and may be created from suitable acids, bases and salts thereof, such as those which are defined below.

Pharmaceutically acceptable acids include inorganic and organic acids which are non toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cycloaliphatic, arylaliphatic, heterocyclic, saturated, unsaturated, mono-, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo[2.2.2]-oct-2-ene-1-carboxylic, glucoheptonic, 4,4'-methylenebis-3-(hydroxy-2-ene-1-carboxylic acid), hydroxynapthoic, etc.

Pharmaceutically-acceptable bases include inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amine, substituted amines, cyclic amines and basic ion exchange resins, [e.g., $N(R')_4^+$ (where R' is independently H or $C_{1-4}$ alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Additional pharmaceutically acceptable acids and bases useable with the present invention include those which are derived from the amino acids, for example, histidine, glycine, phenylalanine, aspartic acid, glutamic acid, lysine and asparagine.

Pharmaceutically acceptable buffers include those derived from both acid and base addition salts of the above indicated acids and bases. In one embodiment of the invention, the buffer of a pharmaceutical formulation of the invention is succinate, histidine, citrate and/or phosphate. In a preferred embodiment, the buffer of a pharmaceutical formulation of the invention is histidine. In another preferred embodiment, the buffer of a pharmaceutical formulation of the invention is citrate.

In another embodiment of the invention, the buffer concentration in a pharmaceutical formulation of the invention is about 5-50 mM, about 5-20 mM, about 5-15 mM, or about 10 mM. Ranges intermediate to the above recited concentrations, e.g., about 6-48 mM, are also intended to be part of the invention. For example, ranges of values using a combination of any of the above recited values as upper and/or lower limits are intended to be included. In this context "about" includes the particularly recited ranges, and ranges that are larger or smaller by several (5, 4, 3, 2, or 1) mM, at the upper and/or lower limits of the range.

A surfactant may also be added to a pharmaceutical formulation of the invention. Exemplary surfactants include nonionic surfactants such as polysorbates (e.g., polysorbates 20 or 80) or poloxamers (e.g., poloxamer 188). Other pharmaceutically acceptable surfactants are well known in the art and are also contemplated. In a specific embodiment, an amount of surfactant is added in an amount sufficient to reduce aggregation of a therapeutic agent (such as that which occurs upon shaking or shipping), to minimize the formation of particulates in a pharmaceutical formulation of the invention, and/or to reduce non-specific adsorption of a therapeutic agent. In a preferred embodiment, a pharmaceutical formulation of the invention includes a surfactant which is a polysorbate.

In one embodiment, a pharmaceutical formulation of the invention contains the surfactant polysorbate 20. In one preferred embodiment, a pharmaceutical formulation of the invention contains between at least 0.007% and about 0.07% of polysorbate 20. In another preferred embodiment, a pharmaceutical formulation of the invention contains between about 0.01% and about 0.05% of polysorbate 20. In another preferred embodiment, a pharmaceutical formulation of the invention contains between about 0.01% and about 0.03% of polysorbate 20. In another preferred embodiment, about 0.01% polysorbate 20 is found in a pharmaceutical formulation of the invention. In this context "about" includes the particularly recited ranges, and ranges that are larger or smaller by 0.01%, 0.009%, 0.008%, 0.007%, 0.006% or 0.005%, at the upper and/or lower limits of the range, with the proviso that the percentage of polysorbate 20 is not lower than 0.007%.

In another preferred embodiment, a pharmaceutical formulation of the invention contains the surfactant polysorbate 80. In one preferred embodiment, a pharmaceutical formulation of the invention contains between about 0.0015% and about 0.07% of polysorbate 80. In another preferred embodiment, a pharmaceutical formulation of the invention contains between about 0.003% and about 0.05% of polysorbate 80. In another preferred embodiment, a pharmaceutical formulation of the invention contains between about 0.005% and about 0.03% of polysorbate 80. In another preferred embodiment, a pharmaceutical formulation of the invention contains between about 0.01% and about 0.03% of polysorbate 80. In another preferred embodiment, about 0.01% polysorbate 80 is found in a pharmaceutical formulation of the invention. In this context "about" includes the particularly recited ranges, and ranges that are larger or smaller by 0.01%, 0.009%, 0.008%, 0.007%, 0.006% or 0.005%, at the upper and/or lower limits of the range, with the proviso that the percentage of polysorbate 80 is not lower than 0.0015%.

A tonicity modifier may also be added to a pharmaceutical formulation of the invention. Useful tonicity modifiers include salts and amino acids. Salts that are pharmaceutically acceptable and suitable for pharmaceutical formulations of the invention include sodium chloride, sodium succinate, sodium sulfate, potassium chloride, magnesium chloride, magnesium sulfate, and calcium chloride. Preferred salts for use in pharmaceutical formulations of the invention are NaCl and $MgCl_2$. NaCl may improve stability of a therapeutic agent by protecting the agent from deamidation and aggregation. In one preferred embodiment, a pharmaceutical formulation of the invention contains NaCl. In another preferred embodiment, a pharmaceutical formulation of the invention contains between about 150 and about 500 mM NaCl. In another preferred embodiment, a pharmaceutical formulation of the invention contains about 150 mM NaCl. In this context "about" includes the particularly recited ranges, and ranges that are larger or smaller by 1, 2, 3, 4, 5, 10, 25 or 50 mM, at the upper and/or lower limits of the range. In a preferred embodiment, pharmaceutical formulations of the invention are isotonic. By isotonic, it is meant that a pharmaceutical formulation of the invention has essentially the same osmotic pressure as human blood. Isotonic formulations will generally have an osmotic pressure from about 250 to about 350 mOsm, preferably from about 290 to about 310 mOsm. In this context "about" includes the particularly recited ranges, and ranges that are larger or smaller by several (5, 4, 3, 2, or 1) mOsm, at the upper and/or lower limits of the range. Isotonicity can be measured using a vapor pressure or ice-freezing type osmometer, for example.

In one embodiment, a pharmaceutical formulation of the invention contains the above-identified agents (i.e. therapeutic agent, buffer, surfactant and tonicity modifier) and is essentially free of one or more preservatives, such as benzyl alcohol, phenol, m-cresol, chlorobutanol and benzethonium Cl. In another embodiment, a preservative may be included in a pharmaceutical formulation of the invention, particularly where the formulation is a multidose formulation. One or more other pharmaceutically acceptable carriers, excipients or stabilizers such as those described in Remington's Pharmaceutical Sciences 16th edition, Osol, A. Ed. (1980) may be included in a pharmaceutical formulation of the invention provided that they do not significantly adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g., Zn-protein complexes); biodegradable polymers such as polyesters; preservatives; cryoprotectants; lyoprotectants; bulking agents and the like. Examples of suitable cryoprotectants include polyols, polyethylene glycol (PEG), Bovine Serum Albumin (BSA), glutamic acid, other amino acids and the like. Additional suitable cryoprotectants include sugars and sugar alcohols such as sucrose, mannose, trehalose, glucose, sorbitol, and mannitol and the like. Suitable lyoprotectants can encompass sugars including sucrose, trehalose, lactose, and maltose and the like. Suitable bulking agents include mannitol, glycine, and sorbital and the like.

In a specific embodiment, a pharmaceutical formulation of the invention does not comprise a cryoprotectant. In a further embodiment, a pharmaceutical formulation of the invention does not comprise sucrose.

EDTA, which is commonly used to stabilize a protein formulation, may also be included in a pharmaceutical formulation of the invention. EDTA, as a chelating agent, may inhibit the metal-catalyzed oxidation of the sulfhydryl groups, thus reducing the formation of disulfide-linked aggregates. A preferred concentration of EDTA is from about 0.01% to about 0.2%.

A pharmaceutical formulation of the invention may also be combined with one or more other therapeutic agents as necessary, for the particular indication being treated, preferably those with complementary activities that do not adversely affect a therapeutic agent in a pharmaceutical formulation of the invention. Combinations are contemplated where the additional therapeutic agents are formulated as a mixture with the immunomodulatory agents. In addition, combinations are contemplated where the additional therapeutic agents are formulated independently but are intended for simultaneous or overlapping administration with an immunomodulatory agent. Such additional therapeutic agents are suitably present in combination in amounts that are effective for the purpose intended. Additional therapeutic agents which can be combined with the formulation of the invention are further described herein.

The present invention provides, in a preferred embodiment, a pharmaceutical formulation comprising, or alternatively consisting of, 10 mM histidine buffer, 150 mM NaCl, and 0.01% polysorbate 80, pH 6.0 (±0.5). In another preferred embodiment, a pharmaceutical formulation of the invention comprises, or alternatively consists of, an antibody in an amount from about 1 mg/ml to about 160 mg/ml, preferably from about 80 mg/ml to about 120 mg/ml, 10 mM histidine buffer, 150 mM NaCl, and 0.01% polysorbate 80, pH 6.0 (±0.5). In another preferred embodiment, a pharmaceutical formulation of the invention comprises, or alternatively consists of, an antibody in an amount from about 1 mg/ml to about 160 mg/ml, preferably from about 80 mg/ml to about 120 mg/ml, 10 mM histidine buffer, 150 mM NaCl, and 0.01% polysorbate 80, pH 6.0 (±0.5) for intravenous administration. In another preferred embodiment, a pharmaceutical formulation of the invention comprises, or alternatively consists of, an antibody in an amount from about 1 mg/ml to about 160 mg/ml, preferably from about 80 mg/ml to about 120 mg/ml, 10 mM histidine buffer, 150 mM NaCl, and 0.01% polysorbate 80, pH 6.0 (±0.5) for subcutaneous administration. In this context "about" includes the particularly recited ranges, and ranges that are larger or smaller by several (5, 4, 3, 2, or 1) mg/ml, at the upper and/or lower limits of the range.

In a preferred embodiment, a pharmaceutical formulation of the invention comprises, or alternatively consists of, 100 mg/ml of an antibody, 10 mM histidine buffer, 150 mM NaCl, and 0.01% polysorbate 80, pH 6.0 (±0.5). In another preferred embodiment, a pharmaceutical formulation of the invention comprises, or alternatively consists of, 100 mg/ml of an antibody, 10 mM histidine buffer, 150 mM NaCl, and 0.01% polysorbate 80, pH 6.0 (±0.5) for intravenous administration. In another preferred embodiment, a pharmaceutical formulation of the invention comprises, or alternatively consists of, 100 mg/ml of an antibody, 10 mM histidine buffer, 150 mM NaCl, and 0.01% polysorbate 80, pH 6.0 (±0.5) for subcutaneous administration.

The present invention provides, in a preferred embodiment, a pharmaceutical formulation comprising, or alternatively consisting of, 0.74 mg/ml L-histidine, 1.1 mg/ml L-histidine monohydrochloride, 8.8 mg/ml NaCl, and 0.1 mg/ml polysorbate 80, pH 6.0 (±0.5). In another preferred embodiment, a pharmaceutical formulation of the invention comprises, or alternatively consists of, an antibody in an amount from about 1 mg/ml to about 160 mg/ml, preferably from about 80 mg/ml to about 120 mg/ml, 0.74 mg/ml L-histidine, 1.1 mg/ml L-histidine monohydrochloride, 8.8 mg/ml NaCl, and 0.1 mg/ml polysorbate 80, pH 6.0 (±0.5). In another preferred embodiment, a pharmaceutical formulation of the invention comprises, or alternatively consists of, an antibody in an amount from about 1 mg/ml to about 160 mg/ml, preferably from about 80 mg/ml to about 120 mg/ml, 0.74 mg/ml L-histidine, 1.1 mg/ml L-histidine monohydrochloride, 8.8 mg/ml NaCl, and 0.1 mg/ml polysorbate 80, pH 6.0 (±0.5) for intravenous administration. In another preferred embodiment, a pharmaceutical formulation of the invention comprises, or alternatively consists of, an antibody in an amount from about 1 mg/ml to about 160 mg/ml, preferably from about 80 mg/ml to about 120 mg/ml, 0.74 mg/ml L-histidine, 1.1 mg/ml L-histidine monohydrochloride, 8.8 mg/ml NaCl, and 0.1 mg/ml polysorbate 80, pH 6.0 (±0.5) for subcutaneous administration. In this context "about" includes the particularly recited ranges, and ranges that are larger or smaller by several (5, 4, 3, 2, or 1) mg/ml, at the upper and/or lower limits of the range.

In a preferred embodiment, a pharmaceutical formulation of the invention comprises, or alternatively consists of, 100 mg/ml of an antibody, 0.74 mg/ml L-histidine, 1.1 mg/ml L-histidine monohydrochloride, 8.8 mg/ml NaCl, and 0.1 mg/ml polysorbate 80, pH 6.0 (±0.5). In another preferred embodiment, a pharmaceutical formulation of the invention comprises, or alternatively consists of, 100 mg/ml of an antibody, 0.74 mg/ml L-histidine, 1.1 mg/ml L-histidine monohydrochloride, 8.8 mg/ml NaCl, and 0.1 mg/ml polysorbate 80, pH 6.0 (±0.5) for intravenous administration. In another preferred embodiment, a pharmaceutical formulation of the invention comprises, or alternatively consists of, 100 mg/ml of an antibody, 0.74 mg/ml L-histidine, 1.1 mg/ml L-histidine monohydrochloride, 8.8 mg/ml NaCl, and 0.1 mg/ml polysorbate 80, pH 6.0 (±0.5) for subcutaneous administration.

In a preferred embodiment, the antibody in a pharmaceutical formulation of the invention is a monoclonal antibody. In another preferred embodiment, the antibody in a pharmaceutical formulation of the invention is an IgG antibody. In another preferred embodiment, the antibody in a pharmaceutical formulation of the invention is an IgG1 antibody. In another preferred embodiment, the antibody in a pharmaceutical formulation of the invention is an IgG1/λ antibody. In another preferred embodiment, the antibody in a pharmaceutical formulation of the invention is a human or humanized antibody.

In a preferred embodiment, a pharmaceutical formulation of the invention is stable for at least 6 months at 2-8° C. In another preferred embodiment, a pharmaceutical formulation of the invention is stable for at least 9 months at 2-8° C. In another preferred embodiment, a pharmaceutical formulation of the invention is stable for at least 1 year at 2-8° C. In another preferred embodiment, a pharmaceutical formulation of the invention is stable for at least 1.5 years at 2-8° C. In another preferred embodiment, a pharmaceutical formulation of the invention is stable for at least 2 years at 2-8° C. In another preferred embodiment, a pharmaceutical formulation of the invention is stable for at least 3 years at 2-8° C. In another preferred embodiment, a pharmaceutical formulation of the invention is stable for at least 4 years at 2-8° C. In another preferred embodiment, a pharmaceutical formulation of the invention is stable for at least 5 years at 2-8° C.

In a preferred embodiment, an antibody in a pharmaceutical formulation of the invention can display significant stability over repeated freeze-thaw cycles, and following such treatment can remain stable after being thawed. In general, a formulation to be frozen is rapidly frozen, for example, frozen in liquid nitrogen. Thawing can be at a range of temperatures, e.g., from about 0° C. to about 25° C., which is slow thawing; or from about 26° C. to 40° C., which is rapid thawing. In this context "about" includes the particularly recited ranges, and ranges that are larger or smaller by several (5, 4, 3, 2, or 1) degrees Celsius, at the upper and/or lower limits of the range. An example of rapid thawing is thawing a pharmaceutical formulation of the invention in a 37° C. water bath. In a preferred embodiment, an antibody in a pharmaceutical formulation of the invention is stable for at least one freeze-thaw cycle. In another preferred embodiment, an antibody in a pharmaceutical formulation of the invention is stable for at least two freeze-thaw cycles. In another preferred embodiment, an antibody in a pharmaceutical formulation of the invention is stable for at least three freeze-thaw cycles. In another preferred embodiment, an antibody in a pharmaceutical formulation of the invention is stable for at least four freeze-thaw cycles. In another preferred embodiment, an antibody in a pharmaceutical formulation of the invention is stable for at least five freeze-thaw cycles. In another preferred embodiment, an antibody in a pharmaceutical formulation of the invention is stable for at least ten freeze-thaw cycles.

It may be desirable to determine an optimal regime for freeze-thawing a pharmaceutical formulation of the invention to preserve stability, or it may be desirable to identify a pharmaceutical formulation of the invention that provides the greatest stability for an antibody that will be subjected to a particular freeze-thaw cycle. Accordingly, in an embodiment of the invention, this parameter is assessed. For example, a pharmaceutical formulation of the invention can be assayed for stability under a variety of freeze-thaw conditions such as rapid freezing, slow freezing, rapid thawing, slow thawing in various combinations to determine the procedure that produces the fewest degradation products (e.g., that has the greatest stability).

A concentration study has shown that an IgG1/λ antibody may be concentrated up to at least 160 mg/ml in a pharmaceutical formulation of the invention comprising 10 mM histidine buffer, 150 mM NaCl, and 0.01% polysorbate 80, pH 6.0 without detrimental effects on purity (as determined by SEC-HPLC) and aggregation (no particulates were observed) (data not shown). In addition, an increase in viscosity was observed with concentration. As viscosity increases, the possibility of administration difficulties increases. Studies have shown that samples with viscosities less than 7.75 cP can be easily injected through a 30G ½ inch needle in less than 10 seconds. As shown in Table X, even at an IgG1/λ antibody concentration of 160 mg/ml, the viscosity of the pharmaceutical formulation is below 7.75 cP and thus is still easily injected through a syringe.

TABLE X

Viscosity as a Function of IgG1/λ Antibody Concentration

| Concentration (mg/ml) | Viscosity (cP) |
|---|---|
| 0.0 | 0.93 |
| 18.9 | 0.97 |
| 35.5 | 1.13 |
| 65.7 | 1.48 |
| 79.2 | 1.80 |
| 89.4 | 1.96 |
| 104.0 | 2.38 |
| 113.2 | 2.68 |
| 122.2 | 3.15 |
| 128.0 | 3.43 |
| 136.5 | 3.89 |
| 144.1 | 4.58 |
| 161.7 | 6.74 |

The formulations to be used for in vivo administration is most preferably sterile. This is readily accomplished by filtration through sterile filtration membranes, prior to, or following, preparation of the formulation.

In a preferred embodiment the antibody of the invention is formulated in 10 mM sodium citrate, 1.9% glycine, 0.5% sucrose, 0.01% polysorbate 80, pH 6.5 (±0.3). In another preferred embodiment, the antibody of the invention is formulated in 10 mM sodium citrate, 1.9% glycine, 0.5% sucrose, 0.01% polysorbate 80, pH 6.5 (±0.3) for intravenous administration.

In a preferred embodiment the antibody of the invention is formulated in 10 mM sodium citrate, 8% sucrose, 0.04% (w/v) polysorbate 80 (pH 6.5) (±0.3). In another preferred embodiment, the antibody of the invention is formulated in 10 mM sodium citrate, 8% sucrose, 0.04% (w/v) polysorbate 80 (pH 6.5) for intravenous administration. In another preferred embodiment, the antibody of the invention is formulated in 10 mM sodium citrate, 8% sucrose, 0.04% (w/v) polysorbate 80 (pH 6.5) for subcutaneous administration.

Generally, the formulations are prepared by contacting the Neutrokine-alpha antagonist or other immunomodulatory agent known in the art and/or described herein uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, sucrose, or dextrins; chelating agents such as EDTA; sugar alcohols such as mannitol or sorbitol; counterions such as sodium; preservatives, such as cresol, phenol, chlorobutanol, benzyl alcohol and parabens, and/or nonionic surfactants such as polysorbates, poloxamers, or PEG.

Compositions comprising immunomodulatory polypeptides are typically formulated in such vehicles at a concentration of about 0.001 mg/ml to 100 mg/ml, or 0.1 mg/ml to 100 mg/ml, preferably 1-10 mg/ml or 1-10 mg/ml, at a pH of about 3 to 10, or 3 to 8, more preferably 5-8, most preferably 6-7. It will be understood that the use of certain of the foregoing excipients, carriers, or stabilizers will result in the formation of polypeptide salts.

Compositions to be used for therapeutic administration are most preferably sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

Pharmaceutical compositions comprising immunomodulatory agents that may be used the methods of the present invention ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Neutrokine-alpha polypeptide solution, and the resulting mixture is lyophilized. The infusion solution is prepared by reconstituting the lyophilized Neutrokine-alpha polypeptide using bacteriostatic Water-for-Injection.

Alternatively, pharmaceutical compositions comprising immunomodulatory agents that may be used the methods of the present invention are stored in single dose containers in lyophilized form. The infusion selection is reconstituted using a sterile carrier for injection.

In specific embodiments, immunomodulatory agents that maybe used in the present invention are radiolabelled polypeptides such as a radiolabelled form of Neutrokine-alpha or anti-CD20 antibody. Such pharmaceutical compositions comprising radiolabelled molecules may also comprise radioprotectants and plasma expanders such as sodium ascorbate, gentran-40, and glycerol. In specific embodiments, compositions that may be used in the methods of the present invention comprise iodinated forms of Neutrokine-alpha polypeptides or fragments or variants thereof which are formulated in 10.0 mM sodium citrate, 140.0 mM sodium chloride, 8.7 μM HEPES, 4% (w/v) sodium ascorbate, 3.3% (w/v) Genetran-40.

In specific embodiments, a composition that may be used in the methods of the present invention comprises at least 1 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition that may be used in the methods of the present invention comprise at least 2 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition that may be used in the methods of the present invention comprise at least 3 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition that may be used in the methods of the present invention comprise at least 4 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition that may be used in the methods of the present invention comprise about 4.6 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40.

In specific embodiments, a composition that may be used in the methods of the present invention comprise about between 0.1 mg/mL and 20 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition that may be used in the methods of the present invention comprise between 1 mg/mL and 10 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition that may be used in the methods of the present invention comprise between 2 mg/mL and 8 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40. In specific embodiments, a composition that may be used in the methods of the present invention comprise between 3 mg/mL and 6 mg/mL of an iodinated form of amino acid residues 134-285 of SEQ ID NO:2, 10.0 mM sodium citrate, 140.0 mM sodium chloride, 8.7 mM HEPES, 4% (w/v) sodium ascorbate, 3.3% (w/v) Gentran-40.

In preferred embodiments, a composition that may be used in the methods of the present invention comprises an anti-Neutrokine-alpha antibody. In other embodiments, a composition that may be used in the methods of the present invention comprises an antibody that specifically binds Neutrokine-alpha. In other embodiments, a composition that may be used in the methods of the present invention comprises an antagonistic anti-Neutrokine-alpha antibody. In other embodiments, a composition that may be used in the methods of the present invention comprises antibody that specifically binds Neutrokine-alpha and neutralizes Neutrokine-alpha biological activity. In other embodiments, a composition that may be used in the methods of the present invention comprises an anti-Neutrokine-alpha antibody that binds a recombinant Neutrokine-alpha protein purified from a cell culture wherein said recombinant Neutrokine-alpha protein is encoded by a polynucleotide encoding at least amino acids 134 to 285 of SEQ ID NO:2. In other embodiments, a composition that may be used in the methods of the present invention comprises an antibody that specifically binds Neutrokine-alpha wherein said antibody binds a recombinant Neutrokine-alpha protein purified from a cell culture wherein said recombinant Neutrokine-alpha protein is encoded by a polynucleotide encoding at least amino acids 134 to 285 of SEQ ID NO:2.

Pharmaceutical compositions containing immunomodulatory agents may be administered orally, rectally, parenterally, subcutaneously, intracisternally, intravaginally, intraperitoneally, topically (as by powders, ointments, drops or transdermal patch), bucally, or as an oral or nasal spray (e.g., via inhalation of a vapor or powder).

The term "parenteral" as used herein refers to modes of administration which include intravenous, intramuscular, intraperitoneal, intrasternal, subcutaneous and intraarticular injection and infusion.

In a preferred embodiment, compositions containing immunomodulatory agents are administered subcutaneously.

In another preferred embodiment, compositions containing immunomodulatory agents are administered intravenously.

Compositions containing immunomodulatory agents may also be administered by sustained-release systems. Suitable examples of sustained-release compositions include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988).

In a specific embodiment, compositions containing immunomodulatory agents are formulated in a biodegradable, polymeric drug delivery system, for example as described in U.S. Pat. Nos. 4,938,763; 5,278,201; 5,278,202; 5,324,519; 5,340,849; and 5,487,897 and in International Publication Numbers WO01/35929, WO00/24374, and WO00/06117 which are hereby incorporated by reference in their entirety. In specific embodiments compositions containing immunomodulatory agents are formulated using the ATRIGEL® Biodegradable System of Atrix Laboratories, Inc. (Fort Collins, Colo.). In other specific embodiments, compositions containing immunomodulatory agents are formulated using the ProLease® sustained release system available from Alkermes, Inc. (Cambridge, Mass.).

Examples of biodegradable polymers which can be used in the pharmaceutical formulations, include but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), polyvinylpyrrolidone, polyethylene glycol, polyhydroxycellulose, chitin, chitosan, and copolymers, terpolymers, or combinations or mixtures of the above materials. The preferred polymers are those that have a lower degree of crystallization and are more hydrophobic. These polymers and copolymers are more soluble in the biocompatible solvents than the highly crystalline polymers such as polyglycolide and chitin which also have a high degree of hydrogen-bonding. Preferred materials with the desired solubility parameters are the polylactides, polycaprolactones, and copolymers of these with glycolide in which there are more amorphous regions to enhance solubility. In specific preferred embodiments, the biodegradable polymers which can be used in the formulation of compositions containing immunomodulatory agents are poly(lactide-co-glycolides). Polymer properties such as molecular weight, hydrophobicity, and lactide/glycolide ratio may be modified to obtain the desired drug release profile (See, e.g., Ravivarapu et al., Journal of Pharmaceutical Sciences 89:732-741 (2000), which is hereby incorporated by reference in its entirety).

It is also preferred that the solvent for the biodegradable polymer be non-toxic, water miscible, and otherwise biocompatible. Examples of such solvents include, but are not limited to, N-methyl-2-pyrrolidone, 2-pyrrolidone, C2 to C6 alkanols, C1 to C15 alchohols, dils, triols, and tetraols such as ethanol, glycerine propylene glycol, butanol; C3 to C15 alkyl ketones such as acetone, diethyl ketone and methyl ethyl ketone; C3 to C15 esters such as methyl acetate, ethyl acetate, ethyl lactate; alkyl ketones such as methyl ethyl ketone, C1 to C15 amides such as dimethylformamide, dimethylacetamide and caprolactam; C3 to C20 ethers such as tetrahydrofuran, or solketal; tweens, triacetin, propylene carbonate, decylmethylsulfoxide, dimethyl sulfoxide, oleic acid, 1-dodecylazacycloheptan-2-one, Other preferred solvents are benzyl alchohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of the solvating ability and their compatibility.

Additionally, formulations compositions containing immunomodulatory agents and a biodegradable polymer may also include release-rate modification agents and/or pore-forming agents. Examples of release-rate modification agents include, but are not limited to, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as C.sub.6-C.sub.12 alkanols, 2-ethoxyethanol, and the like. The release rate modification agent may be used singly or in combination with other such agents. Suitable combinations of release rate modification agents include, but are not limited to, glycerin/propylene glycol, sorbitol/glycerine, ethylene oxide/propylene oxide, butylene glycol/adipic acid, and the like. Preferred release rate modification agents include, but are not limited to, dimethyl citrate, triethyl citrate, ethyl heptanoate, glycerin, and hexanediol. Suitable pore-forming agents that may be used in the polymer composition include, but are not limited to, sugars such as sucrose and dextrose, salts such as sodium chloride and sodium carbonate, polymers such as hydroxylpropylcellulose, carboxymethylcellulose, polyethylene glycol, and polyvinylpyrrolidone. Solid crystals that will provide a defined pore size, such as salt or sugar, are preferred.

In specific embodiments compositions containing immunomodulatory agents are formulated using the BEMA™ Bio-Erodible Mucoadhesive System, MCA™ MucoCutaneous Absorption System, SMP™ Solvent MicroParticle System, or BCP™ BioCompatible Polymer System of Atrix Laboratories, Inc. (Fort Collins, Colo.).

Sustained-release compositions also include liposomally entrapped compositions (see generally, Langer, Science 249: 1527-1533 (1990); Treat et al., in Liposomes in the Therapy of Infectious Disease and Cancer, Lopez-Berestein and Fidler (eds.), Liss, New York, pp. 317-327 and 353-365 (1989)). Liposomes may be prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal immunomodulatory therapy.

In another embodiment sustained release compositions include crystal formulations known in the art.

In yet an additional embodiment, the compositions comprising an immunomodulatory agent are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527-1533 (1990)).

For parenteral administration, in one embodiment, the immunomodulatory agent is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, when the active ingredient is an immunomodulatory protein, the formulation preferably does not include oxidizing agents and other compounds that are known to be deleterious to polypeptides.

In a specific embodiment, it may be desirable to administer the pharmaceutical compounds or compositions locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the immunomodulatory agent can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the immunomodulatory agent can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Press, Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Immunomodulatory agents may be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the immunomodulatory agent which will be effective in the methods of the invention as described herein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. In preferred embodiments, a dose of 1, 4, 10, or 20 mg/kg is administered intravenously to a patient. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

As a general proposition, the total pharmaceutically effective amount of a polypeptide administered parenterally per dose will be in the range of about 1 microgram/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day.

In another embodiment, a polypeptide is administered to a human at a dose between 0.0001 and 0.045 mg/kg/day, preferably, at a dose between 0.0045 and 0.045 mg/kg/day, and more preferably, at a dose of about 45 microgram/kg/day in humans; and at a dose of about 3 mg/kg/day in mice.

If given continuously, the polypeptide is typically administered at a dose rate of about 1 microgram/kg/hour to about 50 micrograms/kg/hour, either by 1-4 injections per day or by continuous subcutaneous infusions, for example, using a mini-pump. An intravenous bag solution may also be employed.

The length of treatment needed to observe changes and the interval following treatment for responses to occur appears to vary depending on the desired effect.

Compositions comprising immunomodulatory agents may be administered as a continuous infusion, multiple discreet injections per day (e.g., three or more times daily, or twice daily), single injection per day, or as discreet injections given intermittently (e.g., twice daily, once daily, every other day, twice weekly, weekly, biweekly, monthly, bimonthly, and quarterly). If given continuously, a polypeptide is typically administered at a dose rate of about 0.001 to 10 microgram/kg/hour to about 50 micrograms/kg/hour, either by 1-4 injections per day or by continuous subcutaneous infusions, for example, using a mini-pump.

Effective dosages of the compositions comprising immunomodulatory agents to be administered may be determined through procedures well known to those in the art which address such parameters as biological half-life, bioavailability, and toxicity. Such determination is well within the capability of those skilled in the art, especially in light of the detailed disclosure provided herein.

Bioexposure of an organism to an immunomodulatory agent may also play an important role in determining a therapeutically and/or pharmacologically effective dosing regime. Variations of dosing such as repeated administrations of a relatively low dose of an immunomodulatory agent for a relatively long period of time may have an effect which is therapeutically and/or pharmacologically distinguishable from that achieved with repeated administrations of a relatively high dose of an immunomodulatory agent for a relatively short period of time.

Using the equivalent surface area dosage conversion factors supplied by Freireich, E. J., et al. (Cancer Chemotherapy Reports 50(4):219-44 (1966)), one of ordinary skill in the art is able to conveniently convert data obtained from the use of immunomodulatory agent in a given experimental system into an accurate estimation of a pharmaceutically effective amount of immunomodulatory agent to be administered per dose in another experimental system. Experimental data obtained through the administration of the immunomodulatory agent in mice, for example, may converted through the conversion factors supplied by Freireich, et al., to accurate estimates of pharmaceutically effective doses of Neutrokine-alpha in rat, monkey, dog, and human. The following conversion table (Table III) is a summary of the data provided by Freireich, et al. Table III gives approximate factors for converting doses expressed in terms of mg/kg from one species to an equivalent surface area dose expressed as mg/kg in another species tabulated.

TABLE III

Equivalent Surface Area Dosage Conversion Factors.

| FROM | TO | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 5/3 | 1 | 1/2 |
| Human | 12 | 7 | 3 | 2 | 1 |

Thus, for example, using the conversion factors provided in Table III, a dose of 50 mg/kg in the mouse converts to an appropriate dose of 12.5 mg/kg in the monkey because (50 mg/kg)×(¼)=12.5 mg/kg. As an additional example, doses of 0.02, 0.08, 0.8, 2, and 8 mg/kg in the mouse equate to effect doses of 1.667 micrograms/kg, 6.67 micrograms/kg, 66.7 micrograms/kg, 166.7 micrograms/kg, and 0.667 mg/kg, respectively, in the human.

In certain embodiments, administration of radiolabeled forms of Neutrokine-alpha or anti-Neutrokine-alpha antibody is contemplated. The radiometric dosage to be applied can vary substantially. The radiolabeled Neutrokine-alpha or anti-Neutrokine-alpha antibody composition can be administered at a dose of about 0.1 to about 100 mCi per 70 kg body weight. In another embodiment, the radiolabeled Neutrokine-alpha or anti-Neutrokine-alpha antibody composition can be administered at a dose of about 0.1 to about 50 mCi per 70 kg body weight. In another embodiment, the radiolabeled Neutrokine-alpha or anti-Neutrokine-alpha antibody composition can be administered at a dose of about 0.1, 0.5, 1, 5, 10, 15, 20, 25, 30, 35, 40, 50, 60, 70, 80, 90 or 100 mCi per 70 kg body weight.

The radiolabeled Neutrokine-alpha or anti-Neutrokine-alpha antibody composition can be administered at a dose of about 0.1 to about 10 mCi/kg body weight. In another embodiment, the radiolabeled Neutrokine-alpha or anti-Neutrokine-alpha antibody composition can be administered at a dose of about 0.25 to about 5 mCi/kg body weight. In specific embodiments, the radiolabeled Neutrokine-alpha or anti-Neutrokine-alpha antibody composition can be administered at a dose of about 0.35, 0.70, 1.35, 1.70, 2.0, 2.5 or 3.0 mCi/kg.

The radiolabeled Neutrokine-alpha or anti-Neutrokine-alpha antibody composition can be administered at a dose of about 1 to about 50 mCi/m$^2$. In another embodiment, the radiolabeled Neutrokine-alpha or anti-Neutrokine-alpha antibody composition can be administered at a dose of about 10 to about 30 mCi/m$^2$. In specific embodiments, the radiolabeled Neutrokine-alpha or anti-Neutrokine-alpha antibody composition can be administered at a dose of about 10, 15, 20, 25, or 30 mCi/m2.

The concentration of total Neutrokine-alpha protein, Neutrokine-alphaSV protein, anti-Neutrokine-alpha antibody and/or anti-Neutrokine-alphaSV antibody in a radiolabelled Neutrokine-alpha or anti-Neutrokine-alpha antibody composition may also vary, for example from about 1 microgram/kg to about 1 mg/kg. In specific embodiments, the total concentration of Neutrokine-alpha protein, Neutrokine-alphaSV protein, anti-Neutrokine-alpha antibody and/or anti-Neutrokine-alphaSV antibody in a radiolabelled Neutrokine-alpha or anti-Neutrokine-alpha antibody composition may be about 5, 10, 15, 20, 25, 30, 35, 40, 45, 50, 55, 60, 65, 70, 75, 80, 85, 90, 95 100 micrograms/kg.

For example, lymphomas are known to be radiosensitive tumors. For immunodiagnostic imaging, trace-labeling by the complex may be used, typically 1-20 mg of Neutrokine-alpha protein is labeled with about 1 to 60 mCi of radioisotope. The dose may be somewhat dependent upon the isotope used for imaging; amounts in the higher end of the range, preferably 40 to 60 mCi, may be used with $^{99m}$Tc; amounts in the lower end of the range, preferably 1-20 mCi, may be used with $^{111}$In. For imaging purposes, about 1 to about 30 mg of Neutrokine-alpha complex can be given to the subject. For radioimmunotherapeutic purposes, the Neutrokine-alpha complex is administered to a subject in sufficient amount so that the whole body dose received is up to about 1100 cGy, but preferably less than or equal to 500 cGy. The total amount of Neutrokine-alpha protein administered to a subject, including Neutrokine-alpha protein, Neutrokine-alpha conjugate and Neutrokine-alpha complex, can range from 1.0 µg/kg to 1.0 mg/kg of patient body weight. In another embodiment, total amount of Neutrokine-alpha protein administered to a subject, can range from 20 µg/kg to 100 µg/kg of patient body weight.

An amount of radioactivity which would provide approximately 500 cGy to the whole body of a human is estimated to be about 825 mCi of $^{131}$I. The amounts of radioactivity to be administered depend, in part, upon the isotope chosen. For $^{90}$Y therapy, from about 1 to about 200 mCi amounts of radioactivity are considered appropriate, with preferable amounts being 1 to 150 mCi, and 1 to 100 mCi (e.g., 60 mCi) being most preferred. The preferred means of estimating tissue doses from the amount of administered radioactivity is to perform an imaging or other pharmacokinetic regimen with a tracer dose, so as to obtain estimates of predicted dosimetry. In determining the appropriate dosage of radiopharmaceutical to administer to an individual, it is necessary to consider the amount of radiation that individual organs will receive compared to the maximum tolerance for such organs. Such information is known to those skilled in the art, for example, see Emami et al., International Journal of Radiation Oncology, Biology, Physics 21:109-22 (1991); and Meredith, Cancer Biotherapy & Radiopharmaceuticals 17:83-99 (2002), both of which are hereby incorporated by reference in their entireties.

A "high-dose" protocol, for example in the range of 200 to 600 cGy (or higher) to the whole body, may require the support of a bone-marrow replacement protocol, as the bone-marrow is the tissue which limits the radiation dosage due to toxicity.

In specific embodiments, a patient receives multiple administrations of a composition (e.g., antibody that specifically binds Neutrokine-alpha or other immunomodulatory agent known in the art and/or described herein). One set of multiple administrations is referred to as a cycle. A single cycle may comprise, for example 1, 2, 3, 4, 5, 6, 7, 8, 9, 10, 11, 12 or more administrations. For any one administration, the dose may be fixed or variable to allow for initial drug loading and/or to account for patient-specific differences in mass, body surface area, disease activity, disease responsiveness, drug tolerability, recovery times, PK parameters, and/or pharmacological response(s).

The time between any two administrations within a given cycle may be may be fixed or variable to accommodate patient-specific differences in disease activity, disease responsiveness, drug tolerability, recovery times, PK parameters, and/or pharmacological response(s). In specific embodiments, patients are given an initial loading dose that is twice the amount given in subsequent administrations. In other embodiments, the time between any two administrations may be 1, 2, 3, 4, 5, 6, or 7 days (1 week) or greater. In specific embodiments, the time between any two administrations may be 1, 2, 3, 4, 5, 6, 7, or 8 weeks or greater. Patients may also receive multiple cycles of treatment. If more than one cycle is needed, the time between any two treatment cycles may be fixed or variable to accommodate patient-specific differences in disease activity, disease responsiveness, drug tolerability, recovery times, PK parameters, and/or pharmacological response(s). In specific embodiments, the time between any two cycles may be 1, 2, 3, 4, 5, 6 weeks or greater. In specific embodiments, the time between any two cycles may be 1, 2, 3, 4, 5, 6, 7, 8, 9, 10, 11, 12 months or greater. In specific embodiments, the time between any two cycles may be 1, 2, 3, 4, 5 years or greater. In specific embodiments, a patient receives an initial bolus administration followed by one or multiple cycle treatments.

In one embodiment, the initial bolus administration comprises a dose of more than or equal to 2 mg/kg of an antibody antagonist of Neutrokine-alpha administered intravenously to a patient. In one embodiment, the initial bolus administration comprises a dose of more than or equal to 5 mg/kg of an antibody antagonist of Neutrokine-alpha administered intravenously to a patient. In preferred embodiments, the initial bolus administration is a dose of more than or equal to 10 mg/kg of an antibody antagonist of Neutrokine-alpha administered intravenously to a patient. In other embodiments, the initial bolus administration is a dose of more than or equal to 15 mg/kg of an antibody antagonist of Neutrokine-alpha administered intravenously to a patient. In one embodiment, the initial bolus administration comprises a dose of more than or equal to 20 mg/kg of the antibody of the invention administered intravenously to a patient.

In other specific embodiments, the initial bolus comprises an anti-CD20 antibody.

In other specific embodiments, the initial bolus comprises a B-cell depleting agent.

The invention also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

An immunomodulatory agent may be administered alone or in combination with other therapeutic agents, including but not limited to, one or more additional immunomodualory agents, chemotherapeutic agents, antibiotics, antivirals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In the succeeding paragraphs, it is disclosed that an immunomodulatory agent may be administered in combination with another compound. In certain instances, the additional compound is itself also an immunomodulatory agent. The disclosure in those paragraphs is intended to convey that it is specifically contemplated that two or more distinct immunomodulatory agents may be administered in combination with one another in conjunction with the methods of the present invention. For example, it is specifically contemplated that an anti-Neutrokine-alpha antibody may be used in conjunction with an anti-CD20 antibody in conjunction with the methods of the present invention.

Conventional nonspecific immunosuppressive agents, that may be administered in combination an immunomodulatory agent include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells. Other immunosuppressive agents, that may be administered in combination with an immunomodulatory agent include, but are not limited to, prednisolone, methotrexate, thalidomide, methoxsalen, rapamycin, leflunomide, mizoribine (BREDININ™), brequinar, deoxyspergualin, and azaspirane (SKF 105685).

In specific embodiments, an immunomodulatory agent is administered in combination with an immunosuppressant. Immunosuppressant preparations that may be administered with an immunomodulatory agent include, but are not limited to, ORTHOCLONE OKT® 3 (muromonab-CD3), SANDIMMUNE™, NEORAL™, SANGDYA™ (cyclosporine), PROGRAF® (FK506, tacrolimus), CELLCEPT® (mycophenolate motefil, of which the active metabolite is mycophenolic acid), IMURAN™ (azathioprine), glucorticosteroids, adrenocortical steroids such as DELTASONE™ (prednisone) and HYDELTRASOL™ (prednisolone), FOLEX™ and MEXATE™ (methotrxate), OXSORALEN-ULTRA™ (methoxsalen) and RAPAMUNE™ (sirolimus). In a specific embodiment, immunosuppressants may be used to prevent rejection of organ or bone marrow transplantation.

In another embodiment, an immunomodulatory agent is administered in combination with steroid therapy. Steroids that may be administered in combination with an immunomodulatory agent, include, but are not limited to, oral corticosteroids, prednisone, and methylprednisolone (e.g., IV methylprednisolone). In a specific embodiment, an immunomodulatory agent is administered in combination with prednisone. In a further specific embodiment, an immunomodulatory agent is administered in combination with prednisone and an immunosuppressive agent. Immunosuppressive agents that may be administered with an immunomodulatory agent and prednisone are those described herein, and include, but are not limited to, azathioprine, cylophosphamide, and cyclophosphamide IV. In another specific embodiment, an immunomodulatory agent is administered in combination with methylprednisolone. In a further specific embodiment, an immunomodulatory agent is administered in combination with methylprednisolone and an immunosuppressive agent. Immunosuppressive agents that may be administered with an immunomodulatory agent and methylprednisolone are those described herein, and include, but are not limited to, azathioprine, cylophosphamide, and cyclophosphamide IV.

In a preferred embodiment, an immunomodulatory agent is administered in combination with an antimalarial. Antimalarials that may be administered with an immunomodulatory agent include, but are not limited to, hydroxychloroquine (e.g., PLAQUENIL™), chloroquine, and/or quinacrine.

In a preferred embodiment, an immunomodulatory agent is administered in combination with an NSAID.

In a nonexclusive embodiment, an immunomodulatory agent is administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In one embodiment, an immunomodulatory agent is administered in combination with one or more of the following drugs: Infliximab (also known as Remicade™ Centocor, Inc.), Trocade (Roche, RO-32-3555), Leflunomide (also known as Arava™ from Hoechst Marion Roussel), Kineret™ (an IL-1 Receptor antagonist also known as Anakinra from Amgen, Inc.), SCIO-469 (p38 kinase inhibitor from Scios, Inc), Humira® (adalimumab from Abbott Laboratories) and/or ASLERA™ (prasterone, dehydroepiandrosterone, GL701) from Genelabs Technologies Inc.

In another embodiment, an immunomodulatory agent is administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, LJP 394 (La Jolla Pharmaceutical Company, San Diego, Calif.), and prednisolone.

In another embodiment, an immunomodulatory agent is administered in combination with an antimalarial, methotrexate, anti-TNF antibody, ENBREL™ and/or sulfasalazine. In one embodiment, an immunomodulatory agent is administered in combination with methotrexate. In another embodiment, an immunomodulatory agent is administered in combination with anti-TNF antibody. In another embodiment, an immunomodulatory agent is administered in combination with methotrexate and anti-TNF antibody. In another embodiment, an immunomodulatory agent is administered in combination with sulfasalazine. In another specific embodiment, an immunomodulatory agent is administered in combination with methotrexate, anti-TNF antibody, and sulfasalazine. In another embodiment, an immunomodulatory agent is administered in combination ENBREL™. In another embodiment, an immunomodulatory agent is administered in combination with ENBREL™ and methotrexate. In another embodiment, an immunomodulatory agent is administered in combination with ENBREL™, methotrexate and sulfasalazine. In another embodiment, an immunomodulatory agent is administered in combination with ENBREL™, and sulfasalazine. In other embodiments, one or more antimalarials is combined with one of the above-recited combinations. In a specific embodiment, an immunomodulatory agent is administered in combination with an antimalarial (e.g., hydroxychloroquine), ENBREL™, methotrexate and sulfasalazine. In another specific embodiment, an immunomodulatory agent is administered in combination with an antimalarial (e.g., hydroxychloroquine), sulfasalazine, anti-TNF antibody, and methotrexate.

In an additional embodiment, an immunomodulatory agent is administered alone or in combination with one or more intravenous immune globulin preparations. Intravenous immune globulin preparations that may be administered with an immunomodulatory agent include, but are not limited to, GAMMAR™, IVEEGAM™, SANDOGLOBULIN™, GAMMAGARD S/D™, and GAMIMUNE™. In a specific embodiment, an immunomodulatory agent is administered in combination with intravenous immune globulin preparations in transplantation therapy (e.g., bone marrow transplant).

In an additional embodiment, an immunomodulatory agent is administered alone or in combination with an anti-inflammatory agent. Anti-inflammatory agents that may be administered with an immunomodulatory agent include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In specific embodiments, an immunomodulatory agent is administered alone or in combination with anti-CD4 antibody. In one embodiment, coadministration of an immunomodulatory agent with anti-CD4 antibody is envisioned for treatment of rheumatoid arthritis. In one embodiment, coadministration of an immunomodulatory agent with anti-CD4 antibody is envisioned for treatment of systemic lupus erythematosus.

In specific embodiments, an immunomodulatory agent is administered alone or in combination with anti-IL-15 antibody. In one embodiment, coadministration of an immunomodulatory agent with anti-IL-15 antibody is envisioned for treatment of rheumatoid arthritis. In one embodiment, coadministration of an immunomodulatory agent with anti-IL-15 antibody is envisioned for treatment of systemic lupus erythematosus.

In specific embodiments, an immunomodulatory agent is administered alone or in combination with CTLA4-Ig and LEA29Y. In one embodiment, coadministration of an immunomodulatory agent with CTLA4-Ig and LEA29Y is envisioned for treatment of rheumatoid arthritis. In one embodiment, coadministration of an immunomodulatory agent with CTLA4-Ig and LEA29Y is envisioned for treatment of systemic lupus erythematosus.

In specific embodiments, an immunomodulatory agent is administered alone or in combination with anti-IL-6 Receptor antibody. In one embodiment, coadministration of an immunomodulatory agent with anti-IL-6 Receptor antibody is envisioned for treatment of rheumatoid arthritis. In one embodiment, coadministration of an immunomodulatory agent with anti-IL-6 Receptor antibody is envisioned for treatment of systemic lupus erythematosus.

In specific embodiments, an immunomodulatory agent is administered alone or in combination with anti-C5 (complement component) antibody. In one embodiment, coadministration of an immunomodulatory agent with anti-C5 antibody is envisioned for treatment of rheumatoid arthritis. In one embodiment, coadministration of an immunomodulatory agent with anti-C5 antibody is envisioned for treatment of systemic lupus erythematosus.

In specific embodiments, an immunomodulatory agent is administered alone or in combination with complement cascade inhibitors. Complement cascade inhibitors include, but are not limited to, anti-properdin antibodies (Gliatech); TP-10, a recombinant soluble type I complement receptor (AVANT Immunotheragenetics Inc.); Pexelizmab, a Complement C5 inhibitor (Alexion Pharmaceuticals Inc.); and 5G1.1, a monoclonal antibody that prevents cleavage of complement component C5 into its pro-inflammatory components. In one embodiment, coadministration of an immunomodulatory agent with complement cascade inhibitors is envisioned for treatment of Inflammation, Rheumatoid arthritis and/or systemic lupus erythematosus.

In another embodiment, an immunomodulatory agent is administered in combination with a chemotherapeutic agent. Chemotherapeutic agents that may be administered with an immunomodulatory agent include, but are not limited to, antibiotic derivatives (e.g., doxorubicin, bleomycin, daunorubicin, and dactinomycin); antiestrogens (e.g., tamoxifen); antimetabolites (e.g., fluorouracil, S-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlortrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, an immunomodulatory agent is administered in combination with CHOP (cyclophosphamide, doxorubicin, vincristine, and prednisone) or combination of one or more of the components of CHOP. In one embodiment, an immunomodulatory agent is administered in combination with anti-CD20 antibodies, such as human monoclonal anti-CD20 antibodies. In another embodiment, an immunomodulatory agent is administered in combination with anti-CD20 antibodies and CHOP, or anti-CD20 antibodies and any combination of one or more of the components of CHOP, particularly cyclophosphamide and/or prednisone. In a specific embodiment, an immunomodulatory agent is administered in combination with Rituximab. In a further embodiment, an immunomodulatory agent is administered with Rituximab and CHOP, or Rituximab and any combination of one or more of the components of CHOP, particularly cyclophosphamide and/or prednisone. In a specific embodiment, an immunomodulatory agent is administered in combination with tositumomab (anti-CD20 antibody from Coulter Pharmaceuticals, San Francisco, Calif.). In a further embodiment, an immunomodulatory agent is administered with tositumomab and CHOP, or tositumomab and any combination of one or more of the components of CHOP, particularly cyclophosphamide and/or prednisone. Tositumomab may optionally be associated with 131I. The anti-CD20 antibodies may optionally be associated with radioisotopes, toxins or cytotoxic prodrugs.

In another specific embodiment, an immunomodulatory agent is administered in combination Zevalin™. In a further embodiment, an immunomodulatory agent is administered with Zevalin™ and CHOP, or Zevalin™ and any combination of one or more of the components of CHOP, particularly cyclophosphamide and/or prednisone. Zevalin™ may be associated with one or more radioisotopes. Particularly preferred isotopes are $^{90}$Y and $^{111}$In.

In additional embodiments, an immunomodulatory agent is administered in combination with Rituximab (Rituxan™) and/or Ibritumomab Tiuxetan (Zevalin™, e.g., either (In-111) Ibritumomab Tiuxetan or (Y-90) Ibritumomab Tiuxetan). In a specific embodiment, an immunomodulatory agent is administered in combination with Rituximab and/or Ibritumomab Tiuxetan for the treatment of non-Hodgkin's lymphoma In specific embodiments, an immunomodulatory agent is administered as a chronic treatment that is supplemented with anti-CD20 administration following disease flare, e.g., after a lupus flare.

In additional embodiments, an immunomodulatory agent is administered in combination with imatinib mesylate (Gleevec®: 4-[(4-Methyl-1-piperazinyl) methyl]-N-[4-methyl-3-[[4-(3-pyridinyl)-2-pyrimidinyl]amino]-phenyl]benzamide methanesulfonate).

In additional embodiments, an immunomodulatory agent is administered in combination with bortezomib (Velcade™ [(1R)-3-methyl-1-[[(2S)-1-oxo-3-phenyl-2-[(pyrazinylcarbonyl)amino]propyl]amino]butyl]boronic acid).

In additional embodiments, an immunomodulatory agent is administered in combination with Alemtuzumab (Campath®).

In additional embodiments, an immunomodulatory agent is administered in combination with fludarabine phosphate (Fludara®: 9H-Purin-6-amine, 2-fluoro-9-(5-O-phosphono-β-D-arabinofuranosyl) (2-fluoro-ara-AMP)).

An immunomodulatory agent may be administered in combination with one or more therapeutic agents useful in the treatment of multiple myeloma including but not limited to, Alkylating agents, Anthracyclines, Carmustine (DTI-015, BCNU, BiCNU, Gliadel Wafer®), Cyclophosphamide (Cytoxan®, Neosar®, CTX), Dexamethasone (Decadron®), Doxorubicin (Adriamycin®, Doxil®, Rubex®), Melphalan (L-PAM, Alkeran®, Phenylalanine mustard), Prednisone, Thalidomide and Vincristine (Oncovorin®, Onco TCS®, VCR, Leurocristine®).

Preferred combinations of therapeutic agents useful in the treatment of multiple myeloma which may be administered in combination with an immunomodulatory agent include, but are not limited to, Cyclophosphamide+Prednisone, Melphalan+Prednisone (MP), Vincristine+Adriamycin®+Dexamethasone (VAD), Vincristine+Carmustine+Melphalan+Cyclophosphamide+Prednisone (VBMCP; the M2 protocol), and Vincristine+Melphalan+Cyclophosphamide+Prednisone alternating with Vincristine+Carmustine+Doxorubicin+Prednisone (VMCP/VBAP).

An immunomodulatory agent may be administered in combination with one or more therapeutic agents useful in the treatment of non-Hodgkin's lymphoma including but not limited to, 2-chlorodeoxyadenosine, Amifostine (Ethyol®, Ethiofos®, WR-272), Bexarotene (Targretin®, Targretin Gel®, Targretin Oral®, LGD1069), Bleomycin (Blenoxane®), Busulfan (Busulfex®, Myleran®), Carboplatin (Paraplatin®, CBDCA), Carmustine (DTI-015, BCNU, BiCNU, Gliadel Wafer®), Chlorambucil (Leukeran®), Cisplatin (Platinol®, CDDP), Cladribine (2-CdA, Leustatin®), Cyclophosphamide (Cytoxan®, Neosar®, CTX), Cytarabine (Cytosar-U®, ara-C, cytosine arabinoside, DepoCyt®), Dacarbazine (DTIC), Daunorubicin (Daunomycin, DaunoXome®, Daunorubicin®, Cerubidine®), Denileukin diftitox (Ontak®), Dexamethasone (Decadron®), Dolasetron mesylate (Anzemet®), Doxorubicin (Adriamycin®, Doxil®, Rubex®), Erythropoietin (EPO®, Epogen®, Procrit®), Etoposide phosphate (Etopophos®), Etoposide (VP-16, Vepesid®), Fludarabine (Fludara®, FAMP), Granisetron (Kytril®), Hydrocortisone, Idarubicin (Idamycin®, DMDR, IDA), Ifosfamide (IFEX®), Interferon alpha (Alfaferone®, Alpha-IF®), Interferon alpha 2a (Intron A®), Mechlorethamine (Nitrogen Mustard, HN$_2$, Mustargen®), Melphalan (L-PAM, Alkeran®, Phenylalanine mustard), Methotrexate® (MTX, Mexate®, Folex®), Methylprednisolone (Solumedrol®), Mitoxantrone (Novantrone®, DHAD), Ondansetron (Zofran®), Pentostatin (Nipent®, 2-deoxycoformycin), Perfosfamide (4-hydroperoxycyclophosphamide, 4-HC), Prednisone, Procarbazine (Matulane®), Rituximab® (Rituxan®, anti-CD20 MAb), Thiotepa (triethylenethiophosphaoramide, Thioplex®), Topotecan (Hycamtin®, SK&F-104864, NSC-609699, Evotopin®), Vinblastine (Velban®, VLB), Vincristine (Oncovin®, Onco TCS®, VCR, Leurocristine®) and Vindesine (Eldisine®, Fildesin®).

Preferred combinations of therapeutic agents useful in the treatment of non-Hodgkin's lymphoma which may be administered in combination with an immunomodulatory agent include, but are not limited to, Adriamycin®+Blenoxane+

Vinblastine+Dacarbazine (ABVD), Anti-idiotype therapy (BsAb)+Interferon alpha, Anti-idiotype therapy (BsAb)+Chlorambucil, Anti-idiotype therapy (BsAb)+Interleukin-2, BCNU (Carmustine)+Etoposide+Ara-C (Cytarabine)+Melphalen (BEAM), Bleomycin+Etoposide+Adriamycin+Cyclophosphamide+Vincristine+Procarbazine+Prednisone (BEACOPP), Bryostatin+Vincristine, Cyclophosphamide+BCNU (Carmustine)+VP-16 (Etoposide) (CBV), Cyclophosphamide+Vincristine+Prednisone (CVP), Cyclophosphamide+Adriamycin® (Hydroxyldaunomycin)+Vincristine (Oncovorin)+Prednisone (CHOP), Cyclophosphamide+Novantrone® (Mitoxantrone)+Vincristine (Oncovorin)+Prednisone (CNOP), Cyclophosphamide+Doxorubicin+Teniposide+Prednisone, Cyclophosphamide+Adriamycin® (Hydroxyldaunomycin)+Vincristine (Oncovorin)+Prednisone+Rituximab (CHOP+Rituximab), Cyclophosphamide+Doxorubicin+Teniposide+Prednisone+Interferon alpha, Cytarabine+Bleomycin+Vincristine+Methotrexate (CytaBOM), Dexamethasone+Cytarabine+Cisplatin (DHAP), Dexamethasone+Ifosfamide+Cisplatin+Etoposide (DICE), Doxorubicin+Vinblastine+Mechlorethamine+Vincristine+Bleomycin+Etoposide+Prednisone (Stanford V), Etoposide+Vinblastine+Adriamycin (EVA), Etoposide+Methylprednisone+Cytarabine+Cisplatin (ESHAP), Etoposide+Prednisone+Ifosfamide+Cisplatin (EPIC), Fludarabine, Mitoxantrone+Dexamethasone (FMD), Fludarabine, Dexamethasone, Cytarabine (ara-C), +Cisplatin (Platinol®) (FluDAP), Ifosfamide+Cisplatin+Etoposide (ICE), Mechlorethamine+Oncovin® (Vincristine)+Procarbazine+Prednisone (MOPP), Mesna+Ifosfamide+Idarubicin+Etoposide (MIZE), Methotrexate with leucovorin rescue+Bleomycin+Adriamycin+Cyclophosphamide+Oncovorin+Dexamethasone (m-BACOD), Prednisone+Methotrexate+Adriamycin+Cyclophosphamide+Etoposide (ProMACE), Thiotepa+Busulfan+Cyclophosphamide, Thiotepa+Busulfan+Melphalan, Topotecan+Paclitaxel, and Vincristine (Oncovin®)+Adriamycin®+Dexamethasone (VAD).

Further examples of therapeutic agents useful in the treatment of non-Hodgkin's lymphoma which may be administered in combination with an immunomodulatory agent include, but are not limited to, A007 (4-4'-dihydroxybenzophenone-2,4-dinitrophenylhydrazone), AG-2034 (AG-2024, AG-2032, GARFT [glycinamide ribonucleoside transformylase] inhibitor), Aldesleukin (IL-2, Proleukin®), Alemtuzumab (Campath®), Alitretinoin (Panretin®, LGN-1057), Altretamine (Hexylen®, hexamethylmelamine, Hexastat®), Aminocamptothecin (9-AC, 9-Aminocamptothecin, NSC 603071), Anti-CD19/CD3 MAb (anti-CD19/CD3 scFv, anti-NHL MAb), Anti-idiotype therapy (BsAb), Arabinosylguanine (Ara-G, GW506U78), Arsenic trioxide (Trisenox®, ATO), B43-Genistein (anti-CD19 Ab/genistein conjugate), B7 antibody conjugates, Betathine (Beta-LT), BLyS antagonists, Bryostatin-1 (Bryostatin®, BMY-45618, NSC-339555), CHML (Cytotropic Heterogeneous Molecular Lipids), Clofarabine (chloro-fluoro-araA), Daclizumab (Zenapax®), Depsipeptide (FR901228, FK228), Dolastatin-10 (DOLA-10, NSC-376128), Epirubicin (Ellence®, EPI, 4' epidoxorubicin), Epratuzumab (Lymphocide®, humanized anti-CD22, HAT), Fly3/flk2 ligand (Mobista®), G3139 (Genasense®, GentaAnticode®, Bcl-2 antisense), HuID10 (anti-HLA-DR MAb, SMART 1D10), HumaLYM (anti-CD20 MAb), Ibritumomab tiuxetan (Zevalin®), Interferon gamma (Gamma-interferon, Gamma 100®, Gamma-IF), Irinotecan (Camptosar®, CPT-1, Topotecin®, CaptoCPT-1), ISIS-2053, ISIS-3521 (PKC-alpha antisense), Lmb-2 immunotoxin (anti-CD25 recombinant immuno toxin, anti-Tac(Fv)-PE38), Leuvectin® (cytofectin+IL-2 gene, IL-2 gene therapy), Lym-1 (131-I LYM-1), Lymphoma vaccine (Genitope), Nelarabine (Compound 506, U78), Neugene compounds (Oncomyc-NG®, Resten-NGO, myc antisense), NovoMAb-G2 scFv (NovoMAb-G2 IgM), 06-benzylguanine (BG, Procept®), Oxaliplatin (Eloxatine®, Eloxatin®), Paclitaxel (Paxene®, Taxol®), Paclitaxel-DHA (Taxoprexin®), Peldesine (BCX-34, PNP inhibitor), Rebeccamycin and Rebeccamycin analogues, SCH-66336, Sobuzoxane (MST-16, Perazolin®), SU5416 (Semaxanib®, VEGF inhibitor), TER-286, Thalidomide, TNP-470 (AGM-1470), Tositumomab (Bexxar®), Valspodar (PSC 833), Vaxid (B-cell lymphoma DNA vaccine), Vinorelbine (Navelbine®), WF10 (macrophage regulator) and XR-9576 (XR-9351, P-glycoprotein/MDR inhibitor).

An immunomodulatory agent may be administered in combination with one or more therapeutic agents useful in the treatment of acute lymphocytic leukemia including but not limited to, Amsacrine, Carboplatin (Paraplatin®, CBDCA), Carmustine (DTI-015, BCNU, BiCNU, Gliadel Wafer®), Cholecaliferol, Cyclophosphamide (Cytoxan®, Neosar®, CTX), Cytarabine (Cytosar-U®, ara-C, cytosine arabinoside, DepoCyt®), Daunorubicin (Daunomycin, DaunoXome®, Daunorubicin®, Cerubidine®), Dexamethasone (Decadron®), Doxorubicin (Adriamycin®, Doxil®, Rubex®), Etoposide (VP-16, Vepesid®), Filgrastam® (Neupogen®, G-CSF, Leukine®), Fludarabine (Fludara®, FAMP), Idarubicin (Idamycin®, DMDR, IDA), Ifosfamide (IFEX®), Imatinib mesylate (STI-571, Imatinib®, Glivec®, Gleevec®, Abl tyrosine kinase inhibitor), Interferon gamma (Gamma-interferon, Gamma 100, Gamma-IF), L-asparaginase (Elspar®, Crastinin®, Asparaginase Medac®, Kidrolase®), Mercaptopurine (6-mercaptopurine, 6-MP), Methotrexate® (MTX, Mexate®, Folex®), Mitoxantrone (Novantrone®, DHAD), Pegaspargase® (Oncospar®), Prednisone, Retinoic acid, Teniposide (VM-26, Vumon®), Thioguanine (6-thioguanine, 6-TG), Topotecan (Hycamtin®, SK&F-104864, NSC-609699, Evotopin®), Tretinoin (Retin-A®, Atragen®, ATRA, Vesanoid®) and Vincristine (Oncovorin®, Onco TCS®, VCR, Leurocristine®).

Further examples of therapeutic agents useful in the treatment of acute lymphocytic leukemia which may be administered in combination with an immunomodulatory agent include, but are not limited to, Aminocamptothecin (9-AC, 9-Aminocamptothecin, NSC 603071), Aminopterin, Annamycin (AR-522, annamycin LF, Aronex®), Arabinosylguanine (Ara-G, GW506U78, Nelzarabine®), Arsenic trioxide (Trisenox®, ATO, Atrivex®), B43-Genistein (anti-CD19 Ab/genistein conjugate), B43-PAP (anti-CD19 Ab/pokeweed antiviral protein conjugate), Cordycepin, CS-682, Decitabine (5-aza-2'-deoxyytidine), Dolastatin-10 (DOLA-10, NSC-376128), G3139 (Genasense®, GentaAnticode®, Bcl-2 antisense), Irofulven (MGI-114, Ivofulvan, Acylfulvene analogue), MS-209, Phenylbutyrate, Quinine, TNP-470 (AGM-1470, Fumagillin), Trimetrexate (Neutrexin®), Troxacitabine (BCH-204, BCH-4556, Troxatyl®), UCN-01 (7-hydroxystaurosporine), WHI-P131 and WT1 Vaccine.

Preferred combinations of therapeutic agents useful in the treatment of acute lymphocytic leukemia which may be administered in combination with an immunomodulatory agent include, but are not limited to, Carboplatin+Mitoxantrone, Carmustine+Cyclophosphamide+Etoposide, Cytarabine+Daunorubicin, Cytarabine+Doxorubicin, Cytarabine+Idarubicin, Cytarabine+Interferon gamma, Cytarabine+L-asparaginase, Cytarabine+Mitoxantrone, Cytarabine+Fludarabine and Mitoxantrone, Etoposide+Cytarabine, Etoposide+Ifosfamide, Etoposide+Mitoxantrone, Ifosfamide+Etoposide+Mitoxantrone, Ifosfamide+Teniposide, Methotrexate+Mercaptopurine, Methotrexate+Mercaptopurine+Vincristine+Prednisone, Phenylbutyrate+Cytarabine, Phenylbutyrate+Etoposide, Phenylbutyrate+Topotecan, Phenylbutyrate+Tretinoin, Quinine+Doxorubicin, Quinine+Mitoxantrone+Cytarabine, Thioguanine+Cytarabine+Amsacrine, Thioguanine+Etoposide+Idarubicin, Thioguanine+Retinoic acid+Cholecaliferol, Vincristine+Prednisone, Vincristine+Prednisone and L-asparaginase, Vincristine+Dexamethasone/Prednisone+Asparaginase+Daunorubicin/Doxorubicin, Vincristine+Dexamethasone/Prednisone+Asparaginase+Daunorubicin/Doxorubicin+Filgrastim, Vincristine+Dexamethasone/Prednisone+Asparaginase+Daunorubicin/Doxorubicin+Cyclophosphamide+Methotrexate, and Vincristine+Dexamethasone/Prednisone+Asparaginase+Daunorubicin/Doxorubicin+Cyclophosphamide+Methotrexate+Filgrastim.

An immunomodulatory agent may be administered in combination with one or more therapeutic agents useful in the treatment of chronic lymphocytic leukemia including but not limited to, Chlorambucil (Leukeran®), Cladribine (2-CdA, Leustatin®), Cyclophosphamide (Cytoxan®, Neosar®, CTX), Cytarabine (Cytosar-U®, ara-C, cytosine arabinoside, DepoCyt®, cytarabine ocfosfate, ara-CMP), Doxorubicin (Adriamycin®, Doxil®, Rubex®), Fludarabine (Fludara®, FAMP), Pentostatin (Nipent®, 2-deoxycoformycin), Prednisone and Vincristine (Oncovorin®, Onco TCS®, VCR, Leurocristine®).

Further examples of therapeutic agents useful in the treatment of chronic lymphocytic leukemia which may be administered in combination with an immunomodulatory agent include, but are not limited to, Alemtuzumab (Campath®), Aminocamptothecin (9-AC, 9-Aminocamptothecin, NSC 603071), Aminopterin, Annamycin (AR-522, annamycin LF, Aronex®), Arabinosylguanine (Ara-G, GW506U78, Nelzarabine®, Compound 506U78), Arsenic trioxide (Trisenox®, ATO, Atrivex®), Bryostatin-1 (Bryostatin®, BMY-45618, NSC-339555), CS-682, Dolastatin-10 (DOLA-10, NSC-376128), Filgrastim (Neupogen®, G-CSF, Leukine), Flavopiridol (NSC-649890, HMR-1275), G3139 (Genasense®, GentaAnticode®, Bcl-2 antisense), Irofulven (MGI-114, Ivofulvan, Acylfulvene analogue), MS-209, Phenylbutyrate, Rituximab® (Rituxan®, anti-CD20 MAb), Thalidomide, Theophylline, TNP-470 (AGM-1470, Fumagillin), UCN-01 (7-hydroxystaurosporine) and WHI-P131.

Preferred combinations of therapeutic agents useful in the treatment of chronic lymphocytic leukemia which may be administered in combination with an immunomodulatory agent include, but are not limited to, Fludarabine+Prednisone, and Cyclophosphamide+Doxorubicin+Vincristine+Prednisone (CHOP).

In an additional embodiment, an immunomodulatory agent is administered in combination with cytokines. Cytokines that may be administered with an immunomodulatory agent include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In another embodiment, an immunomodulatory agent may be administered with any interleukin, including but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, an immunomodulatory agent is administered in combination with IL4 and IL10. Both IL4 and IL10 have been observed by the inventors to enhance Neutrokine-alpha mediated B cell proliferation.

In vitro, IFN gamma and IL-10 have each been observed by the inventors to enhance cell surface expression of Neutrokine-alpha in monocytes and macrophages (macrophages were obtained by culturing primary monocytes with 20 ng/mL of M-CSF for 12-15 days), whereas IL-4 treatment decreased cell surface expression of Neutrokine-alpha in monocytes and macrophages. IL-4 administered with IL-10 resulted in a complete inhibition of the IL-10 induced cell surface expression of Neutrokine-alpha. IL-4 administered with IFN-gamma resulted in increased cell-surface expression of Neutrokine-alpha. Treatment of macrophages with IFN-gamma and IL-10 resulted in a 3 fold increase of soluble (active) Neutrokine-alpha released into the culture medium compared to untreated macrophages.

In an additional embodiment, an immunomodulatory agent is administered with a chemokine. In another embodiment, an immunomodulatory agent is administered with chemokine beta-8, chemokine beta-1, and/or macrophage inflammatory protein-4. In a preferred embodiment, an immunomodulatory agent is administered with chemokine beta-8.

In an additional embodiment, an immunomodulatory agent is administered in combination with an IL-4 antagonist. IL-4 antagonists that may be administered with an immunomodulatory agent include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, an immunomodulatory agent is administered in combination with hematopoietic growth factors. Hematopoietic growth factors that may be administered with an immunomodulatory agent include, but are not limited to, LEUKINE™ (SARGRAMOSTIM™) and NEUPOGEN™ (FILGRASTIM™).

In an additional embodiment, an immunomodulatory agent is administered in combination with fibroblast growth factors. Fibroblast growth factors that may be administered with an immunomodulatory agent include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In an additional embodiment, an immunomodulatory agent is administered in combination with an antihypertensive. Antihypertensives that may be administered with an immunomodulatory agent include, but are not limited to, calcium channel blocking agents, such as nifedipine (ADALAT™, PROCARDIA™); peripheral vasodilators, such as hydralazine (APRESOLINE™); Beta-adrenergic blocking agents, such as propranolol (INDERAL™); alpha/beta adrenergic blockers, such as labetolol (NORMODYNE™, TRANDATE™); agents which inhibit the production of angiotensin II, such as captopril (CAPOTEN™); agents which directly inhibit the activity of angiotensin II, such as losartan (COZAAR™); and thiazide diuretics, such as hydrochlorothiazide (HYDRODIURIL™, ESIDREX™).

Immunomodulatory agents may be administered alone or in combination with other adjuvants. Adjuvants that may be administered with an immunomodulatory agent include, but are not limited to, alum, alum plus deoxycholate (ImmunoAg), MTP-PE (Biocine Corp.), QS21 (Genentech, Inc.), BCG, and MPL. In a specific embodiment, an immunomodulatory agent is administered in combination with alum. In another specific embodiment, an immunomodulatory agent is administered in combination with QS-21. Further adjuvants that may be administered with an immunomodulatory agent include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with an immunomodulatory agent include, but are not limited to, vaccines directed toward protection against MMR (measles, mumps, rubella), polio, varicella, tetanus/diptheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. In another specific embodiment, an immunomodulatory agent is used in combination with PNEUMOVAX-23™.

In one embodiment, an immunomodulatory agent is administered in combination with another member of the TNF family. TNF, TNF-related or TNF-like molecules that may be administered with an immunomodulatory agent include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL/AIM-I (International Publication No. WO 97/33899), LIGHT/AIM-II (International Publication No. WO 97/34911), APRIL (J. Exp. Med. 188(6):1185-1190), endokine-alpha (International Publication No. WO 98/07880), FASTR/TR6 (International Publication No. WO 98/30694), Osteoprotegrin (OPG), and Neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), TRAIL-R1/DR4 (International Publication No. WO 98/32856), TRAIL-R3, TR5 (International Publication No. WO 98/30693), TR6 (International Publication No. WO 98/30694), TRAIL-R2/TR7 (International Publication No. WO 98/41629), TRANK, TR9 (International Publication No. WO 98/56892), TRAIL-R4/TR10 (International Publication No. WO 98/54202), 312C2 (International Publication No. WO 98/06842), and TR12.

In another embodiment, an immunomodulatory agent is administered in combination with one or more Neutrokine-alpha receptors (e.g., TACI, BCMA and BAFF-R). In preferred in embodiments, the Neutrokine-alpha receptor is soluble. In other preferred embodiments, the Neutrokine-alpha receptor is fused to the Fc region of an immunoglobulin molecule such as the Fc region of Ian IgG molecule. For example, amino acid residues 1-154 of TACI (GenBank accession number AAC51790), amino acids 1-48 of BCMA (GenBank accession number NP_001183 or amino acids 1 to 81 of BAFF-R (GenBank Accession Number NP_443177 may be fused to the Fc region of an IgG molecule and used in combination with another immunomodulatory agent known in the art and/or described herein. In another embodiment a BAFF-R-Fc protein that may be administered in combination with an immunomodulatory agent is amino acids 1-70 of SEQ ID NO:10 fused to the Fc region of an IgG1 immunoglobulin molecule. Optionally, amino acid 20 (valine) in BAFF-R is substituted with aspargine and amino acid 27 (leucine) in BAFF-R is substituted with proline.

In a preferred embodiment, an immunomodulatory agent is administered in combination with anti-CD40L antibodies and/or anti-CD40 antibodies.

In an additional embodiment, an immunomodulatory agent is administered alone or in combination with an anti-angiogenic agent(s). Anti-angiogenic agents that may be administered with an immunomodulatory agent include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; (Takeuchi et al., Agents Actions 36:312-316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. Brem and J. Folkman J Pediatr. Surg. 28:445-51 (1993)); an integrin alpha v beta 3 antagonist (C. Storgard et al., J Clin. Invest. 103:47-54 (1999)); carboxynaminolmidazole; Carboxyamidotriazole (CAI) (National Cancer Institute, Bethesda, Md.); Conbretastatin A-4 (CA4P) (OXiGENE, Boston, Mass.); Squalamine (Magainin Pharmaceuticals, Plymouth Meeting, Pa.); TNP-470, (Tap Pharmaceuticals, Deerfield, Ill.); ZD-0101 AstraZeneca (London, UK); APRA (CT2584); Benefin, Byrostatin-1 (SC339555); CGP-41251 (PKC 412); CM101; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3340) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with an immunomodulatory agent may work through a variety of mechanisms including but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with an immunomodulatory agent include, but are not limited to, AG-3340 (Agouron, La Jolla, Calif.), BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aeterna, St-Foy, Quebec). Examples of anti-angiogenic inhibitors that act by blocking the function of endothelial cell-extracellular matrix adhesion molecules and which may be administered in combination with an immunomodulatory agent include, but are not limited to, EMD-121974 (Merck KcgaA Darmstadt, Germany) and Vitaxin (Ixsys, La Jolla, Calif./Medimmune, Gaithersburg, Md.). Examples of anti-angiogenic agents that act by directly antagonizing or inhibiting angiogenesis inducers and which may be administered in combination with an immunomodulatory agent include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with an immunomodulatory agent include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In particular embodiments, the use of an immunomodulatory agent in combination with an anti-angiogenic agents is contemplated for the treatment, prevention, and/or amelioration of an autoimmune disease, such as for example, an autoimmune disease described herein.

In a particular embodiment, the use of an immunomodulatory agent in combination with an anti-angiogenic agent is contemplated for the treatment, prevention, and/or amelioration of arthritis. In a more particular embodiment, the use of an immunomodulatory agent in combination with an anti-angiogenic agent is contemplated for the treatment, prevention, and/or amelioration of rheumatoid arthritis.

In another embodiment, an immunomodulatory agent is administered in combination with an anticoagulant. Anticoagulants that may be administered with an immunomodulatory agent include, but are not limited to, heparin, warfarin, and aspirin. In a specific embodiment, an immunomodulatory agent is administered in combination with heparin and/or warfarin. In another specific embodiment, an immunomodulatory agent is administered in combination with warfarin. In another specific embodiment, an immunomodulatory agent is administered in combination with warfarin and aspirin. In another specific embodiment, an immunomodulatory agent is administered in combination with heparin. In another specific embodiment, an immunomodulatory agent is administered in combination with heparin and aspirin.

In another embodiment, an immunomodulatory agent is administered in combination with an agent that suppresses the production of anticardiolipin antibodies. In specific embodiments, an immunomodulatory agent is administered in combination with an agent that blocks and/or reduces the ability of anticardiolipin antibodies to bind phospholipid-binding plasma protein beta 2-glycoprotein I (b2GPI).

In certain embodiments, an immunomodulatory agent is administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with an immunomodulatory agent, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with an immunomodulatory agent, include, but are not limited to, VIRAMUNE™ (nevirapine), RESCRIPTOR™ (delavirdine), and SUSTIVA™ (efavirenz). Protease inhibitors that may be administered in combination with an immunomodulatory agent, include, but are not limited to, CRIXIVAN™ (indinavir), NORVIR™ (ritonavir), INVIRASE™ (saquinavir), and VIRACEPT™ (nelfinavir).

In certain embodiments, an immunomodulatory agent is administered in combination with antiretroviral agents, nucleoside/nucleotide reverse transcriptase inhibitors (NRTIs), non-nucleoside reverse transcriptase inhibitors (NNRTIs), and/or protease inhibitors (PIs). NRTIs that may be administered in combination with an immunomodulatory agent, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). NNRTIs that may be administered in combination with an immunomodulatory agent is, include, but are not limited to, VIRAMUNE™ (nevirapine), RESCRIPTOR™ (delavirdine), and SUSTIVA™ (efavirenz). Protease inhibitors that may be administered in combination with an immunomodulatory agent is, include, but are not limited to, CRIXIVAN™ (indinavir), NORVIR™ (ritonavir), INVIRASE™ (saquinavir), and VIRACEPT™ (nelfinavir).

Additional NRTIs include LODENOSINE™ (F-ddA; an acid-stable adenosine NRTI; Triangle/Abbott; COVIRACIL™ (emtricitabine/FTC; structurally related to lamivudine (3TC) but with 3- to 10-fold greater activity in vitro; Triangle/Abbott); dOTC (BCH-10652, also structurally related to lamivudine but retains activity against a substantial proportion of lamivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/Abbott); D-D4FC (related to 3TC, with activity against AZT/3TC-resistant virus); GW420867X (Glaxo Wellcome); ZIAGEN™ (abacavir/159U89; Glaxo Wellcome Inc.); CS-87 (3'azido-2',3'-dideoxyuridine; WO 99/66936); and S-acyl-2-thioethyl (SATE)-bearing prodrug forms of β-L-FD4C and β-L-FddC (WO 98/17281).

Additional NNRTIs include COACTINON™ (Emivirine/MKC-442, potent NNRTI of the HEPT class; Triangle/Abbott); CAPRAVIRINE™ (AG-1549/S-1153, a next generation NNRTI with activity against viruses containing the K103N mutation; Agouron); PNU-142721 (has 20- to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW-420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; Abbott Laboratories); BMS-232632 (an azapeptide; Bristol-Myres Squibb); TIPRANAVIR™ (PNU-140690, a non-peptic dihydropyrone; Pharmacia & Upjohn); PD-178390 (a nonpeptidic dihydropyrone; Parke-Davis); BMS 232632 (an azapeptide; Bristol-Myers Squibb); L-756,423 (an indinavir analog; Merck); DMP-450 (a cyclic urea compound; Avid & DuPont); AG-1776 (a peptidomimetic with in vitro activity against protease inhibitor-resistant viruses; Agouron); VX-175/GW-433908 (phosphate prodrug of amprenavir; Vertex & Glaxo Welcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643-678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX40-4C (a cationic peptide), T22 (an 18 amino acid peptide; Trimeris) and the T22 analogs T134 and T140; CCR5 antagonists such as RANTES (9-68), AOP-RANTES, NNY-RANTES, and TAK-779; and CCR5/CXCR4 antagonists such as NSC 651016 (a distamycin analog). Also included are CCR2B, CCR3, and CCR6 antagonists. Chemokine receptor agonists such as RANTES, SDF-1, MIP-1α, MIP-1β, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compounds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors such as VX-497 (Vertex); and mycopholic acids such as CellCept (mycophenolate mofetil; Roche).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1α, MIP-1β, SDF-1α, IL-2, PROLEUKIN™ (aldesleukin/L2-7001; Chiron), IL-4, IL-8, IL-10, IL-12, and IL-13; interferons such as IFN-α2a; antagonists of TNFs, NFκB, GM-CSF, M-CSF, and IL-10; agents that modulate immune activation such as cyclosporine and prednisone; vaccines such as Remune™ (HIV Immunogen), APL 400-003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targeted to the ER to block surface expression of newly synthesized CCR5 (Yang et al., PNAS 94:11567-72 (1997); Chen et al., Nat. Med. 3:1110-16 (1997)); antibodies such as the anti-CXCR4 antibody 12G5, the anti-CCR5 antibodies 2D7, 5C7, PA8, PA9, PA10, PA11, PA12, and PA14, the anti-CD4 antibodies Q4120 and RPA-T4, the anti-CCR3 antibody 7B11, the anti-gp120 antibodies 17b, 48d, 447-52D, 257-D, 268-D and 50.1, anti-Tat antibodies, anti-TNF-α antibodies, and monoclonal antibody 33A; aryl hydrocarbon (AH) receptor agonists and antagonists such as TCDD, 3,3',4,4',5-pentachlorobiphenyl, 3,3',4,4'-tetrachlorobiphenyl, and α-naphthoflavone (WO 98/30213); and antioxidants such as γ-L-glutamyl-L-cysteine ethyl ester (γ-GCE; WO 99/56764).

In other embodiments, an immunomodulatory agent may be administered in combination with an anti-opportunistic infection agent. Anti-opportunistic agents that may be administered in combination with an immunomodulatory agent, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, an immunomodulatory agent is used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic *Pneumocystis carnii* pneumonia infection. In another specific embodiment, an immunomodulatory agent is used in any combination with ISONIAZID™, RIFAMPIN™, PYRAZI- NAMIDE™, and/or ETHAMBUTOL™ to prophylactically treat, prevent, and/or diagnose an opportunistic *Mycobacterium avium* complex infection. In another specific embodiment, an immunomodulatory agent is used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, an immunomodulatory agent is used in any combination with GANCICLOVIR™, FOSCARNET™, and/or CIDOFOVIR™ to prophylactically treat, prevent, and/or diagnose an opportunistic cytomegalovirus infection. In another specific embodiment, an immunomodulatory agent is used in any combination with FLUCONAZOLE™, ITRACONAZOLE™, and/or KETOCONAZOLE™ to prophylactically treat, prevent, and/or diagnose an opportunistic fungal infection. In another specific embodiment, an immunomodulatory agent is used in any combination with ACYCLOVIR™ and/or FAMCICOLVIR™ to prophylactically treat, prevent, and/or diagnose an opportunistic herpes simplex virus type I and/or type II infection. In another specific embodiment, an immunomodulatory agent is used in any combination with PYRIMETHAMINE™ and/or LEUCOVORIN™ to prophylactically treat, prevent, and/or diagnose an opportunistic *Toxoplasma gondii* infection. In another specific embodiment, an immunomodulatory agent is used in any combination with LEUCOVORIN™ and/or NEUPOGEN™ to prophylactically treat, prevent, and/or diagnose an opportunistic bacterial infection.

In a further embodiment, an immunomodulatory agent is administered in combination with an antiviral agent. Antiviral agents that may be administered with an immunomodulatory agent include, but are not limited to, acyclovir, ribavirin, amantadine, and remantadine.

In a further embodiment, an immunomodulatory agent is administered in combination with an antibiotic agent. Antibiotic agents that may be administered with an immunomodulatory agent include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Additionally, an immunomodulatory agent may be administered alone or in combination with other therapeutic regimens, including but not limited to, radiation therapy. Such combinatorial therapy may be administered sequentially and/or concomitantly.

Kits

The invention also provides a pharmaceutical pack or kit comprising one or more containers filled with one or more of the ingredients of the pharmaceutical compositions. Optionally, associated with such container(s) is a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds. In a specific embodiment, the kit contains a notice in the form prescribed by a governmental agency regulating the manufacture, use or sale of pharmaceuticals or biological products, which notice reflects approval by the agency of manufacture, use or sale for human administration in patients that have an ANA titer greater than or equal to 1:80 and/or greater than or equal to 30 IU of anti-dsDNA antibodies in his/her blood plasma or serum.

EXAMPLES

Having generally described the invention, the same will be more readily understood by reference to the following examples, which are provided by way of illustration and are not intended as limiting.

Example 1

Summary of Results from a Clinical Trial Testing the Use of an Antibody (Belimumab) that Neutralizes Neutrokine-Alpha Protein to Treat Systemic Lupus Erythematosus (SLE)

A prospective, randomized, double-blind, placebo-controlled trial tested belimumab, an antibody that neutralizes Neutrokine-alpha protein, added to standard of care therapy for SLE. 449 subjects with SLE by ACR criteria (Tan et al., Arthritis Rheum. 25:1271-7, (1982); and Hochberg et al., Arthritis Rheum. 40:1725, (1997)), with a history of measurable autoantibodies and SELENA SLEDAI score ≥4 at screening were dosed.

Study agent (1, 4, 10 mg/kg belimumab) or placebo was administered intravenously on days 0, 14, 28 then every 28 days over 52 weeks. Subjects who completed the 52-week treatment period were given the option to continue the study for a 24-week extension period. Belimumab was formulated in 10 mM sodium citrate, 1.9% glycine, 0.5% sucrose, 0.01% (w/v) polysorbate 80, pH 6.5 (±0.3). Subjects receiving placebo dose received the formulation (10 mM sodium citrate, 1.9% glycine, 0.5% sucrose, 0.01% (w/v) polysorbate 80, pH 6.5 (±0.3) without belimumab. Efficacy was assessed every 1-2 months by SELENA SLEDAI (SS), SLE Flare Index, Physician's Global Assessment (PGA). BILAG and SF-36 disease activity scores were also assessed regularly. Pre-defined primary efficacy endpoints were percent reduction in SS score at week 24 and time to flare over 52 weeks as defined by SLE Flare Index. Biologic markers included ANA, anti-dsDNA antibody (Ab), C3/C4, Ig isotypes, and peripheral B cell FACS. B-cells were analyzed every 1-2 months by 4-color FACS (CD19, CD20, CD27, CD69, CD38, CD138 and CD45). Serum autoantibody, including anti-dsDNA Ab, Ig isotypes, total protein, and albumin levels were obtained at the same visits. The likelihood ratio chi-squared, Wilcoxon test or t-test was used to analyze the changes in the biological markers.

The mean age of the subjects in this study was 42; the mean duration of SLE in these subjects was 8.8 years. The baseline level of disease activity in these subjects was relatively high, with approximately 67% of subjects having an SS score 8 points or greater (mean SS score: 9.6). Ninety-three percent of the subjects enrolled in this study were female. 70% of subjects were Caucasian; 24% of subjects African American; 3% of subjects Asian; and 18% of subjects Hispanic (categories overlap). Ninety-eight percent of subjects had historically scored positive for ANA and 71.5% of subjects were ANA+ at entry (ANA titer ≥1:80 and/or anti-dsDNA Ab ≥30 IU/ml at screen/day 0). 50% of subjects had an anti-dsDNA titer ≥30 IU/ml at entry. The most common concomitant medications for SLE used at baseline included the following: steroids (approximately 70% of subjects), aminoquinolines (e.g., anti-malarials) (70%), COX-2 inhibitors (28%), COX-1 inhibitors (26%), azathioprine (20%), methotrexate (16%)

and mycophenolate mofetil (16%). Thirty-four percent and 42% of active and placebo subjects, respectively, were receiving clinically meaningful doses of systemic corticosteroids (defined as a prednisone or prednisone equivalent dose >7.5 mg/day) at baseline. There were no significant differences in baseline characteristics or completion rates across treatment arms (81% completed).

Primary efficacy endpoints did not reach statistical significance, but SS score was significantly reduced by 29% at week 52 in ANA+ subjects (p=0.0435, see FIG. 1). SLE flares decreased in belimumab subjects during weeks 24-52 using a 24 week baseline (log rank p=0.036). Although no significant differences in composite numerical BILAG scores (BILAG composite calculated by converting organ system grades to numerical scores as follows: A=9, B=3, C=1, D=0, E=0) were observed, in ANA+ subjects, analysis of scores for the 8 individual organ domains revealed fewer increases in score in two organ domains (musculoskeletal, p<0.008; neurological, p<0.038) and a trend toward fewer increases in score in three organ domains (cardiovascular & respiratory, p=0.060; general, p<0.15; renal, p<0.15) in belimumab treated subjects at week 52. The PGA score improved by week 16 (p=0.016) through week 52 (p<0.002, all active vs. placebo.) Improvements occurred despite increases of prednisone in placebo vs. belimumab-treated (increases to >7.5 mg/day, ~15% vs. ~7%). In ANA+ subjects, a significant reduction in the frequency of increase in prednisone, from low dose of ≤7.5 mg/day to high dose of >7.5 mg/day, was observed as early as week 8 (p<0.05 over weeks 8-12 and over weeks 32-40). There was no dose response in efficacy, suggesting all doses are equally active. No clinically significant differences were noted in safety, including adverse events (AE), AE severity, infections or lab toxicity in all belimumab arms vs. placebo. Fewer subjects on belimumab had pleurisy (3.3% vs. 8%, p<0.05), while more had urticaria (4% vs. 0%, p<0.05). Infusion reactions were rare, with only 1 severe event reported. Immunogenicity to belimumab was observed in 1 subject (1 mg/kg).

As shown in Table IX, analysis of ANA+ subjects at week 52, revealed belimumab treatment resulted in significant stabilization of the disease relative to placebo as measured by the BILAG index (row 3) and by PGA (row 4). Further, response rates among the treatment groups in the trial were also analyzed using a combined response endpoint (row 1), which combined a measure of global disease activity as measured by the SS score, with a measure of a patient's overall condition as assessed by the PGA disease activity index and a measure of disease in specific organ systems as measured by the BILAG scale. A patient was scored as responding to treatment in the combined endpoint if they had a reduction in SELENA SLE-DAI score ≥4 points, no worsening in their PGA score defined as <0.3 point increase in PGA score and no worsening in any specific organ system defined as no new BILAG A organ domain score or no 2 new BILAG B organ domain scores. Analysis of ANA+ subjects using the above described composite endpoint revealed a significant response to belimumab (p=0.0058).

Additionally, in ANA+ subjects, significant improvements of PGA and SF-36 Physical Component Scores (SF-36 PCS) were observed early in treatment. The mean percent change from baseline PGA showed significant improvement (p<0.05) as early as week 4 in ANA+ subjects treated with belimumab as compared to ANA+ placebo treated subjects. The values for mean percent change in PGA score at 8 weeks, 16 weeks, 48 weeks and 52 weeks also showed significant improvement in belimumab treated ANA+ subjects compared to ANA+ placebo treated subjects (p<0.05 at 8, 16 and 48 weeks; p<0.01 at week 52). The mean SF-36 PCS also showed significant improvements in quality of life in belimumab treated ANA+ subjects compared to ANA+ placebo treated subjects at weeks 12, 24, 48 and 52 (p<0.05 at each time point).

Significant reductions in B cell counts (expressed as median percent change from baseline) were observed for belimumab-treated subjects over the course of the study, including CD19+ B cells (p<0.01 for each measurement taken during weeks 8-52), activated B cells (CD20+/CD69+; p<0.01 for each measurement taken during weeks 8-52), naïve B cells (CD20+/CD27−; p<0.01 for each measurement taken during weeks 8-52), and plasmacytoid B cells (CD20+/CD138+; p<0.01 for each measurement taken during weeks 16-52). Measurements of B cell counts at week 24 demonstrated that belimumab (all treated combined) significantly reduced B-cell by week 24 compared to placebo treated subjects. At week 24, a significant reduction in cell counts (expressed as median percent change from baseline; p<0.0001) was observed for CD19+ B cells, naïve B cells (CD20+/CD27−), activated B cells (CD20+/CD69+), and plasmacytoid B cells (CD20+/CD138+). Belimumab (all treated combined) significantly reduced B-cell counts at week 52 (medians). At week 52, the median percent change in CD20+ B cells was 54%* for all treatment groups combined with significant reduction observed as early as week 8 (p<0.0001). At week 52, the median percent change in plasmacytoid B cells (CD20+/CD138+) was 62%* for all treatment groups combined. And, the median percent change in activated B cells (CD20+/CD69+ B cells) was 70%* at week 52 (* all p<0.002). At week 52, CD19+ B cells and naïve B cells (CD20+/CD27−) were significantly reduced, while memory cell populations were preserved. In contrast, plasma cells (CD20−/CD138+) increased 72.5% over baseline (2.7%) in belimumab treated subjects vs. 30.6% in placebo/standard of care (p=0.02) at week 52. In addition, the belimumab induced reduction in B cell counts continued through week 76. At week 76, the median percent change in CD20+ B cells was 61% for all treatment groups combined. At week 76, the median percent change in plasmacytoid B cells (CD20+/CD138+) was 60% for all treatment groups combined. And the median percent change in activated B cells (CD20+/CD69+ B cells) at week 76 was 84% for all treatment groups combined. Among subjects that had an anti-dsDNA titer ≥30 IU/ml at entry, a significant reduction in anti-dsDNA titer (expressed as median percent change from baseline) was observed as early as week 4 in belimumab treated subjects versus placebo treated subjects (p<0.01 for each measurement taken during weeks 4-12; p<0.03 for each measurement taken during weeks 16-24 and p<0.01 for each measurement taken during weeks 32-52). Belimumab reduced anti-dsDNA Ab at week 52 by 30% (p<0.002, baseline positive) vs. 9% in placebo. This effect was sustained as measurement at week 76 showed a 28% reduction in anti-dsDNA Ab. Significant belimumab-induced reductions in serum IgG, IgA, IgE and IgM levels (expressed as median percent change from baseline) were evident as early as week 8 (p<0.0001) in belimumab treated subjects compared to placebo treated controls. At week 52, serum IgG, IgA, IgE and IgM were reduced (10%, 14%, 34% and 29%, respectively). The reductions continued through week 76 (12% 15%, 35% and 34%, respectively). Moreover, for those subjects with elevated Ig isotype levels at baseline, 41% (52/128, p=0.0014)) of the subjects receiving belimumab returned to normal Ig isotype levels while only 16% (7/45) of the control subjects normalized. A significant increase was observed in C4 complement levels (expressed as median percent change from baseline) for each measurement taken during weeks 4-52 among patients with low C4 complement at baseline in belimumab-treated arms (p≤0.01). At week 52, C4 had increased by 33% (p=0.0126, low baseline C4) in belimumab-treated arms. Again, the belimumab effect was sustained, with C4 improving to 46% at week 76, in belimumab-treated arms. At week 52, 14.5% (24/165) of anti-dsDNA+ subjects receiving belimumab converted to negative compared with 3.5% (2/58) on placebo (p=0.012). At week 76, 3 additional anti-dsDNA+ subjects receiving belimumab converted to negative.

Belimumab was well tolerated and demonstrated significant bioactivity. Belimumab improved PGA scores, reduced B cell counts, increased C4, reduced anti-dsDNA, and reduced/normalized Ig isotype levels. Belimumab delayed flare onset after 6 months. In subjects with ANA positively at entry, the SS score improved significantly at Week 52. Finally, a combined response endpoint revealed a significant response to belimumab treatment by ANA+ subjects (see TABLE IX).

example, Ruggenenti, et al., BMJ. 316(7130):504-9, 1998. Therefore, in this example, a "24 hour urine sample" can refer to either the grams of protein in the urine based on a 24 hour urine sample, or an estimate of the grams of protein in a 24 hour urine sample. An estimate of the grams of protein in a 24 hour urine sample can be based on, for example, the ratio of the amount of protein in a single urine specimen to the amount of creatinine clearance in a single urine sample.

In the standard SELENA SLEDAI scoring system, a patient that exhibits a new onset of proteinuria or a recent increase in proteinuria that results in a proteinuria value in the current 24 hour urine sample that is at least 0.5 grams higher that the proteinuria value determined in the immediate prior 24 hour urine sample, will be assigned a score of 4 for proteinuria in the published SELENA SLEDAI scale, see, for example, Bombardier, et al., Arthritis Rheum. June; 35(6): 630-40, 1992. Accordingly, under the standard SELENA SLEDAI scoring system, a subject that is assigned 4 points at

TABLE IX

Response Rate in ANA+ Subjects at Week 52

| | Placebo N = 86 | 1.0 mg/kg N = 78 | 4.0 mg/kg N = 79 | 10.0 mg/kg N = 78 | All Active N = 235 | P-value[a] |
|---|---|---|---|---|---|---|
| 1 Response rate (% of subjects with reduction in SELENA SLEDAI ≥4 and no worsening by BILAG index (no new BILAG A organ domain score or 2 new BILAG B organ domain scores) and no worsening by PGA (<0.3 point increase) | 25 (29.1%) | 38 (48.7%) | 34 (43.0%) | 36 (46.2%) | 108 (46.0%) | 0.0058 |
| 2 % of subjects with reduction in SELENA SLEDAI ≥4 | 34 (39.5%) | 41 (52.6%) | 38 (48.1%) | 37 (47.4%) | 116 (49.4%) | 0.1169 |
| 3 % of subjects with no worsening by BILAG index (no new BILAG A organ domain score or 2 new BILAG B organ domain scores) | 70 (81.4%) | 69 (88.5%) | 75 (94.9%) | 71 (91.0%) | 215 (91.5%) | 0.0152 |
| 4 % of subjects with no worsening by PGA (<0.3 point increase from baseline) | 66 (76.7%) | 70 (89.7%) | 70 (88.6%) | 72 (92.3%) | 212 (90.2%) | 0.0027 |

[a]P-value from likelihood ratio test for pairwise comparison between combined all active vs. placebo Example 2

Scoring Proteinuria for SELENA SLEDAI

Kidney malfunction is often associated with Systemic lupus erythematosus. One of skill in the art would be aware of a variety of standard measures that can be used to assess kidney function, for example, progression to end-stage renal disease, sustained doubling of serum creatinine, creatinine clearance, iothalamate clearance, protein concentration in a single urine sample and protein concentration in a 24-hour urine sample.

Changes in proteinuria calculated from "24 hour urine samples" is one of the categories scored in the SELENA SLEDAI. Proteinuria measurements may be performed by any method known in the art. In a specific embodiment, a single urine specimen is collected and the amount of protein and/or creatinine clearance is measured, see, for example, Lemann, et al., Clin Chem., 33:297-9, 1987. and Schwab, et al., Arch Intern Med., May; 147(5):943-4, 1987. In a specific embodiment, urine is collected over 24 hours and the amount of protein and/or creatinine clearance is determined. In a specific embodiment, a single urine specimen is collected, the ratio of the amount of protein to the amount of creatinine clearance is determined, and this ratio is used to estimate the amount of protein in a 24-hour urine sample, see, for baseline for proteinuria will have an improving SELENA SLEDAI at a subsequent visit as long as proteinuria does not continue to rise by >0.5 g in a 24 hour urine sample (i.e., the patient will have 4 points deducted from their total score even in the face of stable proteinuria or increases ≤0.5 g/24).

A modification to the SELENA SLEDAI proteinuria scoring rules is described below. As in the standard SELENA SLEDAI scoring system, a patient that exhibits a new onset of proteinuria or a recent increase in proteinuria that results in a proteinuria value in the current 24 hour urine sample that is at least 0.5 grams higher that the proteinuria value determined in the immediate prior 24 hour urine sample, will be assigned a score of 4 for proteinuria. Further, if a patient's proteinuria value has not improved (i.e., there has not been a decrease in proteinuria in the current 24 hour urine sample by at least 0.5 grams compared to proteinuria value determined for the immediate prior 24 hour urine sample) a patient will continue to be assigned a score of 4 for proteinuria. If however, a patients proteinuria value has improved (i.e., there has been a decrease in proteinuria in the current 24 hour urine sample of at least 0.5 grams compared to proteinuria value determined for the immediate prior 24 hour urine sample) a patient will be assigned a score of 0 for proteinuria.

In a specific embodiment, the previous proteinuria measurement was made on a 24 hour urine sample that was obtained ≤26 weeks before the current measurement.

Example 3

Summary of Results from a Clinical Trial Testing the Use of an Antibody (Belimumab) that Neutralizes Neutrokine-Alpha Protein to Treat Rheumatoid Arthritis (RA)

A Phase 2, multi-center, randomized, double-blind, placebo-controlled study was performed in subjects with RA. Subjects were randomized into 4 treatment groups (placebo, 1 mg/kg, 4 mg/kg and 10 mg/kg). Belimumab or placebo was administered at doses of 1, 4 and 10 mg/kg on Days 0, 14 and 28 and every 28 days thereafter for 24 weeks, followed by an optional 24-week extension period. Belimumab was formulated in 10 mM sodium citrate, 1.9% glycine, 0.5% sucrose, 0.01% (w/v) polysorbate 80, pH 6.5 (±0.3). Subjects receiving placebo dose received the formulation (10 mM sodium citrate, 1.9% glycine, 0.5% sucrose, 0.01% (w/v) polysorbate 80, pH 6.5 (±0.3) without belimumab. A total of 283 subjects participated in the study. Belimumab was administered to 214 subjects at doses of 1, 4, or 10 mg/kg during the 24-week treatment phase of the study. Sixty-nine subjects received placebo.

A statistically superior ACR20 response was achieved in the 1 mg/kg (p=0.0097) treatment group, as well as in all active treatment groups combined (p=0.0213). The ACR20 is an index developed by the American College of Rheumatology (ACR) to assess patient response to treatment for rheumatoid arthritis. An ACR20 response is defined as at least a 20% reduction in tender joint count and swollen joint count, in addition to an improvement of at least 20% on three of five other assessments of symptoms or disease manifestations (i.e., patient pain assessment, patient global assessment, physician global assessment, patient self-assessed disability, acute-phase reactant [ESR or CRP]). Moreover, the result for the 1 mg/kg treatment group remained statistically significant under adjustment for multiple comparisons using the Bonferroni-closed procedure (p<0.0166). As in subjects with SLE, belimumab was associated with improved ACR20 responses in subjects with autoantibody positive disease (rheumatoid factor [RF] or anti-cyclic citrullinated peptide [CCP]), as well as in subjects positive for C-reactive protein (CRP) at baseline. Biological activity was observed including statistically significant reductions in CD20+ B-cells, naïve B-cells, activated B-cells and RF; memory cells increased within first month of treatment and slowly declined with continued treatment. Belimumab was well tolerated at all doses. A dose-response relationship was not apparent in this study for efficacy, safety nor biomarker effects. Continued treatment in the extension period of the study was well tolerated. ACR20 response increased to approximately 40% at Week 48. Effects on biomarkers increased or were sustained with continued treatment, while memory cells continued to decline towards baseline levels. Serum concentrations in this study were within the range expected based on the Phase 1 data and concomitant medications (i.e., methotrexate, leflunomide or hydroxychloroquine) had no significant effect on belimumab exposures.

Example 4

Neutrokine-Alpha Extends B Cell Lifespan Through Two Independent Signaling Pathways Neutrokine-alpha, also called BLyS, (B lymphocyte stimulator), BAFF, TALL-1, THANK, TNFSF13B and zTNF4, is essential for the survival of resting peripheral B lymphocytes (Rolink, A. G., and Melchers, F. (2002). *Curr Opin Immunol* 14, 266-275) The importance of Neutrokine-alpha in naïve B cell homeostasis is demonstrated best by the finding that Neutrokine-alpha deficient mice produced by targeted gene deletion or introduction of soluble decoy receptors have striking deficits in marginal zone and follicular B cells, the major mature peripheral B cell populations (Gross, J. A., et al. (2001). *Immunity* 15, 289-302; Schiemann, B., et al. (2001). *Science* 293, 2111-2114) Conversely, ectopic expression of Neutrokine-alpha from a transgene markedly expands follicular and marginal peripheral zone B cells without affecting T cells, Bi cells, early (TI) transitional peripheral B cells, or developing B cells in the marrow (Mackay, F., et al (2003). *Annu Rev Immunol* 21, 231-264). Neutrokine-alpha is also required for the maintenance of numerous B cell tumors and dysregulated Neutrokine-alpha stimulation rescues autoreactive B cells from deletion, thereby promoting the production of autoantibodies (Kalled, S. L. (2005). *Immunol Rev* 204, 43-54). Thus, Neutrokine-alpha has a critical role in the homeostasis of both normal and pathogenic B cells. This Example details the results of experiments performed to understand the mechanism by which Neutrokine-alpha promotes B cell survival Experimental Procedures Mice: Pim-$1^{+/+}2^{+/+}$, Pim-$1^{-/-}2^{+/+}$, Pim-$1^{+/+}2^{-/-}$ and Pim-$1^{-/-}2^{-/-}$ mice were generated from Pim-$1^{+/-}2^{+/-}$ stock of Paul Rothman Columbia University, New York, N.Y. C57BL/6 (B6) mice were from The Jackson Laboratory, Bar Harbor Me. or from the National Cancer Institute Production Program, NCI-Fredrick, Fredrick Md. Animals were bred and maintained at the Univ. of Pennsylvania, Harvard Medical School, or the Univ. of Massachusetts Medical School in accordance with Institutional Animal Care and Use Committee guidelines.

B cell purification: Splenic B cells were obtained by anti-thy1.2 and complement treatment of splenocytes followed by purification of resting B cells using a step wise percoll gradient and harvesting cells at the 60-70% interface. In some experiments CD23' B cells were obtained by positive selection and magnetic separation of splenocytes suspensions using biotinylated anti-CD23 antibody (BD Biosciences-Pharmingen, San Diego Calif.) and streptavidin-coated microbeads (Miltenyi Biotec, Auburn Calif.). CD23' B cells were not size selected on Percoll as environmental activation in vivo leads to the loss of CD23. B cells prepared by antibody and Percoll were >90% B220$^+$, whereas CD23' B cells were >95% pure.

Cell cultures: Purified B cells or CD23' B cells were cultured in RPMI-1640 supplemented with 2-mercaptoethanol, MEM-non-essential amino acids, glutamine, penicillin and streptomycin (complete media, CM). For B cell survival and other assays recombinant human Neutrokine-alpha made at Human Genome Sciences, Rockville Md. was used at 50-100 ng/ml. FLAG-tagged human Neutrokine-alpha was from Dr. Randolph Noelle, Dartmouth Medical School. Murine Neutrokine-alpha was purchased from Alexis Biochemicals, San Diego Calif. and human interferon alpha (IFNα) from PBL Biomedical, Piscataway, N.J. Rapamycin was used at a final concentration of 50 nM, added to cultures from a stock dissolve in methanol. Control B cells in experiments using rapamycin were treated with methanol as a vehicle control. For kinetic assays B cells were prepared and refrigerated overnight at 4° C. 5-6×10$^6$ purified B cells per sample were spun onto 24-well plates that had been coated with 5 ug/ml monoclonal anti-FLAG M2 antibody (Sigma), washed, blocked with 1% BSA in PBS, followed by the addition of FLAG-tagged human Neutrokine-alpha 2 ug/well an hour prior to washing and cell addition. Unstimulated control B cells were those spun onto wells treated with anti-FLAG antibody alone. B cells were also activated by incubation with anti-murine IgM (5 ug/ml), anti-CD40 (0.5 ug/ml) or 100 ng/ml of recombinant human Neutrokine-alpha added to kinetic assay buffer (Hank's balanced salt solution plus 2% BSA).

Antibodies and Western Blotting: Mouse anti-Pim 2 (1D12), Pim 1 (19F7), goat anti-actin (1-19), anti-mouse Ig, anti-rabbit Ig and anti-goat Ig coupled to HRP were obtained from Santa Cruz Biotechnology, Santa Cruz Calif. Rabbit anti-phosphoserine 473 Akt, phosphothreonine 389 p70 S6 kinase, phosphothreonine 24/32 FKHR/FKRHL1, phosphoGSK3$_{\alpha/\beta}$, GSK, p70S6K, FKHR and Akt were purchased from Cell Signaling, Beverly Mass. Rabbit anti-mouse Mcl-1 was purchased from Rockland, Wilmington Mass. Whole cell lysates were prepared by washing B cells in ice cold PBS and lysing in RIPA (150 mM NaCl, 1% NP-40, 0.5% sodium deoxycholate, 0.1% SDS, 50 mM Tris pH8.0) supplemented with protease inhibitors (minitab, Roche, Indianapolis Ind.) and phosphatase inhibitor cocktails I and II (Sigma). 10-50 ug of protein was resolved on 4-12% NuPage bis-tris polyacrylamide gels (Invitrogen, Carlsbad Calif.) and transferred to nitrocellulose. Blots were blocked with 3% BSA (Sigma, IgG free), 0.2% Tween-20 in PBS and incubated with primary antibody in the same buffer overnight at 4° C. Blots were washed with PBS-0.2% Tween-20, incubated with secondary antibody conjugated with HRP and developed using ECLplus (Amersham Bioscience, Piscataway N.J.). Blots were stripped for reprobing by incubation for 20 minutes at 65° C. in PBS supplemented with 1% SDS and 100 uM β-mercaptoethanol. Blots were then washed and blocked as above.

Survival assays: B cells at $5\times10^6$/ml were cultured in 24-well tissue culture dishes in CM at 37° C. B cells were supplemented with 50-100 ng/ml of rhuNeutrokine-alpha, 50 nM rapamycin, 200 U of human IFNα, or a combination of these reagents. B cells were pretreated with 50 nM rapamycin or vehicle 1 hour before culture with the test supplements, fresh rapamycin was added after 48 hours of culture. Survival was monitored daily by counting viable cells using trypan blue exclusion with each determination done in triplicate.

Results

Investigation into the mechanism by which Neutrokine-alpha promotes B cell survival revealed that Neutrokine-alpha activates the Akt/mTOR pathway in B cells. Purified B cells were stimulated for the 0, 5, 20, 60 or 120 minutes with 100 ng/ml recombinant human or murine Neutrokine-alpha or anti-Ig (positive control) at 37° C. in pregassed medium. Lysates were prepared from iced samples and analyzed by Western Blot. Such stimulation of primary B cells with recombinant Neutrokine-alpha results in activation of the Akt pathway as determined by increased phosphorylation of the serine 473 and threonine 308 residues of Akt. Additional experiments in which purified B cells were stimulated with plate bound FLAG-tagged Neutrokine-alpha, soluble Neutrokine-alpha (100 ng/ml) or 0.5 ug/ml anti-CD40 (positive control) showed that Akt itself had been activated as seen by the phosphorylation of the Akt substrates, GSKβ and the forkhead transcription factors FOXO1 and FOXO3a. mTOR is the major downstream effector of Akt. Subsequent to Neutrokine-alpha stimulation, activation of mTOR in primary B cells was also shown by the phosphorylation of the mTOR substrates, p70 S6 kinase and the translation inhibitor 4E-BP1. Phosphorylation patterns were studied by Western blotting.

Rapamycin is a potent inhibitor of mTOR and a potent suppressor of B cell proliferation and differentiation. Small resting B cells from normal donors were cultured for 4 days with and without 100 ng/ml rhuNeutrokine-alpha, vehicle or 50 nM rapamycin which was used to pretreat B cells before culture, added directly to cultures upon initiation and re-added every 2 days. Viable cells were determined at day 4. Coculture of total B or CD23+ B cells with Neutrokine-alpha and rapamycin did not prevent Neutrokine-alpha-mediated enhancement of survival as measured by the number of viable cells present after 4 days in culture. This result suggested that another survival pathway may be active in Neutrokine-alpha treated B cells.

Pims are a family of three serine/threonine kinases that can provide rapamycin resistant apoptosis protection, induced in hematopoietic cells by a variety of activators (Fox, C. J., et al., (2003). *Genes Dev* 17, 1841-1854. and Fox, C. J., et al., (2005). *J Exp Med* 201, 259-266). It was shown by western blot, that subsequent to 2 days of treatment with 100 ng/ml rhuNeutrokine-alpha, primary B cells upregulate Pim1 and Pim 2 expression.

To test the involvement of Pim1 and 2 in Neutrokine-alpha mediated B cell survival, CD23$^+$ B cells from wild type or Pim 1$^{-/+}$2$^{-/+}$ heterozygotes, Pim 1$^{-/-}$ 2$^{-/-}$ double deficient or Pim 2 deficient (Pim 1$^{+/-}$ 2$^{-/-}$) donors were cultured in CM for 4 days with vehicle, 100 ng/ml rhuNeutrokine-alpha and with or without 50 nM rapamycin. Viability was determined daily by trypan blue exclusion. Interestingly, B cells from mice doubly deficient in Pim 1 and Pim 2 (Pim-1$^{-/-}$2$^{-/-}$ B cells) did exhibit enhanced survival when exposed to Neutrokine-alpha. This result could be explained if mTOR and Pims 1 and 2 operate in distinct signaling pathways that each mediate Neutrokine-alpha promotion of cell survival. To test the theory that two separate pathways were involved, the effect of rapamycin on Neutrokine-alpha mediated survival in Pim-1$^{-/-}$2$^{-/-}$ B cells was tested. The addition of rapamycin abrogated Neutrokine-alpha's ability to enhance B cell survival in Pim-1$^{-/-}$2$^{-/-}$ B cells. Further investigation showed that Pim-1$^{+/-}$2$^{-/-}$ B cells, deficient only in Pim 2 function, were as sensitive to rapamycin as Pim-1$^{-/-}$2$^{-/-}$ B cells, indicating that Pim1 is not necessary for Neutrokine-alpha's effects on B cell survival. All together, these data show that there are two independent pathways which work to mediate Neutrokine-alpha mediated survival, and that either pathway alone is sufficient for this activity of Neutrokine-alpha.

Further experiments indicated that expression of the Mcl-, a Bcl-2 family member that plays a role in promoting peripheral B and T cell homeostasis is required for effective enhancement of B cell survival (protection against apoptosis induction) (data not shown).

Accordingly, a composition comprising an inhibitor of the akt/mTOR pathway (e.g., rapamycin) and an inhibitor of the Pim 2 pathway may be used to mimic the effects induced by a Neutrokine-alpha antagonist. Thus, a composition comprising an inhibitor of the Akt/mTOR pathway (e.g., rapamycin) and an inhibitor of the Pim 2 pathway may be used as an antagonist of Neutrokine-alpha to inhibit B cell survival or to treat one or more of the diseases or disorders disclosed herein. For instance, a composition comprising an inhibitor of the Akt/mTOR pathway (e.g., rapamycin) and an inhibitor of the Pim 2 pathway may be used to decrease B cell lifespan. Additionally, a composition comprising an inhibitor of the Akt/mTOR pathway (e.g., rapamycin) and an inhibitor of the Pim 2 pathway may be used to treat an autoimmune disease. In specific embodiments, a composition comprising an inhibitor of the Akt/mTOR pathway (e.g., rapamycin) and an inhibitor of the Pim 2 pathway may be used to treat B cell mediated autoimmune diseases. In other specific embodiments, a composition comprising an inhibitor of the Akt/ mTOR pathway (e.g., rapamycin) and an inhibitor of the Pim 2 pathway may be used to treat autoimmune diseases in which autoantibodies are prevalent. In specific embodiments, a composition comprising an inhibitor of the Akt/mTOR pathway (e.g., rapamycin) and an inhibitor of the Pim 2 pathway may be used to treat rheumatoid arthritis, systemic lupus erythematosus multiple sclerosis, myasthenia gravis, Sjogren's syndrome, type 1 diabetes, idiopathic thrombocytopenia purpura, Gullian-Barre syndrome, Hashimoto's thyroiditis, or Graves' disease.

Additionally, a composition comprising an inhibitor Mcl-1 may be used to mimic the effects induced by a Neutrokine-alpha antagonist Thus, a composition comprising an inhibitor of Mcl-1 may be used as an antagonist of Neutrokine-alpha to inhibit B cell survival or to treat one or more of the diseases or disorders disclosed herein. For instance, a composition comprising an inhibitor of Mcl-1 may be used to decrease B cell lifespan. Additionally, a composition comprising an inhibitor of Mcl-1 may be used to treat an autoimmune disease. In specific embodiments, a composition comprising an inhibitor of Mcl-1 may be used to treat B cell mediated autoimmune diseases. In other specific embodiments, a composition comprising an inhibitor of Mcl-1 may be used to treat autoimmune diseases in which autoantibodies are prevalent. In specific embodiments, a composition comprising an inhibitor of Mcl-1 may be used to treat rheumatoid arthritis, systemic lupus erythematosus multiple sclerosis, myasthenia gravis, Sjogren's syndrome, type 1 diabetes, idiopathic thrombocytopenia purpura, Gullian-Barre syndrome, Hashimoto's thyroiditis, or Graves' disease.

Example 5

Characterization of Antibody Formulations

Analysis of 1 mg/ml IgG1/λ antibody formulated in 10 mM histidine and 10 mM citrate buffers by differential scanning calorimetry was used to assess the thermal stability of the antibody in each formulation. The particular antibody used in this study was an IgG1/λ antibody that is specific for Neutrokine-alpha and is capable of neutralizing Neutrokine-alpha activity. The analysis revealed that the melting temperature was highest for both buffers in the pH range of 6.0-7.5, and higher melting temperature generally indicates higher thermal stability. The melting temperature of the citrate buffer was ~2° C. higher than the histidine buffer in this pH range, suggesting that the citrate buffer may yield a more stable antibody formulation. However, the thermal reversibility of the antibody was higher in the histidine buffer than the citrate buffer. This suggests that the antibody has greater biophysical stability in histidine than in citrate despite its lower melting temperature. This was confirmed by stability studies of antibody formulations which found that 10 mM histidine resulted in less aggregation than 10 mM citrate when stored at 2-8° C. over 18 months. During the stability study, the buffering capacity of the two buffers was assessed by repeated pH measurements. In addition to providing greater biophysical stability for the antibody, histidine appears to provide greater buffering capacity at pH 6.0-6.5 than citrate in a pH range of 6.5-7.0. In the 18 month stability study, the histidine formulations remained at a stable pH over time at all temperatures tested (2-8° C., 25° C., and 40° C.). In contrast, the citrate formulations had wider variances at the higher temperatures (data not shown).

Example 6

Long-Term Stability Study of an Antibody Formulation

To determine the shelf-life of an antibody formulation, a long-term stability study of 100 mg/ml antibody in 10 mM histidine, 150 mM NaCl, 0.01% (w/v) polysorbate 80, pH 6.0 was performed. The particular antibody used in this study was an IgG1/λ antibody that is specific for Neutrokine-alpha and is capable of neutralizing Neutrokine-alpha activity. Two ml aliquots in 5 ml glass vials were stored upright for 24 months at −80° C., 2-8° C., 25° C. and 40° C. Samples were stored at −80° C. as a control, at 2-8° C. to determine shelf-life, and at accelerated conditions (25° C. and 40° C.) to monitor any possible degradation pathways that could occur. Periodically over 24 months, samples were analyzed by multiple assays, including: visual inspection, pH, concentration, SDS-PAGE, SEC-HPLC, ion-exchange-HPLC (IE-HPLC), bioassay, capillary isoelectric focusing (cIEF), peptide mapping, RP-HPLC and ISOQUANT®.

Analysis of samples stored for 24 months at 2-8° C. and −80° C. by SEC-HPLC, IE-HPLC and RP-HPLC were visually comparable by all three methods, with only minor differences observed. The 2-8° C. sample decreased in SEC-HPLC purity at an approximate rate of 0.03% per month, and increased in early-eluting IE-HPLC peaks (mostly due to deamidation) at an approximate rate of 0.14% per month (data not shown). The 2-8° C. sample showed only small changes in aggregation (<1%), deamidation (~4%), and oxidation (1%) of the antibody after 24 months of storage. However, significant degradation was observed by all assays for samples stored under accelerated conditions. Degradation observed by SEC-HPLC under accelerated conditions included both aggregation and fragmentation. IE-HPLC assays showed that storage at accelerated conditions results in an increase in early eluting peaks. Deamidation and fragmentation were observed by peptide mapping at 25° C.; deamidation, oxidation, fragmentation and rearrangement of aspartate to isoaspartate were observed at 40° C. Thus, 100 mg/ml of an IgG1/λ antibody in a pharmaceutical formulation of the invention is stable at 2-8° C. for at least 24 months of storage.

Example 7

In Vitro Assay to Test for Inhibition of Neutrokine-Alpha-Neutrokine-Alpha Receptor Interaction The following describes an assay that can be used to test if a compound works as an antagonist of Neutrokine-alpha. Specifically, this assay measures the ability of compound to inhibit soluble Neutrokine-alpha binding to its cognate receptor on IM9 cells.

Preparation of Biotinylated Neutrokine-Alpha

One hundred μg of either human or mouse Neutrokine-alpha is dialysed overnight at 4° C. against 50 mM sodium bicarbonate (sodium hydrogen carbonate) pH8.5 using a slide-a-lyzer cassette (Pierce). The next day, NHS-biotin (Pierce) is dissolved in DMSO to 13.3 mg/ml. This is then added to the Neutrokine-alpha at a molar ratio of 20:1 biotin:Neutrokine-alpha, mixed and incubated on ice for 2 hours. The biotinylated Neutrokine-alpha is then dialysed back into sterile PBS (Sigma) using a slide-a-lyzer cassette overnight at 4° C. The biological activity of the biotinylated Neutrokine-alpha is confirmed using the receptor binding inhibition assay (see below).

Maintenance of IM9 Cells

IM9 cells are a human B lymphocyte cell line that express Neutrokine-alpha receptors. IM9 cells can be maintained in RPMI-1640 supplemented with 4 mM L-glutamine, 10% FCS, 10 U penicillin, 100 g/ml streptomycin (all reagents from Sigma). The cells are thawed from frozen stock and can be used in assays after 5 days in culture when they reach a density of $4\text{-}8 \times 10^5$/ml.

Receptor Binding Inhibition Assay

Flat-bottomed 96-well plates (Costar) are coated with 100 µl per well of a 1:10 dilution of poly-L-lysine (Sigma) in PBS for 1 hour at room temperature. The plates are then washed twice with water, allowed to air-dry and placed at 4° C. overnight. One hundred µl of IM9 cells (at $10^6$/ml in RPMI-1640 culture medium) are then added to each well. Plates are then centrifuged at 3200 rpm for 5 mins to pellet the cells. The media is carefully aspirated and 200 µl of MPBS (PBS containing 3% Marvel blocking solution) added to each well. The plates are then allowed to block for 1 hour at room temperature.

In a separate 96-well plate, 10 µl of biotinylated Neutrokine-alpha (at 162.5 ng/ml) in MPBS is added to each well to give a final concentration of 25 ng/ml. Fifty-five µl of each test compound is added to each well. The final volume in each well is 65 µl. Preferably the test compound is also diluted in MPBS. Plates are then incubated at room temperature for 30 minutes.

The IM9 coated plates are washed twice in PBS, tapped dry and immediately 50 µl of the phage/biotinylated-Neutrokine-alpha mix is added and incubated at room temperature for 1 hour. Plates are washed three times in PBST and three times in PBS, tapped dry and 50 µl of streptavidin-Delfia (Wallac) is added to each well at 1:1000 dilution in the Manufacturer's assay buffer. The plates are then incubated at room temperature for 1 hour and washed six times in Delfia wash solution (Wallac). After tapping the plates dry, 100 µl per well of Delfia enhancement solution (Wallac) is added. The plates are gently tapped to encourage micelle formation, incubated at room temperature for 10 minutes, and fluorescence read on a Wallac 1420 workstation at 6520 nM.

Appropriate controls to include this assay include a bio-Neutrokine-alpha only sample to demonstrate what the maximal binding of biotinylated Neutrokine-alpha to its receptor is in this assay and sample that does not contain bio-Neutrokine-alpha to demonstrate the background signal in this assay. An additional useful control is non-Neutrokine-alpha specific, or "irrelevant", compound—a compound that is structurally similar to the test compound but that is not believed to interact with either Neutrokine-alpha or one of Neutrokine-alpha's receptors. If the test compound was an anti-Neutrokine-alpha antibody of the IgG1 isotype, a suitable "irrelevant control would be another IgG1 antibody that is not specific for Neutrokine-alpha or one of its receptors.

Example 8

Human B Cell Proliferation Assay for In Vitro Screening of Neutrokine-Alpha Antagonist Molecules One bioassay for assessing the effects of a putative Neutrokine-alpha antagonist is performed in triplicate in 96 well format by mixing equal volumes of Neutrokine-alpha, responder cells, and putative antagonist each of which is prepared as a 3× stock reagent.

B-lymphocytes are purified from human tonsil by MACS (anti-CD3 depletion), washed, and resuspended in complete medium (CM) (RPMI 1640 with 10% FBS containing 100 U/ml penicillin, 100 µg/ml streptomycin, 4 mM glutamine, 5×10E-5 M beta-mercaptoethanol) at a concentration of $3 \times 10^6$ cells/mL. *Staphylococcus aureus*, Cowan I (SAC, Cal-Biochem) is added to cells at 3× concentration (3X=1:33,333 dilution of stock).

Meanwhile, eight serial dilutions (3-fold) of potential antagonist are prepared in CM such that the diluted antagonists are at 3× the final concentrations to be tested in the assay. For example, antibodies are routinely tested starting at a final concentration of 10 ug/mL and going down to about 1.5 ng/mL.

Human rNeutrokine-alpha is prepared in CM to 3× concentration (3X=300 ng/mL, 30 ng/mL, and 3 ng/mL) in CM. Potential antagonists are routinely tested at several concentrations of Neutrokine-alpha to avoid false negatives due to unexpectedly low affinity or antagonist concentration.

Fifty microliters of diluted antagonist and 50 uL of diluted Neutrokine-alpha are than added to wells containing 50 uL of the cells mixture.

Cells are then incubated for 72 hours (37° C., 5% $CO_2$) in a fully humidified chamber. After 72 hrs, the cells are supplemented with 0.5 µCi/well $^3$H-thymidine (6.7 Ci/mmol) and incubated for an additional 24 hours. Plates are harvested using a Tomtec Cell Harvester and filters counted in a Top-Count Scintillation counter (Packard).

Appropriate controls to include this assay include a sample in which no antagonist was included to demonstrate what the maximal $^3$H-thymidine incorporation is in this assay and a sample that does not contain Neutrokine-alpha to demonstrate the background signal in this assay. An additional useful control is a non-Neutrokine-alpha specific, or "irrelevant", test compound—a compound that is structurally similar to the test compound but that is not believed to interact with either Neutrokine-alpha or one of Neutrokine-alpha's receptors. For instance, if the test compound was an anti-Neutrokine-alpha antibody of the IgG1 isotype, a suitable "irrelevant" control would be another IgG1 antibody that is not specific for Neutrokine-alpha or one of its receptors.

One of skill in the art will be aware of modifications that may be made to this assay, for example, in the order of steps or the reagents used. As a specific example, the B cells may be primed with anti-IgM instead of SAC. One of skill in the art is also aware of other assays that may be used to test the ability of a compound to act as an antagonist of Neutrokine-alpha.

Example 9

Murine B Cell Proliferation Assay for In Vitro Screening of Neutrokine-Alpha Antagonist Molecules To determine if a potential Neutrokine-alpha antagonist inhibits Neutrokine-alpha mediated B cell proliferation, a murine splenocyte proliferation assay may be performed Briefly, murine splenocytes are isolated by flushing a spleen using a 25 g needle and 10 ml of complete medium (RPMI 1640 with 10% FBS containing 100 U/ml penicillin, 100 µg/ml streptomycin, 41 nM glutamine, $5 \times 10^{-5}$M β-mercaptoethanol). The cells are passed through a 100 micron nylon filter to remove cell clumps. The cell suspension is then ficolled at 400×g for 25 minutes at room temperature (one 15 ml conical tube/spleen; 3 ml ficol, 10 ml cell suspension/spleen; Ficol 1083 from Sigma). The recovered cells are washed 3 times in complete medium and counted. Recovered cells are then diluted to a concentration of $3 \times 10^6$/ml in complete medium containing a 3× concentration of SAC (3X=1:

33,333 dilution of stock; stock is a 10% suspension of *Staph. aureus* (Cowan I strain) available from Calbiochem).

For each antibody, 50 microliters of antibody dilutions at 30 µg/ml, 3.0 µg/ml, and 0.3 µg/ml concentrations are aliquoted into individual wells of a 96 well plate in triplicate. Medium containing no antibody (and human isotype controls (purchased commercially) when necessary) are used as negative controls.

Neutrokine-alpha protein is diluted in complete medium to concentrations of 300 ng/ml, 90 ng/ml and 30 ng/ml. 50 microliters of each of the Neutrokine-alpha dilutions are then added to the antibody dilution series in the plates. The plate containing the antibody and Neutrokine-alpha dilutions are then incubated for 30 minutes at 37° C., 5% $CO_2$, after which 50 microliters of the splenocyte cell suspension containing SAC is added to all wells. The plates are then incubated for 72 hours (37° C., 5% $CO_2$).

After 72 hours, each well is supplemented with 50 µl of complete medium containing 0.5 µCi of 3H-thymidine (6.7 Ci/mM; Amersham) and cells are incubated for an additional 20-24 hours at (37° C., 5% $CO_2$). Following incubation cells are harvested using a Tomtec Cell Harvester and filters counted in a TopCount Scintillation counter (Packard).

One of skill in the art will be aware of modifications that may be made to this assay, for example, in the order of steps or the reagents used. As a specific example, the B cells may be primed with anti-IgM instead of SAC. One of skill in the art is also aware of other assays that may be used to test the ability of a compound to act as an antagonist of Neutrokine-alpha.

Example 10

Summary of results from an extended clinical trial testing the use of an aittibody (belimumab) that neutralizes Neutrokine-alpha protein to treat systemic lupus erythematosus (SLE)

As shown in Example 1, 449 SLE subjects were enrolled in a 52 week double-blind clinical trial testing the use of belimumab, an antibody that neutralizes Neutrokine-alpha protein, (at dosages of 1, 4, or 10 mg/kg) to treat SLE. Following 52 weeks of treatment, all subjects had the option to continue the study for a 24-week extension period. The results from this clinical trial and extension period are described in Example 1.

To evaluate the long term clinical effects of belimumab administration in SLE patients, subjects enrolled in the clinical trial, as described in Example 1, continued open-label treatment with belimumab in a continuation trial. During the 24-week extension period as described in Example 1, subjects in the placebo arm (taking placebo) were switched to 10 mg/kg belimumab every 28 days at week 56, while belimumab subjects either remained on their current dose or increased to 10 mg/kg. At week 76, all remaining subjects were given 10 mg/kg of belimumab every 28 days. Of the patients who completed 52 weeks of treatment in the randomized, double-blind, placebo-controlled Phase 2 trial (see example 1), 96% (351/364) elected to enter the 24-week extension phase of the trial, and 92% (321/351) of those who entered completed it. Of those completing the extension phase, 78% (250/321) continue to receive belimumab in a long-term continuation study.

Serum autoantibodies, Ig isotypes and complement (C3, C4) were measured at 1-3 month intervals. In addition, the population with baseline serologic activity (ANA ≥1:80 or anti-dsDNA Ab ≥30IU; 72% of the original cohort herein called seropositive patients or seropositive subjects) was evaluated for SS, physician global assessment (PGA 0-3 units), BILAG, Spondylitis Functional Index (SFI) and autoantibody status at 1-3 month intervals. The percent of subjects who had at least one flare defined according to SFI over the five six-month intervals through 2.5 years of belimumab therapy (the clinical trial as discussed in Example 1 plus the continuation trial as discussed herein) were also assessed.

Results

Serum Autoantibodies

At baseline, the 449 subjects had a mean SS score=9.6. 68% of these subjects had ≥1 BILAG A or 2 BILAG B flares and a mean PGA score=1.5. (See Example 1). Subjects were also positive for a number of autoantibodies. For example, at baseline 50% of the subjects were anti-double-stranded DNA positive (anti-dsDNA+); 47% of the subjects were ribonucleoprotein positive (RNP+); 39% of the subjects were Ro antigen positive (Ro+); and 28% of the subjects were anti-cardiolipin positive (aCl+).

Among the subjects that were anti-dsDNA+ at baseline, anti-dsDNA levels decreased over time in the belimumab-treated subjects from weeks 52-128 (29-44%, placebo week 52=9%). Belimumab-treated subjects were more likely to have a significant anti-dsDNA reduction (≥50% reduction or become negative) than subjects receiving placebo at week 52 (30% vs. 17%; See Example 1) and had further reduction through week 128 (47%). The percent of subjects with significant anti-dsDNA reduction was higher in clinical responders (subjects who achieved the combined response endpoint; see example 1) than non-responders (35% vs. 19% at week 52, 56% vs. 32% at week 128, p≥0.05). In addition, Anti-Sm (antibodies specific against the Sm antigen)(n=85) or RNP (n=205) reverted from positive at baseline to negative more often in subjects treated with belimumab from weeks 52-128 (Anti-Sm: 26-36% vs. placebo week 52=5%; RNP 9-27% vs. placebo at week 52=2%). The combined response rate at weeks 52 and 128 for all subjects with baseline autoantibodies was: Anti-dsDNA (47%/53%), RNP (42%/52%), Ro (41%/51%) and aC1 (51%/51%).

These results support the use of belimumab or other immunomodulatory agents including Neutrokine-alpha antagonists in the treatment of SLE and other autoimmune diseases as well as other disorders wherein patients are positive for anti-dsDNA, anti-Sm, RNP, Ro, or aCl autoantibodies. Accordingly, a preferred embodiment of the present invention is the treatment of patients positive for anti-dsDNA, anti-Sm, RNP, Ro, or aCl autoantibodies with belimumab or immunomodulatory agents including Neutrokine-alpha antagonists.

Ig Isotypes

As described in Example 1, the maximal median reductions in belimumab-treated subjects with regard to each Ig isotype were reached in the first 8-24 weeks. With continued treatment, these levels stabilized or gradually declined. As compared to baseline, median reductions over weeks 52, 76, 104 and 128 were: IgG: 10%, 12%, 10%, 9%, placebo week 52 up 3%; IgA: 14%, 15%, 14%, 14%, placebo week 52=3%; IgM: 29%, 34%, 35%, 40%, placebo week 52=5%; IgE: 34%, 35%, 37%, 41%, placebo week 52=0%.

Also, it was found that subjects with elevated IgE (>114 KU/L) at baseline had an even greater reduction from week 52 to 128 (44% to 57%). Moreover, subjects (n=125) with hypergammaglobulinemia (>1618 mg/dL) at baseline normalized on belimumab from week 52-128 (45%-57%) vs. placebo week 52=17%). The median percent IgG reduction was greater over time in subjects with elevated IgG vs. those with normal IgG at baseline (14-18% vs. 7-8% at weeks 52-128).

Taken together, these results support the use of belimumab or other immunomodulatory agents including Neutrokine-alpha antagonists in the treatment of SLE and other autoimmune diseases as well as disorders wherein patients have: (1) elevated IgE levels (>114 KU/L); (2) hypergammaglobulinemia (>1618 mg/dL); (3) elevated IgG levels; or (4) require long term reductions in serum Ig isotype levels.

Accordingly, a preferred embodiment of the present invention is the treatment of patients with elevated IgE levels with belimumab or immunomodulatory agents including Neutrokine-alpha antagonists. In addition, another preferred embodiment of the present invention is the treatment of patients with hypergammaglobulinemia with belimumab or immunomodulatory agents including Neutrokine-alpha antagonists. Moreover, another preferred embodiment of the present invention is the treatment of patients with elevated IgG levels with belimumab or immunomodulatory agents including Neutrokine-alpha antagonists. Furthermore, a preferred embodiment of the present invention is the treatment of patients requiring a long term reduction in serum Ig isotype levels with belumumab or immunomodulatory agents including Neutrokine-alpha antagonists.

Complement (C3, C4)

In SLE subjects with low C3 (n=135) or C4 (n=180) at baseline, those treated with belimumab increased complement over time at weeks 52, 76, 96 and 128 (C4: 33%, 46%, 57%, 67%; placebo at week 52=14%; C3: 6%, 10%, 15%, 18%; placebo at week 52=−1%). These results support the use of belimumab or immunomodulatory agents including Neutrokine-alpha antagonists in the treatment of SLE and other autoimmune diseases as well as other disorders wherein patients require a long or short term increase in the level of C3 or C4 complement.

Thus, a preferred embodiment of the present invention is the treatment of patients in need of a long or short term increase in C3 or C4 complement levels with belimumab or immunomodulatory agents including Neutrokine-alpha antagonists.

Seropositive Patients

The combined response rate (see example 1) in seropositive subjects (n=321) was 46% and 49% for all belimumab treatment groups combined at weeks 52 and 56 (vs. placebo 29% and 35%, p<0.05). This response rate increased to 55% from weeks 76-128 of continuous therapy (ITT analysis). Of the seropositive subjects (n=175) who completed 128 weeks of the study, 63% responded. At week 52, the percent of seropositive subjects with SS>4 point improvement on belimumab were 49% (vs. placebo 39%) and improved to 58-60% from weeks 76-128. The percent of seropositive subjects with new 1A or 2B BILAG flares at week 52 who were receiving belimumab was 9% (vs. placebo 19%, p=0.0152) and at weeks 96-128 was 6-7%. Seropositive subjects with worsening PGA scores at week 52 who were receiving belimumab was 10% (vs. placebo 23%, p=0.0027), and at weeks 96-128 this dropped to 7-9%.

An analysis of SFI revealed a decreasing SLE flare rate in seropositive subjects treated with belimumab when evaluated at six-month intervals. For example, at the first six-month interval a decreased SLE flare rate was shown to be 72% (vs. placebo at 76%) with a further decrease in the second six-month intervals where a 61% flare rate was exhibited (vs. placebo at 73%). The third, fourth and fifth six-month intervals demonstrated flare rates at 57%, 30%, and 33% respectively.

These results support the use of belimumab or immunomodulatory agents including Neutrokine-alpha antagonists in the treatment of SLE and other autoimmune diseases in seropositive patients (see example 1). Accordingly, a preferred embodiment of the present invention is the treatment of seropositive patients with belimumab or immunomodulatory agents including Neutrokine-alpha antagonists.

CONCLUSION

The extended treatment of SLE patients with belimumab over 2.5 years (trial described in example 1+continuation trial) resulted in: a sustained improvement in SLE disease activity independent of the type of autoantibody status at baseline; a decreased frequency of flares as measured by SFI; a normalization of IgG; a reduction in autoantibodies and Ig isotypes; and an increase in complement. These objective changes demonstrate long-term in vivo biological activity of belimumab that support the clinical use of belimumab in active SLE and other autoimmune diseases or disorders characterized by auto-antibody production, increased Ig isotype levels, decrease in complement levels, or flares.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith in both computer and paper forms are hereby incorporated by reference in their entireties. Additionally, the entire disclosure (including the specification, sequence listing, and drawings) of each of the following U.S. Provisional and Non-Provisional Patent Applications and International Patent Applications are herein incorporated by reference in their entireties: U.S. Provisional Application Nos. 60/929,109, filed Jun. 13, 2007; 60/725,625, filed Oct. 13, 2005; 60/735,967, filed Nov. 14, 2005; 60/776,664, filed Feb. 27, 2006; 60/781,387, filed Mar. 13, 2006; 60/787,557, filed Mar. 31, 2006; 60/797,360, filed May 4, 2006; 60/814,870, filed Jun. 20, 2006; 60/815,558, filed Jun. 22, 2006; 60/815,827, filed Jun. 23, 2006; 60/834,150, filed Jul. 31, 2006; 60/725,626, filed Oct. 13, 2005; 60/735,988, filed Nov. 14, 2005; 60/776,665, filed Feb. 27, 2006; 60/797,351, filed May 4, 2006; 60/814,869, filed Jun. 20, 2006; 60/815,559, filed Jun. 22, 2006; 60/834,152, filed Jul. 31, 2006; 60/725,627, filed Oct. 13, 2005; 60/735,964, filed Nov. 14, 2005; 60/776,658, filed Feb. 27, 2006; 60/725,629, filed Oct. 13, 2005; 60/735,963, filed Nov. 14, 2005; 60/776,660, filed Feb. 27, 2006; 60/725,628, filed Oct. 13, 2005; 60/735,987, filed Nov. 14, 2005; 60/776,659, filed Feb. 27, 2006; 60/543,261 filed Feb. 11, 2004, 60/580,387 filed Jun. 18, 2004, 60/617,191 filed Oct. 12, 2004, 60/368,548 filed Apr. 1, 2002, 60/336,726 filed Dec. 7, 2001, 60/331,478 filed Nov. 16, 2001, 60/330,835 filed Oct. 31, 2001, 60/329,747 filed Oct. 18, 2001, and 60/329,508 filed Oct. 17, 2001, 60/225,628 filed Aug. 15, 2000, 60/227,008 filed Aug. 23, 2000, 60/234,338 filed Sep. 22, 2000, 60/240,806 filed Oct. 17, 2000, 60/250,020 filed Nov. 30, 2000, 60/276,248 filed Mar. 6, 2001, 60/293,499 filed May 25, 2001, 60/296,122 filed Jun. 7, 2001, 60/304,809 filed Jul. 13, 2001,60/122,388 filed Mar. 2, 1999, 60/124,097 filed Mar. 12, 1999, 60/126,599 filed Mar. 26, 2000, 60/127,598 filed Apr. 2, 1999, 60/130,412 filed Apr. 16, 1999, 60/130,696 filed Apr. 23, 1999, 60/131,278 filed Apr. 27, 1999, 60/131,673 filed Apr. 29, 1999, 60/136,784 filed May 28, 1999, 60/142,659 filed Jul. 6, 1999, 60/145,824 filed Jul. 27, 1999, 60/167,239 filed Nov. 24, 1999, 60/168,624 filed Dec. 3, 1999, 60/171,108 filed Dec. 16, 1999, 60/171,626 filed Dec. 23, 1999, 60/176,015 filed Jan. 14, 2000, and 60/036,100 filed Jan. 14, 1997; U.S. Nonprovisional application Ser. No. 11/054,539 filed Feb. 10, 2005, Ser. No. 10/739,042 filed Dec. 19, 2003, Ser. No. 10/735,865 filed Dec. 16, 2003, 10/270,487 filed Oct. 16, 2002, Ser. No. 09/929,493, filed Aug. 14, 2001, Ser. No. 09/588,947 filed Jun. 8, 2000, Ser. No. 09/589,285 filed Jun. 8, 2000, Ser. No. 09/589,286 filed Jun. 8, 2000, Ser. No. 09/589,287 filed Jun. 8, 2000, Ser. No. 09/589,288 filed Jun. 8, 2000, Ser. No. 09/507,968 filed Feb. 22, 2000, Ser. No. 09/255,794 filed Feb. 23, 1999, and Ser. No. 09/005,874 filed Jan. 12, 1998; and International Patent Application Serial Nos. PCT/US01/25549 filed Aug. 15, 2001, PCT/US00/04336, filed Feb. 22, 2000, and PCT/US96/17957, filed Oct. 25, 1996.

---

What is claimed is:

1. A method of reducing the frequency or quantity of corticosteroid administered to a patient with systemic lupus erythematosus comprising:
   (a) providing a patient that has systemic lupus erythematosus and to whom a corticosteroid is being administered at a first frequency or quantity;
   (b) administering a therapeutically effective amount of an antagonist of Neutrokine-alpha to said patient, wherein the antagonist of Neutrokine-alpha is
      an anti-Neutrokine-alpha antibody;
      and
   (c) administering the corticosteroid to said patient at a second frequency or quantity that is less than the first frequency or quantity.

2. The method of claim 1 wherein the antagonist of Neutrokine-alpha is only administered when the patient has at least one characteristic selected from the group consisting of:
   (a) an ANA titer ≥1:80;
   (b) ≥30 IU/mL of anti-dsDNA antibodies in his/her blood plasma or serum;
   (c) a SELENA SLEDAI score ≥6;
   (d) a depressed level of C3 complement factor in his/her blood plasma or serum;
   (e) a depressed level of C4 complement factor in his/her blood plasma or serum;
   (f) the patient is receiving ≥7.5 milligrams/day of prednisone; and
   (g) the patient is receiving or had previously received immunosuppressant therapy for the treatment of lupus-related symptoms.

3. The method of claim 2 wherein the antagonist of Neutrokine-alpha is only administered when the patient has ≥30 IU/mL of anti-dsDNA antibodies in his/her blood plasma or serum.

4. The method of claim 2 wherein the antagonist of Neutrokine-alpha is only administered when the patient has an ANA titer ≥1:80 and ≥30 IU/mL of anti-dsDNA antibodies in his/her blood plasma or serum.

5. The method of claim 2 wherein the antagonist of Neutrokine-alpha is only administered when the patient has a SELENA SLEDAI score ≥6.

6. The method of claim 2 wherein the antagonist of Neutrokine-alpha is only administered when the patient has less than 90 milligrams/deciliter of C3 complement factor in his/her blood plasma or serum.

7. The method of claim 2 wherein the antagonist of Neutrokine-alpha is only administered when the patient has less than 16 milligrams/deciliter of C4 complement factor in his/her blood plasma or serum.

8. The method of claim 2 wherein the antagonist of Neutrokine-alpha is only administered when the patient is receiving ≥7.5 milligrams/day of prednisone.

9. The method of claim 2 wherein the antagonist of Neutrokine-alpha is only administered when the patient is receiving or had previously received immunosuppressant therapy for the treatment of lupus-related symptoms.

10. The method of claim 2 wherein the antagonist of Neutrokine-alpha is only administered when the patient has an ANA titer ≥1:80.

11. The method of claim 1 wherein the corticosteroid is selected from the group consisting of prednisone, prednisolone, hydrocortisone, methylprednisolone and dexamethasone.

12. The method of claim 1 wherein the corticosteroid is prednisone.

13. The method of claim 12 wherein the quantity of prednisone administered to the patient is reduced by at least 25% to ≤7.5 milligrams/day following administration of the antagonist of Neutrokine-alpha.

14. The method of claim 1 wherein the antibody comprises the amino acid sequences of a set of VH and VL domains selected from the group consisting of:
   (a) the VH domain and the VL domain of SEQ ID NO:13;
   (b) the VH domain and the VL domain of SEQ ID NO:14;
   (c) the VH domain and the VL domain of SEQ ID NO:15;
   (d) the VH domain and the VL domain of SEQ ID NO:16;
   (e) the VH domain and the VL domain of SEQ ID NO:17;
   (f) the VH domain and the VL domain of SEQ ID NO:18;
   (g) the VH domain of SEQ ID NO:19 and the VL domain of SEQ ID NO:20; and
   (h) the VH domain of SEQ ID NO:21 and the VL domain of SEQ ID NO:22.

15. The method of claim 1 wherein the antibody comprises the amino acid sequences of the VH domain and the VL domain of SEQ ID NO:17.

* * * * *